(12) United States Patent
Reisner et al.

(10) Patent No.: US 10,668,109 B2
(45) Date of Patent: Jun. 2, 2020

(54) CONDITIONING PROTOCOLS AND USE OF SAME FOR TISSUE REGENERATION

(71) Applicant: Yeda Research and Development Co. Ltd., Rehovot (IL)

(72) Inventors: Yair Reisner, Old Jaffa (IL); Chava Rosen, Rehovot (IL); Elias Shezen, Rehovot (IL); Irit Milman Krentsis, Rehovot (IL)

(73) Assignee: Yeda Research and Development Co. Ltd., Rehovot (IL)

( * ) Notice: Subject to any disclaimer, the term of this patent is extended or adjusted under 35 U.S.C. 154(b) by 0 days.

(21) Appl. No.: 15/737,290

(22) PCT Filed: Jun. 16, 2016

(86) PCT No.: PCT/IL2016/050638
§ 371 (c)(1),
(2) Date: Dec. 17, 2017

(87) PCT Pub. No.: WO2016/203477
PCT Pub. Date: Dec. 22, 2016

(65) Prior Publication Data
US 2018/0169152 A1    Jun. 21, 2018

Related U.S. Application Data

(60) Provisional application No. 62/181,394, filed on Jun. 18, 2015.

(51) Int. Cl.
| | | |
|---|---|---|
| *A61K 35/42* | (2015.01) |
| *A61K 45/06* | (2006.01) |
| *A61K 31/015* | (2006.01) |
| *A61K 35/12* | (2015.01) |
| *A61K 35/28* | (2015.01) |
| *C12N 5/071* | (2010.01) |
| *A61K 9/00* | (2006.01) |
| *A61K 31/255* | (2006.01) |
| *A61K 31/675* | (2006.01) |
| *A61N 5/10* | (2006.01) |

(52) U.S. Cl.
CPC ............ *A61K 35/42* (2013.01); *A61K 9/0019* (2013.01); *A61K 31/015* (2013.01); *A61K 31/255* (2013.01); *A61K 31/675* (2013.01); *A61K 35/12* (2013.01); *A61K 35/28* (2013.01); *A61K 45/06* (2013.01); *A61N 5/10* (2013.01); *C12N 5/0688* (2013.01); *C12N 5/0689* (2013.01)

(58) Field of Classification Search
CPC .................................................. A61K 9/0019
See application file for complete search history.

(56) References Cited

U.S. PATENT DOCUMENTS

| | | |
|---|---|---|
| 2008/0112890 A1 | 5/2008 | Lelkes et al. |
| 2008/0274088 A1 | 11/2008 | Panoskaltsis-Mortari et al. |
| 2013/0216508 A1 | 8/2013 | Anversa et al. |
| 2014/0356335 A1 | 12/2014 | Reisner et al. |
| 2019/0091266 A1 | 3/2019 | Reisner et al. |

FOREIGN PATENT DOCUMENTS

| | | |
|---|---|---|
| EP | 1099754 | 5/2001 |
| JP | 10-509034 | 9/1998 |
| JP | 2002-501513 | 1/2002 |
| JP | 2005-511501 | 4/2005 |
| JP | 2005-520513 | 7/2005 |
| RU | 2369634 | 10/2009 |
| WO | WO 96/14397 | 5/1996 |
| WO | WO 98/54301 | 12/1998 |
| WO | WO 03/022123 | 3/2003 |
| WO | WO 03/078588 | 9/2003 |
| WO | WO 2004/078022 | 9/2004 |
| WO | WO 2006/038211 | 4/2006 |
| WO | WO 2008/100555 | 8/2008 |
| WO | WO 2013/084190 | 6/2013 |
| WO | WO 2013/093920 | 6/2013 |
| WO | WO 2016/203477 | 12/2016 |
| WO | WO 2017/203520 | 11/2017 |

OTHER PUBLICATIONS

Duchesneau et al. Molecular Therapy, 2010, 18(10):1830-1836.*
Kumar et al. Cell, 2011, 147:525-538.*
Examination Report dated Oct. 5, 2016 From the Intellectual Property Office of Singapore Re. Application No. 11201402902V.
International Preliminary Report on Patentability dated Jun. 19, 2014 From the International Bureau of WIPO Re. Application No. PCT/IB2012/057042.
International Preliminary Report on Patentability dated Dec. 28, 2017 From the International Bureau of WIPO Re. Application No. PCT/IL2016/050638. (6 Pages).
International Search Report and the Written Opinion dated Apr. 5, 2013 From the International Searching Authority Re. Application No. PCT/IB2012/057042.
International Search Report and the Written Opinion dated Sep. 12, 2016 From the International Searching Authority Re. Application No. PCT/IL2016/050638.
International Search Report and the Written Opinion dated Aug. 28, 2017 From the International Searching Authority Re. Application No. PCT/IL2017/050569. (15 Pages).
Notice of Reason for Rejection dated Apr. 25, 2017 From the Japan Patent Office Re. Application No. 2014-545442 and Its Translation Into English. (9 Pages).

(Continued)

*Primary Examiner* — Bin Shen

(57) ABSTRACT

A method of conditioning a subject in need of transplantation of progenitor cells in suspension of a tissue of interest is disclosed. The method comprising: (a) administering to a subject a therapeutically effective amount of an agent capable of inducing damage to the tissue of interest, wherein the damage results in proliferation of resident stem cells in the tissue; and subsequently (b) subjecting the subject to an agent which ablates the resident stem cells in the tissue. A method of transplanting progenitor cells in suspension of a tissue of interest to a subject in need thereof is also disclosed.

13 Claims, 55 Drawing Sheets
(55 of 55 Drawing Sheet(s) Filed in Color)

(56) References Cited

OTHER PUBLICATIONS

Notice of Reason for Rejection dated Sep. 30, 2016 From the Japan Patent Office Re. Application No. 2014-545442 and Its Translation Into English.
Notification of Office Action and Search Report dated Feb. 13, 2017 From the State Intellectual Property Office of the People's Republic of China Re. Application No. 201280069291.9. (11 Pages).
Official Action dated Jun. 6, 2017 From the US Patent and Trademark Office Re. U.S. Appl. No. 14/363,814. (19 pages).
Official Action dated Jun. 9, 2016 From the US Patent and Trademark Office Re. U.S. Appl. No. 14/363,814.
Official Action dated Nov. 29, 2016 From the US Patent and Trademark Office Re. U.S. Appl. No. 14/363,814. (31 pages).
Request for Substantive Examination dated Nov. 18, 2016 From the ROSPATENT, Federal Government Institution, Federal Institute of Industrial Property of the Federal Service of Intellectual Property, Patents and Trademarks of the Russian Federation Re. Application No. 2014127338 and Its Translation Into English. (11 Pages).
Restriction Official Action dated Jan. 29, 2016 From the US Patent and Trademark Office Re. U.S. Appl. No. 14/363,814.
Search Report and Written Opinion dated Nov. 25, 2014 From the Intellectual Property Office of Singapore Re. Application No. 11201402902V.
Translation of Notification of Office Action and Search Report dated Feb. 13, 2017 From the State Intellectual Property Office of the People's Republic of China Re. Application No. 201280069291.9. (17 Pages).
Written Opinion dated Jan. 13, 2016 From the Intellectual Property Office of Singapore Re. Application No. 11201402902V.
Adachi et al. "Treatment and Transfer of Emphysema by a New Bone Marrow Transplantation Method From Normal Mice to Tsk Mice and Vice Versa" Stem Cells, 24: 2071-2077, 2006.
Anversa et al. "Tissue-Specific Adult Stem Cells in the Human Lung", Nature Medicine, 17(9): 1038-1029, Sep. 2011.
Baber et al. "Intratracheal Mesenchymal Stem Cell Administration Attenuates Monocrotaline-Induced Pulmonary Hypertension and Endothelial Dysfunction", American Journal of Physiology: Heart and Circulatory Physiology, 292(2): H1120-H1128, Feb. 2007.
Cargnoni et al. "Transplantation of Allogeneic and Xenogeneic Placenta-Derived Cells Reduces Bleomycin-Induced Lung Fibrosis", Cell Transplantation, 18: 405-422, 2009.
Carraro et al. "Human Amniotic Fluid Stem Cells Can Integrate and Differentiate Into Epithelial Lung Lineages", Stem Cells, 26: 2902-2911, 2008.
Chen et al. "Enrichment of Hematopoietic Stem Cells With SLAM and LSK Markers for the Detection of Hematopoietic Stem Cell Function in Normal and Trp53 Null Mice", Experimental Hematology, XP025465827, 36(10): 1236-1243, Published Online Jun. 17, 2008. Abstract.
Eventov-Friedman et al. "Embryonic Pig Liver, Pancreas, and Lung as a Source for Transplantation: Optimal Organogenesis Without Teratoma Depends on Distinct Time Windows", Proc. Natl. Acad. Sci. USA, PNAS, 102(8): 2928-2933, Feb. 22, 2005. p. 2929, Left Col., Para 1-2, p. 2931, Right Col., Para 2, p. 2933, Left Col., Para 2, Fig.7.
Fischer et al. "Pulmonary Passage Is a Major Obstacle for Intravenous Stem Cell Delivery: The Pulmonary First-Pass Effect" Stem Cells and Development, 18(5):683-691, 2009.
Kajstura Supplementary Appendix,"Evidence for Human Lung Stem Cells", The New England Journal of Medicine, 364(19): 1795-1806, May 12, 2011.
Kajstura et al. "Evidence for Human Lung Stem Cells", The New England Journal of Medicine, 364(19): 1795-1806, May 12, 2011.
Lee et al. "Allogeneic Human Mesenchymal Stem Cells for Treatment of E. coli Endotoxin-Induced Acute Lung Injury in the Ex Vivo Perfused Human Lung", Proc. Natl. Acad. Sci. USA, PNAS, 106(38): 16357-16362, Sep. 22, 2009.

Loi et al. "Limited Restoration of Cystic Fibrosis Lung Epithelium In Vivo With Adult Bone Marrow-Derived Cells", American Journal of Respiratory and Critical Care Medicine, 173: 171-179, 2006.
MacPherson et al. "Bone Marrow-Derived SP Cells Can Contribute to the Respiratory Tract of Mice In Vivo", Journal of Cell Science, 118: 2441-2450, 2005.
Mondrinos et al. "A Tissue-Engineered Model of Fetal Distal Lung Tissue", American Journal of Physiology—Lung Cellular and Molecular Physiology, 293: L639-L650, First Published May 25, 2007. Discussion, Figs.2, 3, 6, 7.
Moodley "Evidence for Human Lung Stem Cells", The New England Journal of Medicine, 365(5): 464-466, Aug. 4, 2011.
Moodley et al. "Human Amnion Epithelial Cell Transplantation Abrogates Lung Fibrosis and Augments Repair", American Journal of Respiratory and Critical Care Medicine, 182: 643-651, Jun. 3, 2010.
Moodley et al. "Human Umbilical Cord Mesenchymal Stem Cells Reduce Fibrosis of Bleomycin-Induced Lung Injury", The American Journal of Pathology, 175(1): 303-313, Jul. 2009.
Provost et al. "Elevated Expression of Four Apolipoprotein Genes During the 32-35 Week Gestation Window in the Human Developing Lung, Early Human Development", 86(9): 529-534, Published, Aug. 2, 2010.
Robey et al. "Postnatal Stem Cells in Tissue Engineering". In Principles of Tissue Engineering: Fourth Edition, Ed: Lanza et al.: 639-653, 2013.
Rosen et al. "Preconditioning Allows Engraftment of Mouse and Human Embryonic Lung Cells, Enabling Lung Repair in Mice", Nature Medicine, 21(8): 869-879, Published Online Jul. 13, 2015.
Sakagami et al. "Patient-Derived GM-CSF Autoantibodies Reproduce Pulmonary Alveolar Proteinosis in Nonhuman Primates", Online Supplement, American Journal of Respiratory and Critical Care Medicine, p. 1-23, 2010.
Sakagami et al. "Patient-Derived Granulocyte/Macrophage Colony-Stimulating Factor Autoantibodies Reproduce Pulmonary Alveolar Proteinosis in Nonhuman Primates", American Journal of Respiratory and Critical Care Medicine, 182: 49-61, Mar. 11, 2010.
Schlichenmaier et al. "Expression of Cytokeratin 18 During Pre- and Post-Natal Porcine Lung Development", Anatomia, Histologia, Embryologia 31(5): 273-277, Oct. 2002.
Sueblinvong et al. "Stem Cells and Cell Therapy Approaches in Lung Biology and Diseases", Translational Research, 156(3): 188-205, Published Online Jul. 7, 2010.
Summer et al. "Embryonic Lung Side Population Cells Are Hematopoietic and Vascular Precursors", American Journal of Respiratory Cell and Molecular Biology, 33: 32-40, 2005.
Suzuki et al. "Heredity Pulmonary Alveolar Proteinosis. Pathogenesis, Presentation, Diagnosis, and Therapy", American Journal of Respiratory and Critical Care Medicine, 182: 1292-1304, Jul. 29, 2010.
Sykes "Hematopoietic Cell Transplantation for Tolerance Induction: Animal Models to Clinical Trials", Transplantation, XP055396593, 87(3): 309-316, Feb. 15, 2009. Abstract.
Weiss "Stem Cells and Cell Therapies for Cystic Fibrosis and Other Lung Diseases", Pulmonary Pharmacology & Therapeutics, 21: 588-594, 2008.
Weiss et al. "Stem Cells and Cell Therapies in Lung Biology and Lung Diseases", Proceedings of the American Thoracic Society, 5(5): 637-667, Jul. 15, 2008.
Wong et al. "Identification of a Bone Marrow-Derived Epithelial-Like Population Capable of Repopulating Injured Mouse Airway Epithelium", The Journal of Clinical Investigation, 119(2): 336-348, Feb. 2009.
International Preliminary Report on Patentability dated Dec. 6, 2018 From the International Bureau of WIPO Re. Application No. PCT/IL2017/050569. (8 Pages).
Examination Report Under Sections 12 & 13 of the Patents Act, 1970 and the Patents Rules, 2003 dated Apr. 9, 2019 From the Government of India, Intellectual Property India, Patents, Designs, Trade Marks, Geographical Indications Re. Application No. 1366/MUMNP/2014. (5 Pages).

* cited by examiner

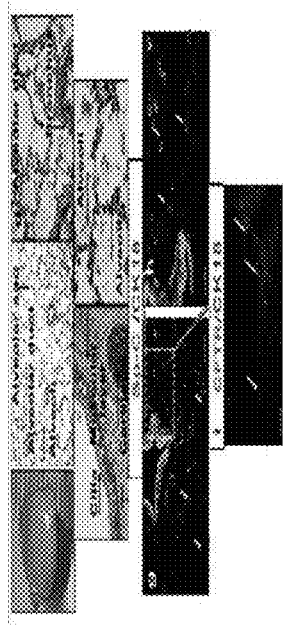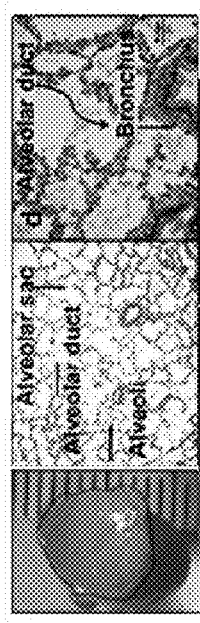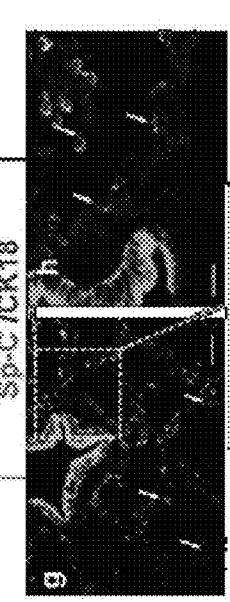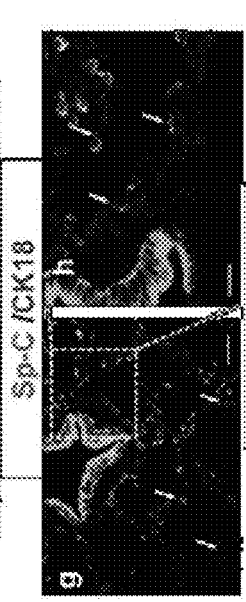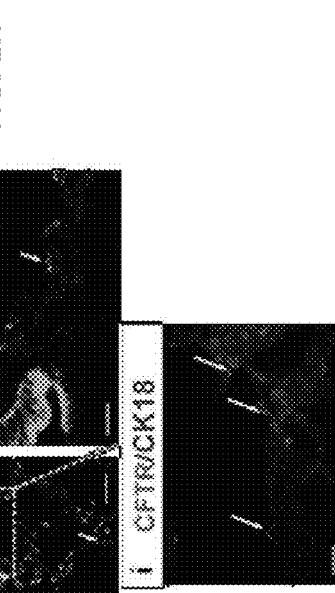

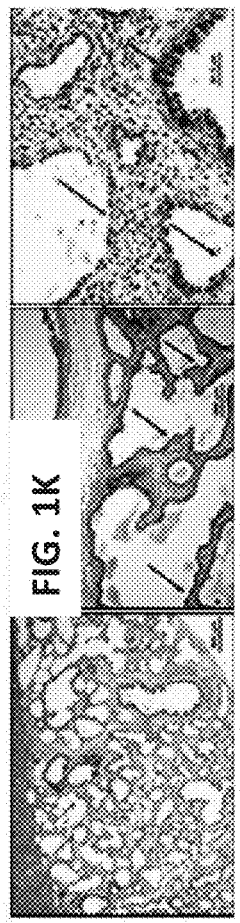
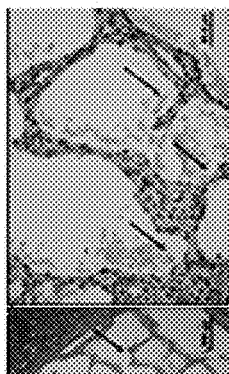
FIG. 1J  FIG. 1K  FIG. 1L
FIG. 1M  FIG. 1N  FIG. 1O
FIG. 1P  FIG. 1Q  FIG. 1R

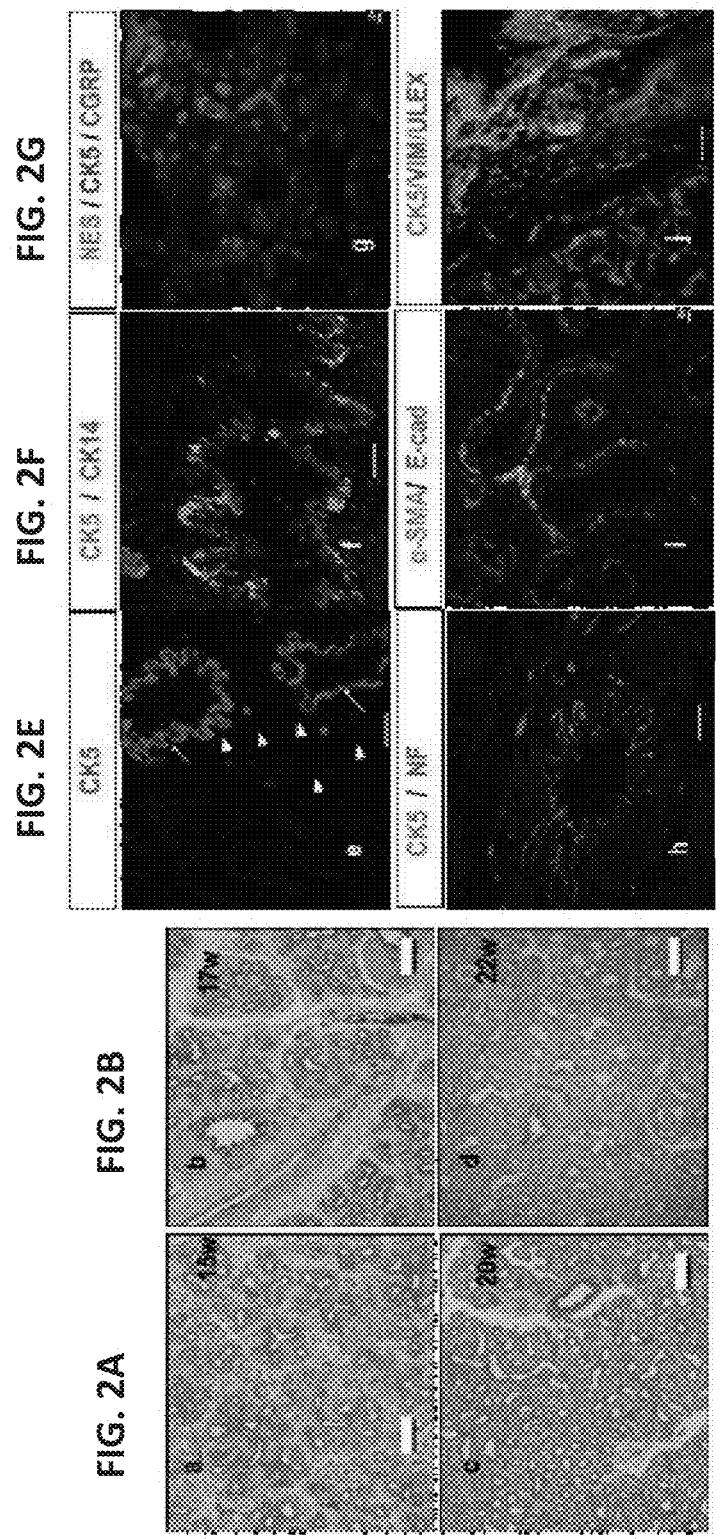

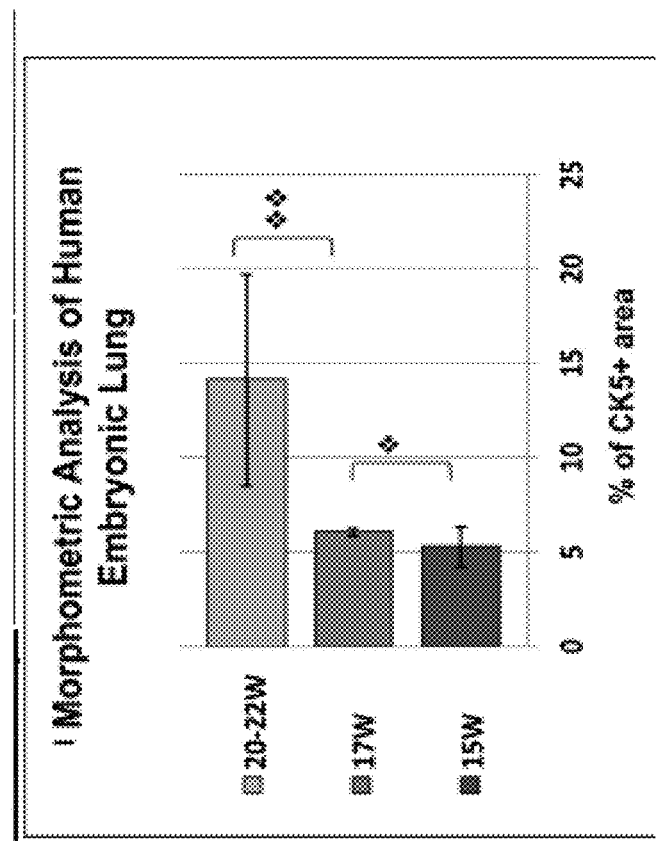
FIG. 2K  FIG. 2L
FIG. 2M  FIG. 2N
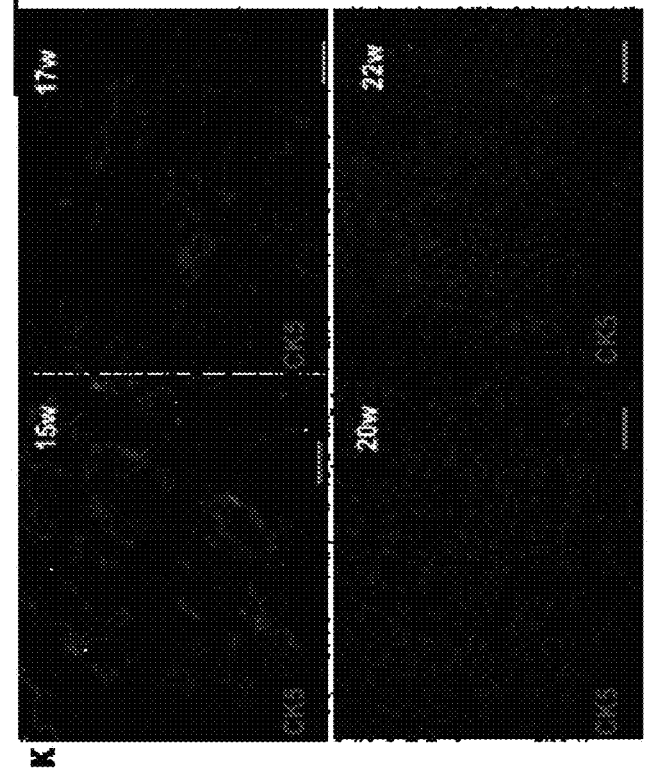
FIG. 2O

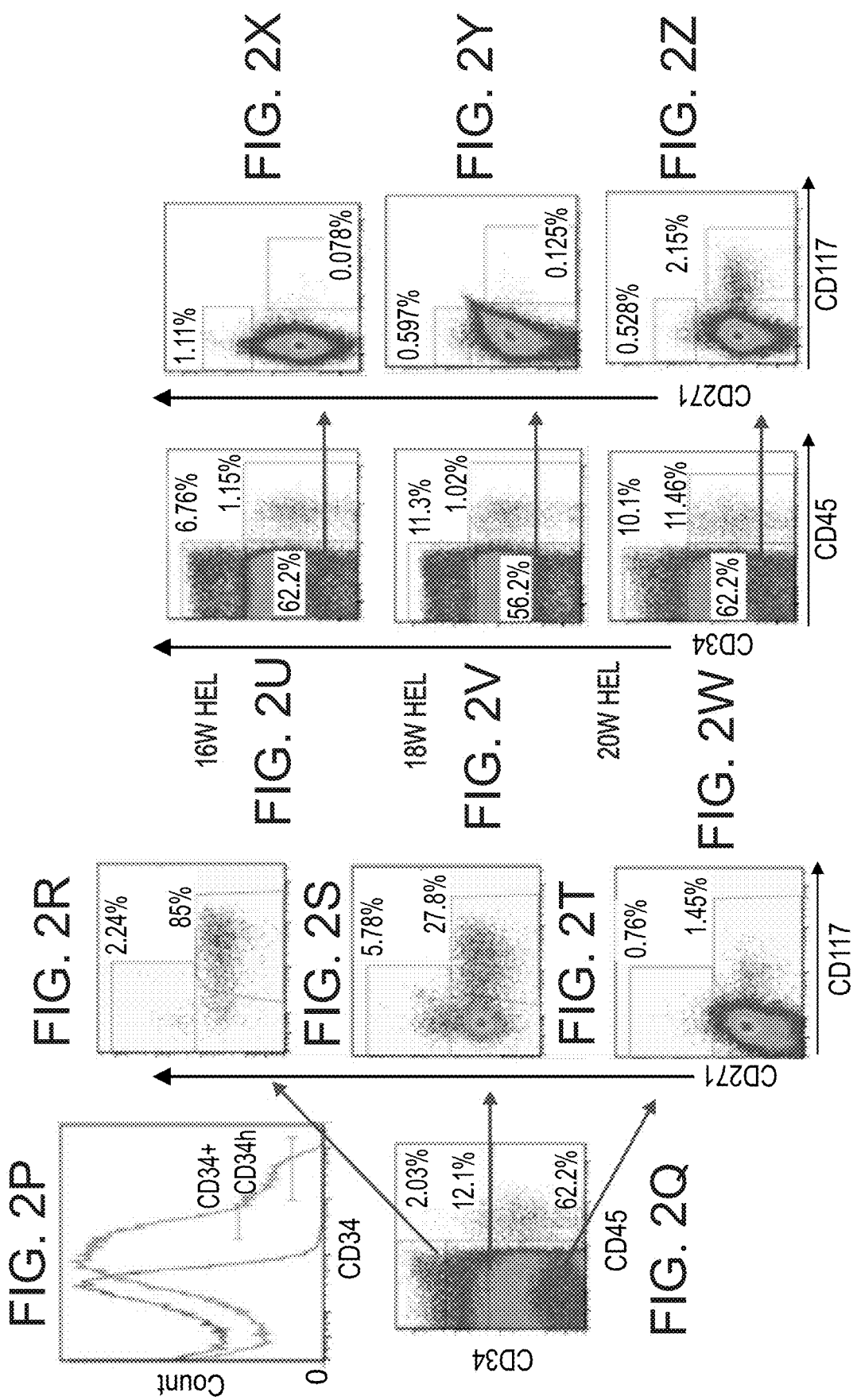

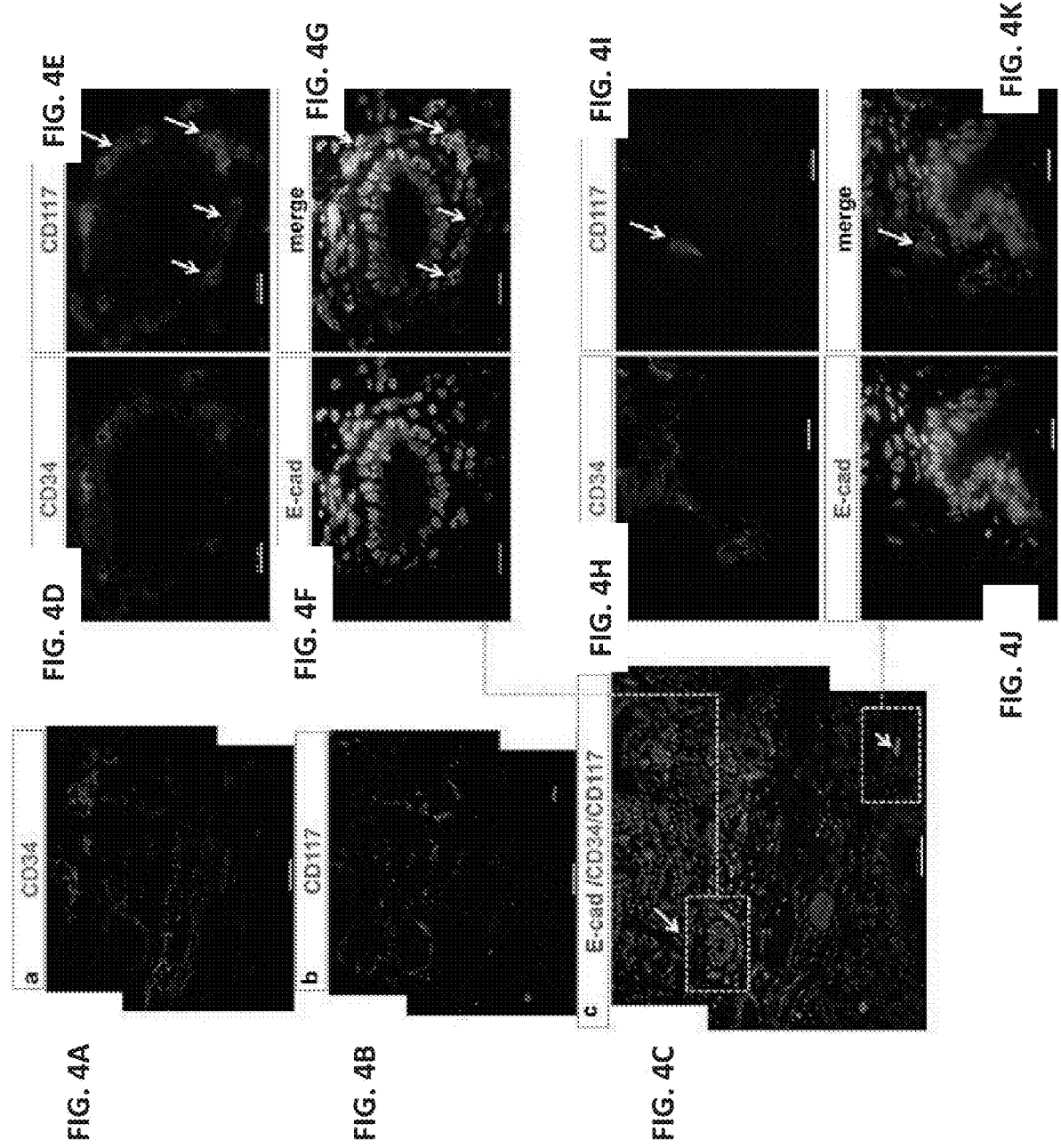

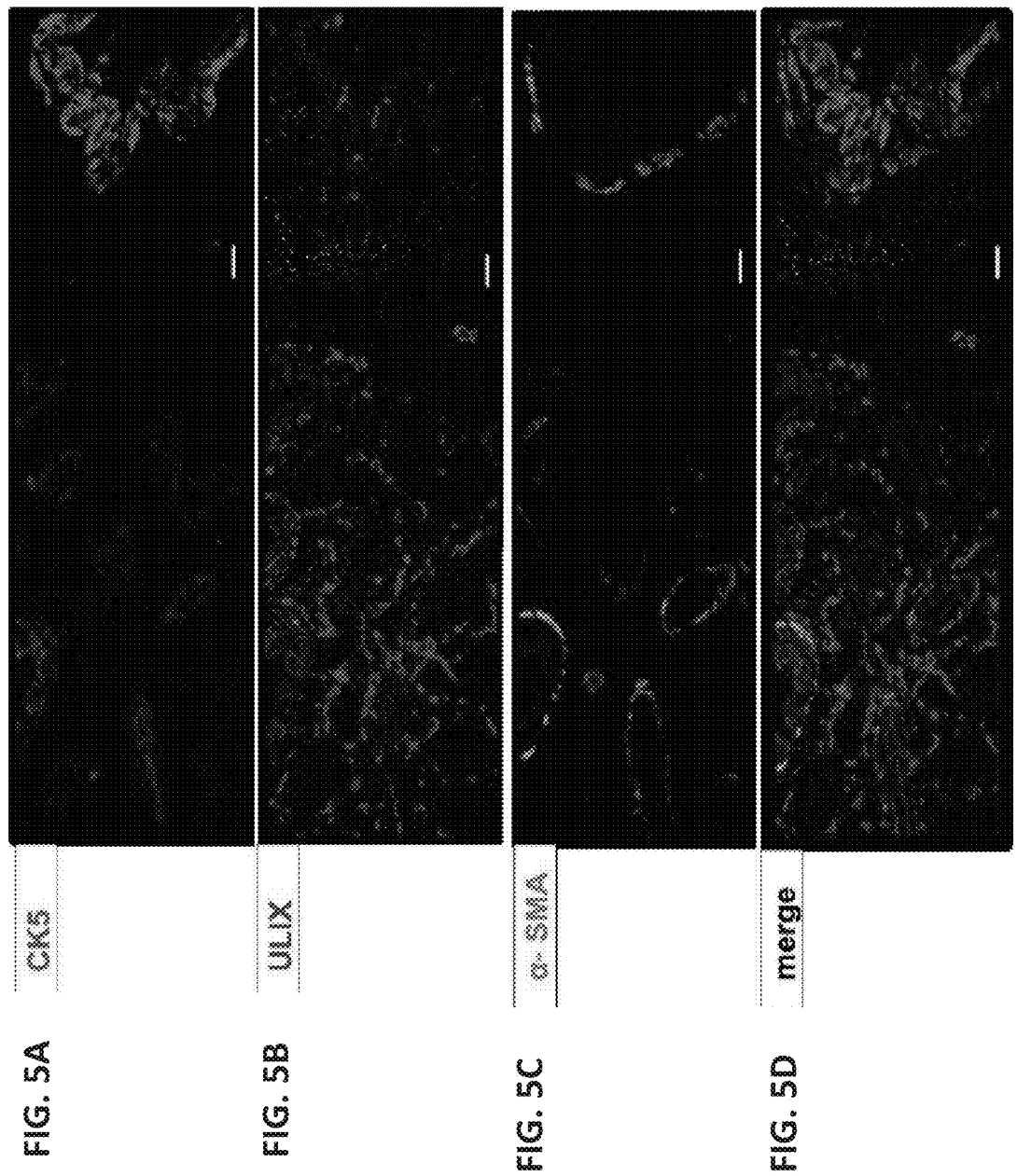
FIG. 5A CK5
FIG. 5B ULIX
FIG. 5C α-SMA
FIG. 5D merge

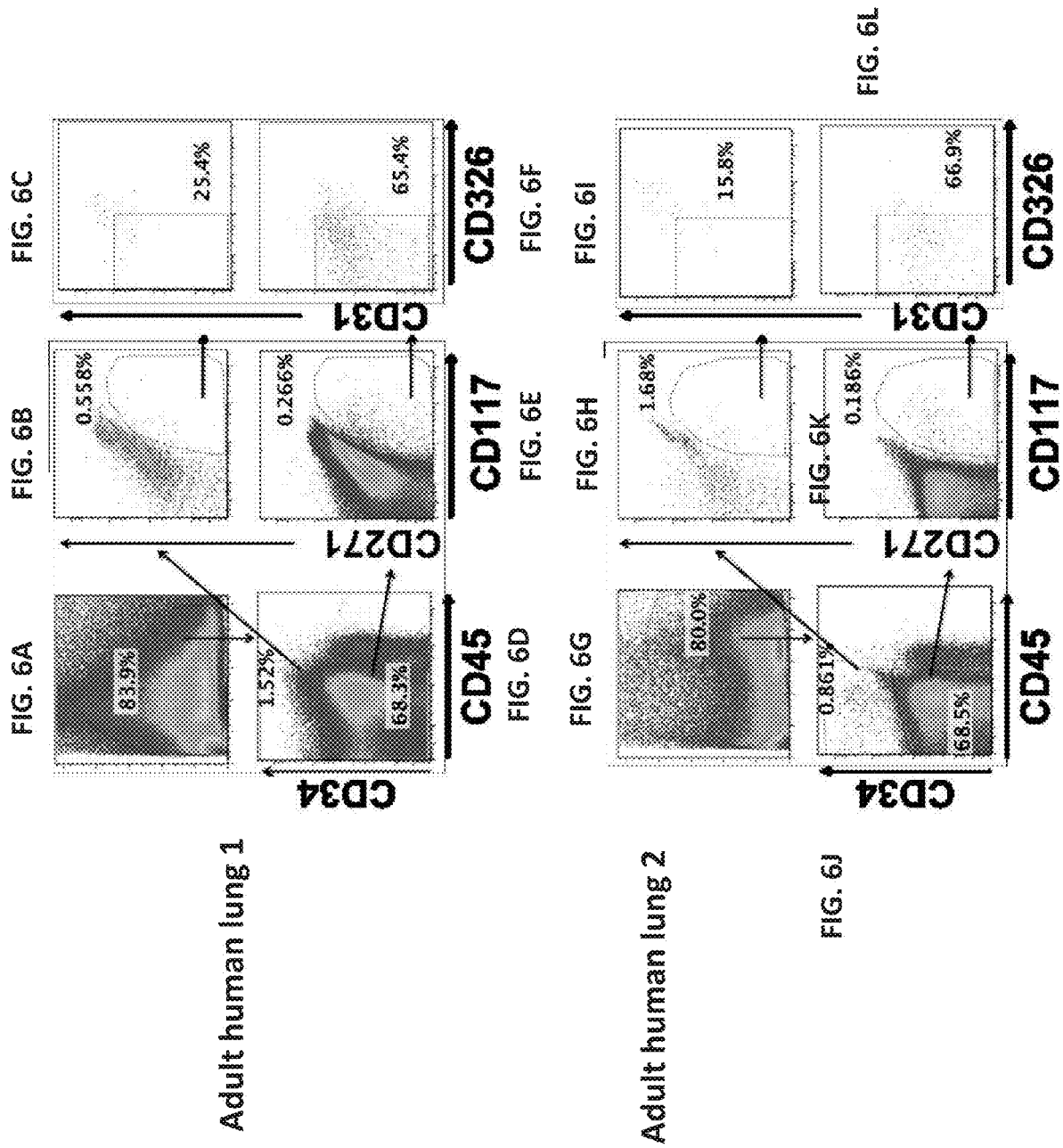

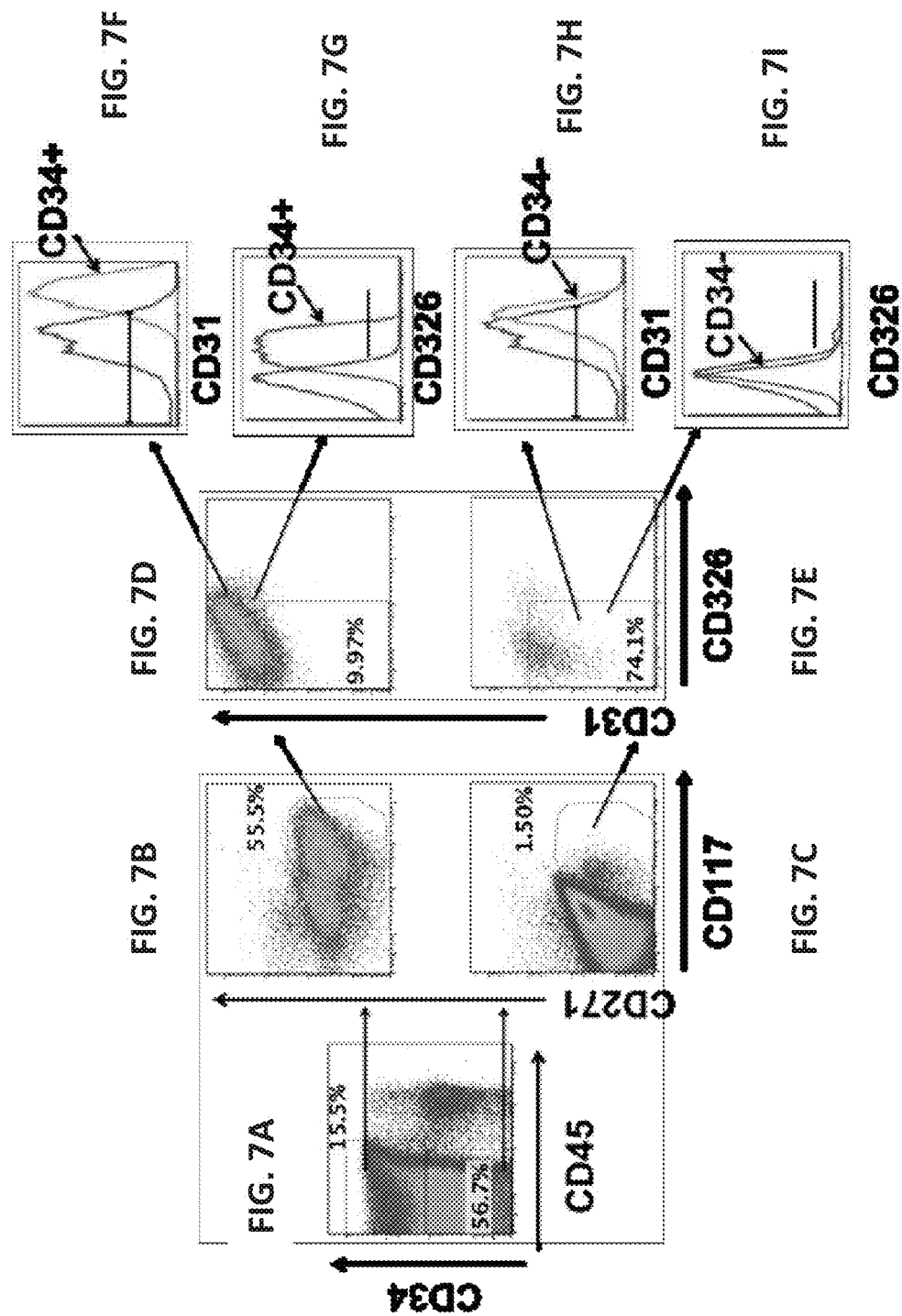

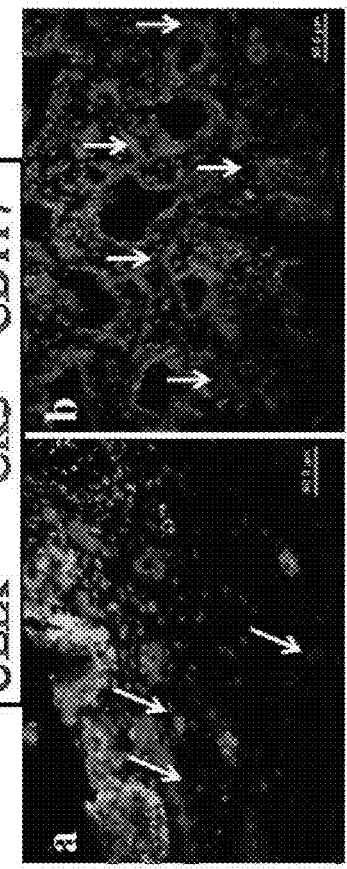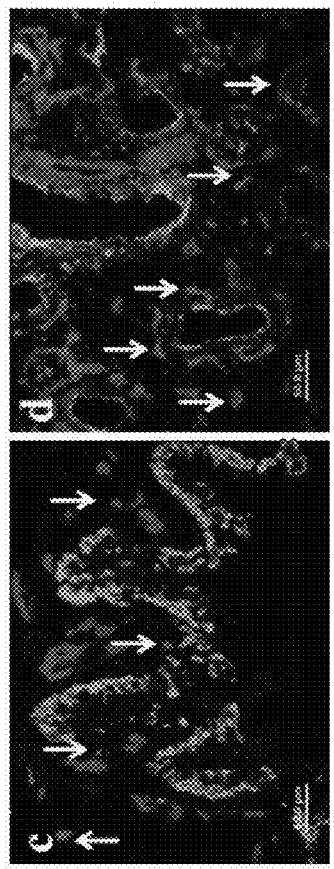
FIG. 8A  FIG. 8B  FIG. 8C  FIG. 8D

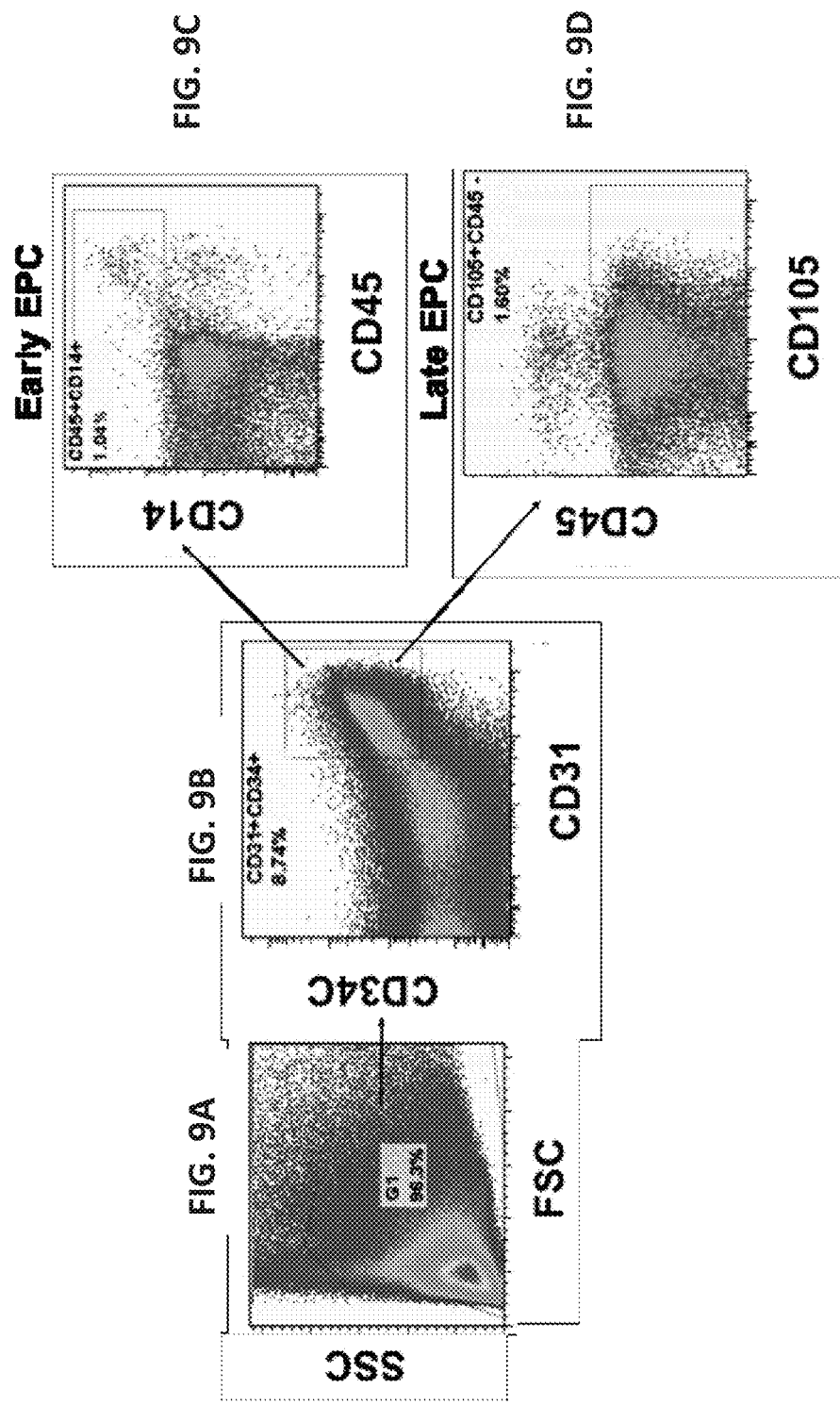

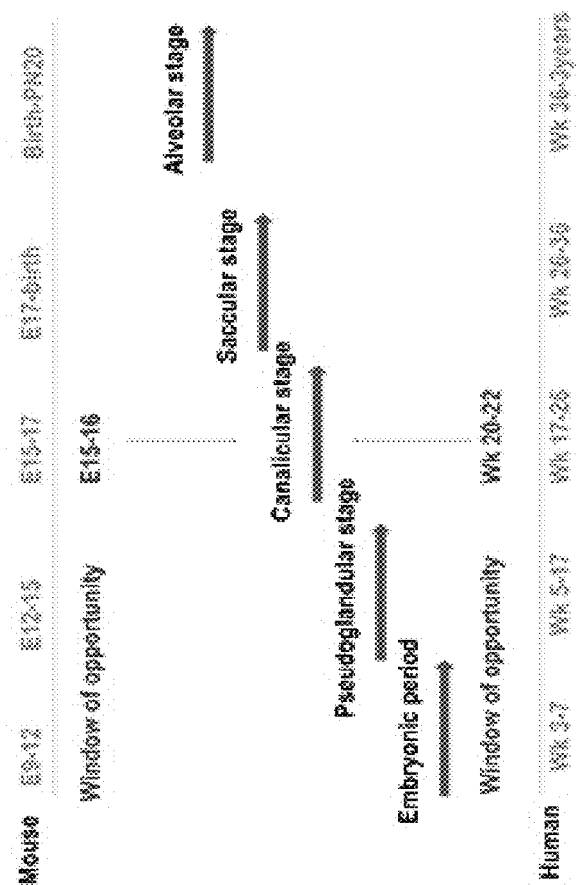
FIG. 10F
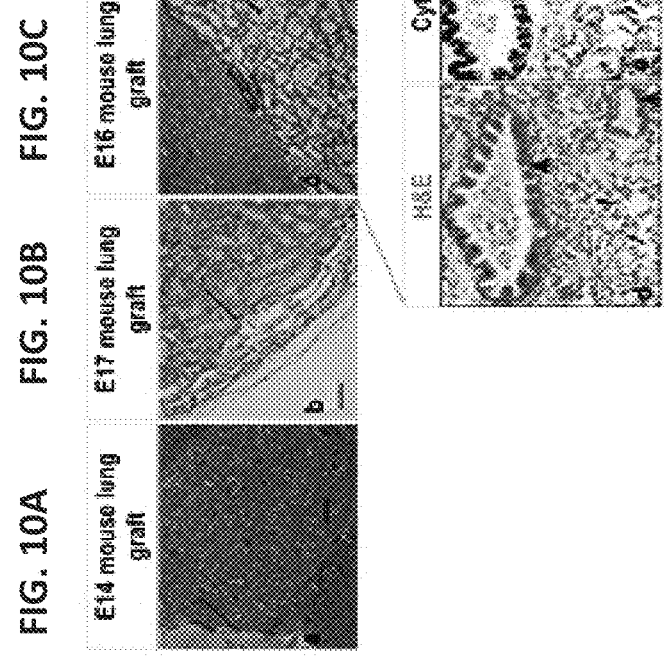
FIG. 10A  FIG. 10B  FIG. 10C
FIG. 10D  FIG. 10E

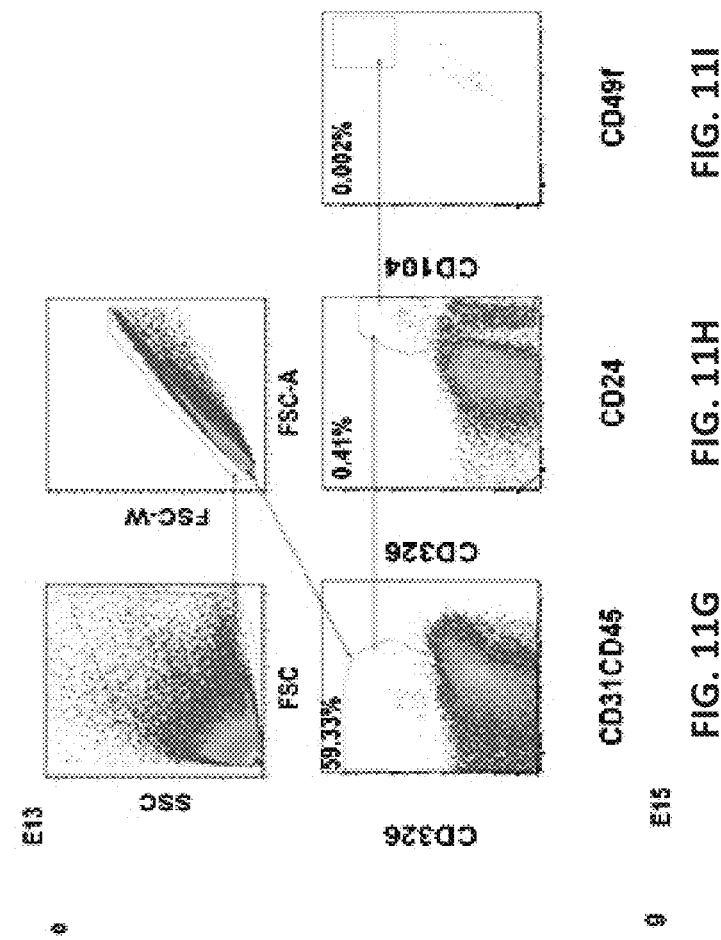
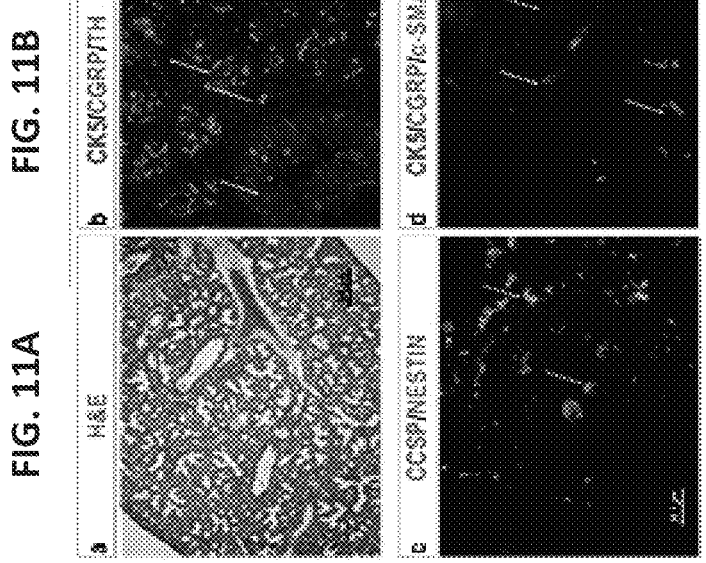
FIG. 11A  FIG. 11B  FIG. 11C  FIG. 11D
FIG. 11E  FIG. 11F  FIG. 11G  FIG. 11H  FIG. 11I

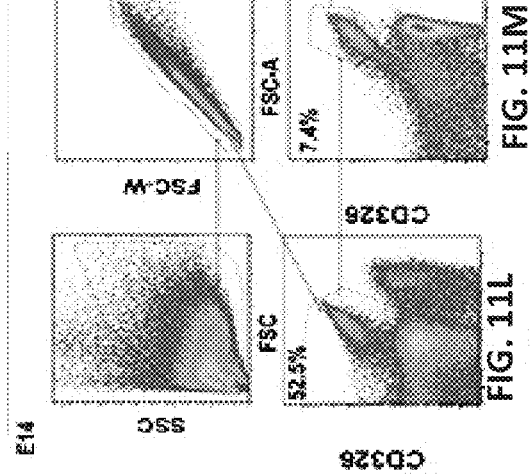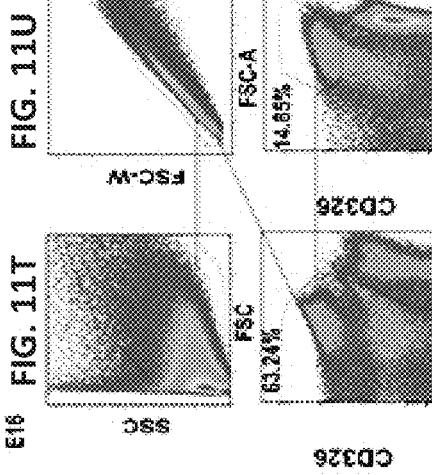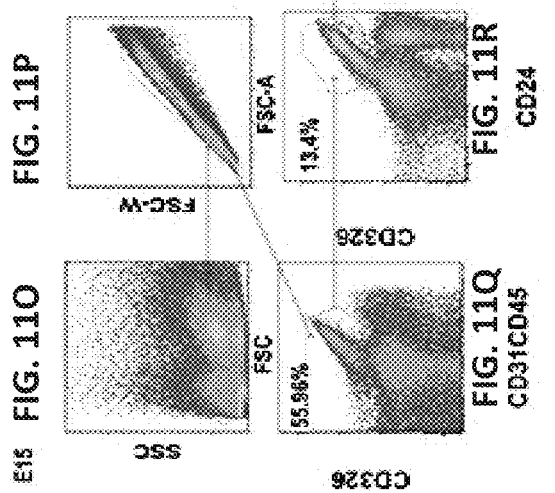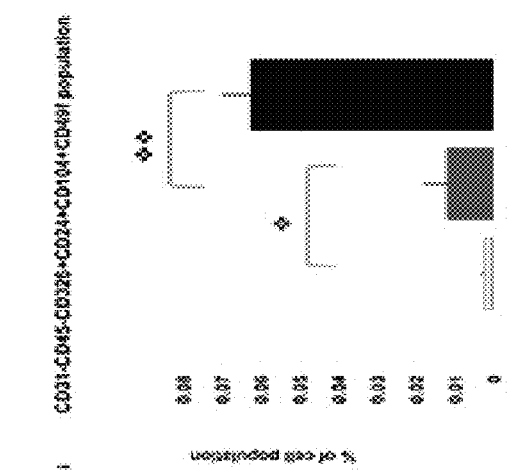

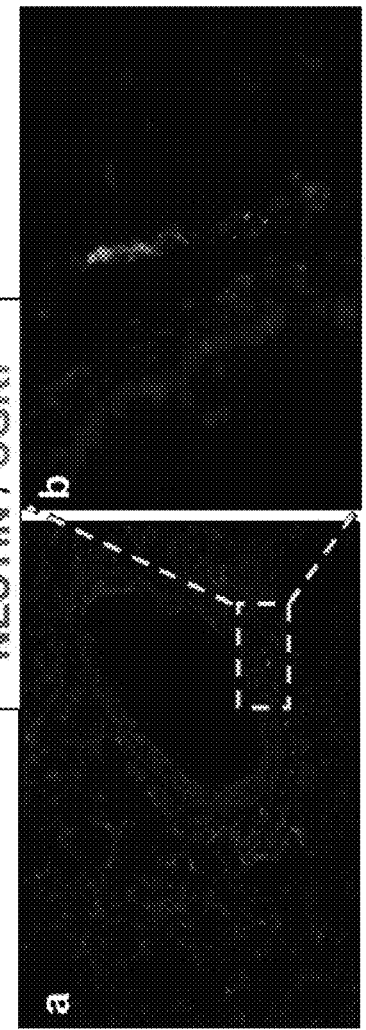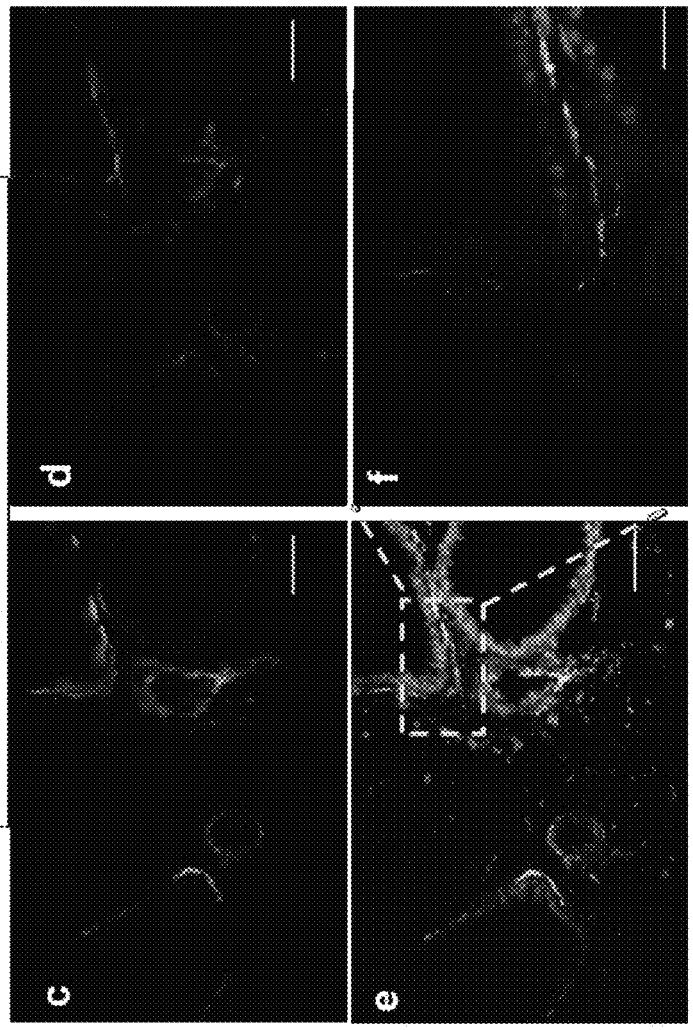

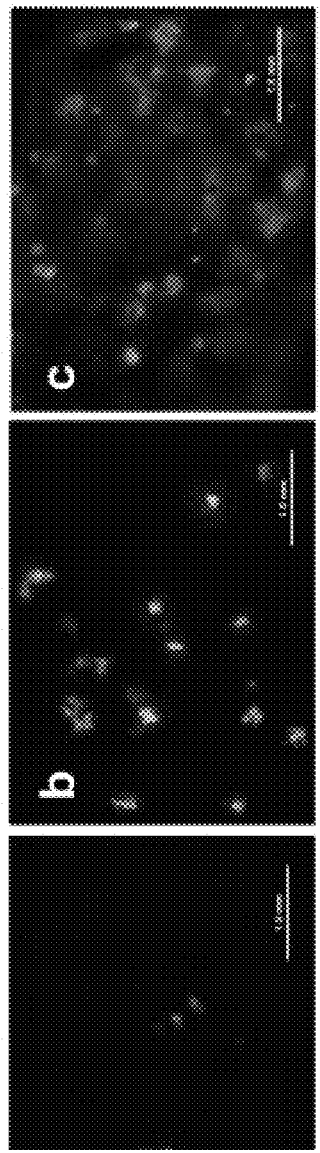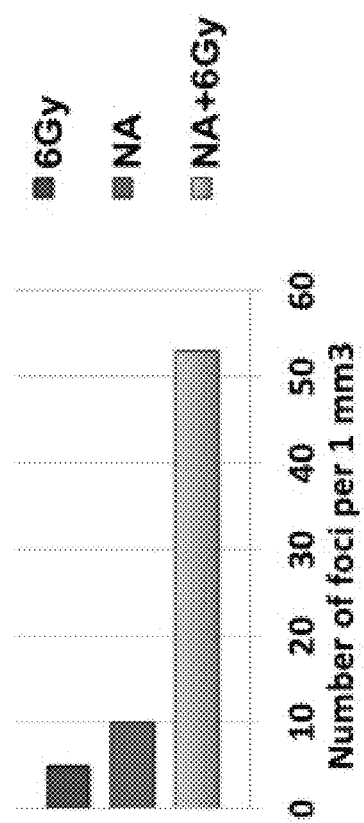
FIG. 13A  FIG. 13B  FIG. 13C
FIG. 13D

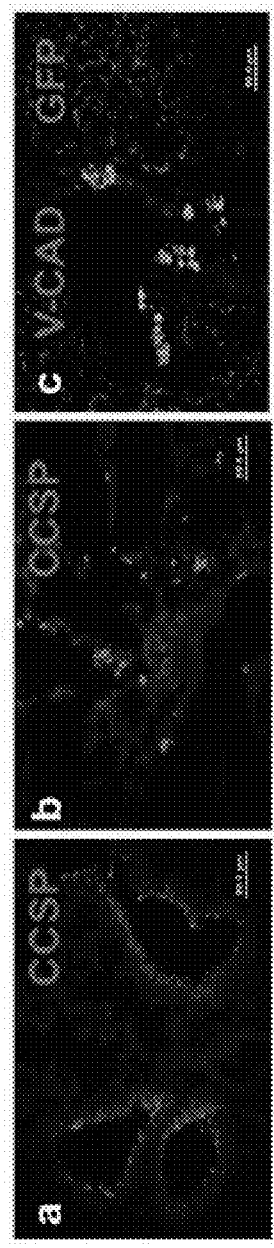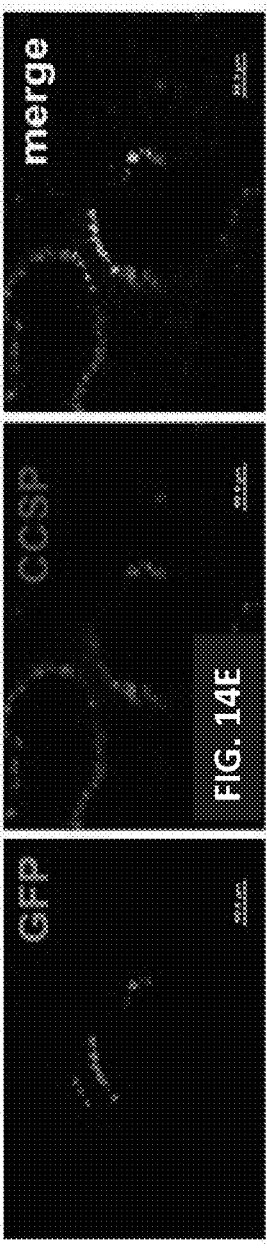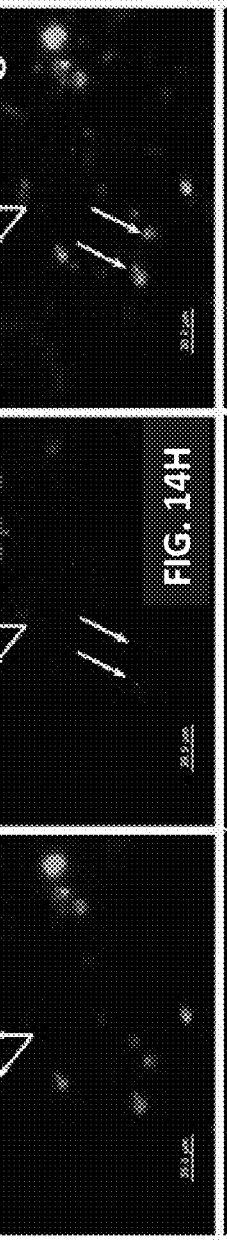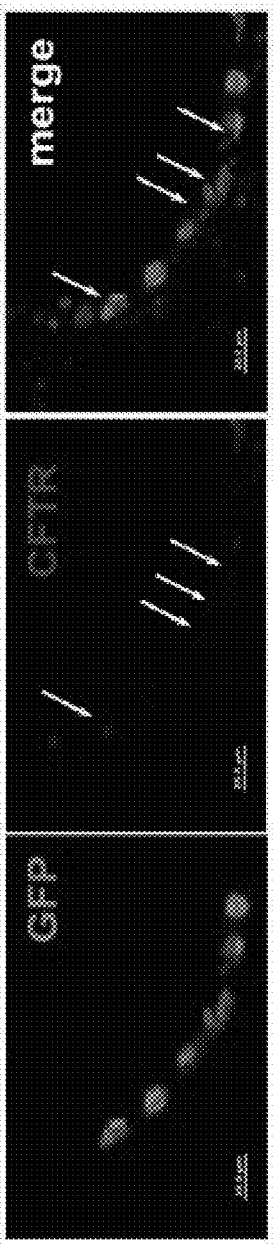

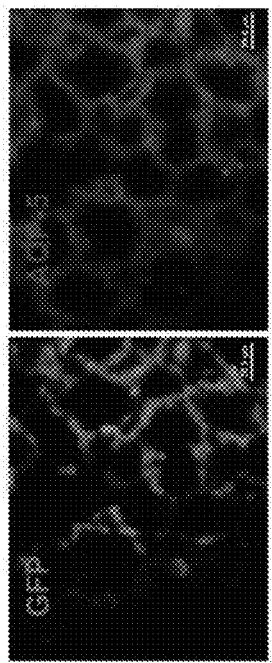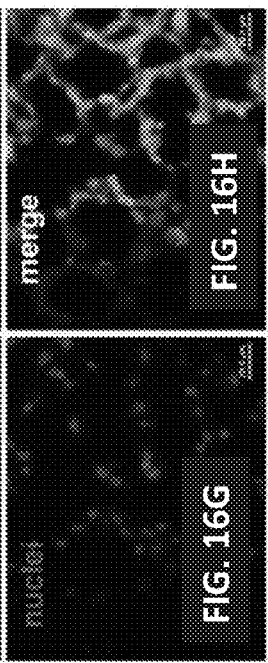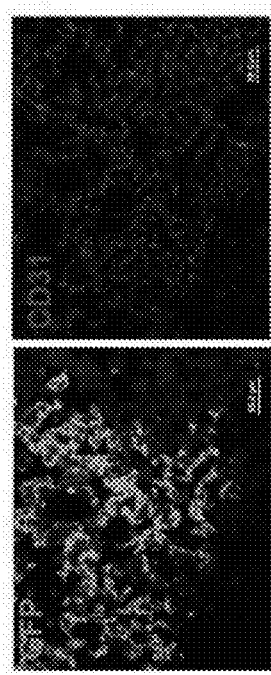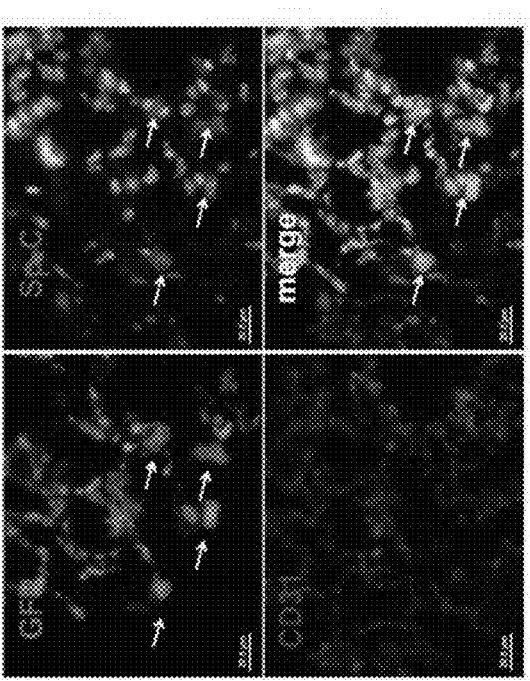

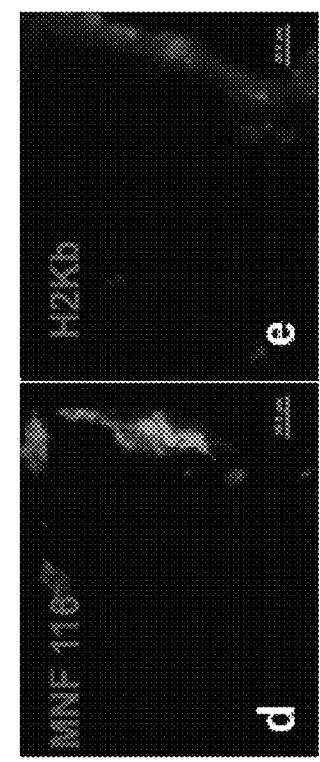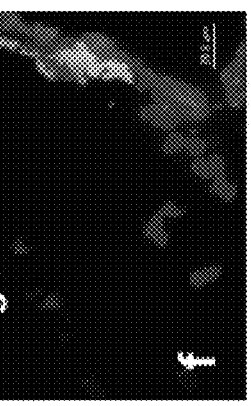
FIG. 18A  FIG. 18B  FIG. 18C
FIG. 18D  FIG. 18E  FIG. 18F
FIG. 18G  FIG. 18H  FIG. 18I

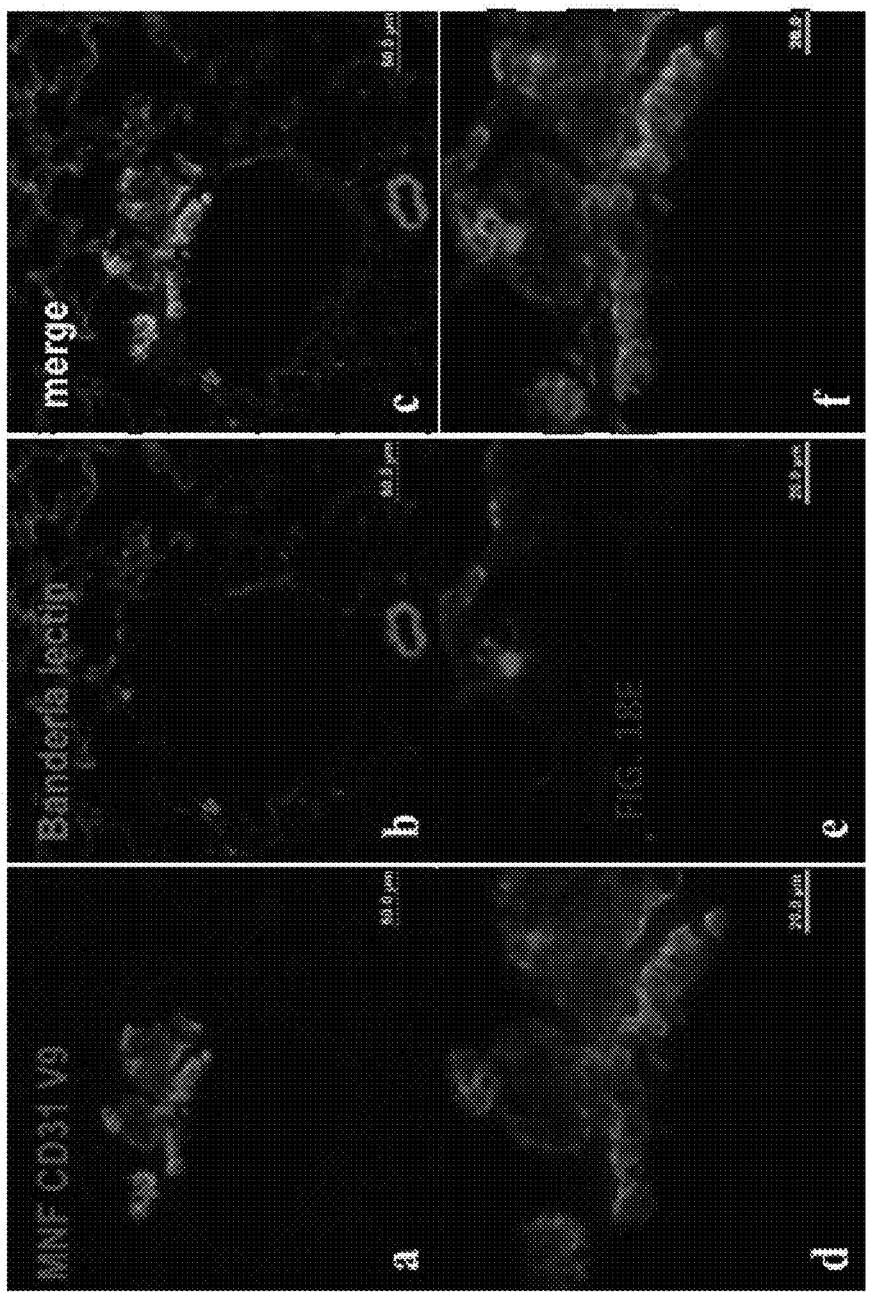

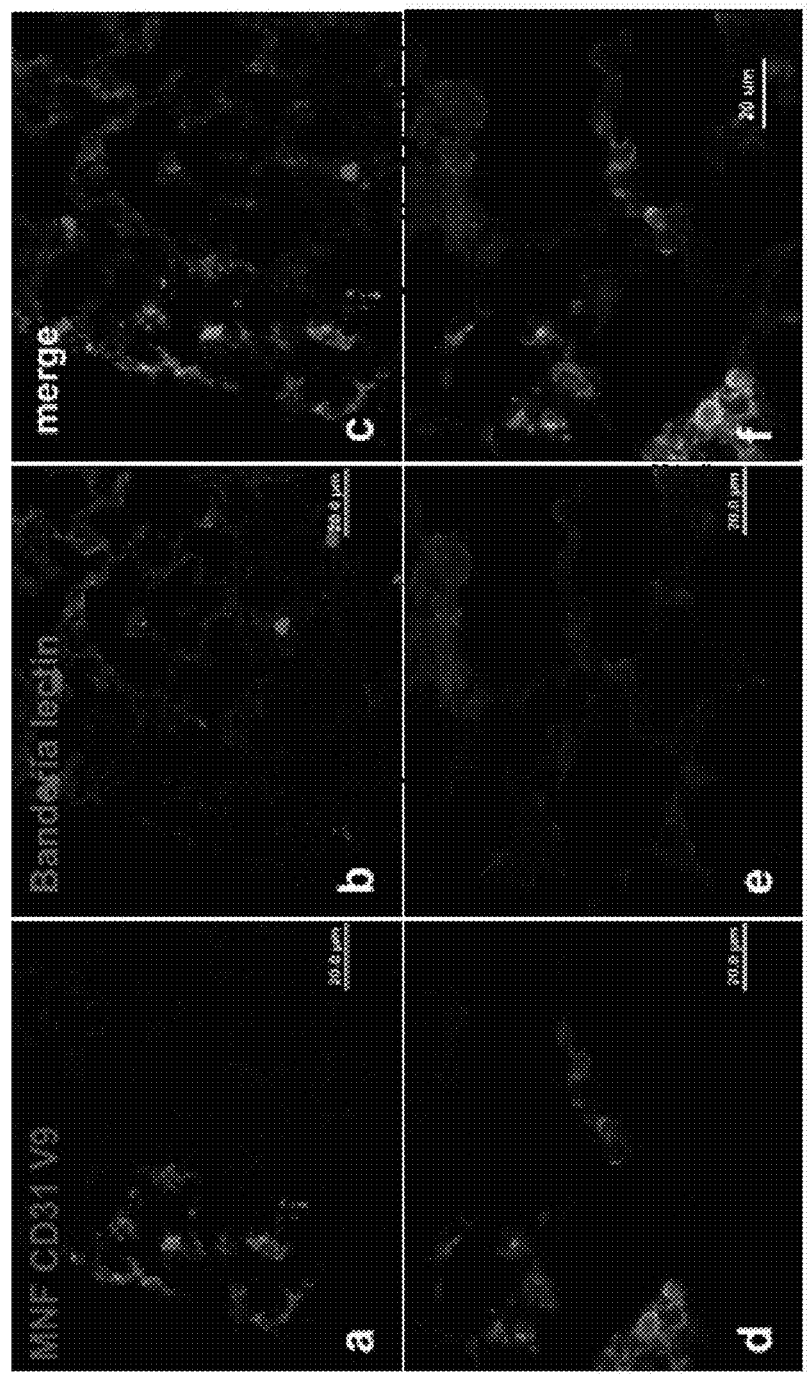

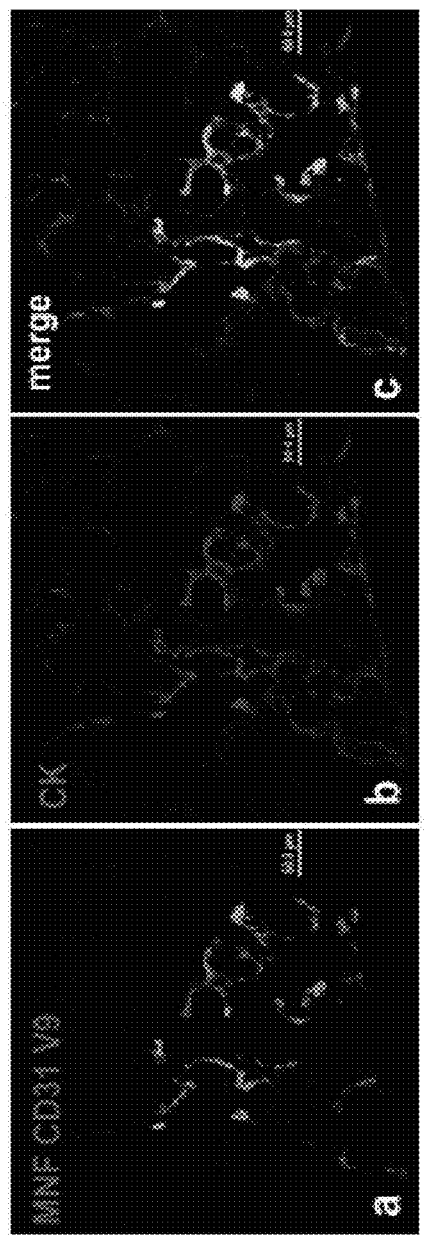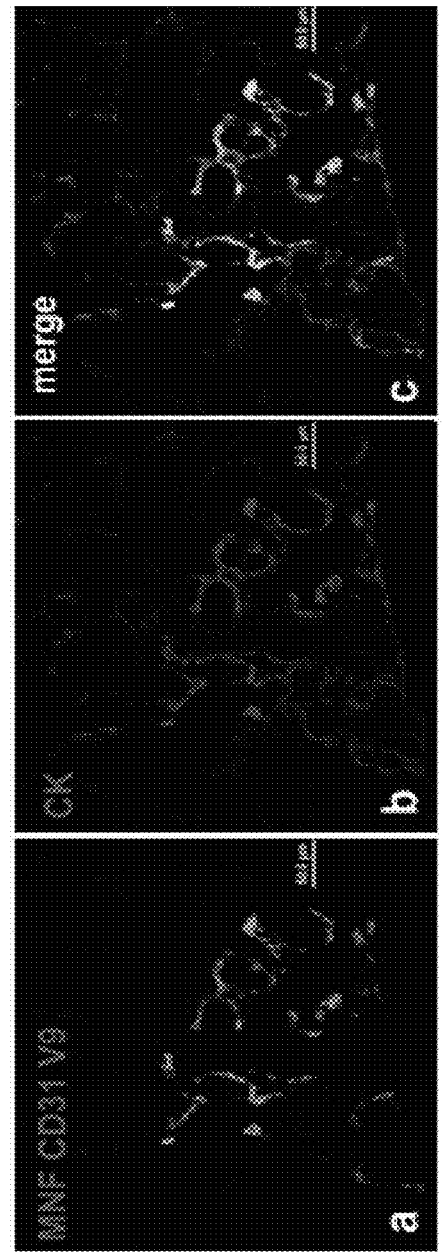

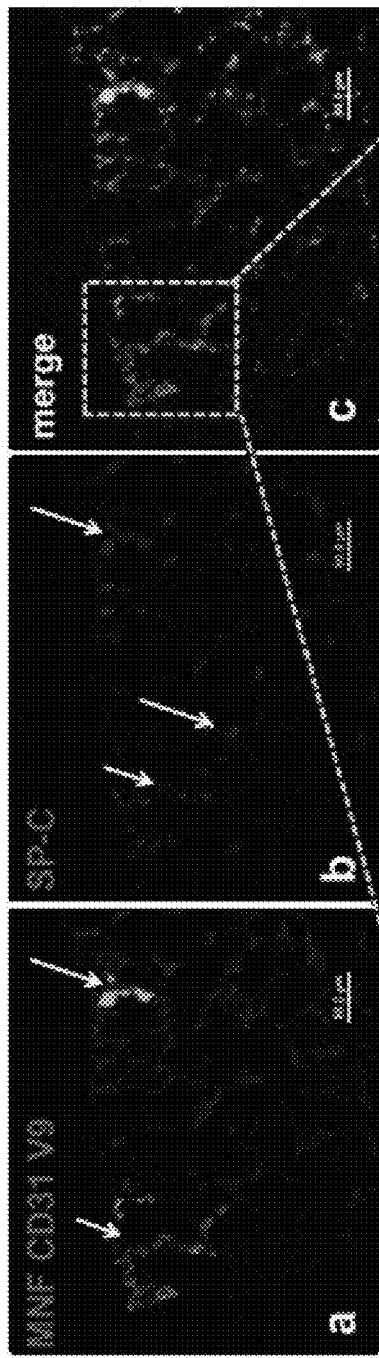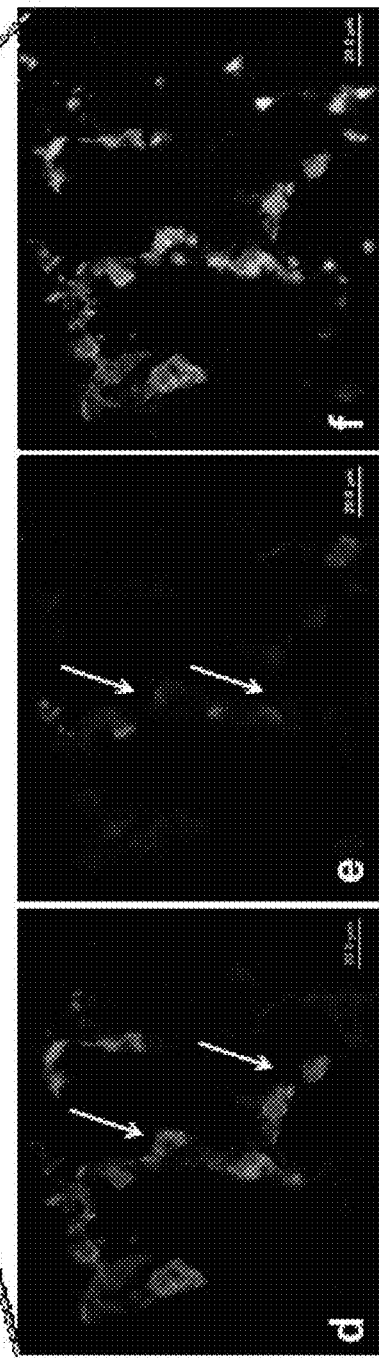

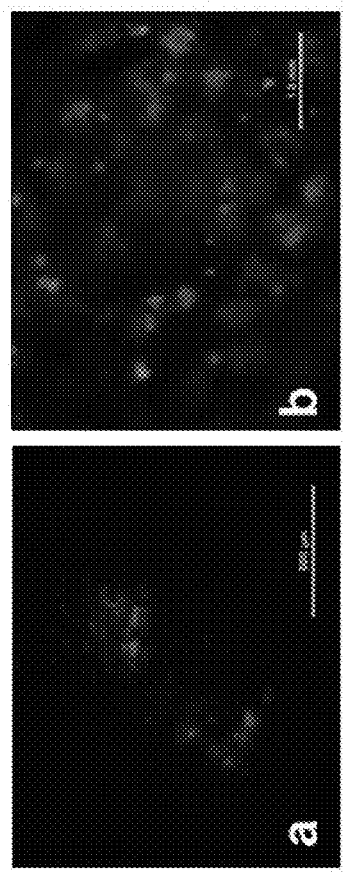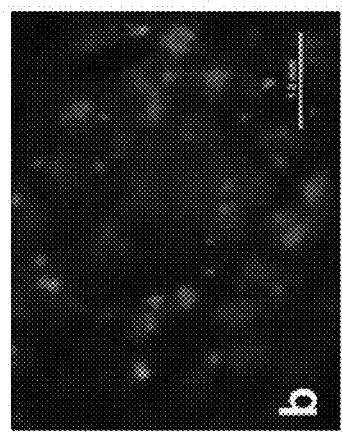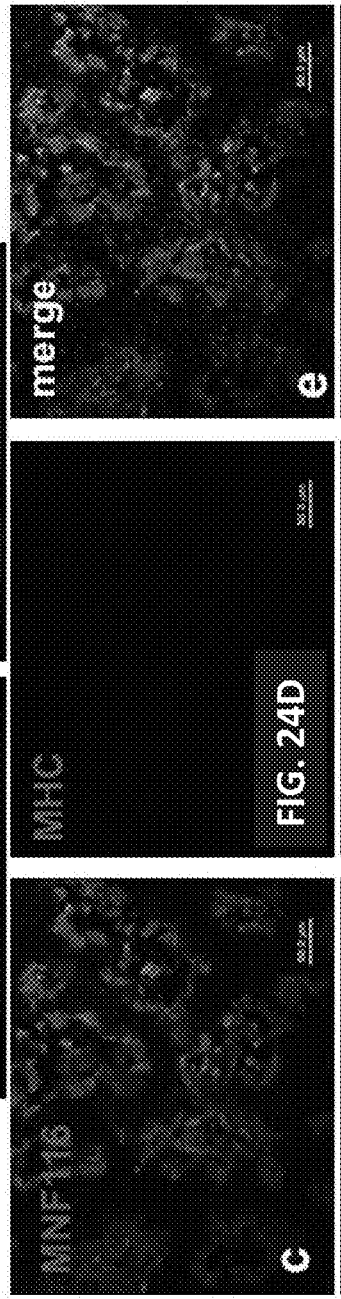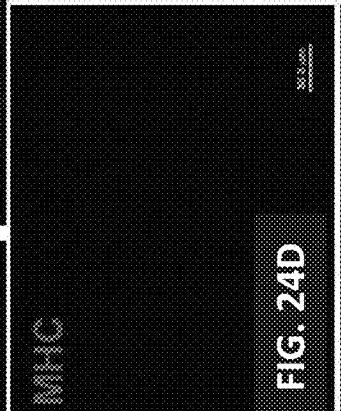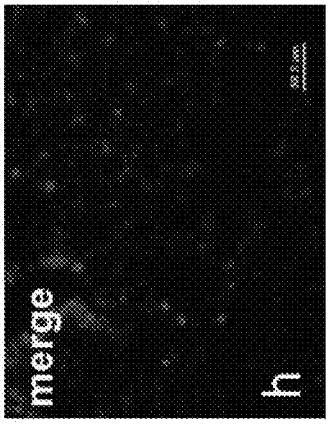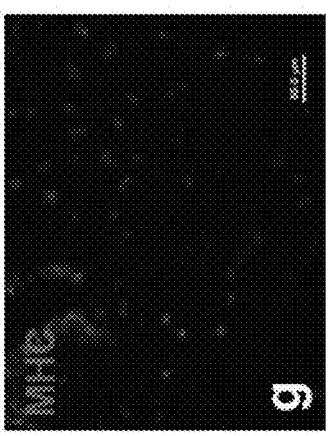

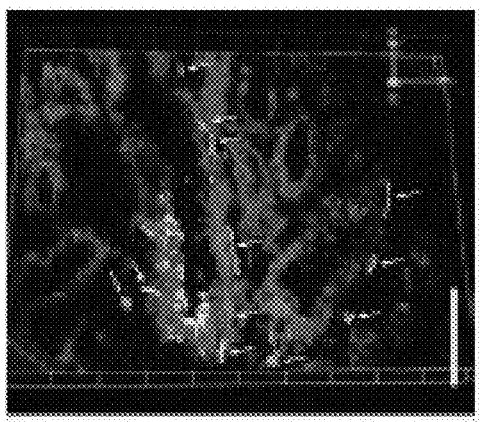
FIG. 26A  FIG. 26B
20 weeks HEL  20 weeks embryonic lung graft
Adult human lung
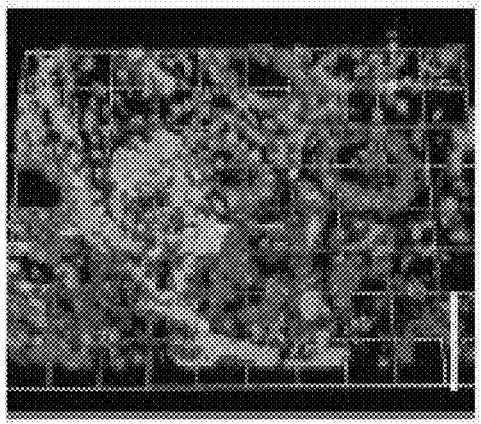
FIG. 26C
CK5 / Nestin / BV / Nuclei
FIG. 26D
CK5 / NF / BV
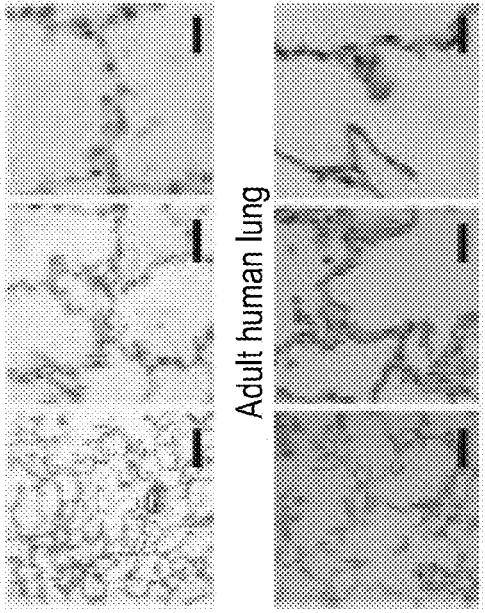
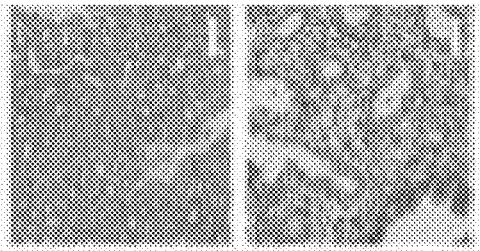
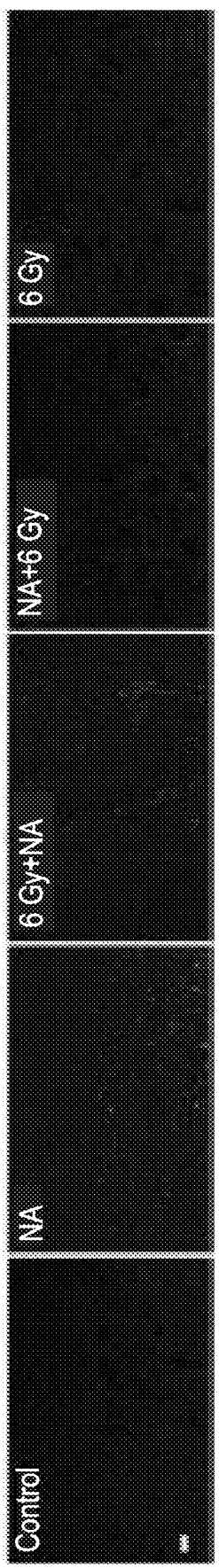
FIG. 26E
BrdU / Nuclei
Control | NA | 6Gy+NA | NA+6 Gy | 6 Gy

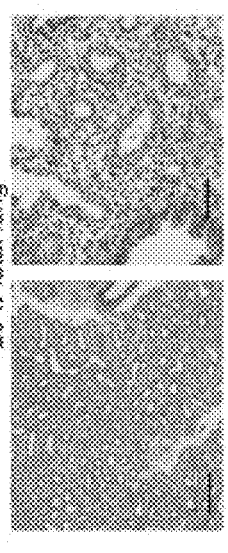
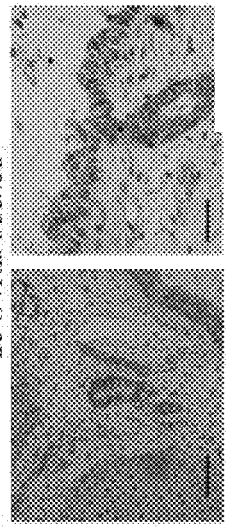
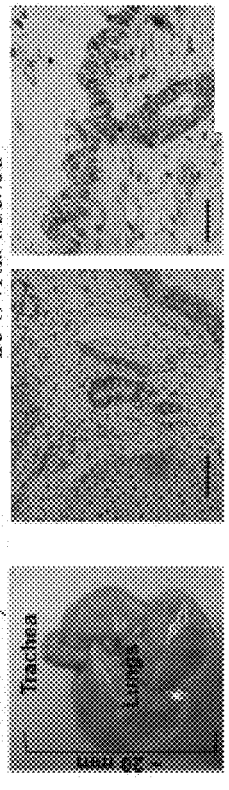
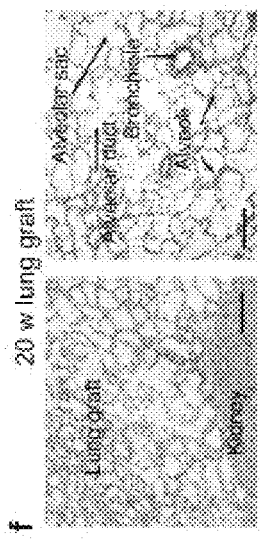
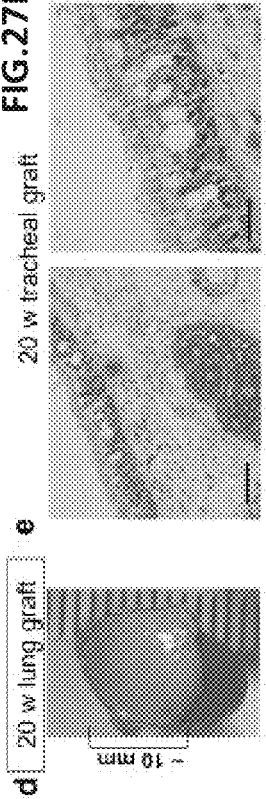
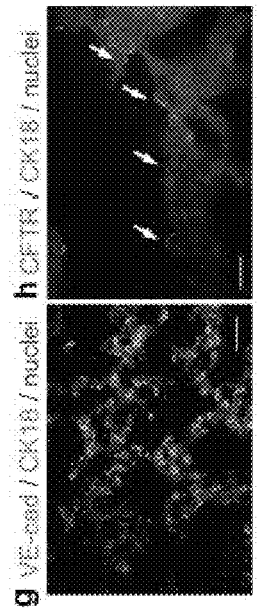
FIG. 27A  FIG. 27B  FIG. 27C  FIG. 27D  FIG. 27E  FIG. 27F  FIG. 27G  FIG. 27H  FIG. 27I

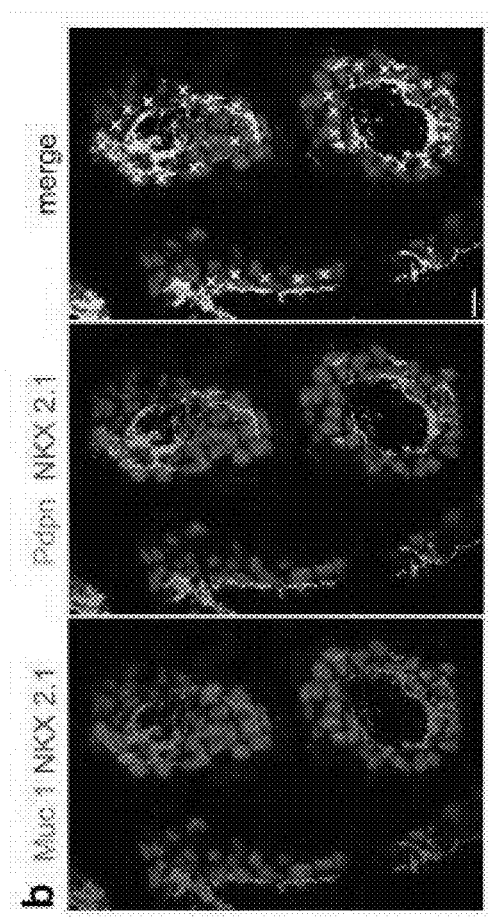
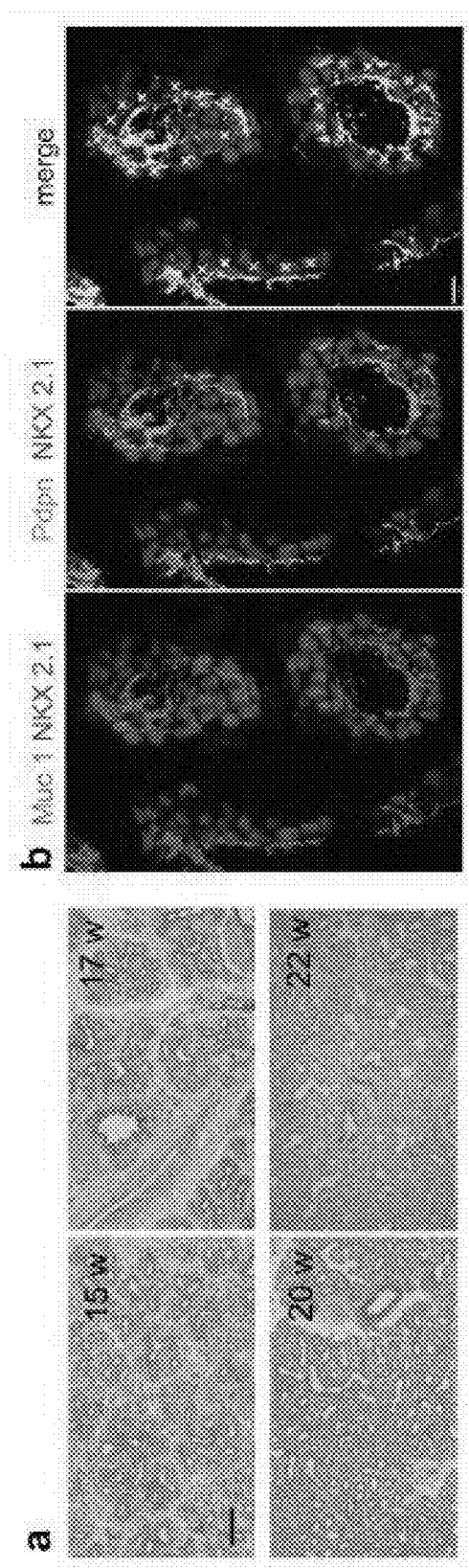
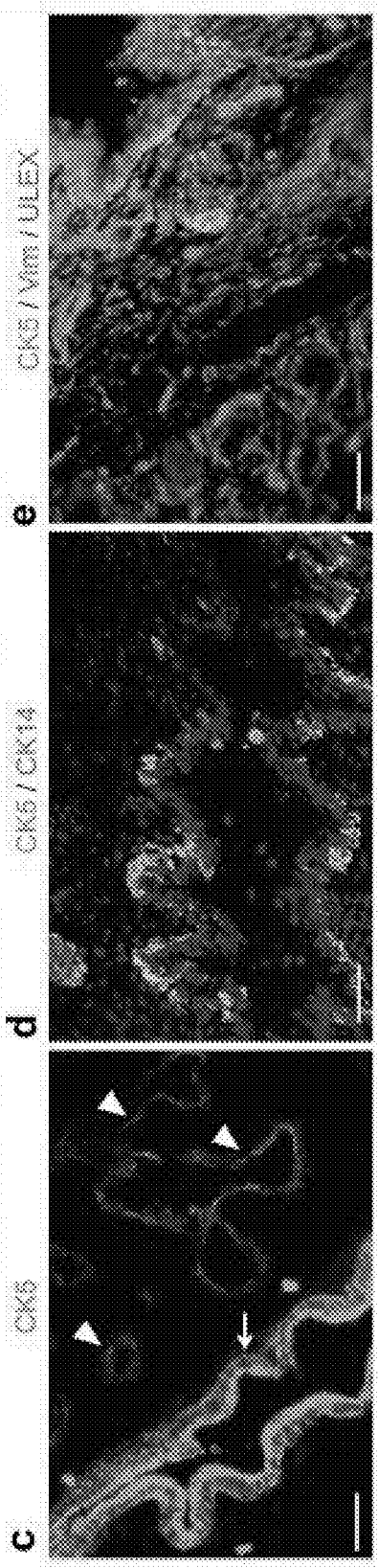
FIG. 28A
FIG. 28B
FIG. 28C
FIG. 28D
FIG. 28E

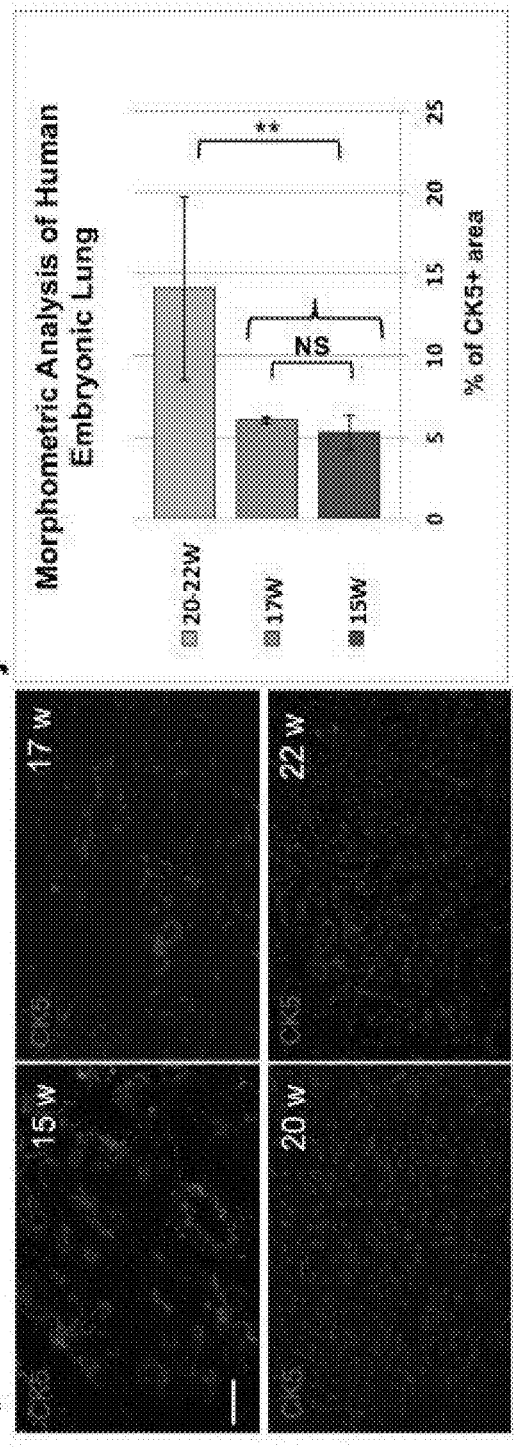
FIG. 28F  FIG. 28G  FIG. 28H  FIG. 28I  FIG. 28J

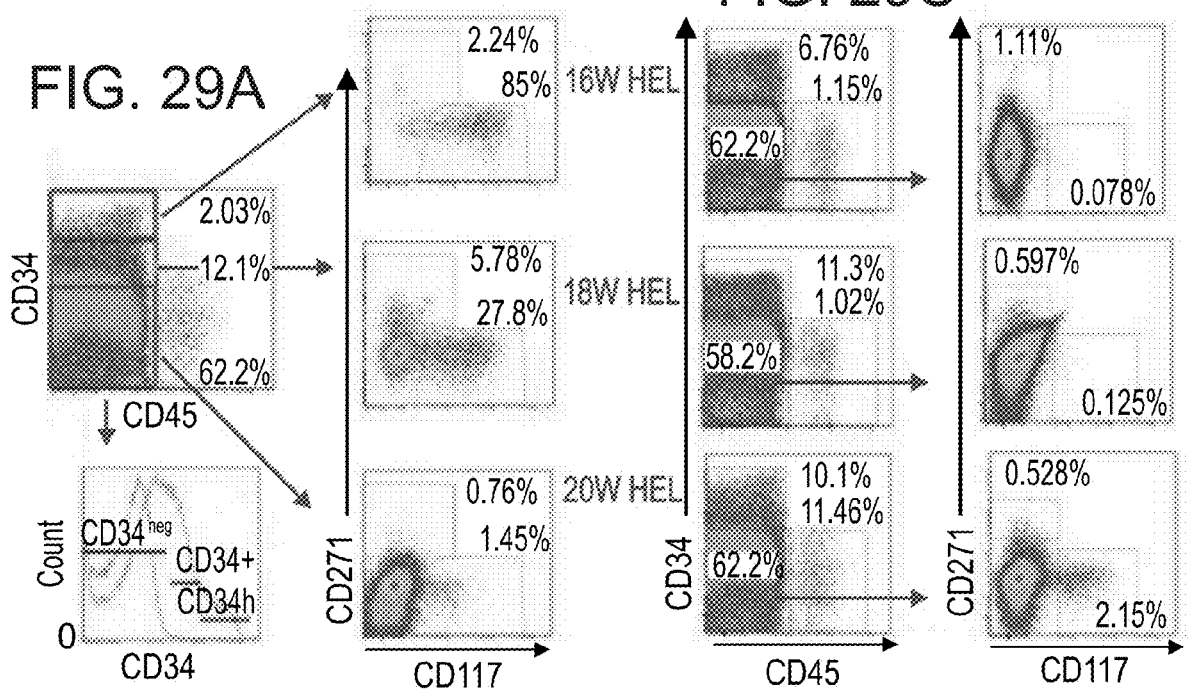
FIG. 29A
FIG. 29B
FIG. 29C
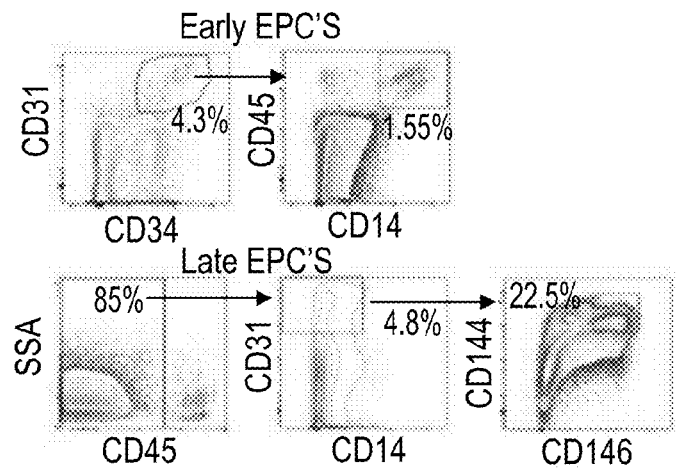
FIG. 29D
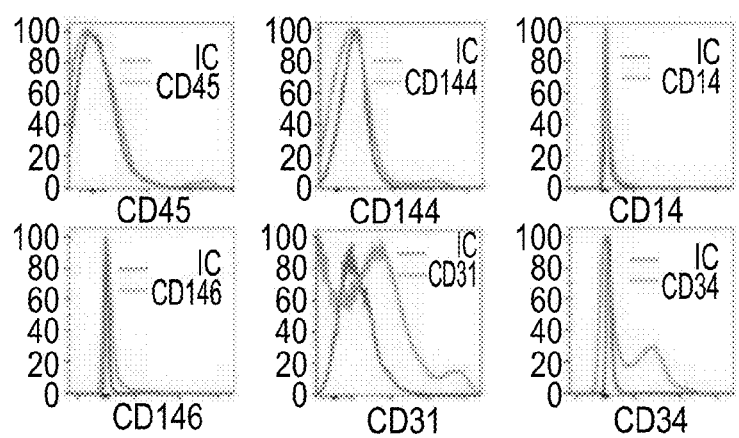
FIG. 29E

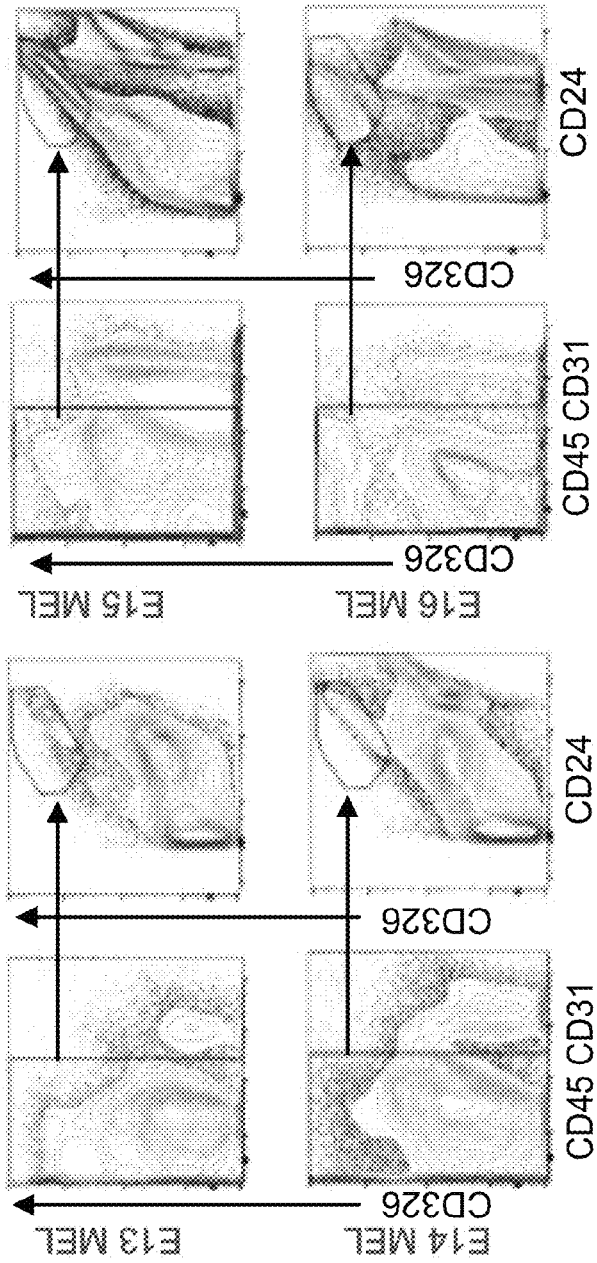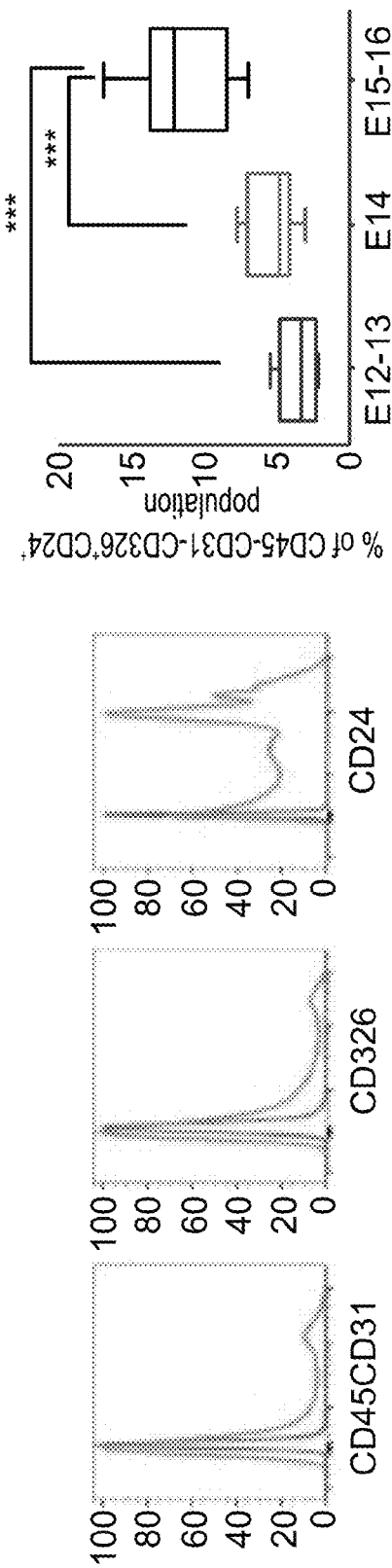

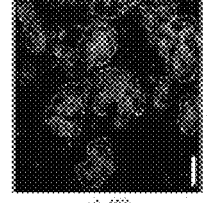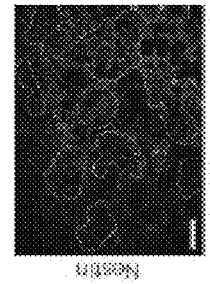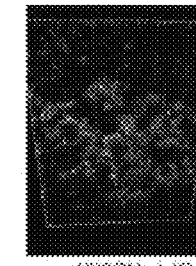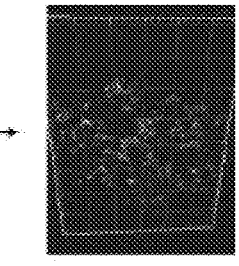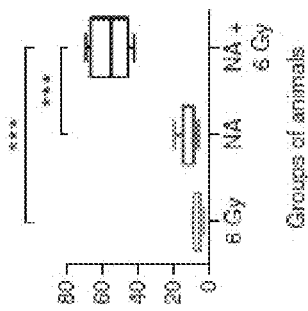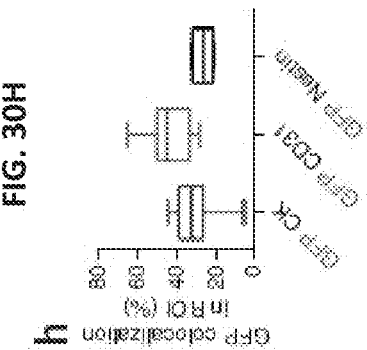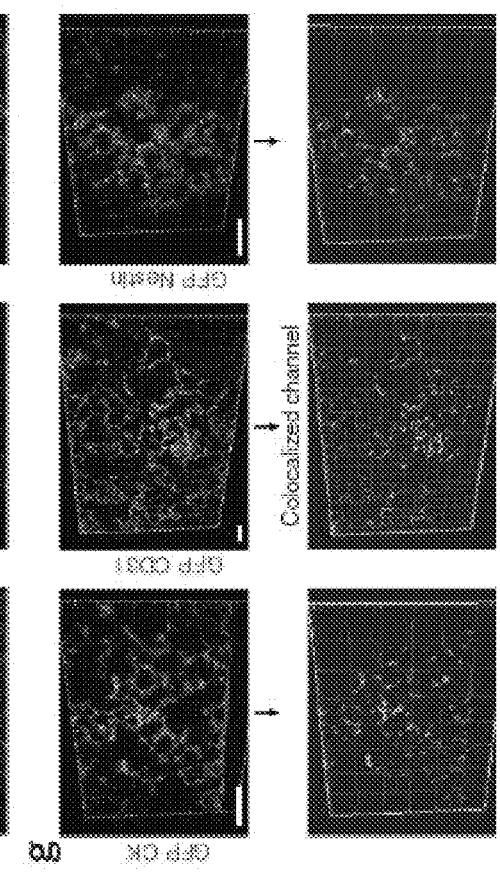

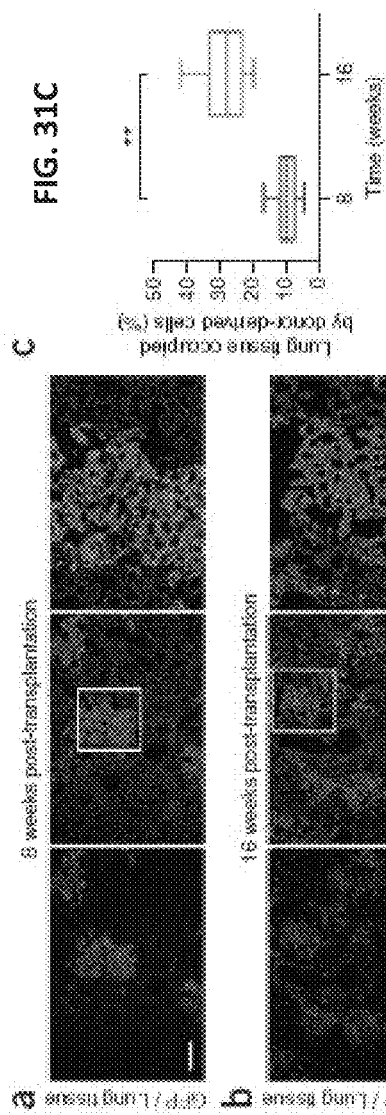
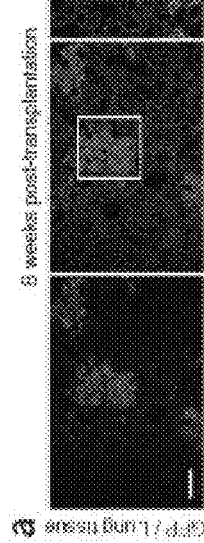
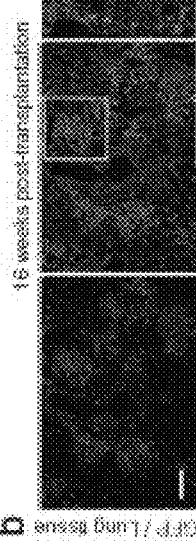
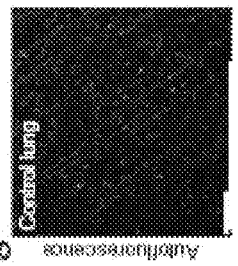
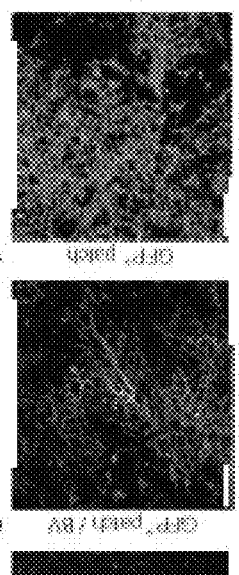
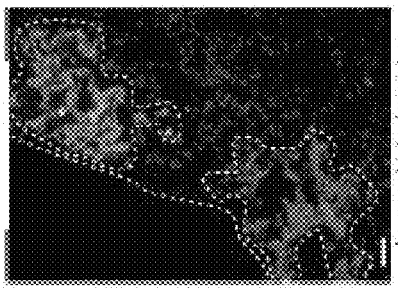
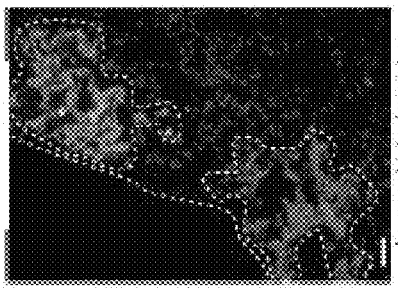
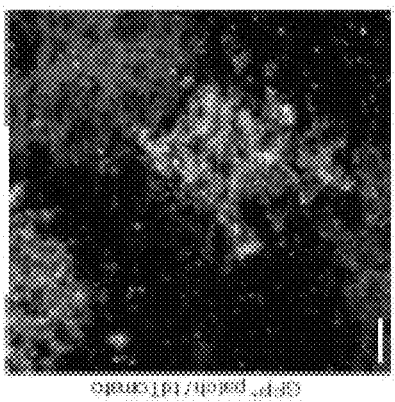
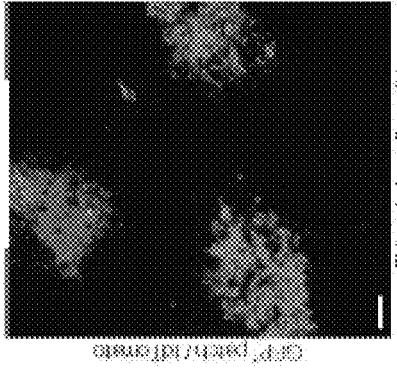
FIG. 31A
FIG. 31B
FIG. 31C
FIG. 31D
FIG. 31E
FIG. 31F
FIG. 31G
FIG. 31H
FIG. 31I
FIG. 31J

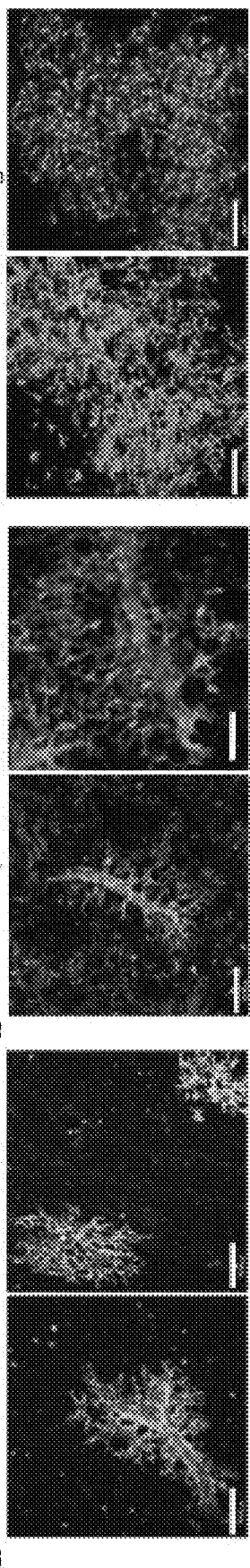
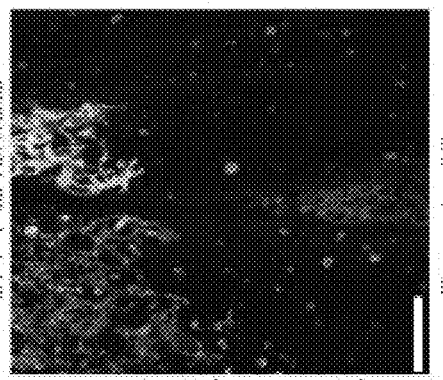

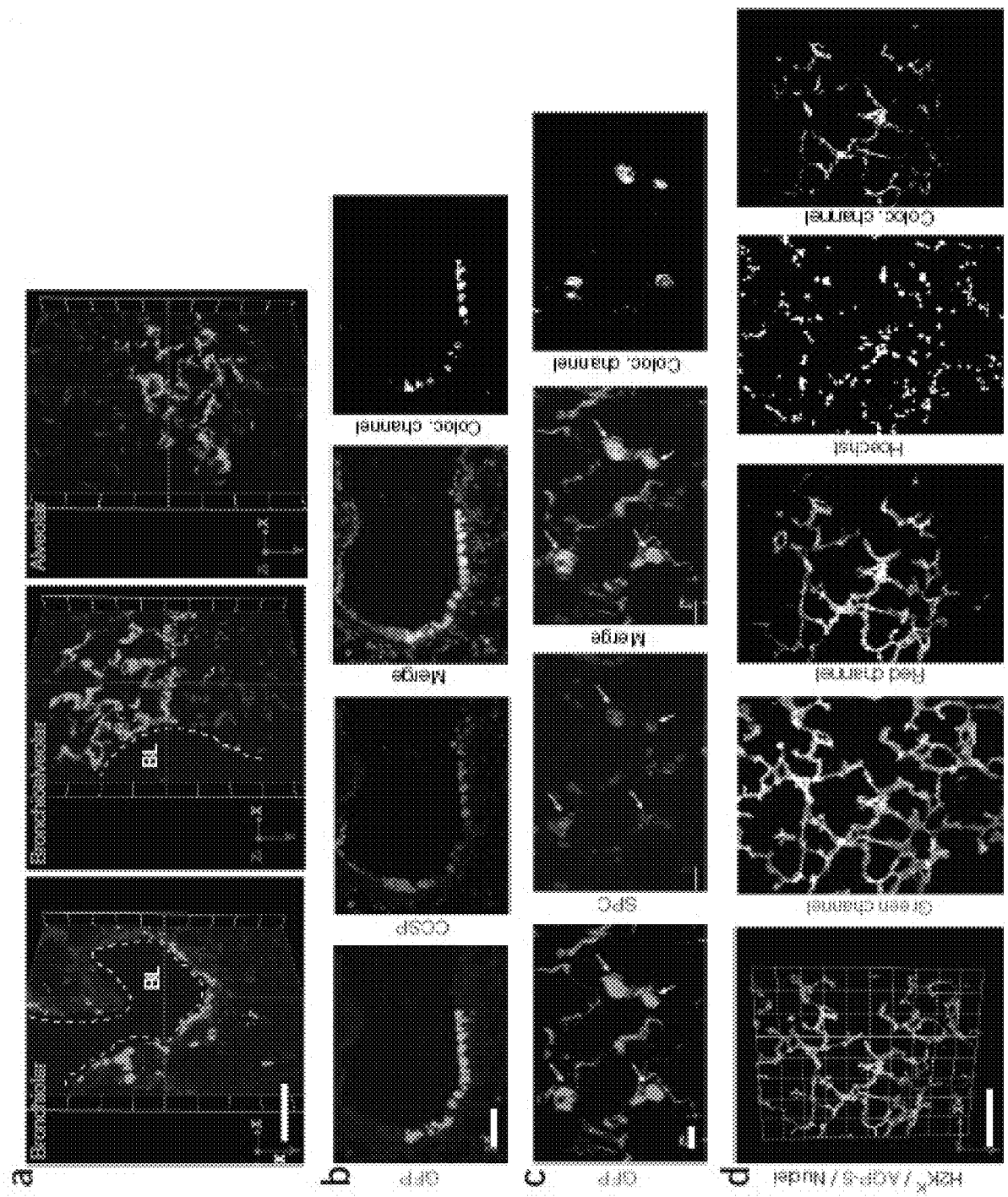

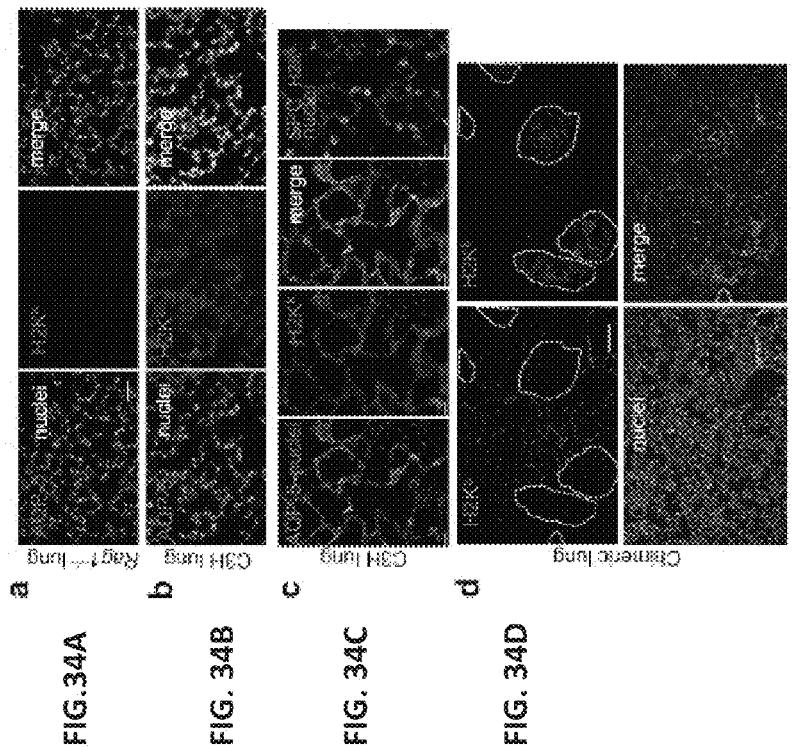
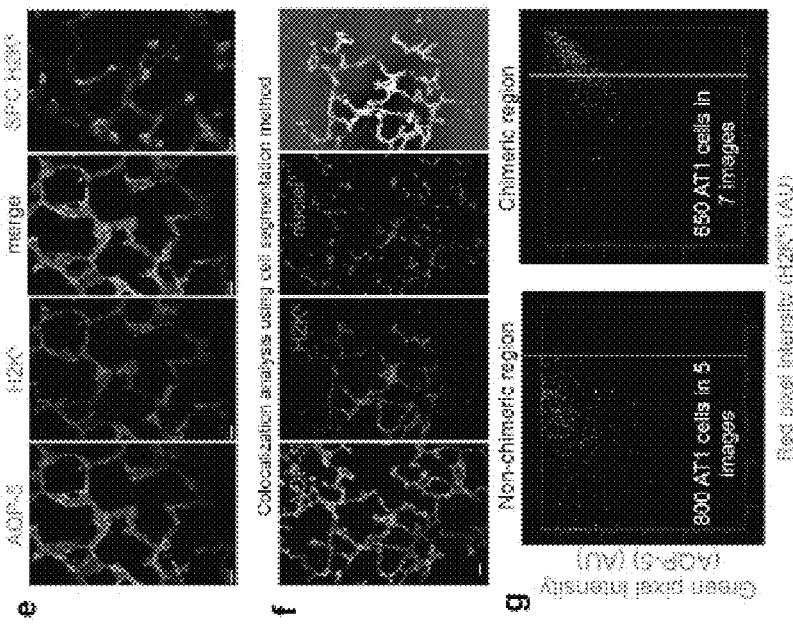
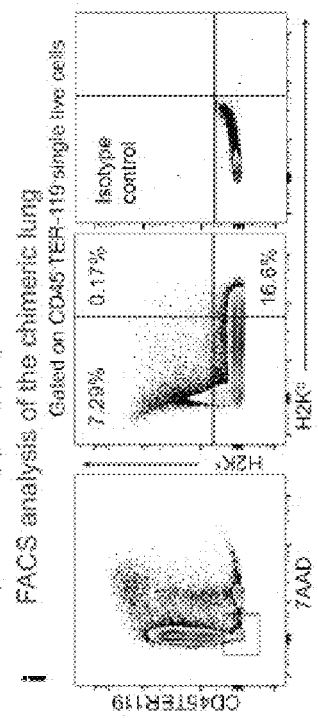
FIG. 34A  FIG. 34B  FIG. 34C  FIG. 34D  FIG. 34E  FIG. 34F  FIG. 34G  FIG. 34H  FIG. 34I

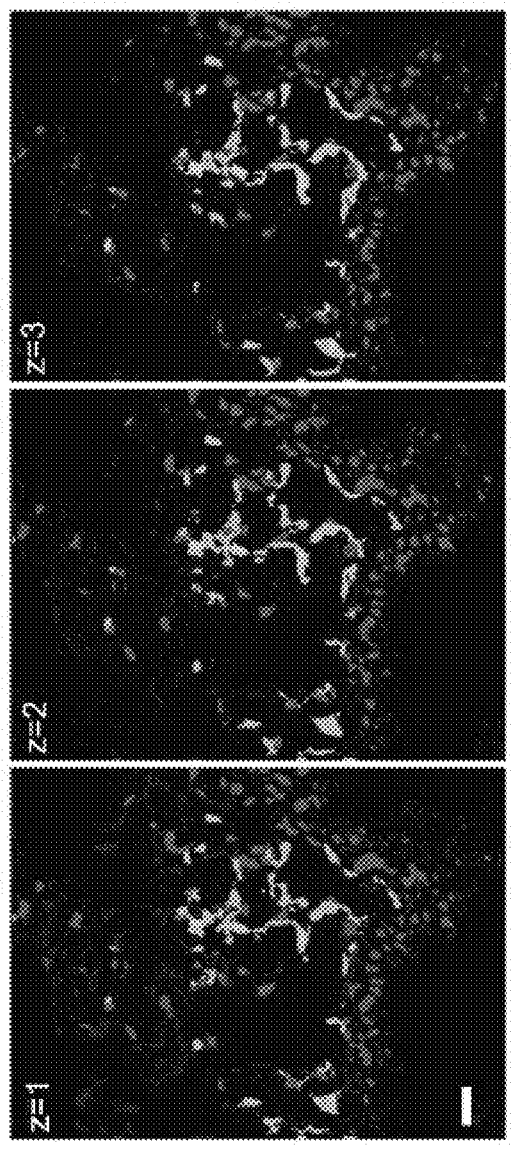

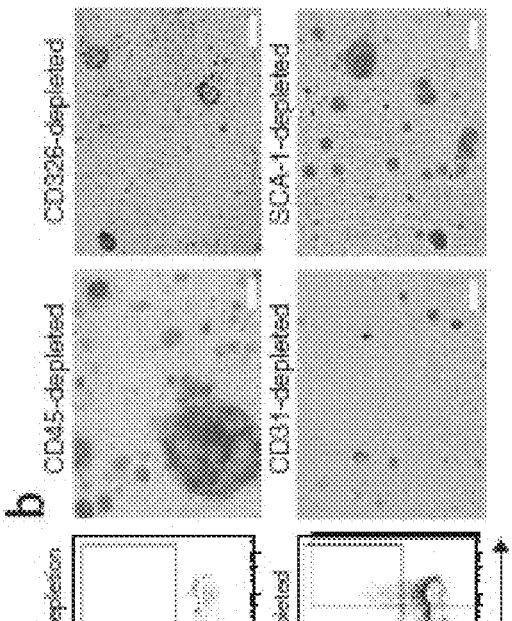
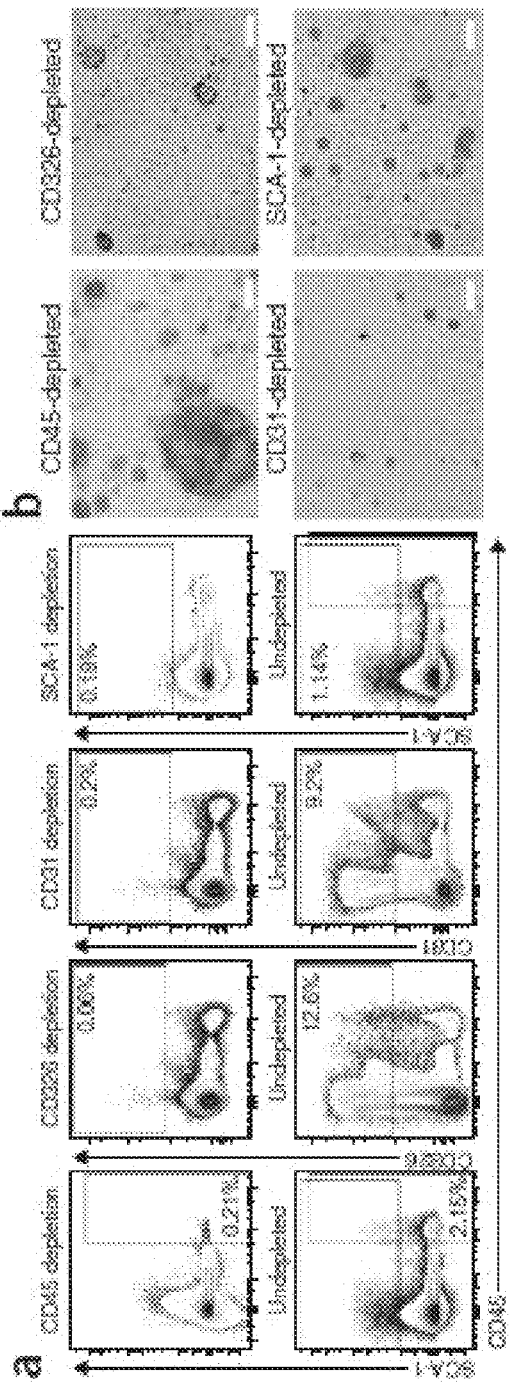
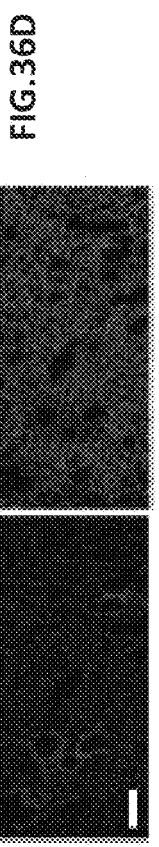
FIG. 36A
FIG. 36B
FIG. 36C
FIG. 36D
FIG. 36E
FIG. 36F

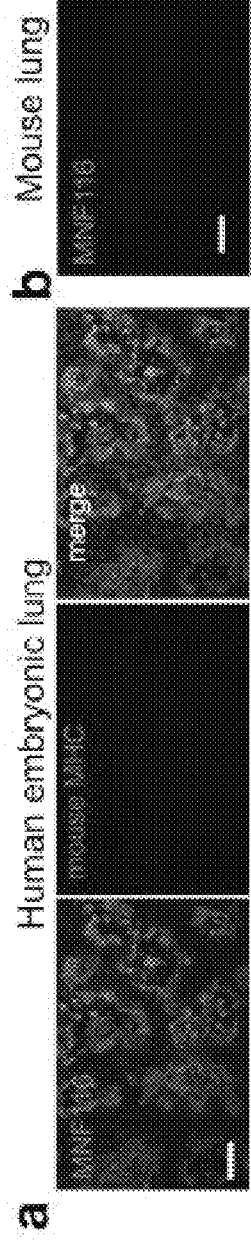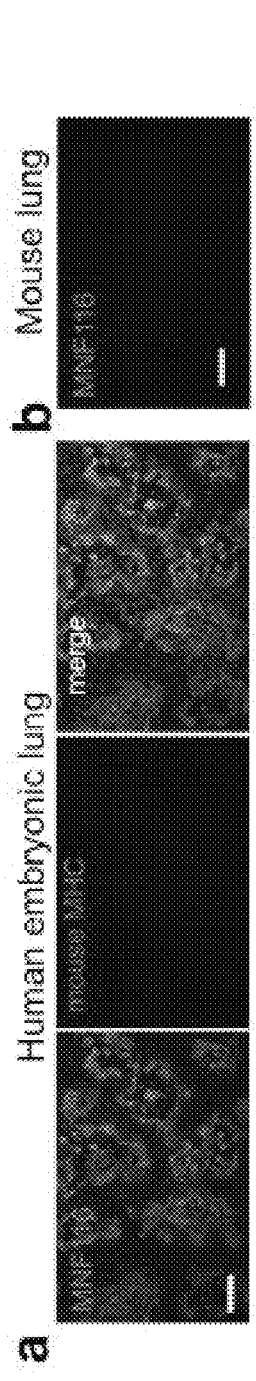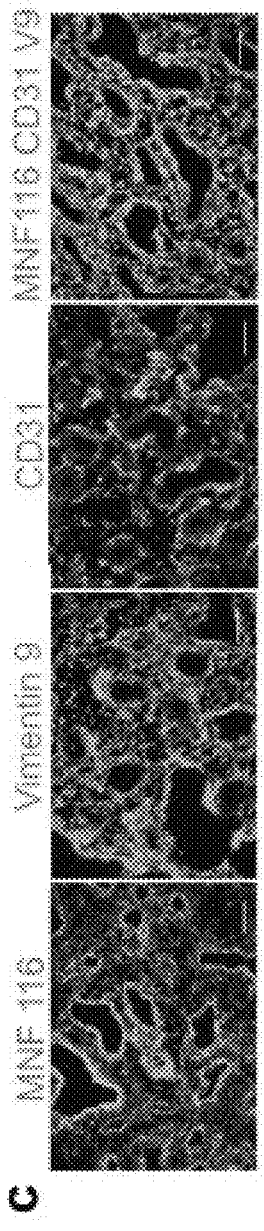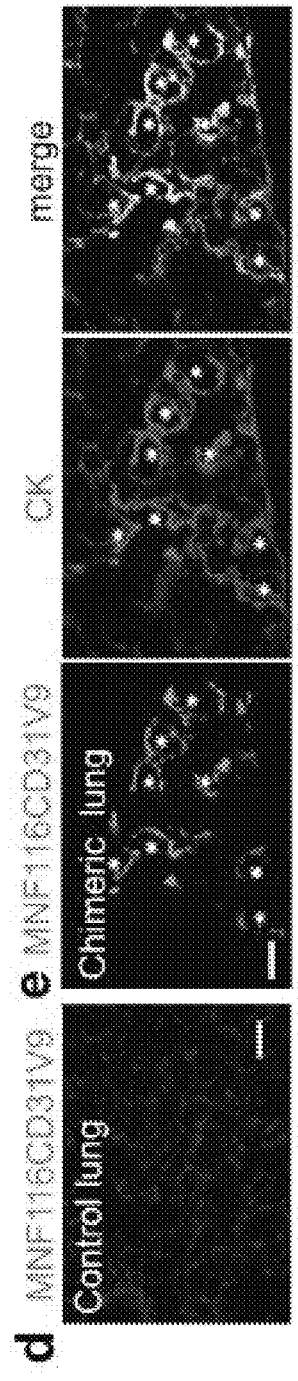
FIG. 37A  FIG. 37B  FIG. 37C  FIG. 37D  FIG. 37E

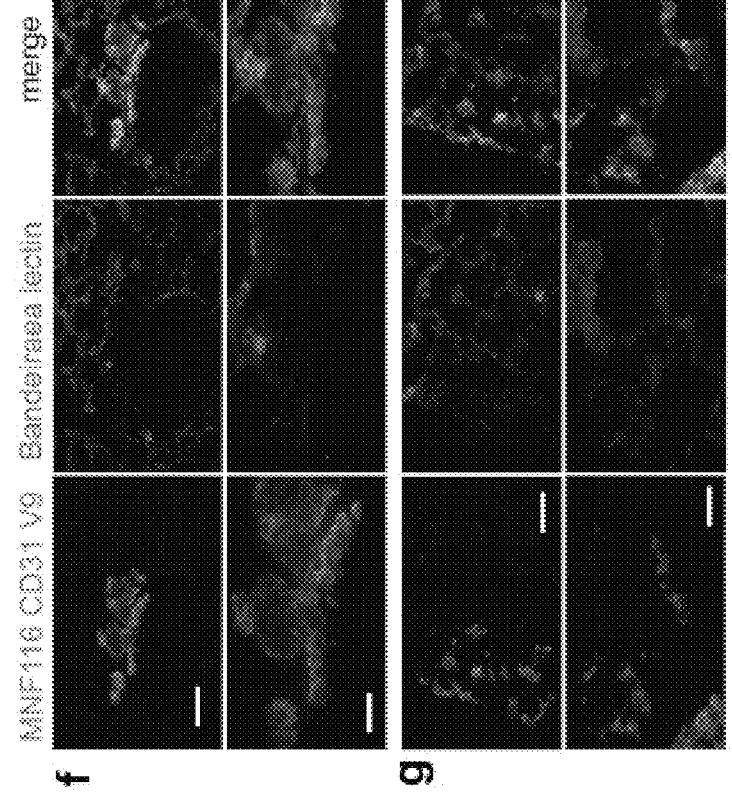
FIG. 37F
FIG. 37G
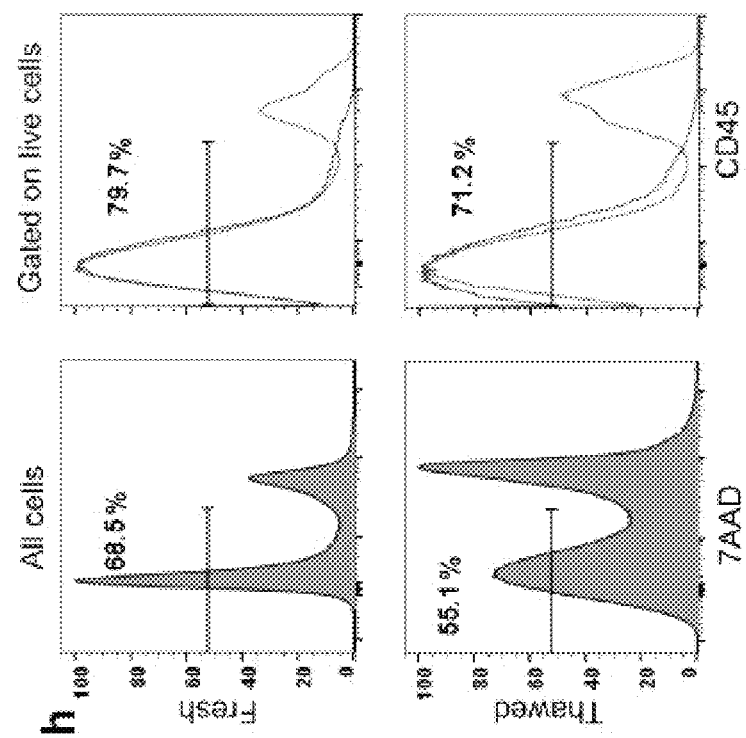
FIG. 37H

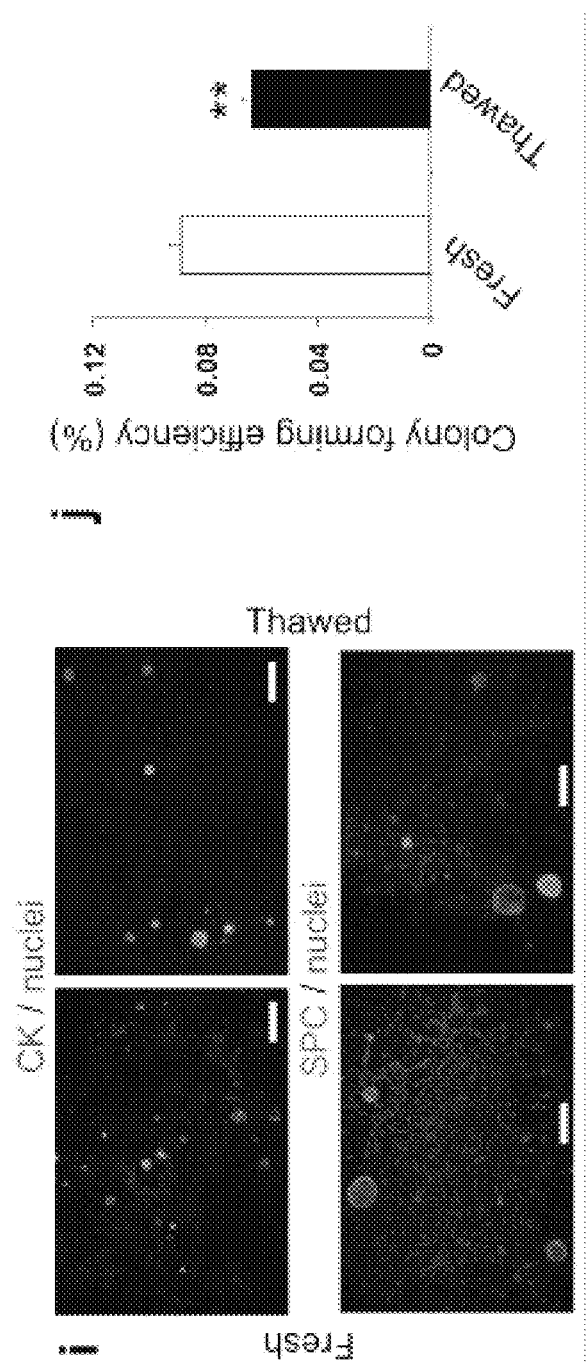

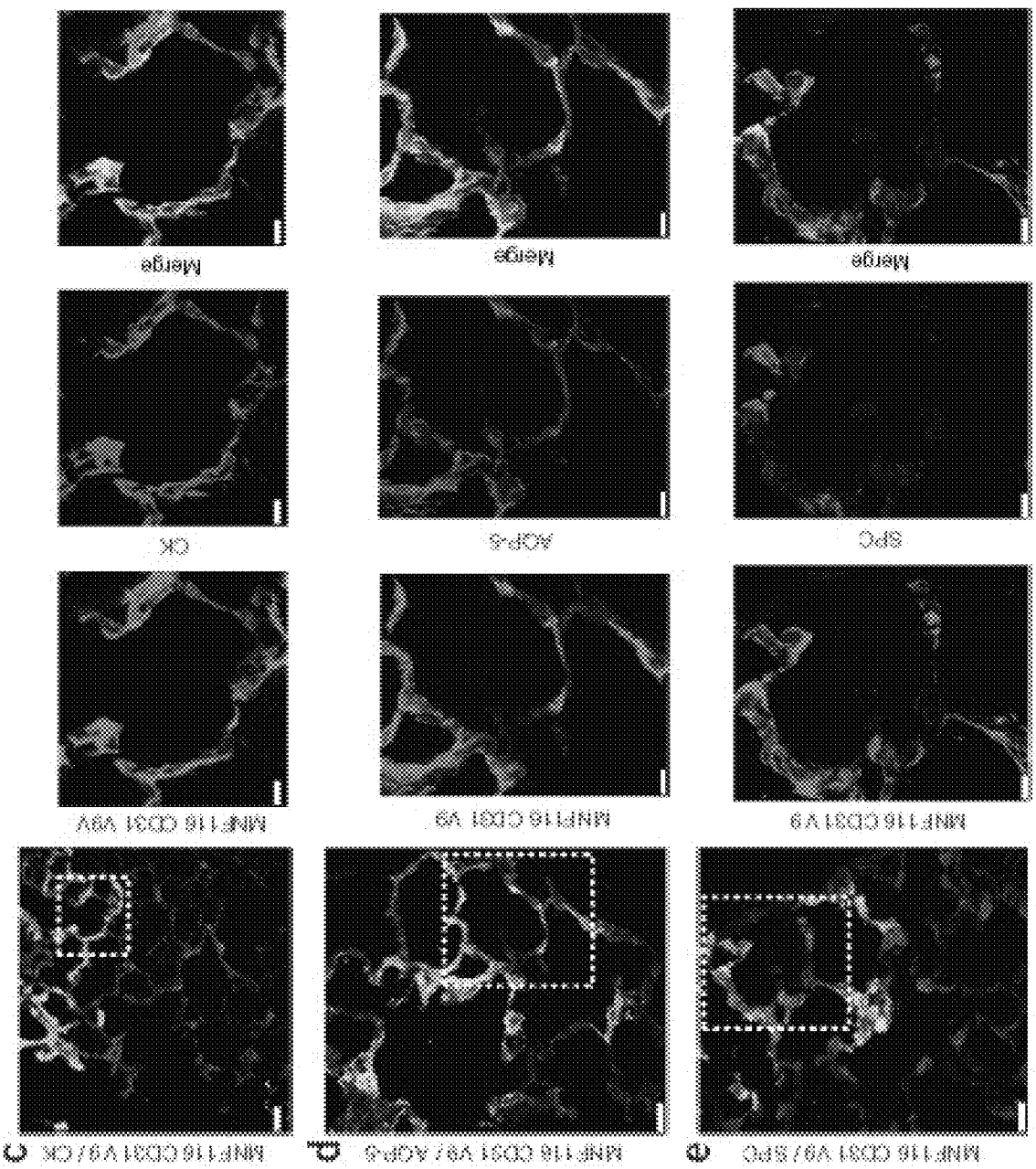

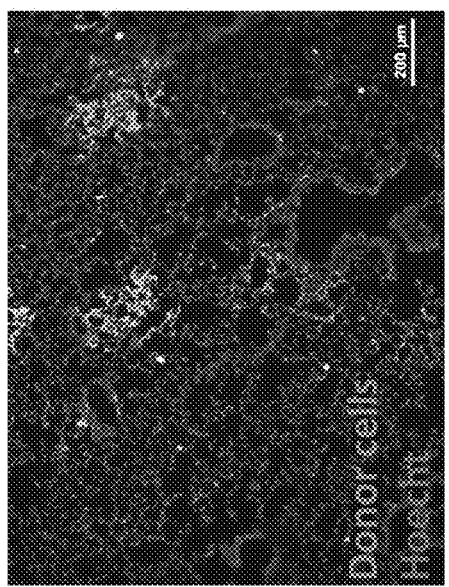
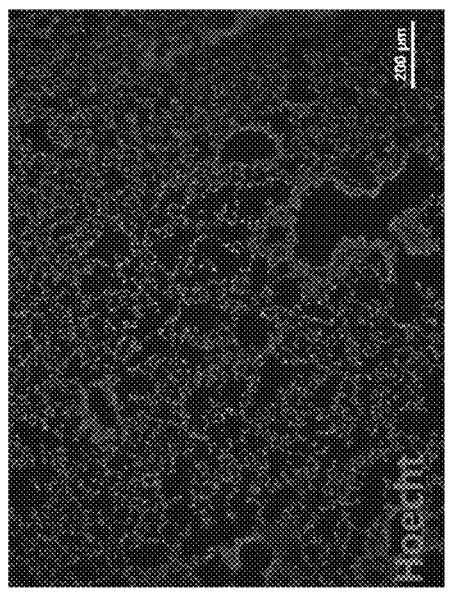
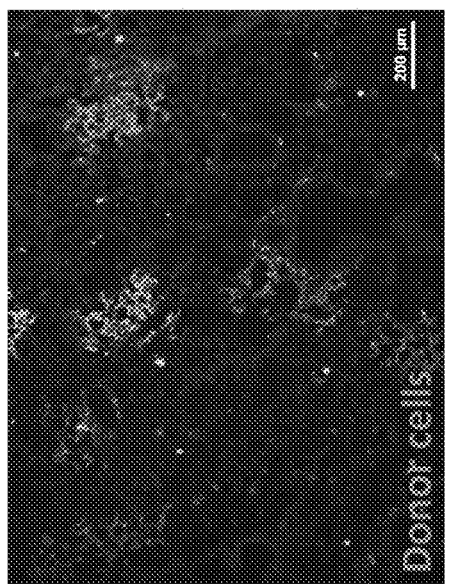
FIG. 39C
FIG. 39B
FIG. 39A

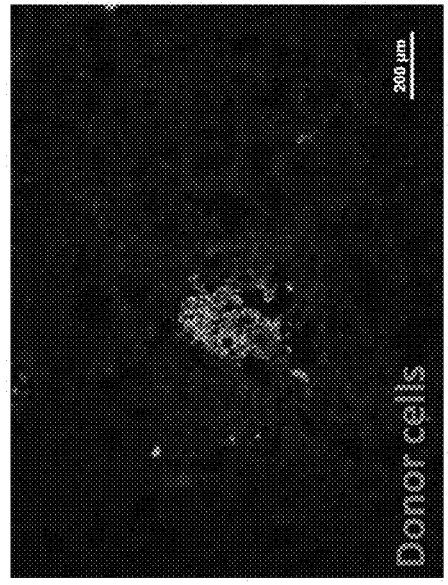
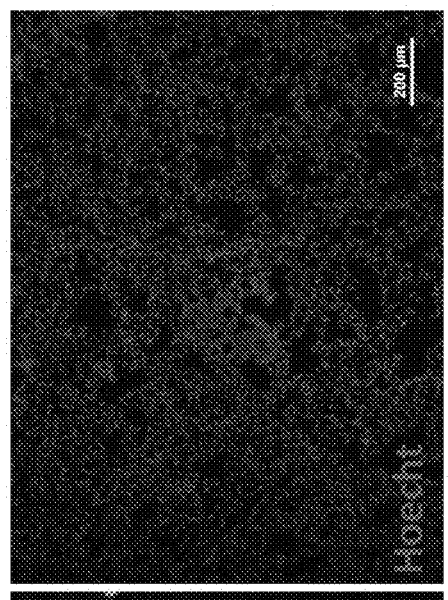
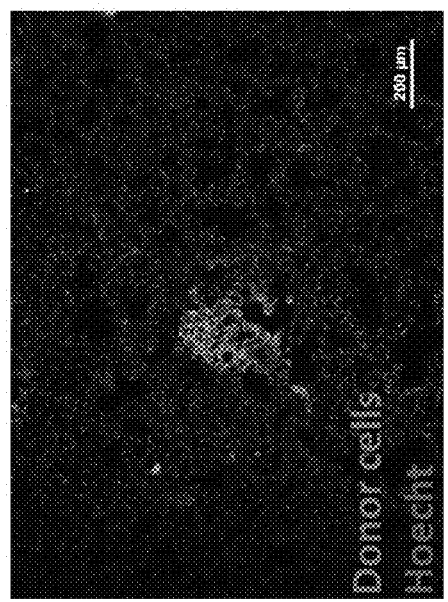

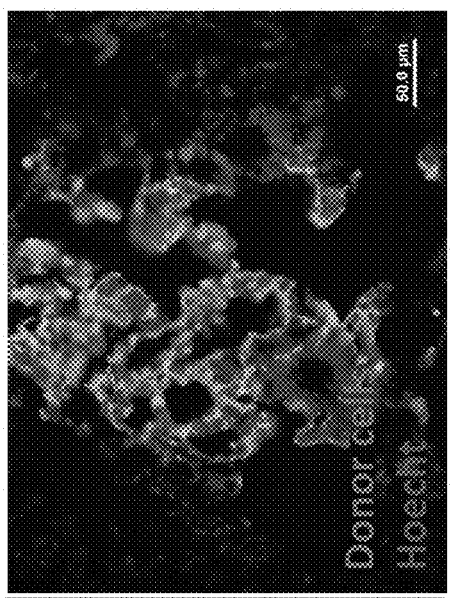
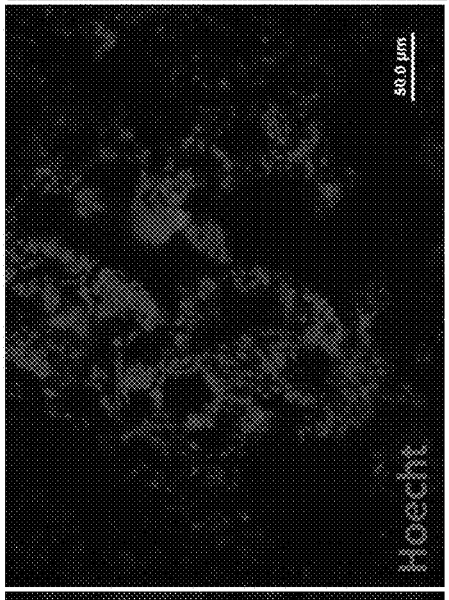
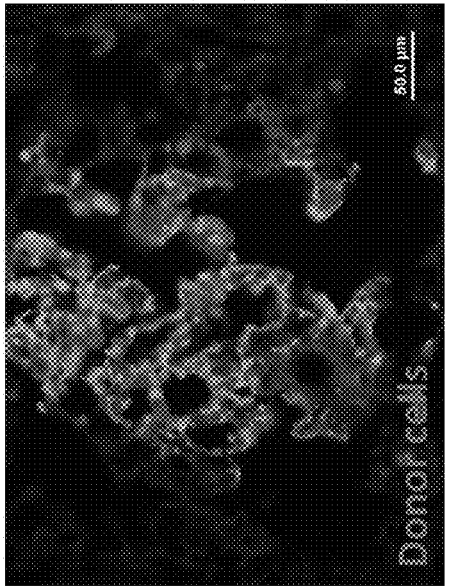
FIG. 40F
FIG. 40E
FIG. 40D

CONDITIONING PROTOCOLS AND USE OF SAME FOR TISSUE REGENERATION

RELATED APPLICATIONS

This application is a National Phase of PCT Patent Application No. PCT/IL2016/050638 having International filing date of Jun. 16, 2016, which claims the benefit of priority under 35 USC § 119(e) of U.S. Provisional Patent Application No. 62/181,394 filed on Jun. 18, 2015. The contents of the above applications are all incorporated by reference as if fully set forth herein in their entirety.

FIELD AND BACKGROUND OF THE INVENTION

The present invention, in some embodiments thereof, relates to conditioning protocols and to the use of same for tissue regeneration.

Pancreatic diseases such as diabetes, pulmonary diseases such as COPD, cystic fibrosis, emphysema, pulmonary fibrosis or pulmonary hypertension, liver diseases such as liver cirrhosis or viral liver diseases (e.g. Hepatitis B or C), heart diseases such as heart failure, and kidney diseases such as kidney failure are diseases of great medical and economic impact for which no satisfactory/optimal treatments are available. Most currently available therapies only slightly improve the quality of life for the patients in need. At present, the only definitive treatment for end-stage lung disease, liver disease, heart disease and kidney disease is the replacement of the damaged organ, but many patients die while on the waiting list due to a severe shortage of organs for transplantation and the limit for inscription being often set at 60 years of age.

Transplantation of fully differentiated haplotype-matched grafts from donors is a life-saving, medical procedure of choice for replacing injured or diseased organs such as pancreas, heart, liver or lung. Such a treatment modality, however, suffers from considerable disadvantages. Allogeneic transplantation of organs/tissues is impossible to implement in a great many cases due to the lack of organ donors (e.g. usually cadavers) and the unavailability of suitable immunologically matched organ donors. Furthermore, the use of living human donors often presents health risks and ethical dilemmas. Thus, large numbers of patients who would otherwise benefit from therapeutic transplantation succumb to diseases associated with pancreatic, liver, lung, kidney and pulmonary failure while awaiting matched transplant donors.

Thus, in view of the unique potential curative benefits of transplantation therapy, there is clearly an urgent and long-standing need for non-syngeneic donor-derived pancreatic, liver, lung, kidney and pulmonary organs/tissues which can be obtained in sufficient quantities, and which can be optimally tolerated immunologically, so as to render feasible the routine and optimally effective therapeutic transplantation of such organs/tissues.

One strategy, which has been proposed to fulfill this aim involves using gestational stage grafts for transplantation.

Additional background art includes:

PCT Publication No. WO2006/038211 relates to methods of providing a pancreatic, lymphoid/hematopoietic or pulmonary organ and/or tissue function to a mammalian subject. The method comprising transplanting into the subject a developing mammalian pancreatic, lymphoid/hematopoietic or pulmonary organ/tissue graft, respectively. The pulmonary graft disclosed in WO 2006/038211 is at a developmental stage essentially corresponding to that of a porcine pulmonary organ/tissue at a gestational stage selected from a range of about 42 to about 80 days of gestation.

PCT Publication No. WO 2004/078022 relates to methods of treating a disorder associated with pathological organ or tissue physiology or morphology. The method is effected by transplanting into a subject a mammalian organ or tissue graft (e.g. renal, pancreatic, hepatic, cardiac or lymphoid organ or tissue graft) selected not substantially expressing or presenting at least one molecule capable of stimulating or enhancing an immune response in the subject.

Another strategy, which has been proposed to fulfill this aim involves using isolated populations of cells, such as hepatocytes, hematopoietic progenitor cells and stem cells (e.g. cord blood and bone marrow).

PCT Publication No. WO 2013/084190 relates to a pharmaceutical composition comprising as an active ingredient an isolated population of cell suspension from a mammalian fetal pulmonary tissue. The fetal pulmonary tissue is at a developmental stage corresponding to that of a human pulmonary organ/tissue at a gestational stage selected from a range of about 20 to about 22 weeks of gestation. Methods of using the pharmaceutical composition are also disclosed.

SUMMARY OF THE INVENTION

According to an aspect of some embodiments of the present invention there is provided a method of conditioning a subject in need of transplantation of progenitor cells in suspension of a tissue of interest, the method comprising: (a) administering to a subject a therapeutically effective amount of an agent capable of inducing damage to the tissue of interest, wherein the damage results in proliferation of resident stem cells in the tissue; and subsequently (b) subjecting the subject to an agent which ablates the resident stem cells in the tissue, thereby conditioning the subject.

According to an aspect of some embodiments of the present invention there is provided a method of transplanting progenitor cells in suspension of a tissue of interest to a subject in need thereof, the method comprising: conditioning the subject according to some embodiments of the invention; and (b) transplanting the progenitor cells in suspension to the subject, wherein when the tissue of interest is a pulmonary tissue the agent capable of inducing damage to the tissue is not naphthalene.

According to some embodiments of the invention, the subject has a disease selected from the group consisting of a malignant disease, a disease of the central nervous system, a gastrointestinal disease, a cardiovascular disease, a hepatic disease, a nephric disease, a pancreatic disease, a pulmonary disease, an infectious disease, an inflammatory disease, an immunodeficiency and an autoimmune disease.

According to some embodiments of the invention, the disease is selected from the group consisting of an organ dysfunction or failure, a cancer, an Alzheimer's disease, a Parkinson's disease, a Huntington's disease, a Multiple Sclerosis, a Crohn's disease, a pancreas damage, a diabetes mellitus, a liver cirrhosis, a hepatitis B, a hepatitis C, a kidney disease, an ischemic cardiac damage, a drug induced cardiac toxicity, an ischemia, an injury, an intestinal injury, a wound and a viral infection.

According to some embodiments of the invention, the pulmonary disease is selected from the group consisting of cystic fibrosis, emphysema, asbestosis, chronic obstructive pulmonary disease (COPD), pulmonary fibrosis, idiopathic pulmonary fibrosis, pulmonary hypertension, lung cancer, sarcoidosis, acute lung injury (adult respiratory distress syndrome), respiratory distress syndrome of prematurity, chronic lung disease of prematurity (bronchopulmonarydysplasia), surfactant protein B deficiency, congenital diaphragmatic hernia, pulmonary alveolar proteinosis, pulmonary hypoplasia and lung injury.

According to some embodiments of the invention, the progenitor cells comprise human progenitor cells.

According to some embodiments of the invention, the progenitor cells are from an adult tissue.

According to some embodiments of the invention, the progenitor cells are from a fetal origin.

According to some embodiments of the invention, the progenitor cells are from an embryonic origin.

According to some embodiments of the invention, the progenitor cells comprise de-differentiated cells.

According to some embodiments of the invention, the progenitor cells comprise ex vivo expanded cells.

According to some embodiments of the invention, the progenitor cells are selected from the group consisting of cardiac progenitor cells, hepatic progenitor cells, pancreatic progenitor cells, brain progenitor cells, nephric progenitor cells, ovarian progenitor cells, spleen progenitor cells and pulmonary progenitor cells.

According to some embodiments of the invention, the progenitor cells from the pulmonary origin are obtained from a fetus at a canalicular stage of development.

According to some embodiments of the invention, the canalicular stage of development corresponds to that of a human organ/tissue at a gestational stage selected from a range of about 16 to about 25 weeks of gestation.

According to some embodiments of the invention, the progenitor cells are non-syngeneic with the subject.

According to some embodiments of the invention, the progenitor cells are allogeneic with the subject.

According to some embodiments of the invention, the allogeneic cells are selected from the group consisting of HLA identical, partially HLA identical and HLA non-identical with the subject.

According to some embodiments of the invention, the progenitor cells are xenogeneic with the subject.

According to some embodiments of the invention, the progenitor cells are capable of regenerating a structural/functional tissue.

According to some embodiments of the invention, the structural/functional tissue comprises generation of a chimeric tissue.

According to some embodiments of the invention, the tissue of interest is a parenchymal tissue.

According to some embodiments of the invention, the tissue of interest is selected from the group consisting of a cardiac tissue, a hepatic tissue, a pancreatic tissue, a brain tissue, a nephric tissue, an ovarian tissue, a lung tissue and a spleen tissue.

According to some embodiments of the invention, the agent capable of inducing damage to the tissue is selected from the group consisting of a chemical, an antibiotic, a therapeutic drug, a toxin, a surgical intervention and an herbal remedy.

According to some embodiments of the invention, the agent capable of inducing damage to the tissue is selected from the group consisting of an agent causing renal cell toxicity, an agent causing hepatic cell toxicity, an agent causing cardiac cell toxicity, an agent causing pancreatic cell toxicity, an agent causing brain cell toxicity, an agent causing spleen cell toxicity, an agent causing ovarian cell toxicity and an agent causing pulmonary cell toxicity.

According to some embodiments of the invention, the agent causing renal cell toxicity is selected from the group consisting of an aminoglycoside antibiotic, a calcineurin inhibitor, an acetaminophen, a nonsteroidal anti-inflammatory drug (NSAID), an antidepressant, an antihistamine, an anti-microbial agent, an anti-retroviral agent, a benzodiazepine, a cardiovascular agent, a chemotherapeutic agent, a herbal remedy and a partial nephrectomy.

According to some embodiments of the invention, the agent causing hepatic cell toxicity is selected from the group consisting of an acetaminophen, a nonsteroidal anti-inflammatory drug (NSAID), a glucocorticoid, an isoniazid, a hydrazine derivative drug, an industrial toxin, a herbal remedy and a partial hepatectomy.

According to some embodiments of the invention, the agent causing cardiac cell toxicity is selected from the group consisting of a chemotherapeutic agent, a cytostatic agent, an antidepressant drug, an immunomodulating drug, an anesthetic, a calcium channel blocking agent, a nonsteroidal anti-inflammatory drug (NSAID), a beta-adrenoceptor antagonist and an antiarrhythmic.

According to some embodiments of the invention, the agent causing pancreatic cell toxicity is selected from the group consisting of an ACE inhibitor, an azathioprine, an estrogen, a furosemide, a methyldopa, a mesalazine, a pentamidine, a procainamide, a propofol, a statin, a streptozotocin, a sulfonamide, a thiazide diuretic, a valproate and a partial pancreatectomy.

According to some embodiments of the invention, the agent causing brain cell toxicity is selected from the group consisting of an antihistamine, a bladder relaxant, a muscle relaxant, an antidepressant and a chemotherapeutic agent.

According to some embodiments of the invention, the agent causing ovarian cell toxicity is selected from the group consisting of a chemotherapeutic agent and an immunosuppressive agent.

According to some embodiments of the invention, the agent causing pulmonary cell toxicity is selected from the group consisting of a chemotherapeutic agent, an immunosuppressive agent, an amiodarone, a beta blockers, an ACE inhibitor, a nitrofurantoin, a procainamide, a quinidine, a tocainide, and a minoxidil.

According to some embodiments of the invention, the agent which ablates the resident stem cells comprises a sublethal or lethal conditioning regimen.

According to some embodiments of the invention, the sublethal or lethal conditioning regimen comprises a partial body irradiation.

According to some embodiments of the invention, the partial body irradiation comprises irradiation treatment specific to the tissue.

According to some embodiments of the invention, the sublethal or lethal conditioning regimen comprises an Alkylating agent.

According to some embodiments of the invention, the Alkylating agent is selected from the group consisting of a cyclophosphamide and a busulfan.

According to some embodiments of the invention, the agent capable of inducing damage to the tissue is administered to the subject 1-3 days prior to the agent which ablates the resident stem cells.

According to some embodiments of the invention, the subject is a human being.

According to some embodiments of the invention, the transplanting is effected by an intravenous route.

According to some embodiments of the invention, the transplanting is effected by a route selected from the group consisting of intratracheal, intrabronchial, intraalveolar, intravenous, intraperitoneal, intranasal, subcutaneous, intramedullary, intrathecal, intraventricular, intracardiac, intramuscular, intraserosal, intramucosal, transmucosal, transnasal, rectal and intestinal.

According to some embodiments of the invention, the method further comprises treating the subject with an immunosuppressive regimen.

Unless otherwise defined, all technical and/or scientific terms used herein have the same meaning as commonly understood by one of ordinary skill in the art to which the invention pertains. Although methods and materials similar or equivalent to those described herein can be used in the practice or testing of embodiments of the invention, exemplary methods and/or materials are described below. In case of conflict, the patent specification, including definitions, will control. In addition, the materials, methods, and examples are illustrative only and are not intended to be necessarily limiting.

BRIEF DESCRIPTION OF THE SEVERAL VIEWS OF THE DRAWINGS

The patent or application file contains at least one drawing executed in color. Copies of this patent or patent application publication with color drawing(s) will be provided by the Office upon request and payment of the necessary fee.

Some embodiments of the invention are herein described, by way of example only, with reference to the accompanying drawings. With specific reference now to the drawings in detail, it is stressed that the particulars shown are by way of example and for purposes of illustrative discussion of embodiments of the invention. In this regard, the description taken with the drawings makes apparent to those skilled in the art how embodiments of the invention may be practiced.

In the drawings:

Figures 3A, 3B, 3C:
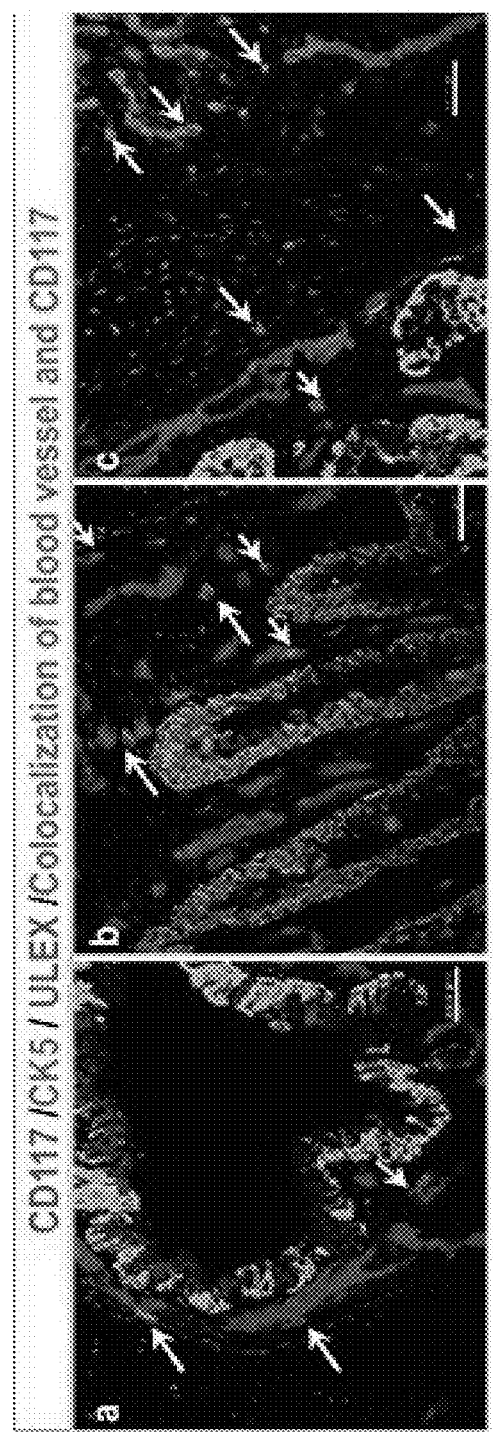

FIGS. 1A-R depict growth and development of human embryonic precursor tissues harvested at different gestational time points. Human embryonic tissues were implanted under the renal capsule of NOD-SCID mice. The implants were evaluated macroscopically or by immunohistological staining after 8 weeks. FIG. 1A is a summary of macroscopic size of implants from different gestational time points implants: Mean (±SD) size, based on long (L) and short (W) axes and height (H) of the implants, 6-8 weeks post-transplant (data shown are average of six independent experiments); FIG. 1B is a photograph illustrating a typical macroscopic appearance of the implants harvested at 20 weeks of gestation; FIGS. 1C-F are photographs of microscopic hematoxylin and eosin stain (H&E) examination of the implant derived from 20 week tissue, showing normal appearance of alveolar ducts, alveoli, trachea covered with ciliated epithelium, muscular layer and cartilage, and alveolar/epithelial monolayer; FIGS. 1G-H are photographs illustrating immunostaining for surfactant protein C (sp-C) in red, and cytokeratin-18 (CK-18) in green, at lower (FIG. 1G) and higher magnification (FIG. 1H); FIG. 1I is a photograph illustrating immunostaining for CFTR-cystic fibrosis transmembrane regulator in red and CK-18 in green; FIGS. 1J-R are photographs illustrating typical H&E staining of implants derived from 15 week (FIGS. 1J-L), 18 week (FIGS. 1P-R), and 24 week (FIGS. 1M-O) tissues, respectively. Arrows indicate cyst. In (FIG. 1M) macroscopic image of a cyst is illustrated.

FIGS. 2A-O depict identification of early progenitors and their niches in the human embryonic lung. FIGS. 2A-D are photographs illustrating H&E staining of human embryonic lung tissues at different gestational time points, revealing bronchial and bronchiolar structures without any alveolar structures; FIGS. 2E-F are photographs illustrating immunohistological staining showing high expression of $CK5^+$ cells in large airways and co-expression of CK5 and CK14 in the large bronchus. Arrows and arrow heads indicate regions with high and low CK5 expression, respectively. $CK5^+$ cells in bronchial and developing alveolar structures are associated with rich innervation, illustrated by contact with $nestin^+$ and $CGRP^+$ cells (FIG. 2G), as well as by staining for neurofilaments (NF) (FIG. 2H); FIG. 2I is a photograph illustrating alpha-smooth muscle actin positive cells; FIG. 2J is a photograph illustrating $Vimentin^+$ mesenchymal cells residing in close proximity to the $CK5^+$ progenitors; FIGS. 2K-N are photograph illustrating staining for CK5 (red) at different time points including 15 (FIG. 2K), 17 (FIG. 2L), 20 (FIG. 2M), and 22 (FIG. 2N) weeks of human gestation demonstrating differences in CK5 expression level; FIG. 2O is a graph illustrating quantitative morphometric analysis of tissue area occupied by $CK5^+$ progenitors showing significantly (t-test) higher levels at 20-22 weeks one diamond represents a p-value that is non-significant, two diamonds represent $p<0.002$).

FIGS. 2P-Z depict FACS analysis of early non-hematopoietic progenitors in human embryonic lung tissue harvested at different gestational time points. FIGS. 2P-Q illustrate representative FACS analysis of 20 week lung cells showing double staining with anti-CD45 and anti-CD34. Three subpopulations within the non-hematopoietic CD45− cells, including CD45−$CD34^{high}$, CD45− $CD34^{intermediate}$, and CD45− $CD34^{neg}$ cells, are depicted; FIGS. 2R-T illustrate double staining with anti-CD117 (c-kit) and anti-CD271 (mesenchymal differentiation marker) revealing the level of each subpopulation; FIGS. 2U-Z illustrate the percentage of single positive $CD117^+$ cells within the CD45−$CD34^{neg}$ population in different human embryonic lung tissues.

FIGS. 3A-C depict triple staining with CK5, ULEX lectin, and CD117 prior to transplantation of lung tissues harvested at 21 weeks. Central airway (FIG. 3A) and main bronchus (FIG. 3B) showing high expression of CK5 in large airways, surrounded by large blood vessels. Rare $CD117^+$ cells reside in perivascular spaces. In the region of smaller airways (FIG. 3C), lower expression of CK5 is observed, in close contact with smaller blood vessels, while numerous $CD117^+$ cells reside within these blood vessels (pink; double positive for the ULEX lectin and CD117).

FIGS. 4A-K depict triple staining with E-cadherin, CD34 and CD117 prior to transplantation of lung tissues harvested at 21 weeks. FIG. 4A illustrates single staining for CD34; FIG. 4B illustrates single staining for CD117; FIG. 4C illustrates a merge with E-cadherin staining. Panoramic images of two neighboring regions, which include large bronchus and developing alveolar structures are depicted. The majority of $CD34^+$ cells in the region of developing alveolar structures co-express CD117 (FIGS. 4D-G), while in the large airway region, rare single positive $CD117^+$ cells may be seen in close proximity to blood vessels (FIGS. 4H-K).

FIGS. 5A-D are photographs depicting a panoramic view of three neighboring fields in 20 week human lung illustrating presence of CK5 positive regions (red, FIG. 5A) with different intensity of expression, which are surrounded by blood vessels (blue, FIG. 5B) and alpha-SMA positive cells (green, FIG. 5C) both in large bronchus and in developing alveoli, (blue, FIG. 5B), suggestive of distinct niches (the overlay of all 3 compartments is shown in FIG. 5D). Bar=50 µm.

FIGS. 6A-L depict polychromatic FACS analysis of two different adult human lung samples. Polychromatic FACS analysis of adult human lung tissues was performed in parallel to human embryonic lung tissues. Single cell suspension was stained, after enzymatic dissociation with collagenase and dispase of the tissues, and stained by CD34 (specific for hematopoietic and endothelial progenitors), CD45 (hematopoietic cells), CD31 (marker for endothelial cells), CD117 (c-KIT, to identify early progenitors), CD271 (NGFR– mesenchymal stem cell marker), and CD326 (EP-CAM– epithelial differentiation marker) specific antibodies or equivalent isotype controls. In both samples, $CD34^+$ and $CD34^-$ populations were identified (FIGS. 6A, 6D, 6G and 6J). Prominent differences were observed between adult and embryonic lung tissues. Much lower levels of $CD34^+$ cells were identified in adult lungs. When tested for the presence of the c-kit$^+$ population, very small $CD34^+CD117^+$ and $CD34^-CD117^+$ populations were identified (FIGS. 6B, 6E, 6H and 6K); the majority of CD34+CD117$^+$ cells were positive for the CD31 marker and only small percentage negative for CD31 marker (FIGS. 6C, 6F, 6I and 6L), and most of $CD34^-CD117^+$ population was found negative for CD31 and CD326 (FIGS. 6F and 6L).

FIGS. 7A-I depict FACS analysis of 20 week HEL, demonstrating $CD45^-CD34^+$ and $CD45^-CD34^-$ subpopulations (FIG. 7A). $CD117^+$ staining within the CD34 positive (FIG. 7B) and negative (FIG. 7C) cell subpopulations. The majority of $CD34^+CD117^+$ subpopulation is positive for CD31 or CD326 markers (FIGS. 7D, 7F-G). The majority of $CD34^-CD117^+$ cells are negative for CD31 and CD326 markers (FIGS. 7E, 7H-I). In FIGS. 7F-I, representative histograms are demonstrated, where red line marks isotype control of CD31 and CD326 markers, blue line shows the $CD34^+CD31^+$ subpopulation and green line shows the $CD34^+CD326^+$ subpopulation (FIGS. 7F-G); in FIGS. 7H-I, blue line marks the CD34–CD31$^+$ subpopulation and green line marks the $CD34^-CD326^+$ subpopulation. These findings confirm the existence of two different $CD117^+$ populations, as demonstrated by immunohistochemistry.

FIGS. 8A-D depict immunohistological staining of 15 week (FIGS. 8A-B) and 17 week (FIGS. 8C-D) HEL for ulix-vascular marker (blue), CK5 (green) and CD117 (red), showing the dual CD117 expression pattern. Several single $CD117^+$ cells are found in close proximity to large airways and blood vessels, while most of them are co-localized within blood vessels around the developing alveolar structures.

FIGS. 9A-D depict analysis of 20 week human lung for the presence of early and late endothelial progenitors (EPC). This figure identifies presence of two minor distinct $CD34^+CD31^+$ subpopulations (FIG. 9B). The first one identified by positive staining for CD14 and CD45 (FIG. 9C), whereas the second subpopulation is $CD45^-CD105^+$ (FIG. 9D).

FIGS. 10A-E depict characterization of embryonic tissues before and after implantation under the renal capsule of syngeneic mice. FIGS. 10A-C are photographs illustrating a typical H&E staining demonstrating the poor growth of E14 (FIG. 10A) and E17 (FIG. 10B) lung tissues at 12 weeks post transplant under the renal capsule of SCID mice (n=7), compared to marked growth and differentiation attained following E16 mouse embryonic implants (n=5) (FIGS. 10C-E); FIGS. 10D-E are photographs illustrating H&E staining demonstrating large airways (large arrows) and alveolar structures (small arrows) and cytokeratin staining in implants of E16 mouse fetal lung.

FIG. 10F depicts a schematic representation of parallel stages in mouse and human lung development. The "optimal window" for transplantation is within the canalicular stage of development.

FIGS. 11A-Y depict characterization of lung progenitors in E16 mouse embryonic lung prior to transplantation. FIG. 11A is a photograph illustrating H&E staining of E16 embryonic lung demonstrating immature structures and absence of alveolar structures; FIG. 11B is a photograph illustrating CK-5 positive cells (blue) in E16 mouse tissue, similar to human embryonic lung, have higher expression in large airways. Numerous neuroepithelial bodies, stained positively by CGRP (red), and tyrosine hydroxylase (TH, green) are found within the entire sample, and are localized in niches; FIG. 11C is a photograph illustrating CCSP-positive cells are found in the regions of large airways, also rich in nestin-positive cells and surrounded by alpha-SMA positive cells (FIG. 11D, white arrows), suggestive of stem cell niches; FIGS. 11E-G are representative polychromatic FACS analysis of $CD45^-CD31^-CD326^+$ $CD24^+CD49f^+$ $CD104^+$ cells in E13, E14, E15 and E16 lung-derived single cell suspensions following treatment with collagenase and dispase (n=10, 10, 12 and 10 respectively, values represent mean±SD from two different experiments). A significantly higher abundance of this cell population in E15-16 lung is demonstrated (p<0.007); FIG. 11Y is a summary of $CD45^-CD31^-CD326^+CD24^+CD49f^+CD104^+$ cell levels showing statistical significance calculated by Student's t-test (one diamond represents p<0.037, two diamonds represent p<0.007, cell gating strategies are described in the Examples section hereinbelow).

FIGS. 12A-F are photographs depicting immunohistochemical staining of adult C57Bl lung, demonstrating presence of nestin and CGRP (FIGS. 12A-B), similar to their expression in stem cell niches in the embryonic mouse lung (FIG. 12A—lower magnification—bar=50 µm, FIG. 12B— higher magnification—bar=20 µm). Box in (FIG. 12A) indicates the position of the enlargement shown in (FIG. 12B); FIGS. 12C-F are photographs illustrating triple staining of adult C57Bl lung for alpha-SMA (green, FIG. 12C), CGRP (red, FIG. 12D) and E-cadherin (blue overlay with alpha-SMA and CGRP, FIG. 12E), bar=50 µm; and FIG. 12F illustrates an enlarged area of the square marked in FIG. 12E, bar=20 µm.

FIGS. 13A-D depict fluorescent microscopy of chimeric lungs under low power magnification demonstrating different numbers of foci of engrafted GFP$^+$ cells following different conditioning regimens. FIGS. 13A-C are photographs of representative images of chimeric lungs of animals treated with 6 Gy TBI (FIG. 13A), NA only (FIG. 13B), and NA plus 6 GY TBI (FIG. 13C); FIG. 13D is quantitative morphometric analysis of GFP$^+$ patches of engrafted cells per mm$^3$, following different conditioning regimens (n=10 in each group). The results of 3 independent experiments are presented.

FIGS. 14A-L are photographs depicting staining of CCSP$^+$ cells before and after infusion of E16 cells. FIG. 14A illustrates lumens of large airways of untreated control mice; FIG. 14B illustrates lungs of experimental animals 1 day after conditioning with naphthalene and 6 Gy TBI, showing peeling of CCSP+ cells; FIG. 14C illustrates lungs of animals conditioned with naphthalene and 6 Gy TBI 30 days after infusion of E16 cells, showing marked regeneration of the epithelial layer with engrafted GFP+ cells (green) in the bronchial lumens, which are vascularized, as indicated by staining for V-E cadherin; FIGS. 14D-L illustrate that transplanted cells (FIGS. 14D-F) incorporate into the epithelial layer, regenerate CCSP+ cells (red), are able to produce surfactant (FIGS. 14G-I), and exhibit ion transport potential, as indicated by staining for CFTR (FIGS. 14J-L).

Figures 15A, 15B, 15C:
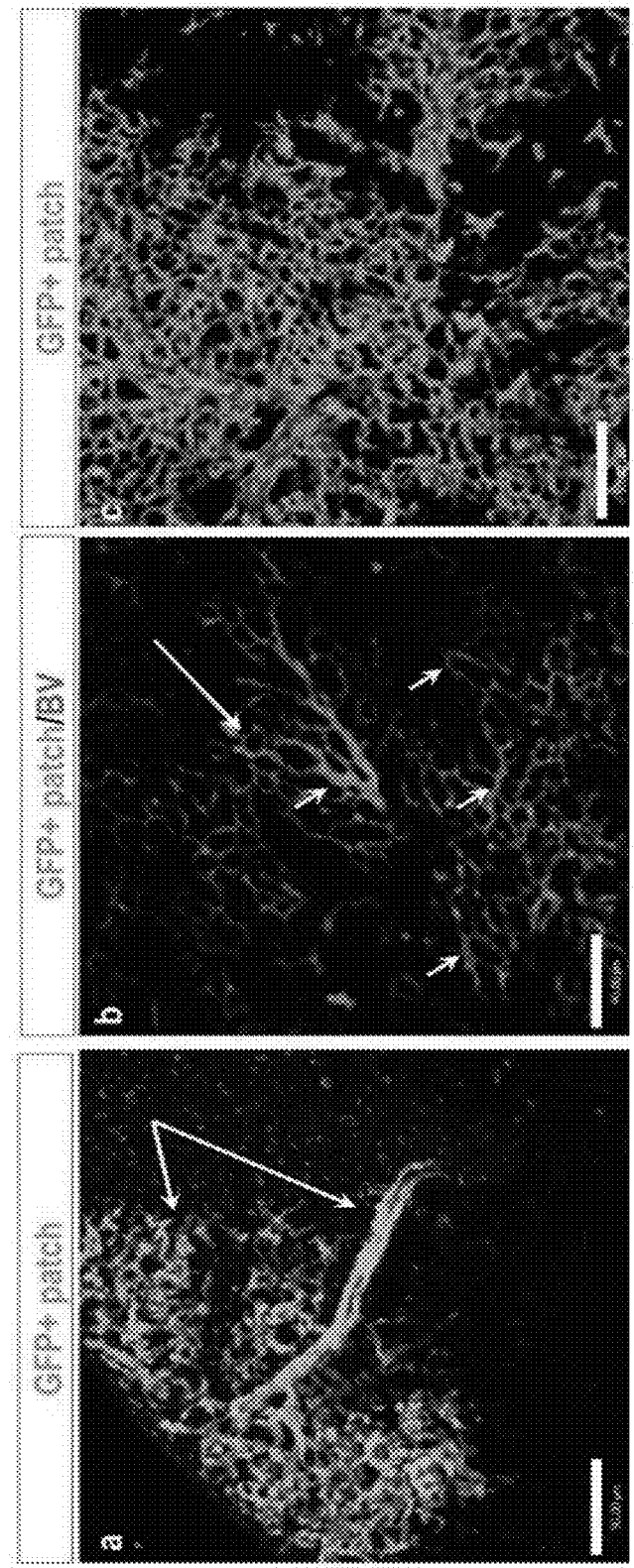

FIGS. 15A-C are photographs depicting two-photon microscopy revealing chimerism level in implanted lungs. Representative two-photon microscopy lung images of transplanted mice at 6 (FIGS. 15A-B) and 16 (FIG. 15C) weeks after transplantation, without (FIG. 15A), and with co-staining of blood vessels with non-targeted Quantum dots (red) (FIG. 15B).

FIGS. 16A-L are photographs depicting immunohistological characterization of chimeric lungs at 16 weeks after transplantation. FIGS. 16A-D are representative images of chimeric lung stained with anti-GFP antibody (green), anti-CD31 antibody (red), and anti-pancytokeratin antibody (blue), demonstrating incorporation of GFP+ cells in vascular and epithelial compartments of transplanted lungs, without signs of scarring or fibrosis; FIGS. 16E-H are representative images of chimeric lungs stained with anti-GFP (green) and anti AQP-5 antibody (red), showing incorporation of transplanted tissue into the gas-exchange surface of type I alveocytes; FIGS. 16I-L are images of chimeric lung stained with anti-GFP (green), anti-CD31 (red) and anti-sp-C antibody (blue), demonstrating type II alveocyte participation of transplanted cells in surfactant synthesis.

Figure 17A:
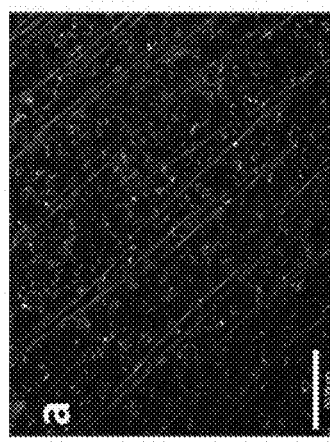
Figures 17B, 17C, 17D, 17E:
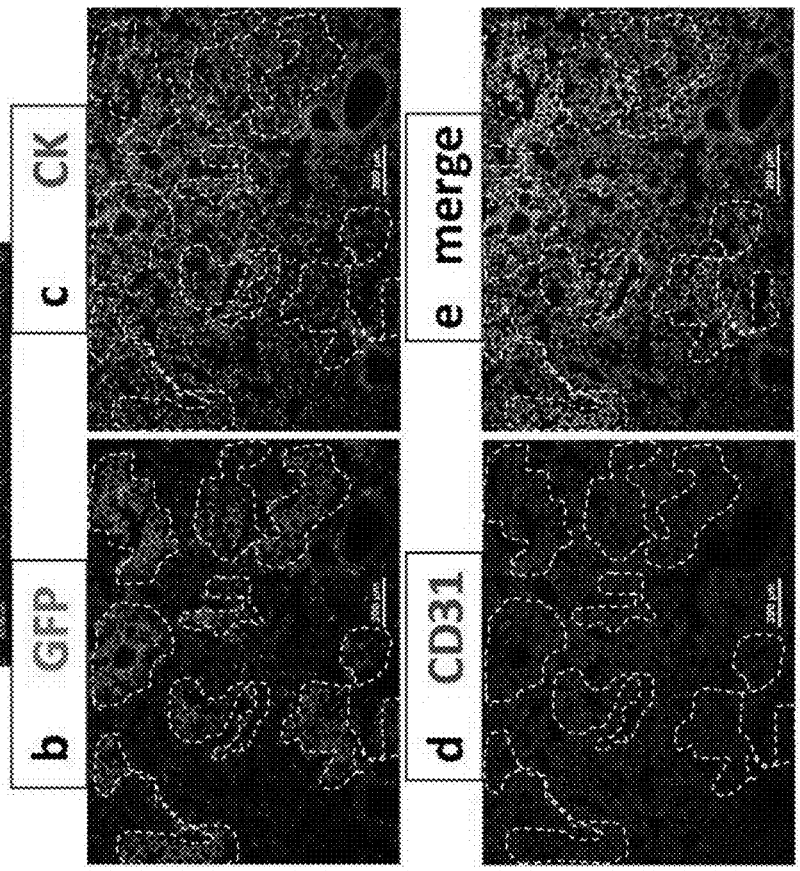

FIGS. 17A-E are photographs depicting appearance of control non-transplanted C57B1 lung analyzed by two-photon microscopy, bar=90 μm (control lung, FIG. 17A) or triple staining of chimeric lung with anti-GFP (green), anti-cytokeratin (blue), and anti-CD31 antibodies, demonstrating chimerism in both epithelial and vascular compartments of the lung, and full incorporation in the structures, without signs of scarring or fibrosis, under low magnification, bar=200 μm (FIGS. 17B-E). In green fluorescent channel GFP+ chimeric foci are indicated by dotted line (FIG. 17B). In red and blue channels the same chimeric regions are also indicated by dotted line, demonstrating smooth transition from recipient to donor tissue in both vascular (FIG. 17C) and epithelial (FIG. 17D) compartments, and overlay of all the layers is shown in (FIG. 17E).

FIGS. 18A-I are photographs depicting engraftment and incorporation of human derived lung cells into the mouse lung at different time points post transplantation. FIGS. 18A-C illustrate chimerism in the mouse lung at 6 weeks post transplantation, showing staining for mouse MHC (red) and human tissue positive for MNF-116 (green) under low magnification; FIGS. 18D-F illustrate chimerism in the mouse lung at 6 weeks post transplantation, showing staining for mouse MHC (red) and human tissue positive for MNF-116 (green), under high magnification; FIGS. 18G-I illustrate an additional field, stained as in. (FIGS. 18D-F).

FIGS. 19A-F are photographs depicting typical chimerism in the lung bronchus of transplanted mouse at 7 weeks post transplant. FIGS. 19A and 19D illustrate human cells originating from human embryonic cells which were selectively stained with a cocktail of mouse anti-human antibodies including anti-MNF (epithelial marker), anti-human Vimentin 9 (typical of stromal cells), and mouse anti-human CD31 (endothelial cell marker) labeled with Daylight 488 (green); FIGS. 19B and 19E illustrate cells of mouse origin in the mouse lung which were stained with Banderia lectin labeled with Alexa-fluor 546 (red). The latter is known to bind to a-Gal expressed on mouse epithelial and endothelial cells. Upper panel shows chimeric field under low magnification (FIG. 19C), the lower panel shows the same region under high magnification (FIG. 19F).

FIGS. 20A-F are photographs depicting typical chimerism in the lung alveoli of a transplanted mouse at 7 weeks post transplant. FIGS. 20A and 20D illustrate human cells originating from human embryonic cells which were selectively stained with a cocktail of mouse anti-human antibodies including anti-MNF (epithelial marker), anti-human Vimentin 9 (typical of stromal cells), and mouse anti-human CD31 (endothelial cell marker) labeled with Day light 488 (green); FIGS. 20B and 20E illustrate cells of mouse origin in the mouse lung which were stained with Banderia lectin labeled with Alexa-fluor 546 (red). The latter is known to bind to a-Gal expressed on mouse epithelial and endothelial cells, but not on their human counterparts. Upper panel shows chimeric field under low magnification (FIG. 20C); the lower panel shows the same region under high magnification (FIG. 20F).

FIGS. 21A-C are photographs depicting incorporation of human cells into the lung parenchyma. FIG. 21A illustrates human cells which were stained (green) with a mixture of anti-human antibodies including anti-MNF117, anti-V9, anti-CD31 as described above, and with rabbit anti-cytokeratin antibody (red), which stains both mouse and human cytokeratin (FIG. 21B). Merging of both colors demonstrates human cells within the lung parenchyma (FIG. 21C).

FIGS. 22A-C are photographs depicting incorporation of human cells into the lung gas-exchange surface. Human cells were stained (green) with a mixture of anti-human antibodies including anti-MNF117, anti-V9, and anti-CD31, as described above (FIG. 22A) and with goat anti-AQP-5 (red), which stains both mouse and human AQP-5 (FIG. 22B). Merging of both colors demonstrates human cells within the lung gas-exchange surface (FIG. 22C).

FIGS. 23A-F are photographs depicting that engrafted human lung cells within the alveoli of a chimeric mouse participate in production of surfactant. Human cells were stained (green) with a mixture of anti-human antibodies including anti-MNF117, anti-V9, and anti-CD31 as described above (FIGS. 23A and 23D), and with rabbit anti-SPC antibody (red), which stains both mouse and human surfactant protein C (FIG. 23B). Merging of both colors demonstrates participation of the transplanted human tissue in production of surfactant (FIG. 23C). The lower panel (FIGS. 23D-F) shows staining at high magnification of the square area denoted in (FIG. 23C).

FIGS. 24A-H are photographs depicting engraftment of 20 week human lung derived single cell suspension stained with CMTMR in the lung of a NOD-SCID mouse, bar=500 μm (FIG. 24A); GFP+ patches denoting lung cells originating from transplanted mouse embryonic lung cells in the syngeneic transplantation model, bar=1 mm (FIG. 24B); FIGS. 24C-E illustrate control staining with mouse anti-human cytokeratin MNF 116 antibody (green, FIG. 24C) and rat anti-mouse MHC (red, FIG. 24D) of human embryonic lung tissue, which is positive to MNF116 and negative to mouse MHC (overlay of two is shown in FIG. 24E); FIGS. 24F-H illustrate control staining of mouse lung cells with anti-human MNF116 anti-mouse MHC antibodies, demonstrating negative staining for MNF116 and positive staining for mouse MHC, bar=50 μm.

Figures 25A, 25B, 25C, 25D:
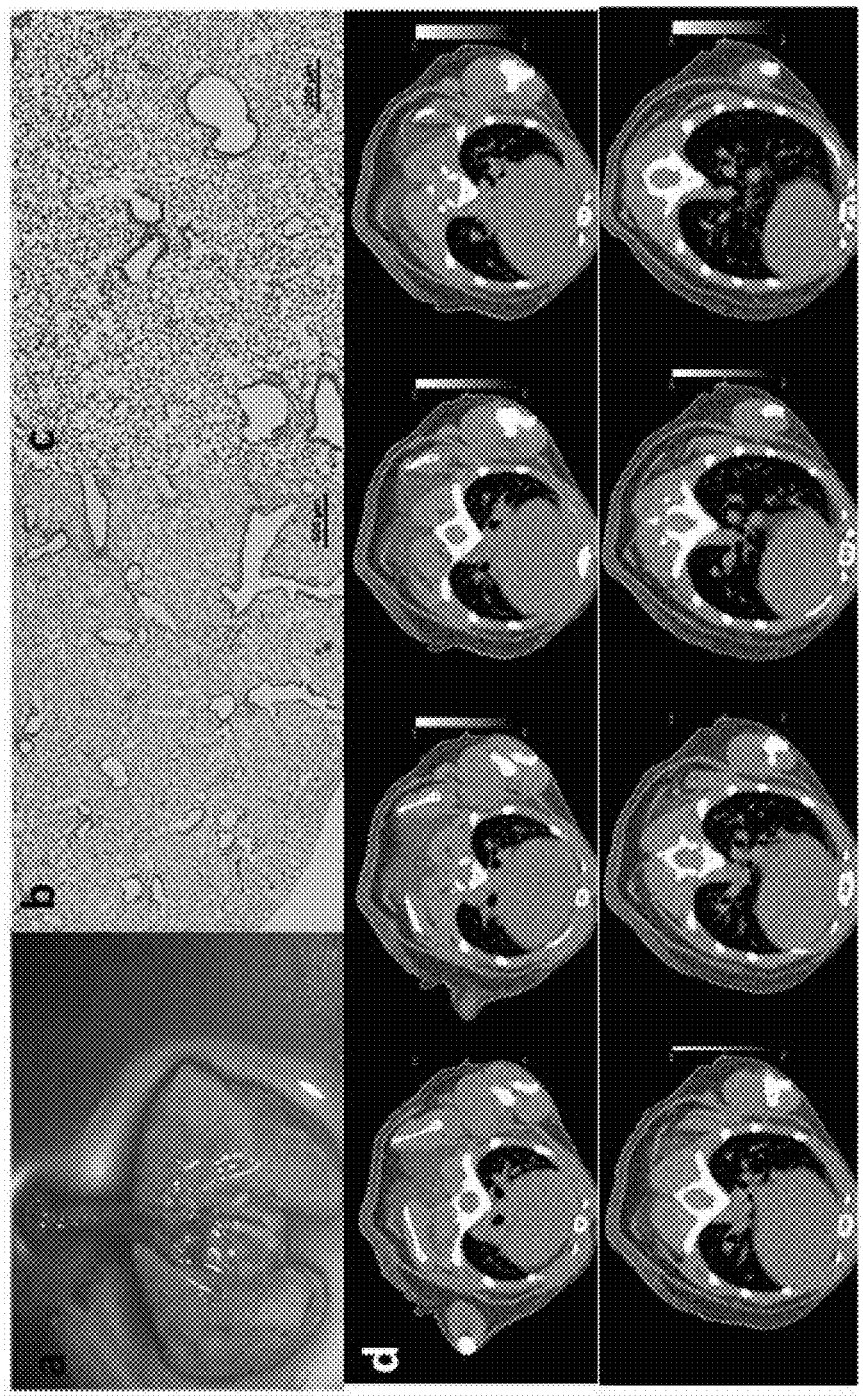

FIGS. 25A-D are photographs depicting long term follow-up of mice implanted with E16 mouse embryonic lung tissue showing no evidence of teratoma. FIG. 25A illustrates a macroscopic appearance of the transplanted lung one year after transplantation showing smooth borders and absence of tumors; FIGS. 25B-C illustrate H&E staining showing normal morphology of the transplanted lung under lower (FIG. 25B) and higher magnification (FIG. 25C) one year after transplantation; FIG. 25D illustrates coronal views of in-vivo lung CT images of a typical transplanted animal showing normal radiologic appearance of the experimental lung.

FIGS. 26A-J depict a histological comparison between embryonic lung implant and adult human lung, and comparison of conditioning protocols. (FIG. 26A) Hematoxylin and eosin (H&E) staining of human embryonic lung (HEL) tissue harvested at 20 weeks of gestation (20 weeks HEL). Scale bars, 200 µm (top) and 50 µm (bottom). (FIG. 26B) Top, H&E staining of 20 weeks HEL implant under the renal capsule of NOD-SCID mouse 8 weeks after transplantation. n=25 implants obtained at 20-22 weeks (from five donor fetuses). Bottom, H&E staining of human adult lung. Representative images under different magnifications; scale bars, 200 µm (left), 50 µm (middle) and 20 µm (right). (FIGS. 26C-D) Typical niches of $CK5^+$ lung progenitors. (FIG. 26C) Staining of 20 week HEL slice (20 µm) for CK5 (red), nestin (green) and blood vessels (BV, blue). Acquired images reconstructed in three dimensions. (FIG. 26D) Confocal image of 20 week HEL tissue for CK5 (red), BV (blue) and neurofilaments (NF, green), revealing rich innervation (arrows). Scale bars, 90 µm. (FIGS. 26E-J) BrdU incorporation in lungs of C57BL/6 mice (n=5 mice per group) 7 days after conditioning with NA alone; 6 Gy TBI followed by NA (6 Gy+NA); NA followed by 6 Gy TBI (NA+6 Gy); 6 Gy TBI alone or no conditioning (control). (FIG. 26E) Immunohistochemical staining of lungs with anti-BrdU antibody (green). Scale bar, 100 µm. (FIG. 26F) Double staining with anti-CCSP antibody (Club cells, red) and anti-BrdU antibody (green; arrows) assessed by confocal spinning-disc microscopy. Scale bars, 34 µm. (FIG. 26G) Double staining with anti-SPC antibody (AT2 cells, red) and anti-BrdU antibody (green). Scale bars, 50 µm. (FIG. 26H) Quantitative morphometric analysis of $CCSP^+BrdU^+$ and $SPC^+BrdU^+$ cells following different conditioning protocols. Center line, median; box limits, $25^{th}$ and $75^{th}$ percentiles; whiskers, minimal and maximal values. Top, absolute numbers of $CCSP^+BrdU^+$ cells per assessed field (n=78 fields for control, n=40 fields for NA, n=20 fields for 6 Gy+NA, n=54 fields for NA+6 Gy and n=96 fields for 6 Gy treated mice were calculated, for total n=3 mice per conditioning protocol); bottom, number of $SPC^+BrdU^+$ cells per individual field (n=23 fields for control, n=22 fields for NA, n=30 fields for 6 Gy+NA, n=23 fields for NA+6 Gy and n=34 fields for 6 Gy treated mice were calculated, for total n=3 mice per conditioning protocol); per mouse, n=3 mice per group). For morphometric analysis of $CCSP^+BrdU^+$ and $SPC^+BrdU^+$ cells, comparison was done using one-way nested ANOVA (the effect of individual mice was nested with the treatment effect). (FIG. 26I) FACS analysis of anti-BrdU staining of lung cells harvested from mice conditioned using the protocols described above. Representative dot plots (n=5 mice per conditioning protocol) to calculate the abundance of $CD45^-BrdU^+$ cells. (FIG. 26J) Quantitative FACS analysis of $BrdU^+$ cells in different lung cell lineages (box plots show percentage of individual cell populations out of total $CD45^-$ cells; n=5 mice per group). Center line, median; box limits, $25^{th}$ and $75^{th}$ percentiles; whiskers, minimal and maximal values. For FACS analysis, the differences between groups were calculated using one-way ANOVA on the arcsine-transformed proportions followed by Tukey's post hoc test; only comparisons between groups of interest (NA vs. NA+6 Gy; 6 Gy+NA vs. NA+6 Gy) are given. $*P<0.05$; $P<0.01$; $*P<0.001$; $****P<0.0001$. Results shown are from 1 experiment representative of 3.

Figures 27J, 27K, 27L:
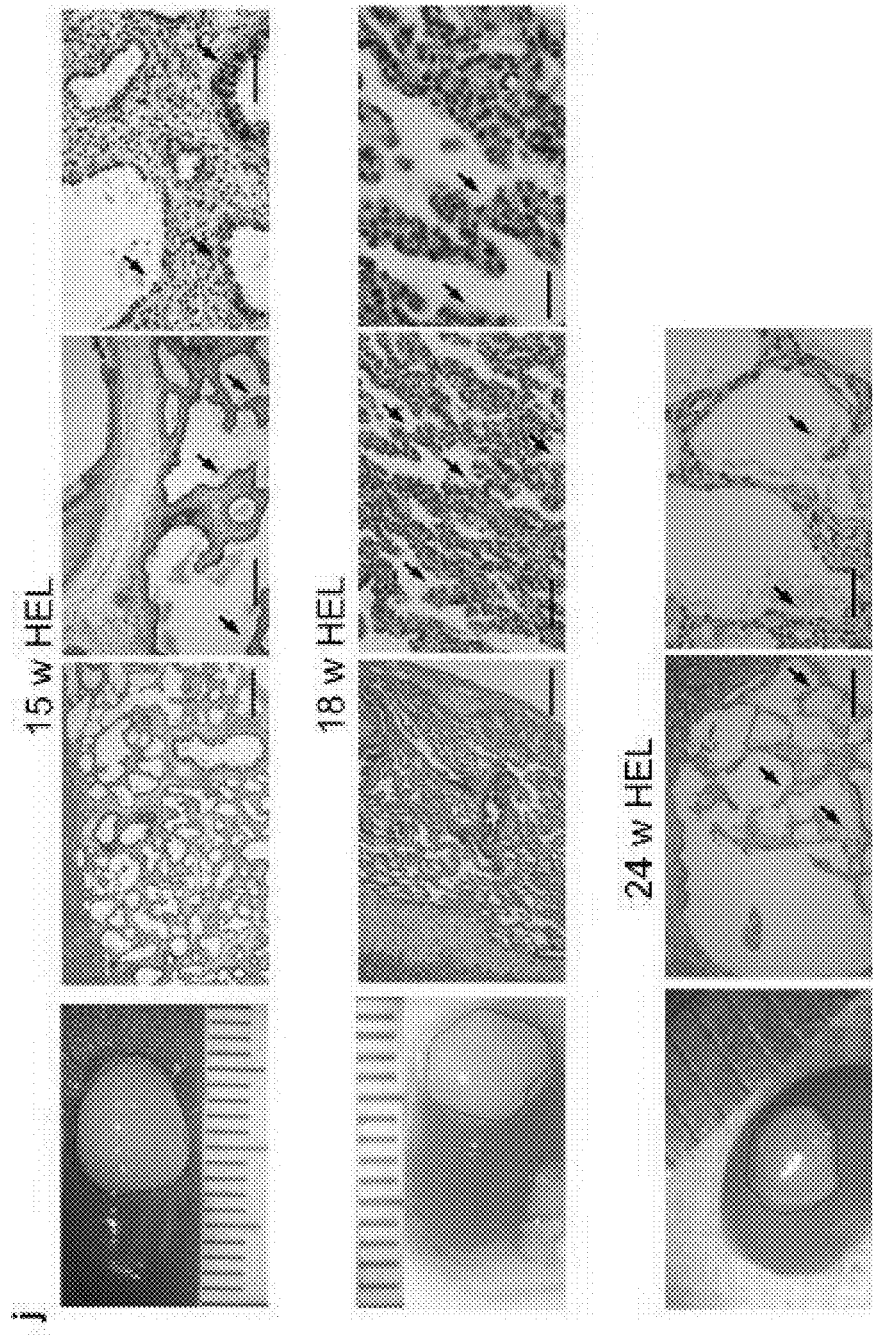

FIGS. 27A-L are photographs depicting human embryonic lung (HEL) tissues harvested at 20 weeks of gestation, before and 8 weeks after transplantation under the kidney capsule of NOD-SCID mice. Human embryonic airway tissues were implanted under the kidney capsule of NOD-SCID mice. The implants were evaluated macroscopically and by immunohistological staining 8 weeks posttransplantation. (FIG. 27A) Appearance of fresh 20 week fetal airway, comprising trachea and lungs. (FIGS. 27B-C) H&E staining of trachea and lungs before transplantation, under lower and higher magnification (left image in (FIG. 27B), scale bar, 50 µm; right image in (FIG. 27B), scale bar, 20 µm; left image in (FIG. 27C), scale bar, 200 µm, right image in (FIG. 27C), scale bar, 50 µm. (FIG. 27D) Typical macroscopic appearance of harvested 20 week lung tissue implant. (FIG. 27E) Microscopic H&E examination of an implant derived from 20 week fetal trachea, showing normal appearance of tracheal structure covered with ciliated epithelium and cartilage identical to pre-transplantation tissue under lower (in left image; scale bar, 50 µm) and higher magnification (in right image; scale bar, 20 µm); (FIG. 27F) The growing lung parenchyma in the same implant is shown under low and high magnification (Scale bar, 500 µm, left, and 200 µm, right). (FIGS. 27G-I) Immunostaining for epithelial differentiation markers 8 weeks post-transplantation. (FIG. 27G) Expression of cytokeratin (CK18) (green) and VE-cadherin (red) in alveoli-like structures; scale bar, 50 µm. (FIG. 27H) Immunostaining for CFTR (red, indicated with arrows) and CK18 (green); scale bar, 20 µm. (FIG. 27I) Immunostaining for surfactant protein C (SPC) (red and arrows) and CK18 (green), at lower (left image, scale bar, 50 µm) and higher (middle image, scale bar, 20 µm) magnification, and for aquaporin-5 (green, right image; scale bar, 20 µm). (FIGS. 27J-L) Growth and development of HEL tissues harvested at different gestational ages 8 weeks after implantation under the kidney capsule of NOD-SCID mice. Differences in macroscopic and microscopic (H&E staining) appearance of the implants derived from 15 week (FIG. 27J), 18 week (FIG. 27K) and 24 week (FIG. 27L) tissues. In FIG. 27J and FIG. 27L row images, arrows indicate cystic structures. In FIG. 27K, arrows indicate alveolar-like structures. In FIG. 27J and FIG. 27K from left to right scale bars, 200, 50 and 20 µm. In the FIG. 27L, scale bar, 50 and 20 µm [left to right]. At least n=7 samples of 15 week implants (from 3 different fetuses), n=8 of 18 week implants (from 3 different fetuses), and n=5 (from 2 different fetuses) of 24 week implants were analyzed. Representative images are shown.

FIGS. 28A-J depict identification and phenotyping of early progenitors and their niches in the human embryonic lung. (FIG. 28A) H&E staining of human embryonic lung tissues at different gestational time points (n=3, 15 week lungs; n=3, 17 week lungs; n=3, 20 week lungs; and n=5, 22 week lungs analyzed), revealing bronchial and bronchiolar structures without any alveolar structures. Scale bar, 200 µm. (FIG. 28B) Staining of 20 week HEL for mucin-1 (red), podoplanin (green), and Nkx2.1 (blue) which mark bipotent alveolar progenitors (marked with x in merged image). Scale bar, 34 µm. (FIGS. 28C-D) Immunohistological staining of 20 week fetal lungs, showing high expression of $CK5^+$ cells in large airways. In (FIG. 28C), arrows and arrowheads indicate regions with high and low CK5 expression, respectively. (FIG. 28D) Co-expression of CK5 and CK14 in the large bronchus. Scale bar, 50 µm. (FIG. 28E) Vimentin$^+$ mesenchymal cells residing in close proximity to the $CK5^+$ progenitors. (FIG. 28F) Alpha-smooth muscle actin positive cells, surrounding epithelial cells stained with anti-E-cadherin antibody (red). Scale bar, 50 µm. (FIG. 28G) CK5+ cells in bronchial and developing alveolar structures are associated with rich innervation, illustrated by staining for neurofilaments (NF), scale bar, 200 µm, and close proximity to nestin+ and CGRP+ cells (FIG. 28H). Scale bar, 50 µm. (FIG. 28I) Staining for CK5 (red) at different time points including 15 (n=3), 17 (n=3), 20 (n=4), and 22 (n=5) weeks of human gestation, demonstrating differences in CK5 expression level. Scale bar, 200 µm. (FIG. 28J) Quantitative morphometric analysis of tissue area occupied by CK5+ progenitors showing significantly higher levels at 20-22 week tissues. ((t-test) non-significant (NS), **P=0.002).

FIGS. 29A-H are graphs depicting FACS analysis of early non-hematopoietic progenitors in human and mouse embryonic lung tissue harvested at different gestational time points. Left panel (FIGS. 29A-B): Representative FACS analysis of 20 week lung cells showing double staining with anti-CD45 and anti-CD34. Three subpopulations within the non-hematopoietic CD45− cells, including $CD45^-CD34^{high}$, $CD45^- CD34^{+intermediate}$, and $CD45^-CD34^{neg}$ cells, are depicted. Double staining with anti-CD117 (c-Kit) and anti-CD271 (mesenchymal differentiation marker, also shown to be expressed in basal cells of human airway epithelium) was used to further define the level of each subpopulation within the different $CD34^{neg}$, $CD34^{interm.}$ and $CD34^{high}$ subpopulations. (FIG. 29C) Percentage of single positive CD117+ cells within the CD45− CD34neg population in different human embryonic lung tissues. Analysis of all tissues was performed within the same experiment. (FIGS. 29D-E) Analysis of 20 week HEL for the presence of early and late Endothelial Progenitor Cells (EPC). (FIG. 29D) FACS analysis illustrating the presence of two distinct minor subpopulations within the CD34+CD31+ cell population, previously demonstrated to represent two types of EPCs. The first one is identified by positive staining for CD14 and CD45 and represents early EPCs, whereas the second subpopulation is CD45−CD14− CD31+CD144+CD146+ and represents late EPCs (n=5 different 20 week lung tissue samples were tested). (FIG. 29E) Staining of the same tissue with an appropriate isotype control (IC). (FIGS. 29F-H) Progenitor cell populations in mouse embryonic lung (MEL) tissues harvested at different gestational time points. (FIG. 29F) Representative FACS analysis of CD45−CD31−CD326+CD24+ cells in E13, E14, E15 and E16 lung-derived single cell suspensions. This cell population was present at significantly higher abundance in E15-E16 lung. (FIG. 29G) Gating strategies based on staining with antibody (blue histogram) and appropriate isotype control (red histogram); the example of E16 cell staining is shown. (FIG. 29H) Box plots demonstrating percent of CD45−CD31−CD326+CD24+ cell levels showing significant differences between embryos of various gestational ages (results of at least n=6 fetal lungs in each group are shown, ***P<0.001, one way ANOVA). Center lines in the boxes show the medians; box limits indicate the 25th and 75th percentiles, whiskers indicate the minimal and maximal values.

FIGS. 30A-H depict engraftment of mouse GFP+ embryonic precursor lung cells following different conditioning protocols. (FIGS. 30A-C) Fluorescence microscopy of chimeric C57BL/6 adult lungs (green, GFP-expressing donor-derived cells). Representative images (n=10 for each group) of chimeric lungs following treatment with 6 Gy TBI alone (FIG. 30A), NA alone (FIG. 30B) or NA+6 Gy TBI (FIG. 30C). Scale bars, 1 mm. (FIG. 30D) Quantitative morphometric analysis of GFP+ patches of engrafted cells per mm³ lung tissue after different conditioning regimens (engraftment of donor cells in NA+6 Gy TBI-treated animals; ***P=0.00012, ANOVA on log-transformed values); average number of patches for each mouse, n=10 mice per group, pooled from three experiments employing identical transplant protocols. The effect of date was not significant and was therefore removed from the final analysis. Center line in box plot is median; box limits, 25th and 75th percentiles; whiskers, minimal and maximal values. (FIGS. 30E-F) Low-magnification images of double staining of chimeric lung with anti-GFP (FIG. 30E) and anti-cytokeratin (CK, left), anti-CD31 (middle) or anti-nestin antibodies (right) (FIG. 30F). Scale bars, 200 µm. GFP+ chimeric foci are indicated by dotted lines. Images shown are representative of three independent experiments and 10 mice. (FIG. 30G) Quantitative colocalization analysis within individual patches in chimeric lungs 2 months after transplantation. Scale bars, 50 µm. (n=8 GFP+ patches from 3 mice were analyzed for CK colocalization, n=8 GFP+ patches from 3 mice were analyzed for CD31 colocalization and n=7 GFP+ patches from 2 mice were analyzed for nestin colocalization) (FIG. 30H) Summary of % ROI with GFP colocalized. Box plots present percentage of GFP colocalized with different markers within indicated ROI. The entire data distribution is shown. Center line, median; box limits, 25th and 75th percentiles; whiskers, minimal and maximal values.

FIGS. 31A-J depict morphometric analysis of the lung area occupied by the engrafted patches and their clonal origin. (FIGS. 31A-B) Typical donor type GFP+ patches (green) used for morphometric analysis at 8 (FIG. 31A) and 16 (FIG. 31B) weeks after transplant. Chimeric lung under ×10 magnification (left), parallel reconstruction in Fiji software (middle) and higher magnification of the marked area (right). Scale bars, 200 µm. (FIG. 31C) Box plots showing percentage of lung tissue occupied by donor-derived GFP cells. Engrafted area measured in n=30 random lung fields of 3 mice at each time point (**P<0.01, nested ANOVA; n=3 mice for each group, 9-10 observations per mouse). Center line in box plot is median; box limits, 25th and 75th percentiles; whiskers, minimal and maximal values. (FIGS. 31D-E) Chimerism assessment at 6 weeks after transplant on whole mount, freshly isolated lung tissue; green indicates donor-derived GFP; blue indicates host autofluorescence. Representative two-photon microscopy extended focus images showing entire scan depth (top to bottom) of chimeric lung in the absence (FIG. 31D, z stack 88 µm) or presence (FIG. 31E) of blood vessel (BV) costaining with Quantum dots (red). Scale bars, 90 µm. Images are representative of n=7 images from 2 mice per group. (FIGS. 31F-G) Two-photon extended focus image at 16 weeks after transplant showing entire scan depth of chimeric lung (FIG. 31F, z stack 96 µm) compared to image of nontransplanted (control) C57BL/6 mouse lung (FIG. 31G). Images are representative n=7 of n=2 mice per group; scale bars, 90 µm). (FIGS. 31H-J) Discrete donor type patches following transplantation of a 1:1 mixture of E16 embryonic lung cells expressing GFP or tdTomato. Typical monochromatic green or red donor patches at 8 weeks after transplant visualized by spinning-disc microscopy (FIG. 31H; extended focus image; scale bar, 70 µm) and two-photon microscopy (FIG. 31I, extended focus image showing entire scan depth of chimeric lung; each z step=3 µm, merge of 60 planes; scale bar, 100 µm). (FIG. 31J) Histological staining of the recipient lung with anti-GFP and anti-DsRed assessed by confocal microscopy. Scale bar, 70 µm. Images representative of n=10 images from n=3 mice are shown.

FIGS. 32A-I are photographs depicting types of donor-derived clones in chimeric lungs and lung chimerism within different cell lineages. (FIGS. 32A-C) Images of two-photon microscopy, showing entire scan depth from top to bottom of chimeric lungs following implantation of E16 lung cells from GFP$^+$ donors at 6 weeks post transplant. Left image shows regenerated bronchioalveolar structure (z-stack 38 µm). Right image shows engrafted alveolar structures (z-stack 34 µm) at 6 weeks post-transplantation. Scale bar, 90 µm. (FIG. 32B) Representative images of blood vessels stained by i.v. injection of Quantum dots immediately before sacrifice, demonstrating generation of chimeric blood vessels. Left and right images: Scale bars, 90 µm and 30 µm, respectively. (FIG. 32C) Chimeric lung images of different animals at 4 or 6 months post-transplantation, respectively (z-stack in left image 96 µm, and in right image 86 µm. Scale bar, 90 µm. (FIG. 32D) Clonogenic potential of lung progenitors. Rag1$^{-/-}$ mice were conditioned with NA and subsequent exposure to 6 Gy TBI prior to i.v. infusion of embryonic cell suspension containing a 1:1 mixture of E16 cells from GFP (green) and tdTomato(Gt(ROSA)26Sortm4 (ACTB-tdTomato,-EGFP)Luo/J mice) (red) donors. E16 embryonic lung whole tissue images, taken by epifluorescence microscopy, immediately after harvesting are shown on left. Scale bar, 500 µm. Right frame shows Rag1$^{-/-}$ mouse chimeric lung evaluated by two-photon microscopy (z=3 µm, merge of 20 planes, scale bar, 100 µm) at 8 weeks after transplantation, illustrating extended focus image of donor-derived monochromatic clones revealing their incorporation within the recipient lung. (FIGS. 32E-H) Types of donor-derived clones in chimeric lungs. (FIG. 32E) Occasional bronchioles colonized by donor derived GFP$^+$ cells were identified. Two different examples acquired by confocal microscopy are shown under lower magnification. Scale bar, 34 µm at left; boxed areas are shown at higher magnification to the right of each image. Scale bar, 11 µm. (FIG. 32F) Staining of chimeric bronchiole with anti-GFP and anti-cytokeratin antibodies, demonstrating the epithelial nature of the engrafted cells. Scale bar, 50 µm. (FIG. 32G) Staining of the chimeric lung with anti-SOX-2 (red) and anti-GFP (green) antibody, demonstrating bronchioalveolar GFP$^+$ patch. Scale bar, 50 µm. (FIG. 32H) Chimeric lung stained with anti-GFP (green), and anti-SPC antibody (blue), demonstrating donor-derived surfactant-positive AT2 cells. Scale bar, 20 µm. Single channel close ups of boxed region demonstrate typical pattern of SPC staining. (FIG. 32I) GFP$^+$ donor derived bronchiolar CFTR positive cells. Close up of the boxed region illustrates double positive cells (marked by arrow heads). Scale bar, 50 µm.

Figure 33E:
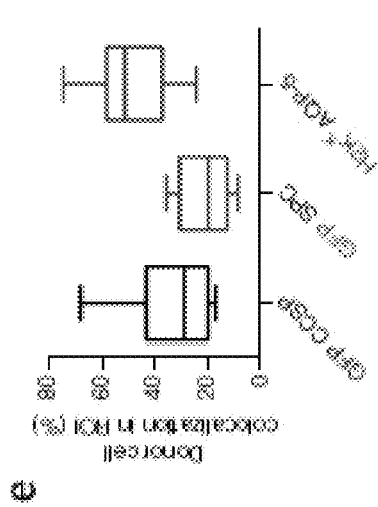
Figure 33F:
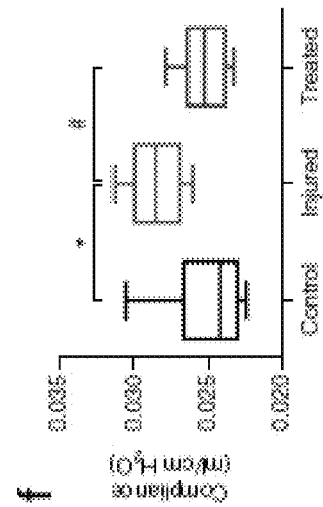
Figure 33G:
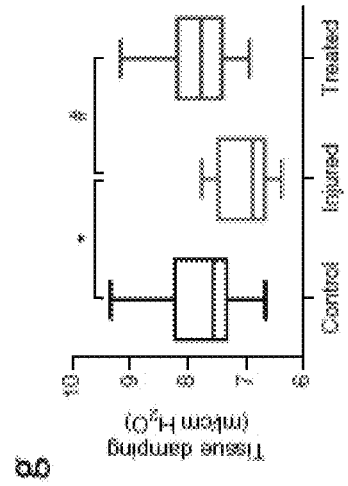

FIGS. 33A-G depict integration of donor-derived cells in epithelial lung compartment and functional repair of injured lungs. (FIG. 33A) Representative 3D view of GFP$^+$ bronchiolar, bronchioalveolar and alveolar clones. Dotted line marks bronchiolar lumen (BL). Scale bar, 17 µm. (FIGS. 33B-C) Colocalization of GFP$^+$ donor cells and CCSP (FIG. 33B) or SPC (FIG. 33C) evaluated by double antibody staining. Representative fluorescent images out of n=7 and n=8 images, respectively, are shown. Scale bars, 50 µm (FIG. 33B) and 11 µm (FIG. 33C). (FIG. 33D) Staining of chimeric lung from Rag1$^{-/-}$ mice transplanted with E16 lung cells from C3H donors for H2K$^k$ (red, donor) and AQP-5 (green). Scale bar, 17 µm. (FIG. 33E) Box plots showing percentage of donor cell colocalization within ROI for different markers. The colocalization analysis was done on n=7 images from 2 mice, for CCSP colocalization, n=8 images from 2 mice for SPC colocalization and n=7 images from 2 mice for AQP-5 colocalization. Center line, median; box limits, 25$^{th}$ and 75$^{th}$ percentiles; whiskers, minimal and maximal values. (FIGS. 33F-G) Analysis of lung function 6 weeks after transplantation. (FIG. 33F) Lung baseline compliance; *P=0.0004, control (uninjured) mice vs. mice with lung injury (and no transplant); # P=0.009, mice with lung injury and no transplant vs. mice receiving transplant after injury; one-way ANOVA. (FIG. 33G) Tissue damping. *P=0.015, control vs. mice with lung injury; # P=0.021, lung injury vs. mice transplanted after injury; one-way ANOVA. n=19 control mice, n=10 injured mice and n=8 transplanted mice in each group, pooled from two independent experiments (FIGS. 33F-G). Box plots show entire data distribution. Center line, median; box limits, 25$^{th}$ and 75$^{th}$ percentiles; whiskers, minimal and maximal values.

FIGS. 34A-I depict donor type chimerism and expression of the AT1 and AT2 markers in lungs of chimeric mice following transplantation of E16 lung cells from C3H donors into Rag1$^{-/-}$ recipients. (FIGS. 34A-C) Control staining of Rag1$^{-/-}$ and C3H lungs for H2K$^k$ (red) and AQP-5 (blue), used to define membrane colocalization of H2K$^k$ (red, donor) and AQP-5 in FIG. 33D Rag1$^{-/-}$ mouse lung alveolar structures are shown in (FIG. 34A), which completely lack staining for H2K$^k$, and positively stain for AQP-5. (FIG. 34B) C3H mouse lung exhibiting strong double positive staining for H2K$^k$ and AQP-5. Scale bar, 50 µm. (FIG. 34C) Distinct staining patterns of C3H lung for H2K$^k$ and AQP-5 or SPC for AT1 and AT2 markers, respectively. Scale bar, 17 µm. (FIG. 34D) Distinct donor derived H2K$^k$ patches are clearly negative for H2K$^b$. Scale bar, 200 µm. (FIG. 34E) Staining of chimeric Rag1$^{-/-}$ lung used to distinguish donor H2K$^k$ AQP-5$^+$ and donor H2K$^k$ SPC$^+$ cells (red, donor), demonstrating an almost identical pattern of staining of AT1 and AT2 cells in positive control C3H lung. Scale bar, 17 µm. (FIGS. 34F-G) Cell segmentation method used for analysis of chimeric AT1 cells (details are described in the 'General Materials and Experimental Methods' section). The same donor-derived patch, shown in FIG. 33D. Briefly, both donor type patches and non-chimeric regions were evaluated in order to compare red fluorescence in H2K$^k$ (red) negative and positive cells. The Hoechst image for each data set was segmented for nuclei. Each nucleus was used as a seed in the green channel to extend it to the entire cell. Cell centers were marked with a red cross. The region of interest was manually drawn (polygon) in each image in order to select tissue areas positive and negative for donor labeling. For each cell segment in the negative and positive areas, the total fluorescence intensity in green and red channels was calculated and displayed in a FACS-like scatterplot. (FIG. 34G) Left scatter plot shows only green fluorescent cells in the non-chimeric region, calculated from five images; the right scatter plot shows double positive red and green fluorescent cells in the chimeric region of seven images from the same animals. Thus, the "Red" total intensity (in arbitrary units [AU]) values were $4\pm1\times10^6$ for AT1 cells in the chimeric areas, and $2\pm1\times10^5$ for the non chimeric areas. The images are representative of n=2 mice, 12 weeks post transplantation. (FIG. 34H) Staining of chimeric patch for RAGE-AT1 marker, (green), H2K$^k$ donor cells (red), and nuclei (blue), assessed by spinning disc microscopy. Scale bar, 17 µm. (FIG. 34I) Chimerism analysis defining the level of single positive H2K$^k$ cells compared to double positive H2K$^k$H2K$^b$ cells within the CD45$^-$TER119$^-$ lung population, using FACS. Lung cells were harvested from Rag1$^{-/-}$ C57BL6 recipient mice transplanted with E16 lung cells from a C3H donor (n=3) at 9 weeks posttransplantation. Detailed percentages of all 3 mice are provided.

FIGS. 35A-F are photographs depicting chimerism analysis following transplantation of GFP$^+$ E16 lung cells into a 'Tomato' recipient. Tissue blocks were triple labeled for 'tdTomato' (red host), GFP (donor) and nuclei (blue). Three-dimensional confocal images were acquired by Nikon Eclipse Ti inverted spinning disc confocal microscope, using Andor iQ software (Mag=X 40 or X 60, NA=1.3 or 1.49 oil, pixel size=0.17 µm or 0.11 µm, respectively, delta-z=µm. Scale bar, 17 µm in presented images), and the 3D image stacks were analyzed as follows: the red images ('Tomato', in contrast to GFP, is restricted to membrane labeling) were thresholded (low value about half the Otsu threshold was taken to include all red image pixels) and the 3D binary image was thinned to outline the cell membranes. Superposition of nuclei and the thinned membranes clearly indicates that nuclei are enclosed by a "contour" of red membrane. This three dimensional analysis revealed co-localization of 7±1% (See 'General Materials and Experimental Methods' section for detailed description of calculations). However, even this low level of co-localization can largely be attributed to resolution limits of the microscope in z at the cell contact sites. Thus, when the green 3D stack of donor cells is superimposed on the red (host)/blue (nuclei) image, some red cell outlines can be seen appearing to cross the green cell volume, while red outlines surrounding a green area can hardly be detected. Rather, they cross the green area as part of the outline of a "red" cell that lies immediately above or below the green cell, recognizable by its higher or lower nucleus. Multiple z stacks are shown.

Figure 36H:
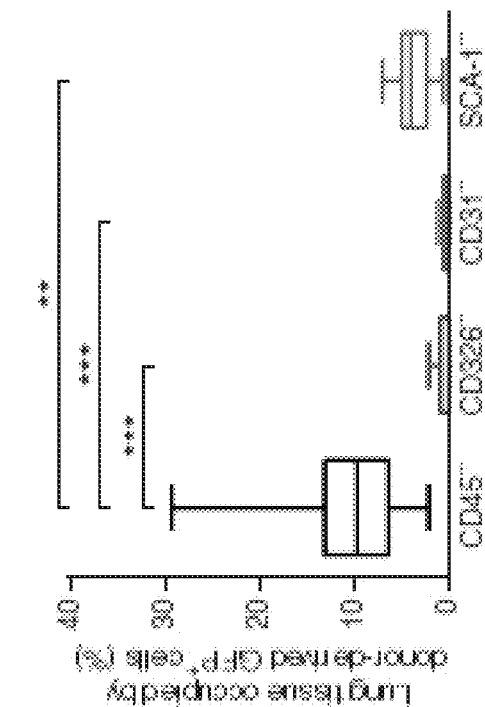
Figure 36G:
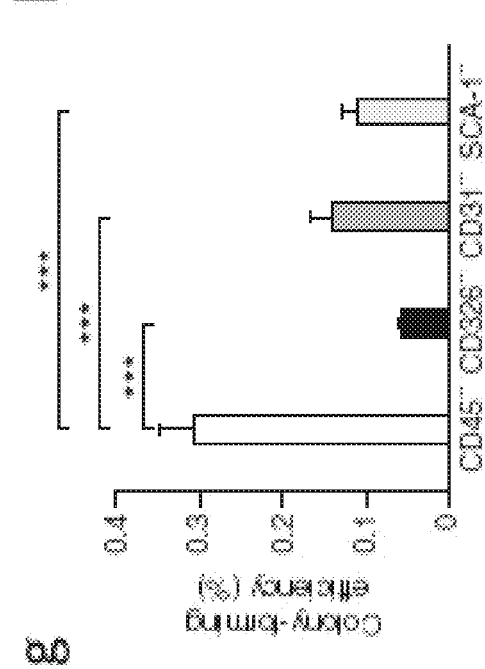

FIGS. 36A-H depict colony-forming efficiency and donor type lung chimerism after fractionation of E16 mouse lung cells. (FIG. 36A) FACS analysis of E16 lung cells from $GFP^+$ C57BL/6 donors after (top) and before magnetic-bead depletion (bottom) of $CD45^+$, $SCA-1^+$, $CD31^+$ or $CD326^+$ cells. Percentages of indicated cell populations are shown within E16 mouse fetal lung single cell suspension after and before depletion. (FIG. 36B) Typical brightfield appearance of 3D colonies generated by seeding cells depleted of different fractions. Scale bars, 200 µm. (FIGS. 36C-F) $GFP^+$ patches formed by depleted cell populations 8 weeks after infusion into C57BL/6 recipients conditioned with NA and 6 Gy TBI. Shown are representative of n=41 images for $CD45^-$ transplanted population, n=18 images for $CD326^-$ transplanted population, n=30 for $CD31^-$ transplanted population and n=19 for SCA-1-transplanted population original images of $GFP^+$ patches (left) and parallel images, reconstructed in Fiji, of donor (red) and recipient (green) tissues (right). Scale bars, 200 µm. (FIG. 36G) Colony-forming efficiency of depleted cell populations assessed in 3D culture. Average colony generation efficiency per $10^5$ cells (errors bars represent mean and s.d. of three wells). Colony-forming efficiency was compared by one-way ANOVA followed by Dunnett's test with the activity of $CD45^-$ cells as the reference. (FIG. 36H) Box plots showing percentage of lung tissue occupied by donor-derived GFP cells. Center line, median; box limits, $25^{th}$ and $75^{th}$ percentiles; whiskers, minimal and maximal values. A total of 41, 18, 30 and 19 fields were scored in 3-4 mice (pooled from two identical transplant procedures done on different dates (the effect of date was not significant and was therefore removed from analysis) for $CD45^-$, $CD326^-$, $CD31^-$ and $Sca-1^-$ depleted fractions, respectively. $P<0.01$, *$P<0.001$, one-way nested ANOVA followed by Tukey's post hoc test (FIGS. 36G-H).

Figures 38A, 38B:
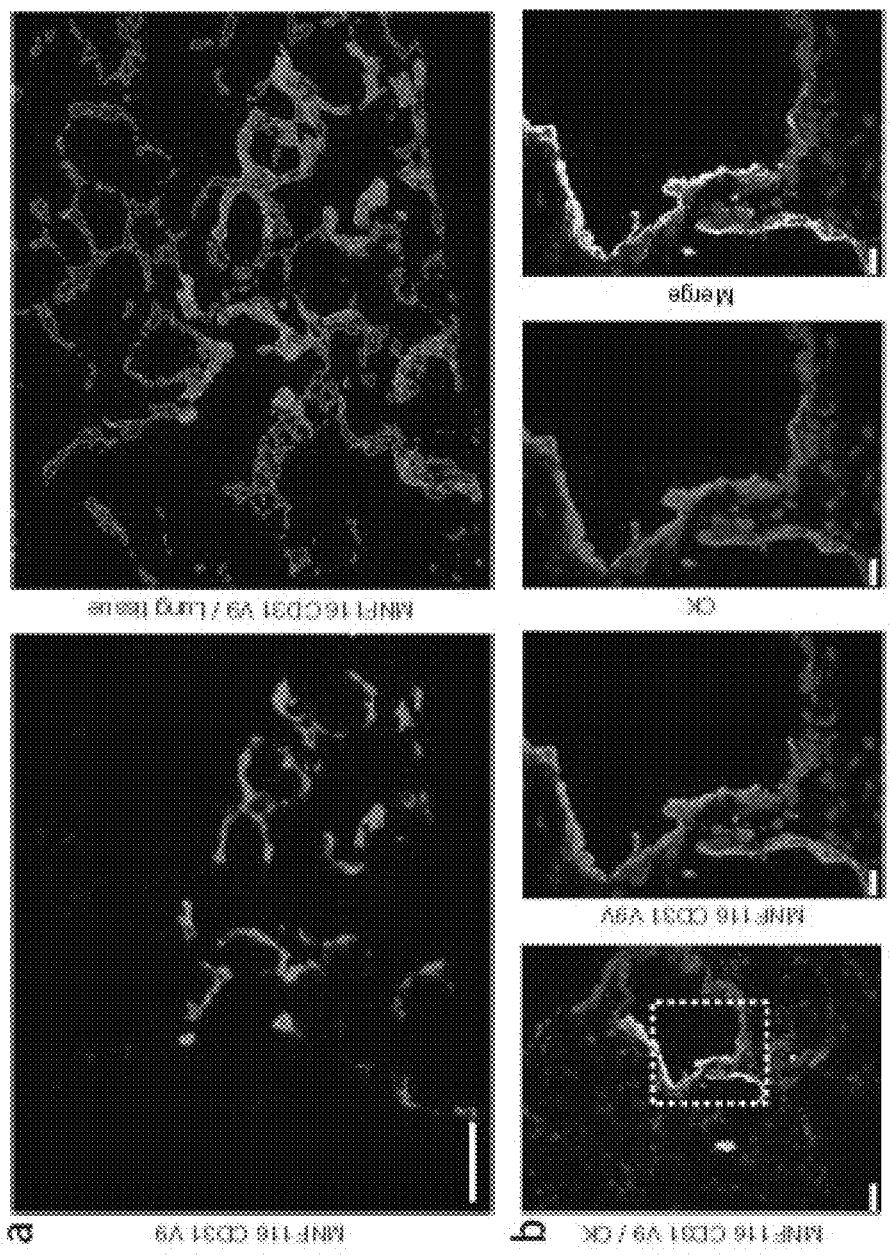
Figure 39D:
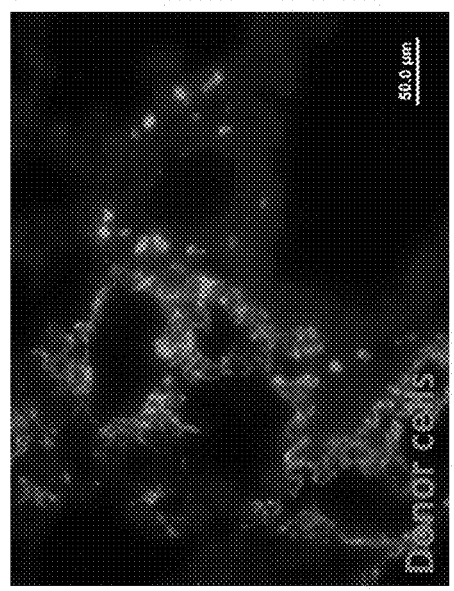
Figure 39E:
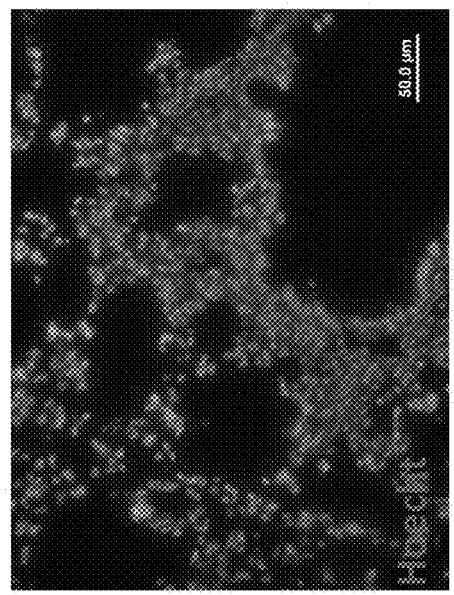
Figure 39F:
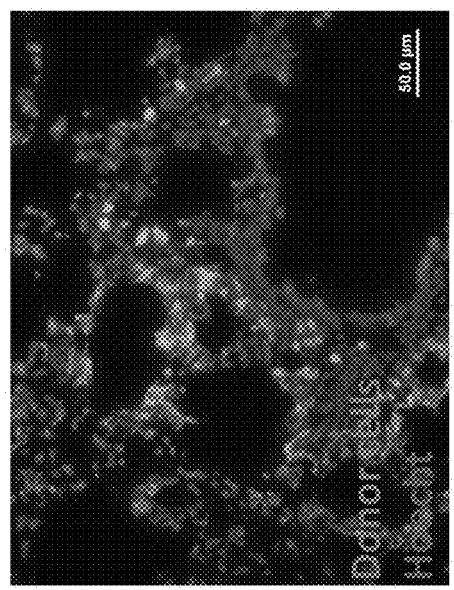

FIGS. 37A-J depict HEL derived cell engraftment in NOD-SCID mice and impact of freezing and thawing on their viability and clonogenicity. (FIG. 37A) Control staining with mouse anti-human cytokeratin MNF116 antibody (green—upper left image), and mouse anti-mouse MHC (red—central upper image), of human embryonic lung tissue (n=5), which is positive only for MNF116, but negative for mouse MHC (overlay is shown in right image). (FIG. 37B) Control staining of adult mouse lung (n=5) with antihuman MNF116, demonstrating lack of staining for MNF116. Scale bar, 50 µm. (FIG. 37C) Staining of 20 week HEL tissue with mouse anti-human cytokeratin, MNF116, CD31 and V9 antibodies alone and as cocktail of all three antibodies (green). (FIG. 37D) Negative control showing lack of staining of NOD-SCID mouse lung cells with the cocktail of anti-human MNF116, CD31 and V9 antibodies. (FIG. 37E) Staining of NOD-SCID chimeric lung with the same cocktail of antihuman antibodies (green), which selectively stain engrafted human cells in alveoli (asterisks), and pan-cytokeratin antibody (red), which positively stains both mouse and human tissues (HEL-derived patch shown in FIG. 38A. Scale bar, 50 µm. (FIGS. 37F-G) Chimerism in the lung bronchiole and alveoli of a NOD-SCID transplanted mouse at 7 weeks post transplant. Human cells originating from human embryonic lung cells were selectively stained with a cocktail of mouse anti-human antibodies including anti-MNF (epithelial marker), anti-human Vimentin 9 (typical of stromal cells), and mouse anti-human CD31 (endothelial cell marker) labeled with DyLight 488 (green). Cells of mouse origin in the mouse lung were stained with *Bandeiraea simplicifolia* isolectin B4, biotin related, labeled with Alexa-fluor 546 (red). The latter binds alfa-Gal expressed on mouse epithelial and endothelial cells. Upper row images show chimeric field under low magnification, scale bar, 50 µm; lower row images show the same region under high magnification, scale bar, 20 µm. (FIGS. 37H-J) Impact of freezing and thawing on viability and clonogenicity of a single cell suspension of canalicular HEL. (FIG. 37H) A single cell suspension of 20 week HEL was prepared as described in 'General Materials and Experimental Methods' section and phenotyped by FACS (FIG. 37H—upper panel) for viability (7AAD), and content of CD45– cells. Thereafter, the cells were frozen for 3 weeks, and then thawed and re-analyzed by FACS (FIG. 37H—lower panel); the thawed population showed similar levels of CD45– cells. (FIG. 37I) $10^5$ fresh or thawed cells were plated in GFR Matrigel on Transwell membranes and grown for 10 days. The resulting clones were stained for SPC (red, scale bar, 200 µm) and CK (green, scale bar, 500 µm) to assess epithelial differentiation properties. (FIG. 37J) Colony forming efficiency, defined as the number of colonies formed/number of cells plated per well as a percentage, was similar for thawed versus fresh cells (**P=0.01, t-test). Bars represent mean±SD of fresh and thawed HEL cells grown in triplicates.

FIGS. 38A-E are photographs depicting lung chimerism in NOD-SCID mice after transplantation of human embryonic lung (HEL) cells. Lungs of NOD-SCID mice conditioned with NA and 4 Gy TBI transplanted with $1 \times 10^6$ HEL cells. (FIG. 38A) Left, staining of human-derived cells in the mouse lung parenchyma with a mixture of anti-human antibodies including anti-MNF116, anti-CD31 and anti-V9. Selected field out of 7 random fields from a single mouse with high human lung cell occupancy. Right, image reconstructed in Fiji software to calculate percentage of lung occupancy. Average lung occupancy in this mouse was 4.4%±1.4%. Scale bars, 50 µm. (FIG. 38B) Confocal images of chimeric lungs in the bronchiolar region stained with anti-human antibodies as in FIG. 38A and anti-cytokeratin (anti-CK) antibody (red). Merged image (left) showing human epithelial cells within the lung bronchiole; scale bars, 34 µm. Inset, close-up of boxed region showing single staining and merged images; scale bars, 11 µm. (FIG. 38C) Epithelial cells in alveolar region, stained as in FIG. 38B.

Left, merged image showing human epithelial cells within the lung parenchyma. Scale bar, 17 μm. Inset, close-up of boxed region showing single staining and merged images; scale bars, 7 μm. (FIG. 38D) AT1 cells. Left, human cells stained with a mixture of anti-human antibodies (green) as in FIG. 38A and goat anti-AQP-5 (red); scale bar, 17 km; inset, close-up of boxed region showing single staining and merged images (scale bars, 7 km). (FIG. 38E) AT2 cells stained with a mixture of anti-human antibodies (green) described in FIG. 38A and rabbit anti-SPC (red), staining both mouse and human cells; scale bar, 17 km. Inset, close-ups of boxed region showing single staining and merged images; scale bars, 7 km.

FIGS. 39A-F are photographs depicting lung chimerism induction following transplantation of fresh adult lung cells. A single cell suspension comprising $8\times10^6$ adult lung cells was harvested from a GFP positive C57BL/6 mouse and injected i.v. into C57BL/6 recipient mice following conditioning with NA and 6 GY TBI. After 8 weeks, lung tissue from transplanted mice was fixed in 4% PFA and GFP positive patches were determined by immune-histology. Green—donor derived cells; Blue—hoechst staining for nuclei. FIGS. 39A-C and FIGS. 39D-F show different magnifications of the same field, respectively.

FIGS. 40A-F are photographs depicting lung chimerism induction following transplantation of E16 lung expanded cells: GFP positive C57BL E16 lung cells were harvested and seeded on tissue culture plates with condition medium (irradiated mouse embryonic feeders (iMEF)) together with epithelial growth factor and Rock inhibitor. Medium was changed every 2 days and Rock inhibitor was added freshly every time. After 4 days, cells were passed by splitting them into 3 plates. After 3 additional days of culture, the cells were used for transplantation. A single cell suspension comprising $2\times10^6$ expanded cells were injected i.v. into C57BL/6 recipient mice following conditioning with NA and 6 GY TBI. After 8 weeks, lung tissue from transplanted mice was fixed in 4% PFA and GFP positive patches were determined by immune-histology. Green—donor derived cells; Blue—hoechst staining for nuclei. FIGS. 40A-C and FIGS. 40D-F show different magnifications of the same field.

DESCRIPTION OF SPECIFIC EMBODIMENTS OF THE INVENTION

The present invention, in some embodiments thereof, relates to conditioning protocols and to the use of same for tissue regeneration.

The principles and operation of the present invention may be better understood with reference to the drawings and accompanying descriptions.

Before explaining at least one embodiment of the invention in detail, it is to be understood that the invention is not necessarily limited in its application to the details set forth in the following description or exemplified by the Examples. The invention is capable of other embodiments or of being practiced or carried out in various ways. Also, it is to be understood that the phraseology and terminology employed herein is for the purpose of description and should not be regarded as limiting.

Diseases associated with organ dysfunction, injury or failure, such as, pancreatic diseases, pulmonary diseases, liver diseases, heart diseases and kidney diseases, regardless of the cause of disease, are diseases of great medical and economic impact for which no satisfactory/optimal treatments are available. Currently, the only definitive treatment for end-stage disease is the replacement of the damaged organ.

While reducing the present invention to practice, the present inventors have identified a conditioning protocol for use in transplantation of progenitor cells in suspension for organ regeneration and repair of injured/diseases organs.

The present inventors have surprisingly uncovered that successful progenitor cell transplantation requires clearing of niches within the organ to be treated (e.g. lung). Such a step is critical to vacate tissue niches for occupancy of the transplanted cells, to attain chimerism and functional repair of injured organs or tissues. The conditioning protocol comprises two steps, in the first step an agent is used which induces tissue damage, the damage results in proliferation of stem cells within the tissue. Next, a second agent is used which ablates the resident stem cells and clears cell niches within the organ. Progenitor cells are then administered (e.g. from an allogeneic cell donor), by simple i.v. injection to the subject so as to produce a chimeric organ comprising both donor and recipient cells.

Thus, the present inventors have shown that conditioning a subject with naphthalene (NA) resulted in a marked signal of endogenous $BrdU^+$ proliferating cells (Example 3, in the Examples section which follows). This endogenous cell recovery, which could potentially compete with donor-derived progenitors and prevent their engraftment in the appropriate niches, was inhibited following exposure to 6 Grey (Gy) total body irradiation (TBI) 48 hours (hrs) after NA treatment. The present inventors have also shown that administration (e.g. intravenous administration) of single cell suspensions obtained from fetal human or mouse tissues at a canalicular 'window' of gestation (see Example 1), obtained from adult tissues (e.g. adult lung, see Example 8) or cells expanded ex vivo (e.g. ex vivo expanded fetal lung cells, see Example 9) can be used to achieve remarkable lung repair. These results were presented in both syngeneic and allogeneic transplantation models (Examples 3 and 5, respectively). Specifically, the lung precursor cells homed, differentiated and integrated in injured lungs of mice resulting in formation of an entire respiratory unit including formation of new epithelial cells and new vasculature (see Example 2). Furthermore, transplantation of single cell suspension following NA and TBI treatment resulted in functional improvement of injured lungs (Example 5). Taken together, these results substantiate the use of the conditioning protocol as well as single cell suspensions of mammalian precursor cells, e.g. fresh or frozen cells, fetal cells (e.g. harvested at the canalicular stage of gestation), adult tissue cells, expanded canalicular stage cells or expanded adult tissue cells, for regeneration of organs or tissues.

Thus, according to one aspect of the present invention, there is provided a method of conditioning a subject in need of transplantation of progenitor cells in suspension of a tissue of interest, the method comprising:

(a) administering to a subject a therapeutically effective amount of an agent capable of inducing damage to the tissue of interest, wherein the damage results in proliferation of resident stem cells in the tissue; and subsequently (b) subjecting the subject to an agent which ablates the resident stem cells in the tissue, thereby conditioning the subject.

As used herein, the term "conditioning" refers to the preparative treatment of a subject prior to transplantation. The conditioning is done to vacate cell niches for transplantation and to increase the rate of a successful transplantation (e.g. the formation of chimerism).

According to one embodiment, conditioning the subject is effected by first administering to a subject a therapeutically effective amount of an agent capable of inducing damage to the tissue of interest, wherein the damage results in proliferation of resident stem cells in the tissue.

The phrase "damage to the tissue" refers to a localized injury to a target organ or a part thereof.

The term "proliferation of resident stem cells" refers to the induction of cell division of endogenous stem cells residing within the specific tissue once subjected to the agent.

As used herein, the term "tissue of interest" refers to any bodily tissue or organ. The tissue may comprise a solid tissue/organ. According to one embodiment, the tissue has been damaged or is malfunctioning as a result of a disease, disorder or injury.

According to one embodiment, the tissue is a parenchymal tissue.

Exemplary tissues include, but are not limited to a cardiac tissue, a pulmonary tissue, a hepatic tissue, a pancreatic tissue, a brain tissue, a nephric tissue, a bone tissue, an ovarian tissue and a spleen tissue.

Various conditioning agents may be used in accordance with the present invention as long as the agent induces damage to at least a part of the tissue which results in proliferation of resident stem cells within the tissue. Thus, for example, the agent may comprise a chemical, an antibiotic, a therapeutic drug, a toxin, a surgical intervention (e.g. a surgical procedure removing at least a part of the tissue or organ) or an herb or an extract thereof.

The conditioning protocol may be adjusted for the specific tissue to be targeted taking into consideration the age and condition (e.g. disease, disease stage) of the subject, such a determination is well within the capacity of those of skill in the art, especially in view of the disclosure provided herein.

Without being bound to theory, a therapeutically effective amount is an amount of the agent sufficient for inducing localized tissue damage and proliferation of resident stem cells, but not being toxic to other organs of the subject being treated.

Determination of the therapeutically effective amount is well within the capability of those skilled in the art, especially in light of the detailed disclosure provided herein.

For any preparation used in the methods of the invention, the therapeutically effective amount or dose can be estimated initially from in vitro and cell culture assays. For example, a dose can be formulated in animal models to achieve a desired concentration or titer. Such information can be used to more accurately determine useful doses in humans.

Thus, according to one embodiment, the agent capable of inducing damage to the tissue is an agent causing renal cell toxicity (e.g. to nephrons), an agent causing hepatic cell toxicity (e.g. to hepatocytes), an agent causing cardiac cell toxicity (e.g. to myocytes), an agent causing pancreatic cell toxicity (e.g. to Islets of Langerhans or Pancreatic acini), an agent causing brain cell toxicity (e.g. to neurons and glial cells), an agent causing spleen cell toxicity (e.g. to red or white pulp), an agent causing ovarian cell toxicity (e.g. to follicles) or an agent causing pulmonary cell toxicity (e.g. to lung parenchyma).

Exemplary agents causing renal cell toxicity (e.g. nephrotoxicity), include but are not limited to, aminoglycoside antibiotics, calcineurin inhibitors, acetaminophen, non-steroidal anti-inflammatory drugs (NSAID), antidepressants, antihistamines, anti-microbial agents, anti-retroviral agents, benzodiazepines, cardiovascular agents, chemotherapeutic agents and herbal remedies.

Additional agents causing nephrotoxicity are listed in Table 1, below [incorporated from Naughton C., Am Fam Physician. (2008) 78(6):743-750].

TABLE 1

Drugs Associated with Nephrotoxicity

| Drug class/drug(s) | Pathophysiologic mechanism of renal injury |
|---|---|
| Analgesics | |
| Acetaminophen, aspirin | Chronic interstitial nephritis |
| Nonsteroidal anti-inflammatory drugs | Acute interstitial nephritis, altered intraglomerular hemodynamics, chronic interstitial nephritis, glomerulonephritis |
| Antidepressants/mood stabilizers | |
| Amitriptyline (Elavil), doxepin (Zonalon), fluoxetine (Prozac) | Rhabdomyolysis |
| Lithium | Chronic interstitial nephritis, glomerulonephritis, rhabdomyolysis |
| Antihistamines | |
| Diphenhydramine (Benadryl), doxylamine (Unisom) | Rhabdomyolysis |
| Antimicrobials | |
| Acyclovir (Zovirax) | Acute interstitial nephritis, crystal nephropathy |
| Aminoglycosides | Tubular cell toxicity |
| Amphotericin B (Fungizone; deoxycholic acid formulation more so than the lipid formulation) | Tubular cell toxicity |
| Beta lactams (penicillins, cephalosporins) | Acute interstitial nephritis, glomerulonephritis (ampicillin, penicillin) |
| Foscarnet (Foscavir) | Crystal nephropathy, tubular cell toxicity |
| Ganciclovir (Cytovene) | Crystal nephropathy |
| Pentamidine (Pentam) | Tubular cell toxicity |
| Quinolones | Acute interstitial nephritis, crystal nephropathy (ciprofloxacin [Cipro]) |
| Rifampin (Rifadin) | Acute interstitial nephritis |
| Sulfonamides | Acute interstitial nephritis, crystal nephropathy |
| Vancomycin (Vancocin) | Acute interstitial nephritis |
| Antiretrovirals | |
| Adefovir (Hepsera), cidofovir (Vistide), tenofovir (Viread) | Tubular cell toxicity |
| Indinavir (Crixivan) | Acute interstitial nephritis, crystal nephropathy |
| Benzodiazepines | Rhabdomyolysis |
| Calcineurin inhibitors | |
| Cyclosporine (Neoral) | Altered intraglomerular hemodynamics, chronic interstitial nephritis, thrombotic microangiopathy |
| Tacrolimus (Prograf) | Altered intraglomerular hemodynamics |
| Cardiovascular agents | |
| Angiotensin-converting enzyme inhibitors, angiotensin receptor blockers | Altered intraglomerular hemodynamics |
| Clopidogrel (Plavix), ticlopidine (Ticlid) | Thrombotic microangiopathy |
| Statins | Rhabdomyolysis |
| Chemotherapeutics | |
| Carmustine (Gliadel), semustine (investigational) | Chronic interstitial nephritis |
| Cisplatin (Platinol) | Chronic interstitial nephritis, tubular cell toxicity |

TABLE 1-continued

Drugs Associated with Nephrotoxicity

| Drug class/drug(s) | Pathophysiologic mechanism of renal injury |
|---|---|
| Interferon-alfa (Intron A) | Glomerulonephritis |
| Methotrexate | Crystal nephropathy |
| Mitomycin-C (Mutamycin) | Thrombotic microangiopathy |
| Contrast dye | Tubular cell toxicity |
| Diuretics | |
| Loops, thiazides | Acute interstitial nephritis |
| Triamterene (Dyrenium) | Crystal nephropathy |
| Drugs of abuse | |
| Cocaine, heroin, ketamine (Ketalar), methadone, methamphetamine | Rhabdomyolysis |
| Herbals | |
| Chinese herbals with aristocholic acid | Chronic interstitial nephritis |
| Proton pump inhibitors | |
| Lansoprazole (Prevacid), omeprazole (Prilosec), pantoprazole (Protonix) | Acute interstitial nephritis |
| Others | |
| Allopurinol (Zyloprim) | Acute interstitial nephritis |
| Gold therapy | Glomerulonephritis |
| Haloperidol (Haldol) | Rhabdomyolysis |
| Pamidronate (Aredia) | Glomerulonephritis |
| Phenytoin (Dilantin) | Acute interstitial nephritis |
| Quinine (Qualaquin) | Thrombotic microangiopathy |
| Ranitidine (Zantac) | Acute interstitial nephritis |
| Zoledronate (Zometa) | Tubular cell toxicity |

According to one embodiment, the damage to the nephric tissue is caused by partial nephrectomy.

Assessing renal damage can be carried out using any method known in the art, e.g. by common laboratory tests measuring kidney function. Such tests include, for example, blood urea nitrogen (BUN), creatinine blood test, creatinine urine test, and/or creatinine clearance test (i.e. comparing the creatinine level in urine with the creatinine level in blood). Determination of renal damage is well within the capability of those skilled in the art, especially in light of the detailed disclosure provided herein. Exemplary agents causing hepatic cell toxicity (e.g. hepatotoxicity), include but are not limited to, acetaminophen, nonsteroidal anti-inflammatory drugs (NSAID) (e.g. aspirin, phenylbutazone, ibuprofen, sulindac, phenylbutazone, piroxicam, diclofenac and indomethacin), glucocorticoids, isoniazids, hydrazine derivative drugs (e.g. the MAOI antidepressant iproniazid), natural products (e.g. amanita mushrooms and aflatoxins) industrial toxins (e.g. arsenic, carbon tetrachloride, and vinyl chloride) and herbal remedies (e.g. Ackee fruit, Bajiaolian, Camphor, Copaltra, Cycasin, Garcinia, Kava leaves, pyrrolizidine alkaloids, Horse chestnut leaves, Valerian, Comfrey, Jin Bu Huan, Ma-huang, Shou Wu Pian and Bai Xian Pi).

Additional agents causing hepatotoxicity are listed in Table 2, below [incorporated from Herrine S. K., www(dot)merckmanuals(dot)com/professional/hepatic-and-biliary-disorders/drugs-and-the-liver/liver-injury-caused-by-drugs].

TABLE 2

Drugs Associated with Hepatotoxicity

| Potential hepatic damage | Drug |
|---|---|
| Hepatocellular damage: | Acarbose |
| | Acetaminophen |
| | Allopurinol |
| | Amiodarone |
| | ART drugs |
| | Bupropion |
| | Fluoxetine |
| | Germander |
| | Green tea extract |
| | Baclofen |
| | Isoniazid |
| | Kava |
| | Ketoconazole |
| | Lisinopril |
| | Losartan |
| | Methotrexate |
| | NSAIDs |
| | Omeprazole |
| | Paroxetine |
| | Pyrazinamide |
| | Rifampin |
| | Risperidone |
| | Sertraline |
| | Statins |
| | Tetracyclines |
| | Trazodone |
| | Troy afloxacin |
| | Valproate |
| Cholestatic damage: | Amoxicillin/clavulanate |
| | Anabolic steroids |
| | Chlorpromazine |
| | Clopidogrel |
| | Oral contraceptives |
| | Erythromycins |
| | Estrogens |
| | Irbesartan |
| | Mirtazapine |
| | Phenothiazines |
| | Terbinafine |
| | Tricyclic antidepressants |
| Mixed liver damage: | Amitriptyline |
| | Azathioprine |
| | Captopril |
| | Carbamazepine |
| | Clindamycin |
| | Cyproheptadine |
| | Enalapril |
| | Nitrofurantoin |
| | Phenobarbital |
| | Phenytoin |
| | Sulfonamides |
| | Trazodone |
| | Trimethoprim/sulfamethoxazole |
| | Verapamil |

According to one embodiment, the damage to the hepatic tissue is caused by partial hepatectomy.

Assessing liver damage can be carried out using any method known in the art, e.g. liver function tests such as prothrombin time (PT/INR), aPTT, albumin, bilirubin (direct and indirect) or by measuring liver transaminases (AST or SGOT and ALT or SGPT). Determination of liver damage is well within the capability of those skilled in the art, especially in light of the detailed disclosure provided herein.

Exemplary agents causing cardiac cell toxicity (e.g. cardiotoxicity), include but are not limited to, chemotherapeutic agents [e.g. Daunorubicin (Cerubidine®), Doxorubicin, Doxorubicin liposome injection (Doxil®), Epirubicin (Ellence®), Idarubicin (Idamycin® PFS), and Valrubicin (Valstar®)], anti-cancer agents [e.g. trastuzumab (Herceptin®), bevacizumab (Avastin®), lapatinib (Tykerb®), sunitinib (Sutent®), and sorafenib (Nexavar®)], cytostatic agents, antidepressant drugs, immunomodulating drugs, anesthetics, calcium channel blocking agents, nonsteroidal anti-inflammatory drugs (NSAID), beta-adrenoceptor antagonists and anti-arrhythmics.

Additional agents causing cardiotoxicity are listed in Table 3, below [incorporated from Feenstra et al., J Am Coll Cardiol. 1999; 33(5):1152-1162].

TABLE 3

Drugs Associated with Cardiotoxicity

Agents associated with the induction of congestive heart failure (CHF)

Anthracyclines
Paclitaxel
Mitoxantrone
Interferons
Interleukin-2

Agents associated with the precipitation of CHF in patients with preexisting ventricular dysfunction Calcium channel blockers
NSAIDs
Antiarrhythmics
Beta-receptor antagonists
Anesthetics
Steroidal hormones with mineralocorticoid effects
Drugs that may increase afterload:
Sympathomimetic drugs; e.g., adrenaline, dobutamine, dopamine
Cyclosporine
Ketoconazol Agents that are only incidentally associated with the onset of CHF in case reports Tricyclic antidepressants
5-Fluorouracil
Cytarabine
Polyethylene glycol-electrolyte lavage solution
Aminocaproic acid
Antidigoxine antibody fragments
Sodium-containing antacids
Amantadine
Bromocriptine
Foscarnet
Megestrol
Mannitol
Hydralazine
Edetic acid
Deferiprone
Dapsone
Carbamazepine
Cibenzoline
Prostaglandin E$_2$
Methyl-sergide
Ifosfamide Assessing cardiac damage can be carried out using any method known in the art, e.g. by a physical exam, chest X-ray, Echocardiogram, ECG (electrocardiogram), MUGA (multi-gated acquisition) scan, and/or by Troponin blood tests. Determination of cardiac damage is well within the capability of those skilled in the art, especially in light of the detailed disclosure provided herein.

Exemplary agents causing pancreatic cell toxicity (e.g. acute pancreatitis), include but are not limited to, ACE inhibitors, alcohol, alloxan, azaserine, azathioprine, dimethylbenzo[a]anthracene, estrogens, ethionine, furosemide, methyldopa, mesalazine, oleic acid, pentamidine, procainamide, propofol, statin, streptozotocin sulfonamide, thiazide diuretic and valproate.

Additional agents causing pancreatic cell toxicity are listed in Table 4, below [incorporated from Kaurich T, Proc (Bayl Univ Med Cent) (2008) 21(1): 77-81].

TABLE 4

Drugs and drug classes associated with acute pancreatitis

| | | |
|---|---|---|
| ACE inhibitors | Estrogens | Pentamidine |
| Acetaminophen | Ethacrynic acids | Pergolide |
| Adrenocorticotrophic hormones | Exenatide | Phenolphthalein |
| | Ezetimibe | Pilocarpine |
| Alendronate | Fibrates | Prazosin |
| All-trans-retinoic acid | Finasteride | Procainamide |
| Alpha-methyldopa | Fluoroquinolones | Propofol |
| Aminosalicylates | 5-Fluorouracil | Propoxyphene |
| Amiodarone | Furosemide | Proton pump inhibitors |
| Amlodipine | Gabapentin | Quinupristin/dalfopristin |
| Ampicillin | Gold | Ranitidine |
| Antivirals | HAART agents | Repaglinide |
| Aspirin | HMG-CoA reductase inhibitors | Rifampin |
| Atypical antipsychotics | | Rifapentine |
| Azathioprine | Ifosfamide | Rivastigmine |
| Bupropion | Indomethacin | Ropinirole |
| Calcitriol | Interferon/ribavirin | Saw palmetto |
| Cannabis | Interleukin-2 | Selective serotonin receptor antagonists |
| Capecitabine | Irbesartan | |
| Carbamazepine | Isoniazid | Sirolimus |
| Ceftriaxone | Isotretinoin | Sodium stibogluconate |
| Cimetidine | Lamotrigine | Somatropin |
| Cisplatin | L-asparaginase | Sulfamethoxazole |
| Clomiphene | Macrolides | Sulfasalazine |
| Codeine | Mefenamic acid | Sumatriptan |
| Colchicine | 6-Mercaptopurine | Tacrolimus |
| Corticosteroids | Mesalamine | Tamoxifen |
| COX-2 inhibitors | Metformin | Tetracyclines |
| Cyclophosphamide | Methimazole | Thiazide diuretics |
| Cyclosporine | Methyldopa | Thrombolytic agents |
| Cyproheptadine | Metronidazole | TNF-alpha inhibitors |
| Cytosine | Mirtazapine | Topiramate |
| Danazol | Montelukast | Trimethoprim-sulfamethizole |
| Dapsone | Mycophenolate | |
| Diazoxide | Nitrofurantoin | Valproic acid |
| Diphenoxylate | NSAIDs | Venlafaxine |
| Dipyridamole | Octreotide | Vincristine |
| Doxercalciferol | Paclitaxel | Voriconazole |
| Doxorubicin | Pegaspargase | Zolmitriptan |
| Ertapenem | Penicillin | |

(ACE, angiotensin-converting enzyme; COX, cyclooxygenase; HMG-CoA, 3-hydroxy-3-methyl-glutaryl coenzyme A; NSAID, nonsteroidal anti-inflammatory drug; TNF, tumor necrosis factor.)

According to one embodiment, the damage to the pancreatic tissue is caused by partial pancreatectomy.

Assessing pancreatic damage can be carried out using any method known in the art, e.g. by blood test measuring amylase and/or lipase; by fecal elastase test; by abdominal ultrasound, by computed tomography (CT) scan e.g. with contrast dye and/or endoscopic retrograde cholangiopancreatography (ERCP). Determination of pancreatic damage is well within the capability of those skilled in the art, especially in light of the detailed disclosure provided herein.

Exemplary agents causing brain cell toxicity (e.g. neurotoxicity), include but are not limited to, antihistamines (e.g. diphenhydramine), bladder relaxants (e.g. oxybutynin and tolterodine), medications for vertigo or motion sickness (e.g. Meclizine), medications for itching (e.g. strong antihistamines such as hydroxyzine and diphendyramine), muscle relaxants (e.g. cyclobenzaprine), medications for nerve pain or antidepressants (e.g. tricyclics), and chemotherapeutic agents.

Assessing brain cell damage can be carried out using any method known in the art, e.g. by measuring cognitive function, by Neurobehavioral Core Test Battery (NCTB)+, by Electromyography (EMG), by Evoked potentials (EP), by Electrocardiography (ECG or EKG), by Positron Emission Tomography (PET), or by Computed tomographic (CT) [as described in detail in Nervous System, Mergler Donna, Editor, Encyclopedia of Occupational Health and Safety, Jeanne Mager Stellman, Editor-in-Chief. International Labor Organization, Geneva. (2011)]. Determination of brain damage is well within the capability of those skilled in the art, especially in light of the detailed disclosure provided herein.

Exemplary agents causing spleen cell toxicity, include but are not limited to, anticancer drugs, hydroxyurea, nitrosobenzene and thioacetamide.

Assessing spleen damage can be carried out using any method known in the art, e.g. by ultrasound imaging or by CT scan.

Exemplary agents causing ovarian cell toxicity, include but are not limited to, chemotherapeutic agents or immunosuppressive agents. Exemplary agents include, but are not limited to, alkylating agents, Sirolimus (e.g. rapamycin), 1,3-butadiene, 4-vinylcyclohexene, vinylcyclohexene deipoxide, nitrofurantoin, nitrofurazone, benzene, delta-9-tetrahydrocannabinol, and tricresylphosphate. According to one embodiment, ovarian cell toxicity is caused by polycystic ovaries.

Assessing ovarian cell damage can be carried out using any method known in the art, e.g. by ultrasound imaging (e.g. measuring hypoplasia, atrophy, follicular necrosis, and/or tubular hyperplasia). Determination of ovarian damage is well within the capability of those skilled in the art, especially in light of the detailed disclosure provided herein.

Exemplary agents causing pulmonary cell toxicity, include but are not limited to, chemotherapeutic agents, immunosuppressive agents, amiodarone, beta blockers, ACE inhibitors, nitrofurantoin, procainamide, quinidine, tocainide, minoxidil, amiodarone, methotrexate, taxanes (e.g. paclitaxel and docetaxel), gemcitabine, bleomycin, mitomycin C, busulfan, cyclophosphamide, chlorambucil, nitrosourea (e.g., carmustine) and Sirolimus.

Additional agents causing pulmonary cell toxicity are listed in Table 5, below [incorporated from Collard, www (dot)merckmanuals(dot)com/professional/pulmonary-disorders/interstitial-lung-diseases/drug-induced-pulmonary-disease].

TABLE 5

Substances with toxic pulmonary effects

| Condition | Drug or Agent |
| --- | --- |
| Asthma | Aspirin, β-blockers (e.g., timolol), cocaine, dipyridamole, IV hydrocortisone, IL-2, methylphenidate, nitrofurantoin, protamine, sulfasalazine, vinca alkaloids (with mitomycin-C) |
| Organizing pneumonia | Amiodarone, bleomycin, cocaine, cyclophosphamide, methotrexate, minocycline, mitomycin-C, penicillamine, sulfasalazine, tetracycline |
| Hypersensitivity pneumonitis | Azathioprine plus 6-mercaptopurine, busulfan, fluoxetine, radiation |
| Interstitial pneumonia or fibrosis | Amphotericin B, bleomycin, busulfan, carbamazepine, chlorambucil, cocaine, cyclophosphamide, diphenylhydantoin, flecainide, heroin, melphalan, methadone, methotrexate, methylphenidate, methysergide, mineral oil (via chronic microaspiration), nitrofurantoin, nitrosoureas, procarbazine, silicone (s.c. injection), tocainide, vinca alkaloids (with mitomycin-C) |

TABLE 5-continued

Substances with toxic pulmonary effects

| Condition | Drug or Agent |
| --- | --- |
| Noncardiac pulmonary edema | β-Adrenergic agonists (eg, ritodrine, terbutaline), chlordiazepoxide, cocaine, cytarabine, ethiodized oil (IV, and via chronic microaspiration), gemcitabine, heroin, hydrochlorothiazide, methadone, mitomycin-C, phenothiazines, protamine, sulfasalazine, tocolytic agents, tricyclic antidepressants, tumor necrosis factor, vinca alkaloids (with mitomycin-C) |
| Parenchymal hemorrhage | Anticoagulants, azathioprine plus 6-mercaptopurine, cocaine, mineral oil (via chronic microaspiration), nitrofurantoin, radiation |
| Pleural effusion | Amiodarone, anticoagulants, bleomycin, bromocriptine, busulfan, granulocyte-macrophage colony-stimulating factor, IL-2, methotrexate, methysergide, mitomycin-C, nitrofurantoin, para-aminosalicylic acid, procarbazine, radiation, tocolytic agents |
| Pulmonary infiltrate with eosinophilia | Amiodarone, amphotericin B, bleomycin, carbamazepine, diphenylhydantoin, ethambutol, etoposide, granulocyte-macrophage colony-stimulating factor, isoniazid, methotrexate, minocycline, mitomycin-C, nitrofurantoin, para-aminosalicylic acid, procarbazine, radiation, sulfasalazine, sulfonamides, tetracycline, trazodone |
| Pulmonary vascular disease | Appetite suppressants (eg, dexfenfluramine, fenfluramine, phentermine), busulfan, cocaine, heroin, methadone, methylphenidate, nitrosoureas, radiation |

According to one embodiment, when the tissue of interest is a pulmonary tissue the agent capable of inducing damage to the tissue is not naphthalene.

Assessing pulmonary cell damage can be carried out using any method known in the art, e.g. by pulmonary function tests, chest X-ray, by chest CT, or by PET scan. Determination of pulmonary damage is well within the capability of those skilled in the art, especially in light of the detailed disclosure provided herein.

As described above, tissue damage results in proliferation of resident stem cells within the tissue.

Assessing proliferation of resident stem cells (e.g. endogenous stem cells within a tissue) can be carried out using any method know to one of skill in the art, such as for example, by in-vivo imaging of cellular proliferation e.g. using a Positron emission tomography (PET) with a PET tracer e.g. 18F labeled 2-fluoro-2-deoxy-D-glucose (18FDG) or [18F] 3'-deoxy-3-fluorothymidine ((18)FLT) as taught by Francis et al., Gut. (2003) 52(11):1602-6 and by Fuchs et al., J Nucl Med. (2013) 54(1):151-8.

Thus, according to one embodiment of the invention, following administration of the agent capable of inducing damage to the tissue of interest, the subject is subjected to a second conditioning agent, i.e. an agent which ablates the resident stem cells in the tissue. As will be apparent to those of ordinary skill in the art of cell biology, sensitivity to radiation is achieved only in a proliferative stage.

According to one embodiment, the agent which ablates the resident stem cells comprises a sublethal or lethal conditioning regimen.

According to one embodiment, the sublethal or lethal conditioning regimen comprises a partial body irradiation or a total body irradiation (TBI).

According to one embodiment, when partial body irradiation is used, exposure is specific to an organ or tissue to be treated (e.g. lungs, kidney, liver, heart, pancreas, brain etc.). In such cases, it is advisable to shield the non-irradiated body organs in order to avoid unwanted organ/tissue damage. Alternatively, irradiation may be effected by a focused beam.

According to one embodiment, the partial body irradiation comprises a single or fractionated irradiation dose within the range of 0.5-1 Gy, 0.5-1.5 Gy, 0.5-2.5 Gy, 0.5-5 Gy, 0.5-7.5 Gy, 0.5-10 Gy, 0.5-15 Gy, 1-1.5 Gy, 1-2 Gy, 1-2.5 Gy, 1-3 Gy, 1-3.5 Gy, 1-4 Gy, 1-4.5 Gy, 1-1.5 Gy, 1-7.5 Gy, 1-10 Gy, 2-3 Gy, 2-4 Gy, 2-5 Gy, 2-6 Gy, 2-7 Gy, 2-8 Gy, 2-9 Gy, 2-10 Gy, 3-4 Gy, 3-5 Gy, 3-6 Gy, 3-7 Gy, 3-8 Gy, 3-9 Gy, 3-10 Gy, 4-5 Gy, 4-6 Gy, 4-7 Gy, 4-8 Gy, 4-9 Gy, 4-10 Gy, 5-6 Gy, 5-7 Gy, 5-8 Gy, 5-9 Gy, 5-10 Gy, 6-7 Gy, 6-8 Gy, 6-9 Gy, 6-10 Gy, 7-8 Gy, 7-9 Gy, 7-10 Gy, 8-9 Gy, 8-10 Gy, 10-12 Gy or 10-15 Gy.

According to a specific embodiment, the partial body irradiation comprises a single or fractionated irradiation dose within the range of 1-7.5 Gy.

According to one embodiment, the TBI comprises a single or fractionated irradiation dose within the range of 0.5-1 Gy, 0.5-1.5 Gy, 0.5-2.5 Gy, 0.5-5 Gy, 0.5-7.5 Gy, 0.5-10 Gy, 0.5-15 Gy, 1-1.5 Gy, 1-2 Gy, 1-2.5 Gy, 1-3 Gy, 1-3.5 Gy, 1-4 Gy, 1-4.5 Gy, 1-1.5 Gy, 1-7.5 Gy, 1-10 Gy, 2-3 Gy, 2-4 Gy, 2-5 Gy, 2-6 Gy, 2-7 Gy, 2-8 Gy, 2-9 Gy, 2-10 Gy, 3-4 Gy, 3-5 Gy, 3-6 Gy, 3-7 Gy, 3-8 Gy, 3-9 Gy, 3-10 Gy, 4-5 Gy, 4-6 Gy, 4-7 Gy, 4-8 Gy, 4-9 Gy, 4-10 Gy, 5-6 Gy, 5-7 Gy, 5-8 Gy, 5-9 Gy, 5-10 Gy, 6-7 Gy, 6-8 Gy, 6-9 Gy, 6-10 Gy, 7-8 Gy, 7-9 Gy, 7-10 Gy, 8-9 Gy, 8-10 Gy, 10-12 Gy or 10-15 Gy.

According to a specific embodiment, the TBI comprises a single or fractionated irradiation dose within the range of 1-7.5 Gy.

According to one embodiment, the agent which ablates the resident stem cells comprises a chemotherapeutic agent (e.g. antineoplastic agent). According to a specific embodiment, the agent comprises an Alkylating agent. Exemplary Alkylating agents include, but are not limited to, Cyclophosphamide, Busulfan, Mechlorethamine or mustine (HN2), Uramustine or uracil mustard, Melphalan, Chlorambucil, Ifosfamide, Bendamustine, Nitrosoureas Carmustine, Lomustine, Streptozocin, Thiotepa, Platinum, Cisplatin, Carboplatin, Nedaplatin, Oxaliplatin, Satraplatin, Triplatin tetranitrate, Procarbazine, Altretamine, Triazenes (dacarbazine, mitozolomide, temozolomide), Dacarbazine, Temozolomide, Myleran, Busulfex, Fludarabine and Dimethyl mileran.

The chemotherapeutic agent may be administered to the subject in a single dose or in several doses e.g. 2, 3, 4, 5, 6, 7, 8, 9, 10 or more doses (e.g. daily doses) as to ablate resident stem cells in the tissue.

According to one embodiment, the agent capable of inducing damage to the tissue is administered to the subject 1-10 days (e.g. 1-3 days, e.g. 3 days) prior to the agent which ablates the resident stem cells.

According to an embodiment, the agent which ablates the resident stem cells is administered to the subject 1-10 days (e.g. 1-3 days, e.g. 2 days) prior to administration of the progenitor cells (discussed below).

According to one embodiment, the agent capable of inducing damage to the tissue is administered to the subject 2-10 days (e.g. 2-3 days) prior to transplantation and the agent which ablates the resident stem cells is administered to the subject 40-48 hours thereafter (e.g. 1-3 days prior to transplantation, e.g. 1 day prior to transplantation).

According to one embodiment, the agent capable of inducing damage to the tissue and the agent which ablates the resident stem cells is the same agent (e.g. Alkylating agent).

The present inventors have illustrated that conditioning of recipient mice using naphthalene treatment, followed by total body irradiation (TBI), lead to substantial and durable chimerism in different cell lineages of the injured lungs (see Examples 2 and 4, in the Examples section which follows).

Thus, the method of the present invention may be applied for conditioning of any subject in need of transplantation of progenitor cells.

Thus, according to one aspect of the present invention there is provided a method of transplanting progenitor cells in suspension of a tissue of interest to a subject in need thereof, the method comprising: (a) conditioning the subject according to the method of some embodiments of the invention; and (b) transplanting the progenitor cells in suspension to the subject.

As used herein, the term "subject" or "subject in need" refers to a mammal, preferably a human being, male or female at any age that is in need of a cell transplantation (i.e. transplantation of progenitor cells) or suffers from a disease which may be treated with a cell transplantation (i.e. transplantation of progenitor cells). Typically the subject is in need of transplantation (also referred to herein as recipient) due to a disorder or a pathological or undesired condition, state, or syndrome, or a physical, morphological or physiological abnormality which is amenable to treatment via cell transplantation. According to a specific embodiment, the subject suffers from or is predisposed to tissue damage or deficiency as a result of a disease, disorder or injury. Examples of such disorders are provided further below.

As used herein, the phrase "transplanting" refers to administering bodily cells, e.g. single cells or a group of cells, into a subject.

As used herein the term "progenitor cells" or "precursor cells" refer to cells which occur in fetal or adult tissues and are committed to a specific cell lineage. These cells give rise to differentiated cells (i.e., terminally differentiated cells).

According to one embodiment, the progenitor cells comprise cardiac progenitor cells, hepatic progenitor cells, pancreatic progenitor cells, brain progenitor cells, nephric progenitor cells, ovarian progenitor cells, spleen progenitor cells or pulmonary progenitor cells.

The phrase "cells in suspension" as used herein, refers to progenitor cells which have been isolated from their natural environment (e.g., the human body) and are extracted from the blood or tissue/organ while maintaining viability but do not maintain a tissue structure (i.e., no vascularized tissue structure) such that they may be injectable such as by intravenous administration. According to a specific embodiment the cells in suspension are not attached to a solid support.

Depending on the application, the method may be effected using progenitor cells which are syngeneic or non-syngeneic with the subject.

As used herein, the term "syngeneic" cells refer to cells which are essentially genetically identical with the subject or essentially all lymphocytes of the subject. Examples of syngeneic cells include cells derived from the subject (also referred to in the art as an "autologous"), from a clone of the subject, or from an identical twin of the subject.

As used herein, the term "non-syngeneic" cells refer to cells which are not essentially genetically identical with the subject or essentially all lymphocytes of the subject, such as allogeneic cells or xenogeneic cells.

As used herein, the term "allogeneic" refers to cells which are derived from a donor who is of the same species as the subject, but which is substantially non-clonal with the subject. Typically, outbred, non-zygotic twin mammals of the same species are allogeneic with each other. It will be appreciated that an allogeneic cell may be HLA identical, partially HLA identical or HLA non-identical (i.e. displaying one or more disparate HLA determinant) with respect to the subject.

As used herein, the term "xenogeneic" refers to a cell which substantially expresses antigens of a different species relative to the species of a substantial proportion of the lymphocytes of the subject. Typically, outbred mammals of different species are xenogeneic with each other.

The present invention envisages that xenogeneic cells are derived from a variety of species. Thus, according to one embodiment, the progenitor cells may be derived from any mammal. Suitable species origins for the progenitor cells comprise the major domesticated or livestock animals and primates. Such animals include, but are not limited to, porcines (e.g. pig), bovines (e.g., cow), equines (e.g., horse), ovines (e.g., goat, sheep), felines (e.g., *Felis domestica*), canines (e.g., *Canis domestica*), rodents (e.g., mouse, rat, rabbit, guinea pig, gerbil, hamster), and primates (e.g., chimpanzee, rhesus monkey, macaque monkey, marmoset).

Progenitor cells of xenogeneic origin (e.g. porcine origin) are preferably obtained from a source which is known to be free of zoonoses, such as porcine endogenous retroviruses. Similarly, human-derived cells or tissues are preferably obtained from substantially pathogen-free sources.

According to one embodiment, the progenitor cells are non-syngeneic with the subject.

According to one embodiment, the progenitor cells are allogeneic with the subject.

According to one embodiment, the progenitor cells are xenogeneic with the subject.

According to one embodiment, the progenitor cells are syngeneic with the subject (e.g. autologous).

According to an embodiment of the present invention, the subject is a human being and the progenitor cells are from a human origin (e.g. syngeneic or non-syngeneic).

According to one embodiment, the subject is a human being and the progenitor cells are from a xenogeneic origin (e.g. porcine origin).

Depending on the application and available sources, the cells of the present invention may be obtained from a prenatal organism, postnatal organism, an adult or a cadaver donor. Such determinations are well within the ability of one of ordinary skill in the art.

According to one embodiment, the progenitor cells are from an embryonic origin (e.g. corresponding to human gestation of one to eight weeks after fertilization).

According to one embodiment, the progenitor cells are from a fetal origin (e.g. corresponding to human gestation starting nine weeks after fertilization).

According to one embodiment, the progenitor cells are from an adult origin (e.g. a mammalian organism at any stage after birth).

Any method known in the art may be employed to obtain cells for transplantation. Thus, for example, progenitor cells may be obtained from an organ or tissue. It will be appreciated that the progenitor cells of the invention may be of fresh or frozen (e.g., cryopreserved) preparations, as discussed below.

According to one embodiment, the organ or tissue is from a fetal organism. The fetal organism may be of any of a human or xenogeneic origin (e.g. porcine) and at any stage of gestation. Such a determination is in the capacity of one of ordinary skill in the art.

According to one embodiment, the fetal organ or tissue comprises a fetal pulmonary tissue, a fetal pancreatic tissue, a fetal nephric tissue, a fetal hepatic tissue, a fetal cardiac tissue, a fetal brain tissue, a fetal spleen tissue and a fetal ovarian tissue.

Various methods may be employed to obtain an organ or tissue from a fetal organism. Thus, for example, obtaining a tissue (e.g. liver, pancreas, heart, kidney or lung tissue) may be effected by harvesting the tissue from a developing fetus, e.g. by a surgical procedure.

According to one embodiment, the pulmonary tissue (i.e. lung tissue) is obtained from a fetus at a stage of gestation corresponding to human canalicular stage of development (e.g. 16-25 weeks of gestation). According to one embodiment, the pulmonary tissue is obtained from a fetus at a stage of gestation corresponding to human 16-17 weeks of gestation, 16-18 weeks of gestation, 16-19 weeks of gestation, 16-20 weeks of gestation, 16-21 weeks of gestation, 16-22 weeks of gestation, 16-24 weeks of gestation, 17-18 weeks of gestation, 17-19 weeks of gestation, 17-20 weeks of gestation, 17-21 weeks of gestation, 17-22 weeks of gestation, 17-24 weeks of gestation, 18-19 weeks of gestation, 18-20 weeks of gestation, 18-21 weeks of gestation, 18-22 weeks of gestation, 18-24 weeks of gestation, 19-20 weeks of gestation, 19-21 weeks of gestation, 19-22 weeks of gestation, 19-23 weeks of gestation, 19-24 weeks of gestation, 20-21 weeks of gestation, 20-22 weeks of gestation, 20-23 weeks of gestation, 20-24 weeks of gestation, 21-22 weeks of gestation, 21-23 weeks of gestation, 21-24 weeks of gestation, 22-23 weeks of gestation, 22-24 weeks of gestation, 22-25 weeks of gestation, 23-24 weeks of gestation, 23-25 weeks of gestation, 24-25 weeks of gestation or 25-26 weeks of gestation. According to a specific embodiment, the pulmonary tissue is obtained from a fetus at a stage of gestation corresponding to human 20-22 weeks of gestation.

According to one embodiment, the hepatic tissue (i.e. liver tissue) is obtained from a fetus at a stage of gestation corresponding to human 5-16 weeks of gestation. According to one embodiment, the hepatic tissue is obtained from a fetus at a stage of gestation corresponding to human 5-7 weeks of gestation, 5-8 weeks of gestation, 5-9 weeks of gestation, 5-10 weeks of gestation, 5-11 weeks of gestation, 5-12 weeks of gestation, 6-7 weeks of gestation, 6-8 weeks of gestation, 6-9 weeks of gestation, 6-10 weeks of gestation, 6-11 weeks of gestation, 6-12 weeks of gestation, 6-14 weeks of gestation, 7-8 weeks of gestation, 7-9 weeks of gestation, 7-10 weeks of gestation, 7-11 weeks of gestation, 7-12 weeks of gestation, 7-14 weeks of gestation, 7-16 weeks of gestation, 8-9 weeks of gestation, 8-10 weeks of gestation, 8-12 weeks of gestation, 8-14 weeks of gestation, 8-16 weeks of gestation, 9-10 weeks of gestation, 9-11 weeks of gestation, 9-12 weeks of gestation, 10-12 weeks of gestation, 10-14 weeks of gestation, 10-16 weeks of gestation, 6 weeks of gestation, 7 weeks of gestation, 8 weeks of gestation, 9 weeks of gestation or 10 weeks of gestation. According to a specific embodiment, the hepatic tissue is obtained from a fetus at a stage of gestation corresponding to human 7-9 weeks of gestation, e.g. 7 weeks of gestation.

According to one embodiment, the pancreatic tissue (i.e. pancreas tissue) is obtained from a fetus at a stage of gestation corresponding to human 5-20 weeks of gestation. According to one embodiment, the pancreatic tissue is obtained from a fetus at a stage of gestation corresponding to human 5-7 weeks of gestation, 5-8 weeks of gestation, 5-9 weeks of gestation, 5-10 weeks of gestation, 5-11 weeks of gestation, 5-12 weeks of gestation, 5-14 weeks of gestation, 5-16 weeks of gestation, 6-7 weeks of gestation, 6-8 weeks of gestation, 6-9 weeks of gestation, 6-10 weeks of gestation, 6-11 weeks of gestation, 6-12 weeks of gestation, 6-14 weeks of gestation, 7-8 weeks of gestation, 7-9 weeks of gestation, 7-10 weeks of gestation, 7-11 weeks of gestation, 8-9 weeks of gestation, 8-10 weeks of gestation, 8-12 weeks of gestation, 8-14 weeks of gestation, 8-16 weeks of gestation, 8-18 weeks of gestation, 8-20 weeks of gestation, 9-10 weeks of gestation, 9-11 weeks of gestation, 9-12 weeks of gestation, 10-12 weeks of gestation, 10-14 weeks of gestation, 10-16 weeks of gestation, 10-18 weeks of gestation, 10-20 weeks of gestation, 12-14 weeks of gestation, 12-16 weeks of gestation, 12-20 weeks of gestation, 14-18 weeks of gestation, 14-20 weeks of gestation, 16-18 weeks of gestation, 16-20 weeks of gestation, 6 weeks of gestation, 7 weeks of gestation, 8 weeks of gestation, 9 weeks of gestation or 10 weeks of gestation. According to a specific embodiment, the pancreatic tissue is obtained from a fetus at a stage of gestation corresponding to human 8-20 weeks of gestation, e.g. 8 weeks of gestation.

According to one embodiment, the cardiac tissue (i.e. heart tissue) is obtained from a fetus at a stage of gestation corresponding to human 5-16 weeks of gestation. According to one embodiment, the cardiac tissue is obtained from a fetus at a stage of gestation corresponding to human 5-7 weeks of gestation, 5-8 weeks of gestation, 5-9 weeks of gestation, 5-10 weeks of gestation, 5-11 weeks of gestation, 5-12 weeks of gestation, 6-7 weeks of gestation, 6-8 weeks of gestation, 6-9 weeks of gestation, 6-10 weeks of gestation, 6-11 weeks of gestation, 6-12 weeks of gestation, 6-14 weeks of gestation, 7-8 weeks of gestation, 7-9 weeks of gestation, 7-10 weeks of gestation, 7-11 weeks of gestation, 8-9 weeks of gestation, 8-10 weeks of gestation, 8-12 weeks of gestation, 8-14 weeks of gestation, 8-16 weeks of gestation, 9-10 weeks of gestation, 9-11 weeks of gestation, 9-12 weeks of gestation, 9-14 weeks of gestation, 9-16 weeks of gestation, 10-12 weeks of gestation, 10-14 weeks of gestation, 10-16 weeks of gestation, 6 weeks of gestation, 7 weeks of gestation, 8 weeks of gestation, 9 weeks of gestation or 10 weeks of gestation. According to a specific embodiment, the cardiac tissue is obtained from a fetus at a stage of gestation corresponding to human 7-9 weeks of gestation, e.g. 9 weeks of gestation.

According to one embodiment, the nephric tissue (i.e. kidney tissue) is obtained from a fetus at a stage of gestation corresponding to human 5-16 weeks of gestation. According to one embodiment, the nephric tissue is obtained from a fetus at a stage of gestation corresponding to human 5-7 weeks of gestation, 5-8 weeks of gestation, 5-9 weeks of gestation, 5-10 weeks of gestation, 5-11 weeks of gestation, 5-12 weeks of gestation, 6-7 weeks of gestation, 6-8 weeks of gestation, 6-9 weeks of gestation, 6-10 weeks of gestation, 6-11 weeks of gestation, 6-12 weeks of gestation, 6-14 weeks of gestation, 7-8 weeks of gestation, 7-9 weeks of gestation, 7-10 weeks of gestation, 7-11 weeks of gestation, 7-12 weeks of gestation, 7-14 weeks of gestation, 7-16 weeks of gestation, 8-9 weeks of gestation, 8-10 weeks of gestation, 8-12 weeks of gestation, 8-14 weeks of gestation, 8-16 weeks of gestation, 10-12 weeks of gestation, 10-14 weeks of gestation, 10-16 weeks of gestation, 6 weeks of gestation, 7 weeks of gestation, 8 weeks of gestation, 9 weeks of gestation or 10 weeks of gestation. According to a specific embodiment, the nephric tissue is obtained from a fetus at a stage of gestation corresponding to human 7-9 weeks of gestation, e.g. 7-8 weeks of gestation.

It will be understood by those of skill in the art that the gestational stage of an organism is the time period elapsed following fertilization of the oocyte generating the organism.

The following table provides an example of the gestational stages of human and porcine tissues at which these can provide fetal tissues which are essentially at corresponding developmental stages:

TABLE 6

Corresponding gestational stages of pigs and humans

| Gestational stage of porcine pulmonary tissue (days) | Gestational stage of human tissue (days*) |
|---|---|
| 18 | 44 |
| 20 | 49 |
| 22 | 54 |
| 23 | 56-57 |
| 25 | 61-62 |
| 26 | 63 |
| 28 | 68-69 |
| 31 | 75 |
| 38 | 92 |
| 42 | 102 |
| 46 | 112 |
| 49 | 119 |
| 56 | 136 |
| 62 | 151 |
| 72 | 175 |
| 80 | 195 |
| 88 | 214 |

The gestational stage (in days) of a tissue belonging to a given species which is at a developmental stage essentially corresponding to that of a porcine tissue can be calculated according to the following formula: [gestational stage of porcine tissue in days]/[gestational period of pig in days] × [gestational stage of tissue of given species in days]. Similarly, the gestational stage (in days) of a tissue belonging to a given species which is at a developmental stage essentially corresponding to that of a human tissue can be calculated according to the following formula: [gestational stage of human in tissue in days]/[gestational period of humans in days] × [gestational stage of tissue of given species in days]. The gestational stage of pigs is about 115 days and that of humans is about 280 days.
*for week calculation divide the numbers by 7.

Likewise, various methods may be employed to obtain an organ or tissue from an adult organism (e.g. live or cadaver). Thus, for example, obtaining a tissue (e.g. liver, pancreas, heart, kidney or lung tissue) may be effected by harvesting the tissue from an organ donor by a surgical procedure e.g. laparotomy or laparoscopy. After the organ/tissue is obtained from the adult organism, stem cells (e.g. adult stem cells) may be isolated therefrom according to methods known in the art, such methods depend on the source and lineage of the cells and may include, for example, flow cytometry and cell sorting as taught for example by www(dot)bio-rad(dot)com/en-uk/applications-technologies/isolation-maintenance-stem-cells.

After organ/tissue is obtained (e.g. fetal tissue), the present invention further contemplates generation of an isolated population of cells therefrom.

The progenitor cells may be comprised in a suspension of single cells or cell aggregates of no more than 5, 10, 50, 100, 200, 300, 400, 500, 1000, 1500, 2000 cells in an aggregate.

The cell suspension of the invention may be obtained by any mechanical or chemical (e.g. enzymatic) means. Several methods exist for dissociating cell clusters to form cell suspensions (e.g. single cell suspension) from primary tissues, attached cells in culture, and aggregates, e.g., physical forces (mechanical dissociation such as cell scraper, trituration through a narrow bore pipette, fine needle aspiration, vortex disaggregation and forced filtration through a fine nylon or stainless steel mesh), enzymes (enzymatic dissociation such as trypsin, collagenase, Acutase and the like) or a combination of both.

Thus, for example, enzymatic digestion of tissue/organ into isolate cells can be performed by subjecting the tissue to an enzyme such as type IV Collagenase (Worthington biochemical corporation, Lakewood, N.J., USA) and/or Dispase (Invitrogen Corporation products, Grand Island N.Y., USA). For example, the tissue may be enzyme digested by finely mincing tissue with a razor blade in the presence of e.g. collagenase, dispase and $CaCl_2$ at 37° C. for about 1 hour. The method may further comprise removal of nonspecific debris from the resultant cell suspension by, for example, sequential filtration through filters (e.g. 70- and 40-μm filters), essentially as described under "General Materials and Experimental Methods" of the Examples section which follows.

Furthermore, mechanical dissociation of tissue into isolated cells can be performed using a device designed to break the tissue to a predetermined size. Such a device can be obtained from CellArtis Goteborg, Sweden. Additionally or alternatively, mechanical dissociation can be manually performed using a needle such as a 27 g needle (BD Microlance, Drogheda, Ireland) while viewing the tissue/cells under an inverted microscope.

Following enzymatic or mechanical dissociation of the tissue, the dissociated cells are further broken to small clumps using 200 μl Gilson pipette tips (e.g., by pipetting up and down the cells).

Alternatively, a tissue may be obtained by in-vitro or ex-vivo culture of cells, organs/tissues. Such controlled in-vitro differentiation of cells, tissues or organs is routinely performed, for example, using culturing of embryonic stem cell lines to generate cultures containing cells of desired lineages.

According to one embodiment, the cells of the present invention are ex-vivo differentiated from adult stem cells or pluripotent stem cells, such as embryonic stem cells (ES cells) or iPS.

The phrase "embryonic stem cells" or "ES cells" refers to embryonic cells which are capable of differentiating into cells of all three embryonic germ layers (i.e., endoderm, ectoderm and mesoderm), or remaining in an undifferentiated state. The phrase "embryonic stem cells" may comprise cells which are obtained from the embryonic tissue formed after gestation (e.g., blastocyst) before implantation of the embryo (i.e., a pre-implantation blastocyst), extended blastocyst cells (EBCs) which are obtained from a post-implantation/pre-gastrulation stage blastocyst (see WO2006/040763), embryonic germ (EG) cells which are obtained from the genital tissue of a fetus any time during gestation, preferably before 10 weeks of gestation, and cells originating from an unfertilized ova which are stimulated by parthenogenesis (parthenotes).

Embryonic stem cells (e.g., human ESCs) originating from an unfertilized ova stimulated by parthenogenesis (parthenotes) are known in the art (e.g., Zhenyu Lu et al., 2010. J. Assist Reprod. Genet. 27:285-291; "Derivation and long-term culture of human parthenogenetic embryonic stem cells using human foreskin feeders", which is fully incorporated herein by reference). Parthenogenesis refers to the initiation of cell division by activation of ova in the absence of sperm cells, for example using electrical or chemical stimulation. The activated ovum (parthenote) is capable of developing into a primitive embryonic structure (called a blastocyst) but cannot develop to term as the cells are pluripotent, meaning that they cannot develop the necessary extra-embryonic tissues (such as amniotic fluid) needed for a viable human foetus.

Another method for preparing ES cells is described in Chung et al., Cell Stem Cell, Volume 2, Issue 2, 113-117, 7 Feb. 2008. This method comprises removing a single cell from an embryo during an in vitro fertilization process. The embryo is not destroyed in this process.

Induced pluripotent stem cells (iPS; embryonic-like stem cells), are cells obtained by de-differentiation of adult somatic cells which are endowed with pluripotency (i.e., being capable of differentiating into the three embryonic germ cell layers, i.e., endoderm, ectoderm and mesoderm). According to some embodiments of the invention, such cells are obtained from a differentiated tissue (e.g., a somatic tissue such as skin) and undergo de-differentiation by genetic manipulation, which re-program the cell to acquire embryonic stem cells characteristics. According to some embodiments of the invention, the induced pluripotent stem cells are formed by inducing the expression of Oct-4, Sox2, Kfl4 and/or c-Myc in a somatic stem cell.

According to one embodiment, the pluripotent stem cells are not a result of embryo destruction.

The phrase "adult stem cells" (also called "tissue stem cells" or a stem cell from a somatic tissue) refers to any stem cell derived from a somatic tissue [of either a postnatal or prenatal animal (especially the human)]. The adult stem cell is generally thought to be a multipotent stem cell, capable of differentiation into multiple cell types. Adult stem cells can be derived from any adult, neonatal or fetal tissue such as adipose tissue, skin, kidney, liver, prostate, pancreas, intestine, bone marrow and placenta.

Cultured embryonic stem cells of the present invention can be differentiated into restricted developmental lineage cells (e.g. progenitor cells).

Differentiation of stem cells can be initiated by allowing overgrowth of undifferentiated human ES cells in suspension culture forming embryoid bodies or by plating ES cells under conditions that promote differentiation in a particular manner.

It will be appreciated that the culturing conditions suitable for the differentiation and expansion of the isolated lineage specific cells include various tissue culture medium, growth factors, antibiotic, amino acids and the like and it is within the capability of one skilled in the art to determine which conditions should be applied in order to expand and differentiate particular cell types and/or cell lineages [reviewed in Fijnvandraat A C, et al., Cardiovasc Res. 2003; 58: 303-12; Sachinidis A, et al., Cardiovasc Res. 2003; 58: 278-91; Stavridis M P and Smith A G, 2003; Biochem Soc Trans. 31(Pt 1): 45-9].

For example, embryonic stem cells can be induced to differentiate in vitro into cardiac progenitor cells [Engels et al., Stem Cells (2014) 00:000-000]. Several factors have been shown to enrich cardiac differentiation such as insulin and insulin-like growth factors (IGF1/2).

Embryonic stem cells have also been induced to differentiate into neural progenitor cells [Kim et al., Dev Biol. (2009) 15; 328(2): 456-471; U.S. Pat. No. 5,851,832]. For their generation, the medium typically includes any of the following factors or medium constituents in an effective combination: retinoic acid (RA), platelet-derived growth factor (PDGF), nerve growth factor (NGF), a macrophage inflammatory protein (MIP), tumor necrosis factor alpha (TNFα) and epidermal growth factor (EGF).

Human pluripotent stem cells have also been induced to differentiate into lung and airway progenitor cells [Huang et al., Nature Protocols 10, 413-425 (2015)]. Thus, the stem cells can be cultured in the presence of high concentrations of activin A.

Subsequently, lung-biased anterior foregut endoderm (AFE) is specified by sequential inhibition of bone morphogenetic protein (BMP), transforming growth factor-β (TGF-β) and Wnt signaling. AFE is then ventralized by applying Wnt, BMP, fibroblast growth factor (FGF) and retinoic acid (RA) signaling to obtain lung and airway progenitors.

Embryonic stem cells have also been induced to differentiate into pancreatic progenitor cells [Chen et al., Cell Biol Int. (2008) 32(4):456-61]. The method utilizes an in vitro differentiation system with a reduced serum concentration plus nicotinamide to generate early pancreatic progenitor cells from embryonic stem cells. Additional methods are described, for example, by Kahan et al., Diabetes (2003) 52(8): 2016-2024.

Embryonic stem cells have also been induced to differentiate into nephric progenitor cells [Takasato et al., Nature Cell Biology 16, 118-126 (2014)] by directed the differentiation of human embryonic stem cells (hESCs) through posterior primitive streak and intermediate mesoderm (IM) under fully chemically defined monolayer culture conditions using growth factors used during normal embryogenesis.

Embryonic stem cells have also been induced to differentiate into hepatic progenitor cells [Pei et al., Tissue Eng Part C Methods. (2009) 15(1): 95-104]. Generating early hepatocytic lineage cells from hES cells was carried out using four sequential inducing steps as follows: first, embryoid bodies (EBs) were generated by growing hES cells in suspension; second, EBs were lineage restricted to definitive endoderm with human activin A; third, cells were differentiated further by co-culturing with human fetal liver stromal cells (hFLSCs) made transgenic to stably release basic fibroblast growth factor (bFGF); fourth, treating the cells with soluble signals comprised of hFLSC-derived bFGF, hepatocyte growth factor, oncostatin M, and dexamethasone.

Differentiation of stem cells can also be directed by genetic modification. For example expression of four factors GATA-4 TBX5, NKX2.5 and BAF60c was shown to induce differentiation of hESCs into cardiac progenitors [Dixon et al., Molecular Therapy (2011) 19 9, 1695-1703].

Monitoring the Differentiation Stage of Embryonic Stem Cells

During the culturing step the stem cells are further monitored for their differentiation state. Cell differentiation can be determined upon examination of cell or tissue-specific markers which are known to be indicative of differentiation. For example, primate ES cells may express the stage-specific embryonic antigen (SSEA) 4, the tumour-rejecting antigen (TRA)-1-60 and TRA-1-81.

Tissue/cell specific markers can be detected using immunological techniques well known in the art [Thomson J A et al., (1998). Science 282: 1145-7]. Examples include, but are not limited to, flow cytometry for membrane-bound markers, immunohistochemistry for extracellular and intracellular markers and enzymatic immunoassay, for secreted molecular markers.

Determination of ES cell differentiation can also be effected via measurements of alkaline phosphatase activity. Undifferentiated human ES cells have alkaline phosphatase activity which can be detected by fixing the cells with 4% paraformaldehyde and developing with the Vector Red substrate kit according to manufacturer's instructions (Vector Laboratories, Burlingame, Calif., USA).

The pluripotency of embryonic stem cells can be monitored in vitro by the formation of embryoid bodies (EBs) as well as in vivo via the formation of teratomas.

Teratomas

The pluripotent capacity of the ES cell line can also be confirmed by injecting cells into SCID mice [Evans M J and Kaufman M (1983). Pluripotential cells grown directly from normal mouse embryos. Cancer Surv. 2: 185-208], which upon injection form teratomas. Teratomas are fixed using 4% paraformaldehyde and histologically examined for the three germ layers (i.e., endoderm, mesoderm and ectoderm).

In addition to monitoring a differentiation state, stem cells are often also being monitored for karyotype, in order to verify cytological euploidity, wherein all chromosomes are present and not detectably altered during culturing. Cultured stem cells can be karyotyped using a standard Giemsa staining and compared to published karyotypes of the corresponding species.

According to the present invention, the cell suspension of progenitor cells comprises viable cells. Cell viability may be monitored using any method known in the art, as for example, using a cell viability assay (e.g. MultiTox Multiplex Assay available from Promega), Flow cytometry, Trypan blue, etc.

Typically, the progenitor cells are immediately used for transplantation. However, in situations in which the cells are to be maintained in suspension prior to transplantation, e.g. for 1-12 hours, the cells may be cultured in a culture medium which is capable of supporting their viability. Such a culture medium can be a water-based medium which includes a combination of substances such as salts, nutrients, minerals, vitamins, amino acids, nucleic acids, proteins such as cytokines, growth factors and hormones, all of which are needed for maintaining the progenitor cells in an viable state. For example, a culture medium according to this aspect of the present invention can be a synthetic tissue culture medium such as RPMI-1640 (Life Technologies, Israel), Ko-DMEM (Gibco-Invitrogen Corporation products, Grand Island, N.Y., USA), DMEM/F12 (Biological Industries, Beit Haemek, Israel), Mab ADCB medium (HyClone, Utah, USA) or DMEM/F12 (Biological Industries, Biet Haemek, Israel) supplemented with the necessary additives. Preferably, all ingredients included in the culture medium of the present invention are substantially pure, with a tissue culture grade.

The progenitor cells may also be stored under appropriate conditions (typically by freezing) to keep the cells (e.g. progenitor cells) alive and functioning for use in transplantation. According to one embodiment, the progenitor cells are stored as cryopreserved populations. Other preservation methods are described in U.S. Pat. Nos. 5,656,498, 5,004,681, 5,192,553, 5,955,257, and 6,461,645. Methods for banking stem cells are described, for example, in U.S. Patent Application Publication No. 2003/0215942.

The progenitor cells may also be expanded, e.g. ex vivo. The term "expanded" refers to increasing the cell number by at least about 2 fold, 4 fold, 10 fold, 20 fold, 40 fold, 80 fold, 120 fold, by 140 fold or more.

According to one embodiment, the progenitor cells are expanded in culture (e.g. ex-vivo expanded) from fetal cells (e.g. fetal pulmonary cells). The fetal cells may be of a gestational age as discussed above (e.g. 16-25 weeks, e.g. 20-22 weeks, of human gestation).

According to one embodiment, the progenitor cells are expanded in culture (e.g. ex-vivo expanded) from adult cells (e.g. adult pulmonary cells).

Thus, for example, the progenitor cells may be obtained from a fetal tissue (e.g. fetal lung tissue) and cultured in tissue culture plates in the presence of a cell medium (e.g. feeder medium, e.g. iMEF) and optionally with additional growth factors and/or cytokines (e.g. epithelial growth factor and Rho-associated kinase (ROCK) inhibitor) for several days (e.g. 7-14 days, such as 9 days), until a suitable number of cells is obtained. Measuring the number of cells (e.g. viable cells) can be carried out using any method known to one of skill in the art, e.g. by a counting chamber, by FACs analysis, or by a spectrophotometer.

The progenitor cells may comprise cells obtained from more than one cell donor.

According to one embodiment, the progenitor cells comprise a heterogeneous population of cells (e.g. unseparated population of cells).

According to another embodiment of the present invention, the progenitor cells comprise a purified population of cells. Accordingly, the progenitor cells may be treated to remove specific population of cells therefrom (e.g. removal of a subpopulation). This subpopulation can then be administered to a subject (as discussed below) or discarded (and the rest of the cell population used, as discussed below).

According to one embodiment of the present invention, the progenitor cells comprise a purified population of epithelial, endothelial and/or mesenchymal cells.

Purification of specific cell types may be carried out by any method known to one of skill in the art, as for example, by affinity based purification (e.g. such as by the use of MACS beads, FACS sorter and/or capture ELISA labeling) using specific antibodies which recognize any specific cell markers (e.g. CD31, CD34, CD41, CD45, CD48, CD105, CD150, CD271, CD326, MUCIN-1, PODOPLANIN).

Administration of the progenitor cells in suspension to the subject may be effected in numerous ways, depending on various parameters, such as, for example, the type, stage or severity of the disease to be treated, the physical or physiological parameters specific to the individual subject, and/or the desired therapeutic outcome. For example, depending on the application and purpose administration of the progenitor cells in suspension may be effected by a route selected from the group consisting of intratracheal, intrabronchial, intraalveolar, intravenous, intraperitoneal, intranasal, subcutaneous, intramedullary, intrathecal, intraventricular, intracardiac, intramuscular, intraserosal, intramucosal, transmucosal, transnasal, rectal and intestinal.

According to one embodiment, administering is effected by an intravenous route.

According to one embodiment, administering is effected by an intratracheal route.

Alternatively, administration of the progenitor cells to the subject may be effected by administration thereof into various suitable anatomical locations so as to be of therapeutic effect. Thus, depending on the application and purpose, the progenitor cells may be administered into a homotopic anatomical location (a normal anatomical location for the organ or tissue type of the cells), or into an ectopic anatomical location (an abnormal anatomical location for the organ or tissue type of the cells).

Accordingly, depending on the application and purpose, the progenitor cells may be advantageously implanted (e.g. transplanted) under the renal capsule, or into the kidney, the testicular fat, the sub cutis, the omentum, the portal vein, the liver, the spleen, the heart cavity, the heart, the chest cavity, the lung, the pancreas, the skin and/or the intra abdominal space.

For example, for the treatment of a liver disease or condition (e.g. liver dysfunction or failure), progenitor cells may be transplanted into the liver, the portal vein, the renal capsule, the sub-cutis, the omentum, the spleen, and the intra-abdominal space. Similarly, for the treatment of a pancreatic disease or condition (e.g. diabetes) transplanting progenitor cells according to the present invention may be advantageously effected by transplanting the cells into the portal vein, the liver, the pancreas, the testicular fat, the sub-cutis, the omentum, an intestinal loop (the subserosa of a U loop of the small intestine) and/or the intra-abdominal space. For treatment of a pulmonary disease or condition, the progenitor cells in suspension may be administered into the lung, under the renal capsule, the liver, the portal vein, the sub-cutis, the omentum, the spleen, the intra-abdominal space, the pancreas and/or the testicular fat. For treatment of a gastrointestinal disease or condition, the progenitor cells of the present invention may be administered into the liver, the portal vein, the renal capsule, the sub-cutis, the omentum, the spleen, the intra-abdominal space, the pancreas, the testicular fat and/or an intestinal loop (the subserosa of a U loop of the small intestine). Likewise, transplantation of progenitor cells may be carried out for the purpose of treating recipients suffering from, for example, renal failure, heart failure or brain damage.

According to one embodiment, transplantation of the progenitor cells results in regenerating of structural/functional tissue.

According to one embodiment, transplantation of the progenitor cells results in generation of a chimeric tissue (i.e. a tissue comprising cells from genetically distinct origins).

Following transplantation of the progenitor cells into the subject according to the present teachings, it is advisable, according to standard medical practice, to monitor the growth functionality and immunocompatibility of the transplanted cells according to any one of various standard art techniques. For example, the functionality of regenerated pulmonary tissues may be monitored following transplantation by standard pulmonary function tests (as discussed in detail hereinabove, e.g. analysis of functional properties of the developing implants, as indicated by the ability to synthesize surfactant, detectable by staining for surfactant protein C (sp-C) and the ability to transport ions, as indicated by staining for CFTR-cystic fibrosis transmembrane regulator). Likewise, the functionality of regenerated hepatic, cardiac, nephritic, brain, ovarian and pancreatic tissues may be monitored following transplantation by standard function tests as described in detail hereinabove.

The method of the present invention may be applied to treat any disease or condition in which transplantation of progenitor cells may be advantageous.

According to one embodiment, the disease is a malignant disease, a disease of the central nervous system, a gastrointestinal disease, a cardiovascular disease, a hepatic disease, a nephric disease, a pancreatic disease, a pulmonary disease, an infectious disease, an inflammatory disease, an immunodeficiency and an autoimmune disease.

Cancerous Diseases

Malignant diseases (also termed cancers) which can be treated by the method of some embodiments of the invention can be any solid or non-solid tumor and/or tumor metastasis.

Examples of cancer include, but are not limited to, carcinoma, lymphoma, blastoma, sarcoma, and leukemia. More particular examples of such cancers include squamous cell cancer, soft-tissue sarcoma, Kaposi's sarcoma, melanoma, lung cancer (including small-cell lung cancer, non-small-cell lung cancer, adenocarcinoma of the lung, and squamous carcinoma of the lung), cancer of the peritoneum, hepatocellular cancer, gastric or stomach cancer (including gastrointestinal cancer), pancreatic cancer, glioblastoma, cervical cancer, ovarian cancer, liver cancer, bladder cancer, hepatoma, breast cancer, colon cancer, colorectal cancer, rectal cancer, endometrial or uterine carcinoma, carcinoid carcinoma, salivary gland carcinoma, kidney or renal cancer, liver cancer, prostate cancer, vulval cancer, thyroid cancer, hepatic carcinoma, mesothelioma, multiple myeloma, post-transplant lymphoproliferative disorder (PTLD), and various types of head and neck cancer (e.g. brain tumor). The cancerous conditions amenable for treatment of the invention include metastatic cancers.

According to one embodiment, the malignant disease is a hematological malignancy. Exemplary hematological malignancies include, but are not limited to, leukemia [e.g., acute lymphatic, acute lymphoblastic, acute lymphoblastic pre-B cell, acute lymphoblastic T cell leukemia, acute—megakaryoblastic, monocytic, acute myelogenous, acute myeloid, acute myeloid with eosinophilia, B cell, basophilic, chronic myeloid, chronic, B cell, eosinophilic, Friend, granulocytic or myelocytic, hairy cell, lymphocytic, megakaryoblastic, monocytic, monocytic-macrophage, myeloblastic, myeloid, myelomonocytic, plasma cell, pre-B cell, promyelocytic, subacute, T cell, lymphoid neoplasm, predisposition to myeloid malignancy, acute nonlymphocytic leukemia, T-cell acute lymphocytic leukemia (T-ALL) and B-cell chronic lymphocytic leukemia (B-CLL)] and lymphoma [e.g., Hodgkin's disease, non-Hodgkin's lymphoma, Burkitt, cutaneous T cell, histiocytic, lymphoblastic, T cell, thymic, B cell, including low grade/follicular; small lymphocytic (SL) NHL; intermediate grade/follicular NHL; intermediate grade diffuse NHL; high grade immunoblastic NHL; high grade lymphoblastic NHL; high-grade small non-cleaved cell NHL; bulky disease NHL; mantle cell lymphoma; AIDS-related lymphoma; and Waldenstrom's Macroglobulinemia].

According to a specific embodiment, the malignant disease is a leukemia, a lymphoma, a myeloma, a melanoma, a sarcoma, a neuroblastoma, a colon cancer, a colorectal cancer, a breast cancer, an ovarian cancer, an esophageal cancer, a synovial cell cancer, a liver cancer or a pancreatic cancer.

Inflammatory Diseases—

Include, but are not limited to, chronic inflammatory diseases and acute inflammatory diseases.

Inflammatory Diseases Associated with Hypersensitivity

Examples of hypersensitivity include, but are not limited to, Type I hypersensitivity, Type II hypersensitivity, Type III hypersensitivity, Type IV hypersensitivity, immediate hypersensitivity, antibody mediated hypersensitivity, immune complex mediated hypersensitivity, T lymphocyte mediated hypersensitivity and DTH.

Type I or immediate hypersensitivity, such as asthma.

Type II hypersensitivity include, but are not limited to, rheumatoid diseases, rheumatoid autoimmune diseases, rheumatoid arthritis (Krenn V. et al., Histol Histopathol 2000 July; 15 (3):791), spondylitis, ankylosing spondylitis (Jan Voswinkel et al., Arthritis Res 2001; 3 (3): 189), systemic diseases, systemic autoimmune diseases, systemic lupus erythematosus (Erikson J. et al., Immunol Res 1998; 17 (1-2):49), sclerosis, systemic sclerosis (Renaudineau Y. et al., Clin Diagn Lab Immunol. 1999 March; 6 (2):156); Chan O T. et al., Immunol Rev 1999 June; 169:107), glandular diseases, glandular autoimmune diseases, pancreatic autoimmune diseases, diabetes, Type I diabetes (Zimmet P. Diabetes Res Clin Pract 1996 October; 34 Suppl:S125), thyroid diseases, autoimmune thyroid diseases, Graves' disease (Orgiazzi J. Endocrinol Metab Clin North Am 2000 June; 29 (2):339), thyroiditis, spontaneous autoimmune thyroiditis (Braley-Mullen H. and Yu S, J Immunol 2000 Dec. 15; 165 (12):7262), Hashimoto's thyroiditis (Toyoda N. et al., Nippon Rinsho 1999 August; 57 (8):1810), myxedema, idiopathic myxedema (Mitsuma T. Nippon Rinsho. 1999 August; 57 (8):1759); autoimmune reproductive diseases, ovarian diseases, ovarian autoimmunity (Garza K M. et al., J Reprod Immunol 1998 February; 37 (2):87), autoimmune anti-sperm infertility (Diekman A B. et al., Am J Reprod Immunol. 2000 March; 43 (3):134), repeated fetal loss (Tincani A. et al., Lupus 1998; 7 Suppl 2:S107-9), neurodegenerative diseases, neurological diseases, neurological autoimmune diseases, multiple sclerosis (Cross A H. et al., J Neuroimmunol 2001 Jan. 1; 112 (1-2):1), Alzheimer's disease (Oron L. et al., J Neural Transm Suppl. 1997; 49:77), myasthenia gravis (Infante A J. And Kraig E, Int Rev Immunol 1999; 18 (1-2):83), motor neuropathies (Kornberg A J. J Clin Neurosci. 2000 May; 7 (3):191), Guillain-Barre syndrome, neuropathies and autoimmune neuropathies (Kusunoki S. Am J Med Sci. 2000 April; 319 (4):234), myasthenic diseases, Lambert-Eaton myasthenic syndrome (Takamori M. Am J Med Sci. 2000 April; 319 (4):204), paraneoplastic neurological diseases, cerebellar atrophy, paraneoplastic cerebellar atrophy, non-paraneoplastic stiff man syndrome, cerebellar atrophies, progressive cerebellar atrophies, encephalitis, Rasmussen's encephalitis, amyotrophic lateral sclerosis, Sydenham chorea, Gilles de la Tourette syndrome, polyendocrinopathies, autoimmune polyendocrinopathies (Antoine J C. and Honnorat J. Rev Neurol (Paris) 2000 January; 156 (1):23); neuropathies, dysimmune neuropathies (Nobile-Orazio E. et al., Electroencephalogr Clin Neurophysiol Suppl 1999; 50:419); neuromyotonia, acquired neuromyotonia, arthrogryposis multiplex congenita (Vincent A. et al., Ann N Y Acad Sci. 1998 May 13; 841:482), cardiovascular diseases, cardiovascular autoimmune diseases, atherosclerosis (Matsuura E. et al., Lupus. 1998; 7 Suppl 2:S135), myocardial infarction (Vaarala O. Lupus. 1998; 7 Suppl 2:S132), thrombosis (Tincani A. et al., Lupus. 1998; 7 Suppl 2:S107-9), granulomatosis, Wegener's granulomatosis, arteritis, Takayasu's arteritis and Kawasaki syndrome (Praprotnik S. et al., Wien Klin Wochenschr 2000 Aug. 25; 112 (15-16):660); anti-factor VIII autoimmune disease (Lacroix-Desmazes S. et al., Semin Thromb Hemost. 2000; 26 (2):157); vasculitides, necrotizing small vessel vasculitis, microscopic polyangiitis, Churg and Strauss syndrome, glomerulonephritis, pauci-immune focal necrotizing glomerulonephritis, crescentic glomerulonephritis (Noel L H. Ann Med Internet (Paris). 2000 May; 151 (3):178); antiphospholipid syndrome (Flamholz R. et al., J Clin Apheresis 1999; 14 (4):171); heart failure, agonist-like β-adrenoceptor antibodies in heart failure (Wallukat G. et al., Am J Cardiol. 1999 Jun. 17; 83 (12A):75H), thrombocytopenic purpura (Moccia F. Ann Ital Med Int. 1999 April-June; 14 (2):114); hemolytic anemia, autoimmune hemolytic anemia (Efremov D G. et al., Leuk Lymphoma 1998 January; 28 (3-4):285), gastrointestinal diseases, autoimmune diseases of the gastrointestinal tract, intestinal diseases, chronic inflammatory intestinal disease (Garcia Herola A. et al., Gastroenterol Hepatol. 2000 January; 23 (1):16), celiac disease (Landau Y E. and Shoenfeld Y. Harefuah 2000 Jan. 16; 138 (2):122), autoimmune diseases of the musculature, myositis, autoimmune myositis, Sjogren's syndrome (Feist E. et al., Int Arch Allergy Immunol 2000 September; 123 (1):92); smooth muscle autoimmune disease (Zauli D. et al., Biomed Pharmacother 1999 June; 53 (5-6):234), hepatic diseases, hepatic autoimmune diseases, autoimmune hepatitis (Manns M P. J Hepatol 2000

August; 33 (2):326) and primary biliary cirrhosis (Strassburg C P. et al., Eur J Gastroenterol Hepatol. 1999 June; 11 (6):595).

Type IV or T cell mediated hypersensitivity, include, but are not limited to, rheumatoid diseases, rheumatoid arthritis (Tisch R, McDevitt H O. Proc Natl Acad Sci USA 1994 Jan. 18; 91 (2):437), systemic diseases, systemic autoimmune diseases, systemic lupus erythematosus (Datta S K., Lupus 1998; 7 (9):591), glandular diseases, glandular autoimmune diseases, pancreatic diseases, pancreatic autoimmune diseases, Type 1 diabetes (Castano L. and Eisenbarth G S. Ann. Rev. Immunol. 8:647); thyroid diseases, autoimmune thyroid diseases, Graves' disease (Sakata S. et al., Mol Cell Endocrinol 1993 March; 92 (1):77); ovarian diseases (Garza K M. et al., J Reprod Immunol 1998 February; 37 (2):87), prostatitis, autoimmune prostatitis (Alexander R B. et al., Urology 1997 December; 50 (6):893), polyglandular syndrome, autoimmune polyglandular syndrome, Type I autoimmune polyglandular syndrome (Hara T. et al., Blood. 1991 Mar. 1; 77 (5):1127), neurological diseases, autoimmune neurological diseases, multiple sclerosis, neuritis, optic neuritis (Soderstrom M. et al., J Neurol Neurosurg Psychiatry 1994 May; 57 (5):544), myasthenia gravis (Oshima M. et al., Eur J Immunol 1990 December; 20 (12): 2563), stiff-man syndrome (Hiemstra H S. et al., Proc Natl Acad Sci USA 2001 Mar. 27; 98 (7):3988), cardiovascular diseases, cardiac autoimmunity in Chagas' disease (Cunha-Neto E. et al., J Clin Invest 1996 Oct. 15; 98 (8):1709), autoimmune thrombocytopenic purpura (Semple J W. et al., Blood 1996 May 15; 87 (10):4245), anti-helper T lymphocyte autoimmunity (Caporossi A P. et al., Viral Immunol 1998; 11 (1):9), hemolytic anemia (Sallah S. et al., Ann Hematol 1997 March; 74 (3):139), hepatic diseases, hepatic autoimmune diseases, hepatitis, chronic active hepatitis (Franco A. et al., Clin Immunol Immunopathol 1990 March; 54 (3):382), biliary cirrhosis, primary biliary cirrhosis (Jones D E. Clin Sci (Colch) 1996 November; 91 (5):551), nephric diseases, nephric autoimmune diseases, nephritis, interstitial nephritis (Kelly C J. J Am Soc Nephrol 1990 August; 1 (2):140), connective tissue diseases, ear diseases, autoimmune connective tissue diseases, autoimmune ear disease (Yoo T J. et al., Cell Immunol 1994 August; 157 (1):249), disease of the inner ear (Gloddek B. et al., Ann N Y Acad Sci 1997 Dec. 29; 830:266), skin diseases, cutaneous diseases, dermal diseases, bullous skin diseases, pemphigus vulgaris, bullous pemphigoid and pemphigus foliaceus.

Examples of delayed type hypersensitivity include, but are not limited to, contact dermatitis and drug eruption.

Examples of types of T lymphocyte mediating hypersensitivity include, but are not limited to, helper T lymphocytes and cytotoxic T lymphocytes.

Examples of helper T lymphocyte-mediated hypersensitivity include, but are not limited to, $T_h1$ lymphocyte mediated hypersensitivity and $T_h2$ lymphocyte mediated hypersensitivity.

Autoimmune Diseases

Include, but are not limited to, cardiovascular diseases, rheumatoid diseases, glandular diseases, gastrointestinal diseases, cutaneous diseases, hepatic diseases, neurological diseases, muscular diseases, nephric diseases, diseases related to reproduction, connective tissue diseases and systemic diseases.

Examples of autoimmune cardiovascular diseases include, but are not limited to atherosclerosis (Matsuura E. et al., Lupus. 1998; 7 Suppl 2:S135), myocardial infarction (Vaarala O. Lupus. 1998; 7 Suppl 2:S132), thrombosis (Tincani A. et al., Lupus 1998; 7 Suppl 2:S107-9), Wegener's granulomatosis, Takayasu's arteritis, Kawasaki syndrome (Praprotnik S. et al., Wien Klin Wochenschr 2000 Aug. 25; 112 (15-16):660), anti-factor VIII autoimmune disease (Lacroix-Desmazes S. et al., Semin Thromb Hemost. 2000; 26 (2):157), necrotizing small vessel vasculitis, microscopic polyangiitis, Churg and Strauss syndrome, pauci-immune focal necrotizing and crescentic glomerulonephritis (Noel L H. Ann Med Internet (Paris). 2000 May; 151 (3):178), antiphospholipid syndrome (Flamholz R. et al., J Clin Apheresis 1999; 14 (4):171), antibody-induced heart failure (Wallukat G. et al., Am J Cardiol. 1999 Jun. 17; 83 (12A):75H), thrombocytopenic purpura (Moccia F. Ann Ital Med Int. 1999 April-June; 14 (2):114; Semple J W. et al., Blood 1996 May 15; 87 (10):4245), autoimmune hemolytic anemia (Efremov D G. et al., Leuk Lymphoma 1998 January; 28 (3-4):285; Sallah S. et al., Ann Hematol 1997 March; 74 (3):139), cardiac autoimmunity in Chagas' disease (Cunha-Neto E. et al., J Clin Invest 1996 Oct. 15; 98 (8):1709) and anti-helper T lymphocyte autoimmunity (Caporossi A P. et al., Viral Immunol 1998; 11 (1):9).

Examples of autoimmune rheumatoid diseases include, but are not limited to rheumatoid arthritis (Krenn V. et al., Histol Histopathol 2000 July; 15 (3):791; Tisch R, McDevitt H O. Proc Natl Acad Sci units S A 1994 Jan. 18; 91 (2):437) and ankylosing spondylitis (Jan Voswinkel et al., Arthritis Res 2001; 3 (3): 189).

Examples of autoimmune glandular diseases include, but are not limited to, pancreatic disease, Type I diabetes, thyroid disease, Graves' disease, thyroiditis, spontaneous autoimmune thyroiditis, Hashimoto's thyroiditis, idiopathic myxedema, ovarian autoimmunity, autoimmune anti-sperm infertility, autoimmune prostatitis and Type I autoimmune polyglandular syndrome. diseases include, but are not limited to autoimmune diseases of the pancreas, Type 1 diabetes (Castano L. and Eisenbarth G S. Ann. Rev. Immunol. 8:647; Zimmet P. Diabetes Res Clin Pract 1996 October; 34 Suppl: S125), autoimmune thyroid diseases, Graves' disease (Orgiazzi J. Endocrinol Metab Clin North Am 2000 June; 29 (2):339; Sakata S. et al., Mol Cell Endocrinol 1993 March; 92 (1):77), spontaneous autoimmune thyroiditis (Braley-Mullen H. and Yu S, J Immunol 2000 Dec. 15; 165 (12): 7262), Hashimoto's thyroiditis (Toyoda N. et al., Nippon Rinsho 1999 August; 57 (8):1810), idiopathic myxedema (Mitsuma T. Nippon Rinsho. 1999 August; 57 (8):1759), ovarian autoimmunity (Garza K M. et al., J Reprod Immunol 1998 February; 37 (2):87), autoimmune anti-sperm infertility (Diekman A B. et al., Am J Reprod Immunol. 2000 March; 43 (3):134), autoimmune prostatitis (Alexander R B. et al., Urology 1997 December; 50 (6):893) and Type I autoimmune polyglandular syndrome (Hara T. et al., Blood. 1991 Mar. 1; 77 (5):1127).

Examples of autoimmune gastrointestinal diseases include, but are not limited to, chronic inflammatory intestinal diseases (Garcia Herola A. et al., Gastroenterol Hepatol. 2000 January; 23 (1):16), celiac disease (Landau Y E. and Shoenfeld Y. Harefuah 2000 Jan. 16; 138 (2):122), colitis, ileitis and Crohn's disease.

Examples of autoimmune cutaneous diseases include, but are not limited to, autoimmune bullous skin diseases, such as, but are not limited to, pemphigus vulgaris, bullous pemphigoid and pemphigus foliaceus.

Examples of autoimmune hepatic diseases include, but are not limited to, hepatitis, autoimmune chronic active hepatitis (Franco A. et al., Clin Immunol Immunopathol 1990 March; 54 (3):382), primary biliary cirrhosis (Jones D E. Clin Sci (Colch) 1996 November; 91 (5):551; Strassburg C P. et al., Eur J Gastroenterol Hepatol. 1999 June; 11 (6):595) and autoimmune hepatitis (Manns M P. J Hepatol 2000 August; 33 (2):326).

Examples of autoimmune neurological diseases include, but are not limited to, multiple sclerosis (Cross A H. et al., J Neuroimmunol 2001 Jan. 1; 112 (1-2):1), Alzheimer's disease (Oron L. et al., J Neural Transm Suppl. 1997; 49:77), myasthenia gravis (Infante A J. And Kraig E, Int Rev Immunol 1999; 18 (1-2):83; Oshima M. et al., Eur J Immunol 1990 December; 20 (12):2563), neuropathies, motor neuropathies (Kornberg A J. J Clin Neurosci. 2000 May; 7 (3):191); Guillain-Barre syndrome and autoimmune neuropathies (Kusunoki S. Am J Med Sci. 2000 April; 319 (4):234), myasthenia, Lambert-Eaton myasthenic syndrome (Takamori M. Am J Med Sci. 2000 April; 319 (4):204); paraneoplastic neurological diseases, cerebellar atrophy, paraneoplastic cerebellar atrophy and stiff-man syndrome (Hiemstra H S. et al., Proc Natl Acad Sci units S A 2001 Mar. 27; 98 (7):3988); non-paraneoplastic stiff man syndrome, progressive cerebellar atrophies, encephalitis, Rasmussen's encephalitis, amyotrophic lateral sclerosis, Sydenham chorea, Gilles de la Tourette syndrome and autoimmune polyendocrinopathies (Antoine J C. and Honnorat J. Rev Neurol (Paris) 2000 January; 156 (1):23); dysimmune neuropathies (Nobile-Orazio E. et al., Electroencephalogr Clin Neurophysiol Suppl 1999; 50:419); acquired neuromyotonia, arthrogryposis multiplex congenita (Vincent A. et al., Ann N Y Acad Sci. 1998 May 13; 841:482), neuritis, optic neuritis (Soderstrom M. et al., J Neurol Neurosurg Psychiatry 1994 May; 57 (5):544) and neurodegenerative diseases.

Examples of autoimmune muscular diseases include, but are not limited to, myositis, autoimmune myositis and primary Sjogren's syndrome (Feist E. et al., Int Arch Allergy Immunol 2000 September; 123 (1):92) and smooth muscle autoimmune disease (Zauli D. et al., Biomed Pharmacother 1999 June; 53 (5-6):234).

Examples of autoimmune nephric diseases include, but are not limited to, nephritis and autoimmune interstitial nephritis (Kelly C J. J Am Soc Nephrol 1990 August; 1 (2):140).

Examples of autoimmune diseases related to reproduction include, but are not limited to, repeated fetal loss (Tincani A. et al., Lupus 1998; 7 Suppl 2:S107-9).

Examples of autoimmune connective tissue diseases include, but are not limited to, ear diseases, autoimmune ear diseases (Yoo T J. et al., Cell Immunol 1994 August; 157 (1):249) and autoimmune diseases of the inner ear (Gloddek B. et al., Ann N Y Acad Sci 1997 Dec. 29; 830:266).

Examples of autoimmune systemic diseases include, but are not limited to, systemic lupus erythematosus (Erikson J. et al., Immunol Res 1998; 17 (1-2):49) and systemic sclerosis (Renaudineau Y. et al., Clin Diagn Lab Immunol. 1999 March; 6 (2):156); Chan O T. et al., Immunol Rev 1999 June; 169:107).

Infectious Diseases

Examples of infectious diseases include, but are not limited to, chronic infectious diseases, subacute infectious diseases, acute infectious diseases, viral diseases, bacterial diseases, protozoan diseases, parasitic diseases, fungal diseases, mycoplasma diseases and prion diseases.

Specific types of viral pathogens causing infectious diseases treatable according to the teachings of the present invention include, but are not limited to, retroviruses, circoviruses, parvoviruses, papovaviruses, adenoviruses, herpesviruses, iridoviruses, poxviruses, hepadnaviruses, picornaviruses, caliciviruses, togaviruses, flaviviruses, reoviruses, orthomyxoviruses, paramyxoviruses, rhabdoviruses, bunyaviruses, coronaviruses, arenaviruses, and filoviruses.

Specific examples of viral infections which may be treated according to the teachings of the present invention include, but are not limited to, human immunodeficiency virus (HIV)-induced acquired immunodeficiency syndrome (AIDS), influenza, rhinoviral infection, viral meningitis, Epstein-Barr virus (EBV) infection, hepatitis A, B or C virus infection, measles, papilloma virus infection/warts, cytomegalovirus (CMV) infection, Herpes simplex virus infection, yellow fever, Ebola virus infection and rabies.

Immunodeficiency Diseases

Examples of immunodeficiency diseases which can be treated by transplantation of a progenitor cells the present invention include, but are not limited to, acquired immunodeficiency syndrome (AIDS) caused by human immunodeficiency virus (HIV), severe combined immunodeficiencies (SCID), such as adenosine deaminase (ADA) deficiency, and immunodeficiencies resulting from therapeutic myeloreduction/myeloablation, such as in the context of therapy of cancers, such as hematological malignancies.

Pulmonary Diseases

Exemplary pulmonary diseases, include but are not limited to, cystic fibrosis, emphysema, asbestosis, chronic obstructive pulmonary disease (COPD), pulmonary fibrosis, idiopatic pulmonary fibrosis, pulmonary hypertension, lung cancer, sarcoidosis, acute lung injury (adult respiratory distress syndrome), respiratory distress syndrome of prematurity, chronic lung disease of prematurity (bronchopulmonarydysplasia), surfactant protein B deficiency, congenital diaphragmatic hernia, pulmonary alveolar proteinosis, pulmonary hypoplasia and lung injury (e.g. induced by ischemia/reperfusion pulmonary hypertension or hyperoxic lung injury).

Diseases of the Central Nervous System (CNS)

Diseases of the CNS include neurodegenerative diseases. Non-limiting examples of neurodegenerative disorders include: (i) chronic neurodegenerative diseases such as familial and sporadic amyotrophic lateral sclerosis (FALS and ALS, respectively), familial and sporadic to Parkinson's disease, Huntington's disease, familial and sporadic Alzheimer's disease, multiple sclerosis, olivopontocerebellar atrophy, multiple system atrophy, progressive supranuclear palsy, diffuse Lewy body disease, corticodentatonigral degeneration, progressive familial myoclonic epilepsy, strionigral degeneration, torsion dystonia, familial tremor, Down's Syndrome, Gilles de la Tourette syndrome, Hallervorden-Spatz disease, diabetic peripheral neuropathy, dementia pugilistica, AIDS Dementia, age related dementia, age associated memory impairment, and amyloidosis-related neurodegenerative diseases such as those caused by the prion protein (PrP) which is associated with transmissible spongiform encephalopathy (Creutzfeldt-Jakob disease, Gerstmann-Straussler-Scheinker syndrome, scrapie, and kuru), and those caused by excess cystatin C accumulation (hereditary cystatin C angiopathy); and (ii) acute neurodegenerative disorders such as traumatic brain injury (e.g., surgery-related brain injury), cerebral edema, peripheral nerve damage, spinal cord injury, Leigh's disease, Guillain-Barre syndrome, lysosomal storage disorders such as lipofuscinosis, Alper's disease, vertigo as result of CNS degeneration; pathologies arising with chronic alcohol or drug abuse including, for example, the degeneration of neurons in locus coeruleus and cerebellum; pathologies arising with aging including degeneration of cerebellar neurons and cortical neurons leading to cognitive and motor impairments; and pathologies arising with chronic amphetamine abuse including degeneration of basal ganglia neurons leading to motor impairments; pathological changes resulting from focal trauma such as stroke, focal ischemia, vascular insufficiency, hypoxic-ischemic encephalopathy, hyperglycemia, hypoglycemia or direct trauma; pathologies arising as a negative side-effect of therapeutic drugs and treatments (e.g., degeneration of cingulate and entorhinal cortex neurons in response to anticonvulsant doses of antagonists of the NMDA class of glutamate receptor), and Wernicke-Korsakoffs related dementia. Neurodegenerative diseases affecting sensory neurons include Friedreich's ataxia, diabetes, peripheral neuropathy, and retinal neuronal degeneration.

Diseases of the CNS also include neurodegenerative diseases of limbic and cortical systems include cerebral amyloidosis, Picks atrophy, and Retts syndrome.

Gastrointestinal Diseases

Exemplary gastrointestinal diseases, include but are not limited to, chronic inflammatory intestinal diseases, inflammatory bowel disease (IBD), Crohn's Disease, Ulcerative Colitis, celiac, colitis, ileitis, gastrointestinal cancer and gastrointestinal injury (e.g. viral, bacterial, radiation enteritis and proctitis).

Cardiovascular Diseases

Exemplary cardiovascular diseases, include but are not limited to, cardiac failure, cardiac tissue injury, coronary artery disease, cerebral stroke (e.g. cerebrovascular disorder), peripheral vascular disease, coronary artery disease. The coronary artery diseases include, for example, myocardial infarction and angina. Cerebral stroke, includes for example, cerebral infarction and cerebral hemorrhage.

Additional exemplary cardiovascular diseases, include but are not limited to, chronic or congestive heart failure (CHF), ischemic heart disease (IHD), rheumatic heart disease, stroke, hypertensive heart disease, rheumatic heart disease (RHD), aortic aneurysms, cardiomyopathy, atrial fibrillation, congenital heart disease, pulmonary heart disease, valvular heart disease, endocarditis, drug induced cardiac toxicity (e.g. doxorubicin hydrochloride (Adriamycin) induced cardiomyopathy), and peripheral artery disease (PAD).

Hepatic Diseases

Exemplary hepatic diseases, include but are not limited to, hepatitis C infection, hepatobiliary malignancies such as hepatocellular carcinoma (Molmenti E P, Klintmalm G B., 2001. J Hepatobiliary Pancreat Surg. 8:427-34), cirrhosis, primary sclerosing cholangitis (Crippin J S., 2002. Can J Gastroenterol. 16:700), alcoholic liver disease (Podevin P. et al., 2001. J Chir (Paris). 138:147), hepatitis B (Samuel D., 2000. Acta Gastroenterol Belg. 63:197-9), drug/toxin-induced hepatotoxicity, hepatic vascular injury, hepatic cancer, autoimmune hepatitis, blunt hepatic trauma, liver damage associated with inborn errors of metabolism, urea cycle defects, hypercholesterolemia, glycogen storage disease, primary hyperoxaluria type I, cryptogenic cirrhosis, Crigler-Najjar syndrome type I, congenital hepatic fibrosis, Neimann-Pick disease, primary biliary cirrhosis, amyloidosis, biliary atresia, hepatoblastoma, Alagille syndrome, hemangioendothelioma, cholestasis, acute/fulminant liver failure, Budd-Chiari syndrome, alpha-1-antitrypsin deficiency, Wilson disease, hemochromatosis, tyrosinemia, disorders of porphyrin metabolism such as protoporphyria, cystic fibrosis, malignant neoplasm of intrahepatic bile ducts, lipidoses, disorders of copper metabolism, disorders of purine and pyrimidine metabolism, disorders of bilirubin excretion, mucopolysaccharidosis, congenital factor VIII disorder, congenital factor IX disorder, necrosis of liver, alcoholic fatty liver, sequelae of chronic liver disease, disorders of gallbladder, bile duct obstruction, biliary atresia, perinatal jaundice due to hepatocellular damage, portal vein thrombosis (PVT), hemophilia (Liu et al., 1994. Transpl Int. 7:201), and lysosomal storage diseases/enzyme deficiencies such as Gaucher disease (Groth C G. et al., Birth Defects Orig Artic Ser. 9:102-5).

Nephric Diseases

Exemplary renal diseases, include but are not limited to, acute kidney failure, acute nephritic syndrome, analgesic nephropathy, atheroembolic kidney disease, chronic kidney failure, chronic nephritis, congenital nephrotic syndrome, end-stage kidney disease, Goodpasture's syndrome, IgM mesangial proliferative glomerulonephritis, interstitial nephritis, kidney cancer, kidney damage, kidney infection, kidney injury, kidney stones, lupus nephritis, membranoproliferative glomerulonephritis I, membranoproliferative glomerulonephritis II, membranous nephropathy, necrotizing glomerulonephritis, nephroblastoma, nephrocalcinosis, nephrogenic diabetes insipidus, IgA-mediated nephropathy, nephrosis, nephrotic syndrome, polycystic kidney disease, post-streptococcal glomerulonephritis, reflux nephropathy, renal artery embolism, renal artery stenosis, renal papillary necrosis, renal tubular acidosis type I, renal tubular acidosis type II, renal underperfusion and renal vein thrombosis.

Pancreatic Diseases

Exemplary pancreatic diseases, include but are not limited to, pancreatic cancer, intraductal papillary mucinous neoplasm (IPMN), mucinous cystic neoplasm (MCN), serous cystic neoplasm (SCN), neuroendocrine tumor (NET), chronic pancreatitis (CP), pancreatitis (e.g. chronic pancreatitis, acute pancreatitis, hereditary pancreatitis), cystic fibrosis, drug induced pancreatic damage, pancreatic alcohol toxicity, and diseases or syndromes which are associated with an insulin deficiency including, but not limited to, type 1 and type 2 diabetes mellitus, metabolic syndrome, type 1 and type 2 diabetes mellitus subtypes, insulin deficiency syndrome, maturity onset diabetes of the young (MODY 1-11), and permanent neonatal diabetes mellitus.

According to one embodiment, the disease is an organ dysfunction or failure, a cancer, an Alzheimer's disease, a Parkinson's disease, a Huntington's disease, a Multiple Sclerosis, a Crohn's disease, a pancreas damage, a diabetes mellitus, a liver cirrhosis, a hepatitis B, a hepatitis C, a kidney disease, an ischemic cardiac damage, a drug induced cardiac toxicity, an ischemia, an injury, an intestinal injury, a wound and a viral infection.

Since non-syngeneic (e.g. allogeneic) cells are likely to induce an immune reaction when administered to the subject several approaches have been developed to reduce the likelihood of rejection of non-syngeneic cells. These include either suppressing the recipient immune system or encapsulating the non-autologous cells in immunoisolating, semipermeable membranes before transplantation. Alternatively, cells may be uses which do not express xenogenic surface antigens, such as those developed in transgenic animals (e.g. pigs).

Thus, according to one embodiment, in order to avoid graft rejection of the progenitor cells, the subject may be administered an immunosuppressive regimen.

Examples of suitable types of immunosuppressive regimens include administration of immunosuppressive drugs and/or immunosuppressive irradiation.

Ample guidance for selecting and administering suitable immunosuppressive regimens for transplantation is provided in the literature of the art (for example, refer to: Kirkpatrick C H. and Rowlands D T Jr., 1992. JAMA. 268, 2952;

Higgins R M. et al., 1996. Lancet 348, 1208; Suthanthiran M. and Strom T B., 1996. New Engl. J. Med. 331, 365; Midthun D E. et al., 1997. Mayo Clin Proc. 72, 175; Morrison V A. et al., 1994. Am J Med. 97, 14; Hanto D W., 1995. Annu Rev Med. 46, 381; Senderowicz A M. et al., 1997. Ann Intern Med. 126, 882; Vincenti F. et al., 1998. New Engl. J. Med. 338, 161; Dantal J. et al. 1998. Lancet 351, 623).

Examples of immunosuppressive agents include, but are not limited to, methotrexate, cyclophosphamide, cyclosporine, cyclosporin A, chloroquine, hydroxychloroquine, sulfasalazine (sulphasalazopyrine), gold salts, D-penicillamine, leflunomide, azathioprine, anakinra, infliximab (REMICADE), etanercept, TNF.alpha. blockers, a biological agent that targets an inflammatory cytokine, and Non-Steroidal Anti-Inflammatory Drug (NSAIDs). Examples of NSAIDs include, but are not limited to acetyl salicylic acid, choline magnesium salicylate, diflunisal, magnesium salicylate, salsalate, sodium salicylate, diclofenac, etodolac, fenoprofen, flurbiprofen, indomethacin, ketoprofen, ketorolac, meclofenamate, naproxen, nabumetone, phenylbutazone, piroxicam, sulindac, tolmetin, acetaminophen, ibuprofen, Cox-2 inhibitors, tramadol, rapamycin (sirolimus) and rapamycin analogs (such as CCI-779, RAD001, AP23573). These agents may be administered individually or in combination.

As used herein the term "about" refers to ±10%.

The terms "comprises", "comprising", "includes", "including", "having" and their conjugates mean "including but not limited to".

The term "consisting of" means "including and limited to".

The term "consisting essentially of" means that the composition, method or structure may include additional ingredients, steps and/or parts, but only if the additional ingredients, steps and/or parts do not materially alter the basic and novel characteristics of the claimed composition, method or structure.

As used herein, the singular form "a", "an" and "the" include plural references unless the context clearly dictates otherwise. For example, the term "a compound" or "at least one compound" may include a plurality of compounds, including mixtures thereof.

Throughout this application, various embodiments of this invention may be presented in a range format. It should be understood that the description in range format is merely for convenience and brevity and should not be construed as an inflexible limitation on the scope of the invention. Accordingly, the description of a range should be considered to have specifically disclosed all the possible subranges as well as individual numerical values within that range. For example, description of a range such as from 1 to 6 should be considered to have specifically disclosed subranges such as from 1 to 3, from 1 to 4, from 1 to 5, from 2 to 4, from 2 to 6, from 3 to 6 etc., as well as individual numbers within that range, for example, 1, 2, 3, 4, 5, and 6. This applies regardless of the breadth of the range.

Whenever a numerical range is indicated herein, it is meant to include any cited numeral (fractional or integral) within the indicated range. The phrases "ranging/ranges between" a first indicate number and a second indicate number and "ranging/ranges from" a first indicate number "to" a second indicate number are used herein interchangeably and are meant to include the first and second indicated numbers and all the fractional and integral numerals therebetween.

As used herein the term "method" refers to manners, means, techniques and procedures for accomplishing a given task including, but not limited to, those manners, means, techniques and procedures either known to, or readily developed from known manners, means, techniques and procedures by practitioners of the chemical, pharmacological, biological, biochemical and medical arts.

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable subcombination or as suitable in any other described embodiment of the invention. Certain features described in the context of various embodiments are not to be considered essential features of those embodiments, unless the embodiment is inoperative without those elements.

Various embodiments and aspects of the present invention as delineated hereinabove and as claimed in the claims section below find experimental support in the following examples.

EXAMPLES

Reference is now made to the following examples, which together with the above descriptions, illustrate the invention in a non limiting fashion.

Generally, the nomenclature used herein and the laboratory procedures utilized in the present invention include molecular, biochemical, microbiological and recombinant DNA techniques. Such techniques are thoroughly explained in the literature. See, for example, "Molecular Cloning: A laboratory Manual" Sambrook et al., (1989); "Current Protocols in Molecular Biology" Volumes I-III Ausubel, R. M., ed. (1994); Ausubel et al., "Current Protocols in Molecular Biology", John Wiley and Sons, Baltimore, Md. (1989); Perbal, "A Practical Guide to Molecular Cloning", John Wiley & Sons, New York (1988); Watson et al., "Recombinant DNA", Scientific American Books, New York; Birren et al. (eds) "Genome Analysis: A Laboratory Manual Series", Vols. 1-4, Cold Spring Harbor Laboratory Press, New York (1998); methodologies as set forth in U.S. Pat. Nos. 4,666,828; 4,683,202; 4,801,531; 5,192,659 and 5,272,057; "Cell Biology: A Laboratory Handbook", Volumes I-III Cellis, J. E., ed. (1994); "Current Protocols in Immunology" Volumes I-III Coligan J. E., ed. (1994); Stites et al. (eds), "Basic and Clinical Immunology" (8th Edition), Appleton & Lange, Norwalk, Conn. (1994); Mishell and Shiigi (eds), "Selected Methods in Cellular Immunology", W. H. Freeman and Co., New York (1980); available immunoassays are extensively described in the patent and scientific literature, see, for example, U.S. Pat. Nos. 3,791,932; 3,839,153; 3,850,752; 3,850,578; 3,853,987; 3,867,517; 3,879,262; 3,901,654; 3,935,074; 3,984,533; 3,996,345; 4,034,074; 4,098,876; 4,879,219; 5,011,771 and 5,281,521; "Oligonucleotide Synthesis" Gait, M. J., ed. (1984); "Nucleic Acid Hybridization" Hames, B. D., and Higgins S. J., eds. (1985); "Transcription and Translation" Hames, B. D., and Higgins S. J., Eds. (1984); "Animal Cell Culture" Freshney, R. I., ed. (1986); "Immobilized Cells and Enzymes" IRL Press, (1986); "A Practical Guide to Molecular Cloning" Perbal, B., (1984) and "Methods in Enzymology" Vol. 1-317, Academic Press; "PCR Protocols: A Guide To Methods And Applications", Academic Press, San Diego, Calif. (1990); Marshak et al., "Strategies for Protein Purification and Characterization—A Laboratory Course Manual" CSHL Press (1996); all of which are incorporated by reference as if fully set forth herein. Other general references are provided throughout this document. The procedures therein are believed to be well known in the art and are provided for the convenience of the reader. All the information contained therein is incorporated herein by reference.

General Materials and Experimental Procedures

Human Fetal Lung Tissues

Human fetal lung tissue was obtained at 15-24 weeks of gestation from legal abortions. Written informed consent for use of lung tissue was obtained according to a protocol approved by the Declaration of Helsinki Ethics Committee of Assaf Harofe Medical Center or Wolfson Medical Center. Fetal age was determined on the basis of clinical information and confirmed by fetal foot-length measurements. All fetal lung samples obtained were processed for histological or flow cytometry analysis and subsequently used for in vitro and in vivo studies as outlined below and in the Example sections which follow.

Animals

Animals were maintained under conditions approved by the Institutional Animal Care and Use Committee at the Weizmann Institute. All of the procedures were monitored by the Veterinary Resources Unit of the Weizmann Institute and approved by the Institutional Animal Care and Use Committee (IACUC). Mouse strains used included: NOD-SCID (NOD.CB 17-Prkdcscid/J), Rag1$^{-/-}$ (B6.129S7-Rag1tm1Mom/J on C57BL/6J background), C57BL/6J (CD45.2) and C57BL/6-Tg (CAG-EGFP)1Osb/J, C3H/HeJ mice (Weizmann Institute Animal Breeding Center, Rehovot, Israel), tdTomato (Gt(ROSA)26Sortm4(ACTB-tdTomato,-EGFP)Luo/J mice (Jackson Labs, Bar Harbor, USA). All mice were 6-12 weeks of age. Mice were kept in small cages (up to five animals in each cage) and fed sterile food and acid water. Randomization: animals of the same age, sex and genetic background were randomly assigned to treatment groups. Pre-established exclusion criteria were based on IACUC guidelines, and included systemic disease, toxicity, respiratory distress, interference with eating and drinking and substantial (more than 15%) weight loss. During the study period most of the animals appeared to be in good health and were included in the appropriate analysis. In all experiments the animals were randomly assigned to the treatment groups.

For kidney capsule transplantation experiments (FIGS. 26A-J), NOD-SCID mice (males and females distributed evenly among groups) aged 8-12 weeks were used. n=25 mice for 20-22 weeks HEL transplantation; n=30 mice for tissue harvested at 15-19 weeks of gestation, and n=10 mice for 23-24 weeks HEL tissue. For BrdU incorporation experiments, female C57BL/6 mice aged 8-12 weeks were used; n=75 mice for three experiments. For FIGS. 30A-H, hosts were C57BL/6 mice, 24 females and 6 males (evenly distributed between the groups), 8-12 weeks old; n=30 for 3 experiments. Donors were E16 GFP$^+$ (C57BL/6-Tg (CAG-EGFP)1Osb/J) embryos. For FIGS. 31A-J, female C57BL/6 mice age 6-7 weeks were used. In experiments using GFP and tdTomato labeling, conditioned Rag1$^{-/-}$-C57BL/6 female mice (aged 8-12 weeks, n=4) were transplanted with a 1:1 mixture of 1×10$^6$ GFP- and tdTomato-positive E15-E16 embryonic lung cells. In experiments with 'red' hosts and 'green' donors, conditioned tdTomato (Gt(ROSA) 26Sortm4(ACTB-tdTomato,-EGFP)Luo/J female mice (age 8-12 weeks, n=3) were transplanted with 1×10$^6$ GFP-positive E15-E16 embryonic lung cells. For FIGS. 33A-G, hosts were female C57BL/6 mice, 8-12 weeks old. Donors were E16 GFP$^+$ embryos. For lung function measurements, n=40 mice C57BL/6 were transplanted in two experiments. In allogeneic experiments, conditioned female Rag1$^{-/-}$-C57BL/6 (H2K$^b$) (age 8-12 weeks) mice were transplanted with 1×10$^6$ E15-E16 lung cells from C3H (H2K$^k$) donors; n=10 mice in two experiments. For FIGS. 36A-H, hosts were female C57BL/6 mice, 6-7 weeks old, n=6 for each group in two experiments. Total n=30 mice. Donors were E16 GFP$^+$ embryos. For FIGS. 38A-E, hosts were female NOD-SCID mice, 8-10 weeks old, n=13 in two experiments. Donors were HEL embryos at 20 weeks of gestation.

Animal Procedures

Transplantation Procedure

Transplantations of the embryonic precursor tissues were performed under general anesthesia (2.5% 2,2,2-tribromoethanol, 97% in PBS, 10 ml/kg administered intraperitoneally) as previously described [Katchman H. et al., Stem Cells. (2008) 26(5):1347-55].

Implantation Under the Kidney Capsule

Host kidney was exposed through a left lateral incision. A 1.5-mm incision was made at the caudal end of the kidney capsule, and donor precursor tissues were grafted under the kidney capsule in fragments 1-2 mm in diameter.

Human fetal lung tissues, ranging from 15 to 24 weeks of gestation, were obtained from legal abortions where written informed consent for use of lung tissue was obtained according to a protocol approved by the Helsinki Ethics Committee. Fetal age was determined based on clinical information and confirmed by fetal foot-length measurements. To ensure that graft tissue was derived from fetal lung, only whole lung lobes were used for preparation of xenograft tissue. Fresh lower airways were cut under sterile conditions into 1-3 mm$^3$ pieces. Surgery was performed on anesthetized immunodeficient mice, and human fetal lung tissue was placed beneath the renal capsule of each mouse (one piece). Xenografts were harvested at different time points after grafting.

For syngeneic transplantation of mouse embryonic lung under the kidney capsule of C57BL mice, lungs from different gestational age embryos (14-17 days of gestation) were harvested and grafted under the kidney capsule in fragments 1-2 mm in diameter. To ensure that graft tissue was derived from fetal lung, only whole lung lobes were used for preparation of graft tissue.

The animals receiving implants were sacrificed at 2-20 weeks after transplantation. Kidneys bearing the transplanted grafts were then removed and fixed in 4% paraformaldehyde or cryopreserved.

Tissue sections were routinely stained by hematoxylin and eosin (H&E). Assessment of graft differentiation and function was performed by histochemical and immunohistochemical labeling.

In some control experiments, human adult lung tissues were used. To that end, normal lung tissue was obtained from the Sheba Medical Hospital Thoracic Surgery Tissue Bank, with approval by the institutional review board. Written informed consent for use of lung tissue was obtained according to a protocol approved by the Declaration of Helsinki Ethics Committee of Sheba Medical Center. Single-cell suspensions were generated with the use of enzymatic digestion by collagenase and dispase.

Morphometric Analysis

Human embryonic lungs of different gestational ages were frozen in Optimal Cutting Temperature compound (OCT) (Sakura Finetek USA, Inc. Tissue-Tek O.C.T.) and sectioned by Leica Cryocut 1800. Consecutive 12 μm sections were stained with different antibodies as outlined in the Examples section below. In some experiments, the areas of interest were quantified using Image Pro software (Media Cybernetics, Crofton, Md., www(dot)mediacy(dot)com). At least 3-5 different samples of lungs of the same gestational age from different fetal donors were analyzed.

Naphthalene Lung Injury

For lung injury studies, mice were given an intraperitoneal injection of naphthalene (NA) (more than 99% pure; Sigma-Aldrich), dissolved in corn oil, 200 mg per kg body weight, 40-48 hours before transplantation of embryonic lung tissue.

For 'double' lung injury, naphthalene-treated animals were further irradiated in a cesium irradiator (Gammacell 40), (40-48 hours after naphthalene administration). C57BL/6, tdTomato (Gt(ROSA)26Sortm4(ACTB-tdTomato,-EGFP)Luo/J mice, and Rag1$^{-/-}$ mice were irradiated with 6 Gy TBI, and NOD-SCID mice were irradiated 3-4 Gy TBI.

Mouse and Human Fetal Lung Single Cell Suspension, Cell Preparation and Transplantation Cell Preparation and Injection Cell suspensions were obtained from enzyme-digested mouse or human fetal lungs. Briefly, lung digestion was performed by finely mincing tissue with a razor blade in the presence of 1 mg/ml collagenase, 2.4 U/ml dispase (Roche Diagnostics, Indianapolis, Ind.) in PBS Ca$^+$Mg$^+$. Removal of nonspecific debris was accomplished by sequential filtration through 70- and 40-μm filters. The cells were then washed with 1×PBS (Ca and Mg free) with 2% FCS and antibiotics. In order to prevent cell clumping before injection 50 units/1 ml heparin was added to the single cell suspension.

Following conditioning with NA, TBI, or both, C57BL/6 mice were transplanted with 1×10$^6$ GFP-positive E15-E16 embryonic lung cells injected into the tail vein 4-8 hours following irradiation.

In experiments using GFP and tdTomato labeling, Rag1$^{-/-}$-C57BL/6 donor mice were transplanted with a 1:1 mixture of 1×10$^6$ GFP- and tdTomato-positive E15-E16 embryonic lung cells injected into the tail vein 4-8 hours following irradiation.

In experiments with mixed 'red' hosts and 'green' donors, conditioned tdTomato (Gt(ROSA)26Sortm4(ACTB-tdTomato,-EGFP)Luo/J mice were transplanted with 1×10$^6$ GFP-positive E15-E16 embryonic lung cells injected into the tail vein 4-8 hours following irradiation.

In allogeneic transplantations, conditioned Rag1$^{-/-}$-C57BL/6 (H2K$^b$) mice were transplanted with 1×10$^6$ E15-E16 lung cells from C3H (H2K$^k$) donors, as described above for syngeneic transplants. For transplantation of HEL, NOD-SCID mice conditioned with NA and 3-4 Gy TBI were transplanted with 1×10$^6$ 20-22 week HEL-derived cells, injected into the tail vein 4-8 hours following irradiation.

Fresh Adult Lung Cells Preparation and Injection

Adult lung cells were harvested from a GFP positive C57BL/6 mice (Jackson Labs, Bar Harbor, USA). All mice were 6-12 weeks of age. A single cell suspension comprising 8×10$^6$ adult lung cells were injected i.v. into C57BL/6 recipient mice following conditioning with NA and 6 GY TBI.

E16 Lung Expanded Cells Preparation and Injection

GFP positive C57BL E16 lung cells were harvested and seeded on tissue culture plates with condition medium [irradiated mouse embryonic feeders (iMEF)] together with epithelial growth factor (1 μM) and Rock inhibitor (Y-27632, 5 μM). Medium was changed every 2 days and Rock inhibitor was added freshly every time. After 4 days cells were passed by splitting them to 3 plates. After 3 additional days on culture the cells were used for transplantation. A single cell suspension comprising 2×10$^6$ expanded cells were injected i.v. into C57BL/6 recipient mice following conditioning with NA and 6 GY TBI.

Assessment of GFP$^+$ Foci in Chimeric Lungs by Morphometry

Lungs were fixed with a 4% PFA solution introduced through the trachea under a constant pressure of 20 cm H$_2$O. Then the lungs were immersed in fixative overnight at 4° C. Lungs were processed after PFA treatment and fixed in 30% sucrose and frozen in Optimal Cutting Temperature (OCT) compound (Sakura Finetek USA, Inc. Tissue-Tek). Serial step sections, 12 μm in thickness, were taken along the longitudinal axis of the lobe. The fixed distance between the sections was calculated so as to allow systematic sampling of at least 20 sections across the whole lung. Lung slices were analyzed by fluorescence microscopy. The actual number of GFP$^+$ foci (a group of more than 5 distinct GFP$^+$ cells was defined as a single patch) was counted per slice using Image Pro software. The area of each slice was estimated by Image Pro software, and the average area of slices and average frequency of GFP$^+$ patches in all the slices were assessed (patch(P)/Area(A) (mm2)), assuming that the frequency per area in a large number of slices reflects distribution per volume.

Flow Cytometry

Human (15-24 week) and mouse (14-17 week) embryonic lung derived single cell suspensions, and adult mouse and adult human single cell suspensions were analyzed by polychromatic flow cytometry. All the samples were stained with conjugated antibodies or matching isotype controls according to manufacturer's instructions. Antibodies were from e-Bioscience, BD, and Biolegend. The complete list of antibodies used in the study is summarized in Table 7, hereinbelow. Data were acquired on an LSRII (BD Biosciences) or BD FACSCanto II flow cytometer, and analyzed using BD FACSDiva 6 or FlowJo software (version 7.6.5, or version vX.0.7 Tree Star Inc).

In chimerism experiments following transplantation of E16 from C3H donors into Rag1$^{-/-}$recipients, a single cell suspension of chimeric lung was prepared by enzymatic treatment of the tissue, as described above, and the cells were stained with anti-CD45, anti-TER19, 7AAD, anti-H2K$^k$, and anti-H2K$^b$, as well as the relevant isotype controls. Doublet discrimination was done by using FCS-Area and FCS-Height. The data were acquired using FACSCanto II flow cytometer and analyzed using FlowJo software (version vX.0.7 Tree Star Inc).

Immunohistochemistry

Animals were sacrificed at different time points following transplantation; the lungs were inflated with 4% PFA solution and kept for 24 hours, then cryopreserved in 30% sucrose and snap-frozen in isopentane pre-cooled by liquid air, or processed for paraffin embedding. The samples for frozen sections were harvested and inflated to full capacity with 1:1 mixture of OCT and PBS and snap frozen in isopentane precooled by liquid air. Frozen samples were cut into 6- or 12-am sections and stained. Paraffin blocks were cut in 4 μm sections, and stained after xylene deparaffinization and rehydration as previously described [Hecht G et al., Proc Nat Acad of Sci. (2009) 106(21): 8659]. The summary of antibodies used in the study is depicted in Table 7, hereinbelow. All secondary antibodies were from Jackson Immunoresearch Laboratories or Abcam. The stained samples were analyzed using an upright Olympus BX51 fluorescent microscope with ×10, ×40 air and ×100 oil objectives, and Olympus digital camera (DP70), or by Nikon Eclipse Ti inverted spinning disc confocal microscope with ×10, ×20 air objectives and ×40, ×60 and ×100 oil objectives for high resolution. Images on fluorescence microscope were acquired by DP Controller and DP Manager software (Olympus). Images on confocal microscope were acquired using Andor iQ software and analyzed and reconstructed in three dimensions (as indicated) with Volocity software (Perkin-Elmer, Coventry, UK). In some cases, images were processed (intensity and contrast adjusted, overlaid) in Adobe Photoshop.

Human and mouse fetal lung tissues were fixed with 4% PFA solution without previous inflation and maintained for 24 hours, then cryopreserved in 30% sucrose and snap frozen in isopentane precooled by liquid air, or processed for paraffin embedding. The samples for frozen sections were snap-frozen in OCT in isopentane precooled by liquid air.

TABLE 7

A list of the antibodies used in the study

| Primary antibodies | Application | Catalog number | Dilution |
|---|---|---|---|
| Rabbit anti-CK5(Abcam) | IHC | Ab53121 Ab52635 | 1:50-100 |
| Rabbit anti-human CK18(Epitomics) | IHC | 1433-1 | 1:100 |
| Rat anti-E-cadherin (Abcam) | IHC | Ab11512 | 1:50-100 |
| Mouse anti-human CK14(Abcam) | IHC | Ab77684 | 1:100 |
| Mouse anti-human MNF (Santa-Cruz) | IHC | Sc-58830 | 1:100 |
| Rabbit anti-Ki-67(Abcam) | IHC | Ab16667 | 1:100 |
| Mouse anti-human nestin(MBL) | IHC | Clone 10C2 KO119-3 | 1:100 |
| Goat anti-mouse nestin (Santa-Cruz) | IHC | Sc-21249 | 1:100 |
| Rabbit anti-CCSP (Seven Hills Labs) | IHC | WRAB-CCSP | 1:1000 |
| Rabbit anti-GFP (MBL) | IHC | Code No. 598 | 1:1000 |
| Chicken anti-GFP (Abcam) | IHC | Ab13970 | 1:500-1000 |
| Goat anti-GFP (Abcam) | IHC | Ab5450 | 1:1000 |
| Rabbit anti-DsRed (Clontech) | IHC | 632496 | 1:200 |
| Goat anti-human CGRP (Santa-Cruz) | IHC | Sc-8857 | 1:50-100 |
| Chicken anti-Thyrosine Hydroxilase (Abcam) | IHC | Ab 76442 | 1:500 |
| Rabbit anti-surfactant protein C (Santa-Cruz) | IHC | Sc-13979 (FL-197) | 1:100 |
| Goat anti-Aquaporin-5 (Santa-Cruz) | IHC | Sc-9890 | 1:50-100 |
| Rabbit Anti-Aquaporin5 (Millipore) | IHC | CALBIOCHEM 178615 | 1:100 |
| Mouse anti-Vimentin V9 (Sigma) | IHC | V 6630 | 1:200 |
| Rabbit anti-CFTR(Abcam) | IHC | Ab-59394 | 1:50-100 |
| Rat anti-mouse CD31(Dianova) | IHC | DIA-310-M Clone SZ31 | 1:50 |
| Rabbit anti-cow Cytokeratin (Dako) | IHC | Code Z0622 | 1:100 |
| Mouse anti-human CD31(Dako) | IHC | M0823 Clone JC70A | 1:100 |
| Rabbit anti-TTF-1(Abcam) | IHC | Ab76013 | 1:100 |
| Rabbit anti-RAGE | IHC | Ab37647 | 1:100 |
| Ulex Europeous Lectin (Vector) | IHC | B-1065 Lot Q0818 | 1:100 |
| Bandeiraea simplisifolia isolectinB4 (Vector) | IHC | B-1205 Lot 0520 | 1:50 |
| Mouse anti-human neurofilament Protein (Dako) | IHC | 2F11 Code No N1591 | Ready for use |
| Anti-mouse Sca-Brilliant violet 711(Biolegend) | FACS | 108131 | 1 μl/10$^6$ cells |
| Anti-mouse CD45 APC (Biolegend) | FACS | 103112 | 1 μl/10$^6$ cells |
| Anti-mouse CD45 APC-Cy7 (Biolegend) | FACS | 103116clone 30-F11 | 1 μl/10$^6$ cells |
| Anti-mouse CD31 APC (Biolegend) | FACS | 102510 | 1 μl/10$^6$ cells |
| Anti-mouse CD31 PE-Cy7 (Biolegend) | FACS | 102418 | 1 μl/10$^6$ cells |
| Anti-mouse CD326 Percp-Cy5.5 (Ep-CAM)(Biolegend) | FACS | 118220 | 1 μl/10$^6$ cells |
| Anti-mouse CD24 PE-Cy, (Biolegend), | FACS | 101822 | 1 μl/10$^6$ cells |
| Anti-mouse CD49f Pacific Blue (Biolegend) | FACS | 313620 | 1 μl/10$^6$ cells |
| Anti-mouse CD104 FITC (Biolegend) | FACS | 123606 | 1 μl/10$^6$ cells |
| Anti-mouse CD90Pacific Blue (Biolegend) | FACS | 105324 | 1 μl/10$^6$ cells |
| Anti-mouse CD34 PE (Biolegend) | FACS | 119308 | 1 μl/10$^6$ cells |
| Anti-mouse SCA-1-Biotin (Biolegend) | Cell separation | Clone D7 108104 | 1 μl/10$^6$ cells |
| Anti-mouse CD45-Biotin (Biolegend) | Cell separation | 102404 | 1 μl/10$^6$ cells |
| Anti-mouse 31-Biotin (Biolegend) | Cell separation | 103104 | 1 μl/10$^6$ cells |
| Anti-mouse CD326-Biotin (Biolegend) | Cell separation | Clone G8.8 118204 | 1 μl/10$^6$ cells |
| Anti-human CD146 PE-Cy7 (Biolegend) | FACS | 342010 | 1 μl/10$^6$ cells |
| Anti-human CD31 Pacific Blue (Biolegend) | FACS | 303114 | 1 μl/10$^6$ cells |
| Anti-human CD117 PE (Biolegend) | FACS, IHC | 313204 | 1 μl/10$^6$ cells |
| Anti-human CD271(Biolegend) | FACS | 345104 | 1 μl/10$^6$ cells |
| Anti-human CD144 APC (VE-Cadherin)(Biolegend) | FACS | 348508 | 1 μl/10$^6$ cells |
| Anti-human CD45 APC-Cy7 (Biolegend) | FACS | 304014 | 1 μl/10$^6$ cells |
| Anti-human CD326 APC (Ep-CAM)(Biolegend) | FACS | 324208 | 1 μl/10$^6$ cells |
| Anti-human CD34 Percp (Biolegend) | FACS | 343520 | 1 μl/10$^6$ cells |
| Anti-human CD14 PE (Biolegend) | FACS | 325606 | 1 μl/10$^6$ cells |
| Mouse anti-alfa SMA-FITC (Abcam) | IHC | Ab8211 | 1:50-100 |
| Anti-H2K$^k$-PE antibody (Biolegend) | FACS IHC | Clone 36-7-5 | 1:50 |
| Anti-H2K$^b$-FITC antibody (Biolegend) | FACS IHC | Clone AF6-88.5 | 1:50 |
| Anti-human Mucin-1-PE (Biolegend) | FACS IHC | 355604 | 1:50 |

TABLE 7-continued

A list of the antibodies used in the study

| Primary antibodies | Application | Catalog number | Dilution |
|---|---|---|---|
| Anti-human Podoplanin-Alexa Fluor 488 (Biolegend) | FACS IHC | NC-08 | 1:50 |
| 7AAD (Biolegend) | FACS | 420404 | 5 µl/$10^6$ cells |
| Secondary antibodies* | | | |
| Anti-mouse Alexa Fluor 488 | IHC | 715-545-150 | 1:200 |
| Anti-mouse DyLight 594 | IHC | 715-545-153 | 1:200 |
| Anti-rat Alexa Fluor 488 | IHC | 712-545-150 | 1:200 |
| Anti-rat Alexa Fluor 594 | IHC | 712-585-150 | 1:200-300 |
| Anti-mouse AMCA | IHC | 715-155-150 | 1:100-200 |
| Anti-rat AMCA | IHC | 712-155-150 | 1:200 |
| Anti-rabbit Alexa Fluor 488 | IHC | 711-545-152 | 1:200 |
| Anti-rabbit Cy3 | IHC | 711-165-152 | 1:200-400 |
| Anti-rat CY2 | IHC | 712-225-153 | 1:100-200 |
| Anti-rabbit Rhodamine Red | IHC | 711-295-152 | 1:200-400 |
| Anti-rabbit AMCA | IHC | 711-155-152 | 1:100-200 |
| Anti-goat AMCA | IHC | 705-155-003 | 1:100-200 |
| Anti-goat Alexa Fluor 488 | IHC | 705-545-003 | 1:200 |
| Anti-goat Rhodamine Red(Abcam) | IHC | Ab7123 | 1:300-400 |
| Anti-Chicken Alexa Fluor 488 | IHC | 703-545-155 | 1:200 |
| Streptavidin-AMCA | IHC | 016-150-084 | 1:100-200 |
| Streptavidin-APC | IHC | 016-130-084 | 1:100-200 |
| BRDU flow kit (BD) | FACS, IHC | 51-2354AK | 1.5 µl/$10^6$ cells |
| Anti-Biotin MicroBeads (Miltenyi Biotec) | Cell separation | 120-000-900 | 2 µl/$10^6$ cells |

*All the secondary antibodies were produced in donkey and purchased from Jackson ImmunoResearch or Abcam (unless indicated otherwise). All the information about the antibodies, their specificity, cross-reactivity, application and isotype controls is available in the manufacturers' websites.

BrdU Incorporation Assay

Lung cell proliferation was measured in vivo by BrdU uptake. Briefly, control and four groups of experimental mice (7 days following naphthalene administration and 5 days after TBI) received a single dose of BrdU (Sigma) intraperitoneally 120 minutes before sacrifice (at a dose of 50 mg per kg of body weight). Lungs were excised, left lungs were enzymatically digested (using the same protocol as for embryonic tissue dissociation) for polychromatic FACS analysis, and right lungs were fixed with 4% PFA and processed for further immunofluorescence staining. Multiple serial slices were costained with anti-BrdU-FITC and anti-CCSP or anti-SPC antibodies. All FACS and immunohistochemical studies were done using the BrdU flow kit (BD Biosciences), according to the manufacturer's instructions. For morphometric analysis of CCSP$^+$BrdU$^+$ and SPC$^+$BrdU$^+$ cells, images were stained with anti-CCSP and anti-BrdU or anti-SPC and anti-BrdU antibodies and nuclei counterstained with Hoechst dye. The images were acquired by an observer blinded to the treatment groups, using an Olympus fluorescent microscope and Olympus digital camera (DP70) with a ×40 objective. At least 20 different stained random fields were counted for each marker.

Separation of Embryonic Lung Cell Subpopulations by MACS

Fetal lung (E15-E16) single cell suspensions were prepared by enzymatic digestion and different cell subpopulations were depleted by MACS using LS columns (Miltenyi Biotec) in MACS buffer (0.5% BSA, 2 mM EDTA in sterile 1×PBS, filtered and degassed) according to the protocol provided by the vendor. The single-cell suspension was passed through a 100-, 70- and 40-µm cell strainer (BD Biosciences). CD45$^+$, SCA-1$^+$, CD31$^+$ or CD326$^+$ cells were depleted by treating the single cell suspension with appropriate antibodies against each of the surface antigens conjugated to biotin (Biolegend) followed by binding with anti-biotin magnetic beads (Miltenyi Biotec). Depleted cell populations were analyzed by FACS, plated on GFR Matrigel (BD) for colony-forming assay, or transplanted (1×$10^6$ cells) into C57BL/6 mice pre-conditioned with NA and 6 Gy TBI.

Epithelial Cell Colony-Forming Assay

Briefly, fetal mouse lung cells were obtained from timed-pregnant C57BL/6 mouse fetuses (Harlan Laboratories), according to an approved protocol (Institutional Animal Care and Use Committee). Following initial isolation, lung digestion was performed by finely mincing tissue with a razor blade in the presence of 0.1% collagenase, 2.4 U/ml dispase (Roche Diagnostics, Indianapolis, Ind.) in PBS Ca$^+$Mg$^+$ and incubating the cells at 37° C. for 30 min. Nonspecific debris was removed by sequential filtration through 70- and 40-µm filters. Whole lung suspensions were washed in 2% FCS in 1×PBS. The resulting single cell suspension was resuspended in 100 µl of growth factor-reduced (GFR) Matrigel (BD Biosciences) prediluted 1:1 (vol/vol) with Epi-CFU medium and cultured in a 12 well Transwell plate (1-1.5×$10^5$ cells per well; Transwell Permeable Supports 0.4 µm, Corning), as previously described [McQualter J L et al., Proceedings of the National Academy of Sciences. (2010) 107(4):1414-9]. The absolute number of epithelial clones was determined after 7-10 days in culture; in some experiments colony-forming efficiency was calculated as the number of growing clones per seeded cell number×100, as a percentage (number of seeded cells that gave rise to growing clones divided by the total number of cells seeded in the well). The growing clones were further characterized as described below. All cell cultures were carried out at 37° C. in a 5% CO2 humidified incubator. The medium was replaced every 48-72 hours.

Morphologic and phenotypic characterization of epithelial organoids grown in culture as described above was carried out using whole mount bright field or fluorescence immunohistochemistry. In brief, 3D structures grown under the culture conditions were fixed in 4% paraformaldehyde (Electron Microscopic Sciences) for 1 hour at room temperature and then overnight at 4° C. Then, the whole mount cultures were washed briefly in 1×PBS and permeabilized and blocked using 0.5% Triton X-100 and 10% horse serum in PBS for 2 hours. Following permeabilization and blocking, the cultures were washed three times with PBS for 20 minutes, followed by incubation with primary antibodies for 48-72 hours at 4° C. Following staining with primary antibodies, the whole mount cultures were washed with PBS and 0.5% Triton-X100 solution and stained with relevant secondary antibodies overnight at 4° C., followed by counterstaining with Hoechst dye. Whole mount cultures were assessed by Nikon Eclipse Ti inverted spinning disc microscope. Images were acquired using Andor iQ software, and reconstructed in three dimensions with Volocity software (Perkin-Elmer, Coventry, UK).

Calculation of GFP$^+$ Engrafted Area

Serial slices of chimeric lungs from different time points after transplantation were prepared and stained with anti-GFP antibody in combination with other markers as indicated in the Examples section below. Multiple random images of the stained serial slices were obtained using Olympus fluorescent microscope and Olympus digital camera (DP70) with ×10 objective. Each analyzed image was individually evaluated for validation of the staining pattern before processing. As large GFP-positive patches containing hundreds of cells were identified in chimeric lungs, computerized calculation of engrafted area by Fiji software was performed. The green channel was extracted from the RGB image. The percentage of the engrafted area was calculated out of the whole lung tissue. Engrafted areas have high values of green intensity, whereas the whole lung tissue has low (autofluorescence) green intensity, and air space areas are dark. Whole lung tissue excluding air spaces filling the lung structure was detected by applying Gauss blur to the green channel (sigma=3), setting a low fixed threshold on the blurred image and further smoothing the edges to remove small artifacts using the dilation and erosion operations. A mask of the whole lung tissue was created whose borders are illustrated in red (FIGS. 31A-B, 36C-F and 38A) and measured its area. The RenyiEntropy global thresholding method [Kapur, et al. Comput. Vis. Graph. Image Process. (1985) 29, 273-285] was used for calculating the intensity threshold of high GFP (engrafted) area and to create a mask whose borders are illustrated in green in FIGS. 31A-B, 36C-F and 38A. The percentage of engrafted GFP+ area was calculated from two measurements as high GFP+ area/total lung tissue×100 as a percentage (sum of engrafted green patch areas divided by the total tissue area). In most experiments, automated software was used, but in a few instances, manual examination of the slides was required. However, in all cases, the reader was blinded to the identity of the sample.

Colocalization Analysis

Colocalization analysis was performed on fluorescent sections using Imaris 7.7.1 software (Bitplane AG, Switzerland, www(dot)bitplane(dot)com). Multiple serial slices from chimeric lungs were costained with (green) anti-GFP antibody and one of a number of markers used for colocalization analysis (always red). The images for analysis were obtained using an Olympus fluorescent microscope and Olympus digital camera (DP70) with ×40 objective. Each analyzed image was individually evaluated for validation of the pattern of the staining used before processing. The images were opened in the Imaris colocalization module and the region of interest (ROI) for colocalization was defined by a fixed threshold on the green channel to concentrate on the relevant parts of the image. Thresholds for colocalization of red (material A, marker of interest) and green (material B, GFP) channels were calculated automatically for each image using the Costes method [Costes et al., Biophys. J. (2004) 86: 3993-4003]. A colocalized channel was created; channel statistics were calculated and exported to Excel files. The extent of colocalization was assessed by the percentage (%) of colocalized ROI material B: (total green intensity in colocalized region/total green intensity in the ROI)×100. The data are presented as mean±s.d. of all analyzed images for each marker.

In the experiment evaluating potential fusion of GFP donor cells following transplantation into 'tdTomato' recipients, colocalization was calculated from the number of pixels labeled by both green and red, divided by green pixels (threshold taken as half the Otsu value). The value was averaged on five fields, each comprising 10 optical sections. Three-dimensional confocal images were acquired by Nikon Eclipse Ti inverted spinning disc confocal microscope, using Andor iQ software (Mag=×40 or ×60, NA=1.3 or 1.49 oil, pixel size=0.17 μm or 0.11 μm, respectively, delta-z=1 μm).

In experiments using allogeneic (H2K$^k$) donors, the colocalization analysis was done as described above, except that the frozen sections (12 μm) from chimeric lungs were stained with anti-mouse H2K$^k$-PE conjugated antibody and AQP-5 labeled with DyLight 488. Thresholds for colocalization of red (material A, H2K$^k$) and green (material B, AQP-5) channels were calculated automatically for each image using the Costes method (Costes, supra). A colocalized channel was created; channel statistics were calculated and exported to Excel files.

Cell segmentation analysis of the colocalized AT1 cells was done as follows: images were acquired with confocal spinning-disc microscopy, with staining of donor MHC (H2K$^k$) in the red channel, AQP-5 in the green channel, and nuclei (Hoechst dye) in the blue channel. Both donor type patches and nonchimeric regions were evaluated in order to compare red fluorescence in H2K$^k$ (red) negative and positive cells. The Hoechst image for each data set was segmented for nuclei. Each nucleus was used as a seed in the green channel to extend it to the whole cell. Cell centers were marked with a red cross. Overlapping cells could define a larger or smaller cell area, compensated by the smaller or larger area of the neighboring cell. For each cell segment, the total fluorescence intensities in green and red channels were calculated and displayed in a FACS-like scatterplot.

The region of interest was manually drawn (polygon) in each image in order to select tissue areas positive and negative for donor labeling.

Assessment of Mouse Lung Function

Mice were anesthetized by intraperitoneal ketamine-xylazine, tracheotomized, paralyzed, and ventilated with FlexiVent mouse lung function unit (SCIREQ, Montreal, Quebec, Canada). Resistance and compliance at baseline were collected with FlexiVent software (SCIREQ). The investigators were blinded to the identity of the experimental mouse groups.

Two-Photon Microscopy

Before imaging, mice were euthanized or injected i.v. with the blood tracer Quantum dot 655 nanoparticles for vascular labeling (Invitrogen-Molecular Probes (cat # Q21021MP)) and then euthanized. Lungs were excised and put under a glass-covered imaging chamber. Imaging was performed using an Ultima Multiphoton Microscope (Prairie Technologies Middleton, Wis.) incorporating a pulsed Mai Tai Ti-Sapphire laser (Newport Corp, CA). The laser was tuned to 850-900 nm to either excite EGFP or to simultaneously excite EGFP and the blood tracer, or to simultaneously excite EGFP and tdTomato. A water-immersed 20× (NA 0.95) or 40× objective (NA 0.8) or 10× air objective (NA 0.3) from Olympus was used. To create a typical Z stack, sections of the lung containing GFP-labeled cells (the donor embryos express GFP under the β-actin promoter; thus all engrafted cells were GFP-positive) were scanned at a depth of approximately 30-150 μm with 2- or 3 μm z-steps. The data were analyzed using Volocity software (Perkin-Elmer, Coventry, UK). All 3D rendering of the images was performed in Volocity software.

Micro-CT Imaging

Micro-CT imaging was performed under general anesthesia (2.5% 2,2,2-tribromoethanol, 97% in PBS, 10 ml/kg administered intraperitoneally.

In vivo micro-CT experiments were performed on TomoScope® 30S Duo scanner (CT Imaging, Germany) equipped with two source-detector systems. The operation voltage of both tubes were 40 kV. The integration time of the first and second protocols was 90 ms (360 rotation) and 5 min (3600 rotation) and axial images were obtained at an isotropic resolution of 80 µm. The processing of the CT data was analyzed using the ImageJ software.

Freezing and Thawing of HEL-Derived Single Cell Suspension

For cryopreservation and thawing of HEL-derived cells, a standard protocol for cryopreservation of peripheral blood mononuclear cells was used. Briefly, enzymatically derived HEL cells were diluted to a concentration of $100 \times 10^6$ cells per ml. The same volume of freezing buffer (20% DMSO diluted in 80% FCS) was gently added, and the cells were then divided into cryotubes ($50 \times 10^6$ cells per ml in each). For the freezing process, a chamber containing cold propanol was used to achieve a $-1°$ C. per min rate of cooling. The cryotubes were kept in the chamber for 24 hours at $-70°$ C. and then transferred to liquid nitrogen container for extended preservation.

Before use, the cells were thawed quickly and then diluted slowly to remove DMSO. Gradual dilution of DMSO helped avoid osmotic stress. Briefly, the cryotubes were removed from the liquid nitrogen and transferred to a $37°$ C. water bath. The cells were gradually diluted in modified Epi-CFU medium containing 10% FCS. After thawing, the cells were phenotyped by FACS, assessed for viability and plated under 3D culture conditions for colony-forming assay in triplicate. After 10 days in culture, the colonies were counted to determine colony-forming efficiency.

Statistical Analysis

Differences between groups were evaluated by one-way ANOVA with a priori contrasts between the groups or by one-way ANOVA on the arcsine-transformed proportions followed by a Tukey's post hoc test or followed by a Dunnett's test, nested ANOVA, or two-tailed t-test, as indicated in relevant figure legends. For every ANOVA the residuals were tested for normality using Shapiro-Wilk test. Additionally, the homogeneity of variances was tested using Levene's test. For cases in which Levene's test showed significant differences in variances between the groups, specific transformation was done to address violations of the homogeneity of variance assumptions (as indicated in relevant figure legends). In situations where Tukey's post hoc test was used, all pairwise comparisons were performed, but only the P values of the difference between groups of interest are shown in the figures. In situations where Dunnett's test was used, the pairwise comparisons were done against the appropriate control group, as indicated in the relevant figure legends. In situations where nested ANOVA was performed, at least seven observations for each mouse were analyzed (in some cases more, as indicated in relevant figure legends).

For each data set, mean±s.d. was calculated and is presented in the Examples section which follows. For graphical presentation of the same data sets, box plots were generated, using GraphPad Prism software (Version 6.01), which present the entire data set distribution. The center line in the boxes shows the medians; box limits indicate the $25^{th}$ and $75^{th}$ percentiles, whiskers indicate the minimal and maximal values. The differences between the groups were considered statistically significant for $P<0.05$. Sample size was determined on the basis of IACUC limitations and previous experience with transplantation experiments in the lab. Thus the sample size was not calculated as to ensure adequate statistical power to detect hypothesized effect sizes.

EXAMPLE 1

Canalicular 'Window' for Human and Mouse Lung Progenitors

Growth Potential of Human Embryonic Lung Tissues Harvested at Different Gestational Time Points To evaluate a suitable window for human fetal lung progenitors, the present inventors initially characterized the growth and differentiation potential of lung precursor tissues harvested at different gestational time points (tissues originating from 15- to 24-week human fetuses). Using implantation of whole human (FIGS. 1A-I, FIGS. 26A-B and FIGS. 27A-L) or mouse (data not shown) fetal lung fragments under the renal capsule of immune-deficient (NOD-SCID) or syngeneic mice, respectively, it was found that use of human or mouse lung fetal tissue harvested at the canalicular stage of development enabled optimal growth and differentiation.

Overall, upon examination at 8 weeks post transplant, more than 98% of the grafts from donor tissue of all ages survived and all recovered grafts demonstrated increased size, with no evidence of neoplasia in any of the recovered grafts. Nevertheless, results were distinctly different when similar transplantation was attempted using earlier or later-gestation lungs as donor tissues.

As can be seen in FIG. 1A, tissue harvested at 20-22 weeks, (n=25, 1-3 mm in size) exhibited enhanced growth at 8 weeks after transplantation (reaching a size of 300.7+/−15.2 mm), compared to tissue harvested at 15-19 or 23-24 weeks of gestation (61.6+/−3.5 mm and 10.6+/−2.0 mm, respectively).

To obtain a quantitative evaluation of the different structural attributes in the growing lung implant, shown macroscopically in FIG. 1B, morphometric analysis was employed. As shown in FIGS. 1C-F, all elements of the respiratory tree, similar in their appearance to adult human lung tissue, were detected in implants growing from week 20-22 tissue. Thus, formation of alveolar ducts with alveoli (FIGS. 1C-F), trachea covered with ciliated epithelium (FIG. 1E), muscular layers and cartilage (FIG. 1E), and alveolar epithelial monolayers (FIG. 1F), were all exhibited by the growing implants. Likewise, parameters which define functional properties of the developing implants, as indicated by the ability to synthesize surfactant, detectable by staining for surfactant protein C (sp-C) (FIGS. 1G-H), and ability to transport ions, as indicated by staining for CFTR-cystic fibrosis transmembrane regulator (FIG. 1I), were clearly expressed. Typically, these functional markers appearing relatively late during the maturation process, coincide with the more differentiated elements expressing cytokeratin 18 (CK18) and they are not expressed in 20 week tissue prior to transplantation (data not shown).

Surprisingly, and in contrast to the above results, implants originating from tissue harvested at 15 weeks (FIGS. 1J-L) or 24 weeks (FIGS. 1M-O) developed cysts and were negative for sp-C and CFTR staining (data not shown), while implants originating from 18 week tissue, although exhibiting all the patterns of differentiation and maturation, including staining for sp-C and CFTR (data not shown), were still defective, in that the formed alveolar ducts were narrower, and alveolar walls were thicker (FIGS. 1P-R). Taken together, these results suggest that the optimal 'window' for harvesting human embryonic lung tissue for transplantation is between 20-22 weeks of gestation.

Identification of Stem Cell Progenitors and their Niches in Human Embryonic Lung Tissue at Different Gestational Time Points Following the identification of optimal 'window' human embryonic lung tissue for transplantation, the presence of putative stem cells in this 'window' tissue was evaluated compared to tissues harvested at earlier or later gestational time points. Accordingly, extensive phenotypic characterization of putative epithelial, endothelial and mesenchymal progenitors was carried out in human and mouse fetal lungs, which indicated marked enrichment of these putative progenitors in the canalicular lung tissue compared to tissues harvested at different gestational time points (FIGS. 28A-J and FIGS. 29A-H).

As shown in FIGS. 2A-D, H&E staining revealed that more bronchial and bronchiolar structures are found in tissues harvested at 20-22 weeks compared to tissues harvested at earlier time points. To define potential differences in progenitor levels in these tissues, the presence of the putative progenitor subpopulation of basal epithelial lung cells, shown to express cytokeratins 5 (CK5) and 14 (CK14), was examined. These distinct markers are down-regulated upon differentiation, in parallel to expression of the more mature CK8/CK18 positive phenotype.

As can be seen in FIG. 2E, marked frequency of CK5 positive cells was found in the large airways along with expression of CK14 (FIG. 2F), while a somewhat lower abundance was found in the developing alveoli. Furthermore, this immunohistological staining revealed that the $CK5^+$ cells were surrounded by $nestin^+$ cells (FIG. 2G), and some of them exhibited properties of neuroepithelial bodies marked by calcitonin gene related protein (CGRP). As can be seen in FIG. 2H, this innervation was further revealed by staining for neurofilaments (NF), suggesting an architecture of stem cell niches similar to those defined for hematopoietic stem cells in the bone marrow, and in adult mouse airways. Furthermore, in line with a very recent report regarding the BM niche, the epithelial $CK5^+$ niche also contained alpha-smooth muscle actin positive cells (FIG. 2I and FIGS. 5A-D) and $Vimentin^+$ mesenchymal cells (FIG. 2J).

Importantly, morphometric analysis demonstrated a relative abundance of $CK5^+$ progenitors at the 'window' tissue of 20-22 weeks of gestation, suggesting that the optimal window is likely associated with a higher number of these progenitors. Thus, in the tissue harvested at 20-22 weeks of gestation, the $CK5^+$ area was found to represent an average of 14.1%±5.6 of the total lung tissue, compared to 5.26%±1.06 (P=0.0006) or 6.05%±0.18 (P=0.002), in 15 week and 17 week tissues, respectively (FIGS. 2K-O).

In addition, both human and mouse canalicular lung cells exhibited marked clonogenic activity in three-dimensional (3D) cultures in the absence of exogenous growth factors (data not shown). Notably, cytokeratin $5^+$ ($CK5^+$) human embryonic lung cells, considered to represent committed epithelial progenitors were commonly surrounded by mesenchymal cells in close proximity to blood vessels (FIG. 26C and FIGS. 28A-J). Furthermore, clear evidence of niche innervations was obtained, as indicated by the presence of neurofilaments (FIG. 26D and FIG. 28G) and neuroepithelial bodies marked by calcitonin gene-related peptide (CGRP) expression (FIG. 28H). This unique structure of progenitor cells surrounded by mesenchyme and endothelial and innervating cells, again suggests a stem cell niche architecture similar to that defined for hematopoietic stem cells in the BM.

Taken together, this "window of opportunity" for harvesting embryonic lung as a source for transplantation can be explained in part by the frequency of CK5 positive epithelial progenitor cells, and their respective niches. To further investigate other putative progenitors in different embryonic tissues, a FACS analysis was used to determine the presence of several phenotypes recently attributed to pluripotential human lung stem cells. In particular, attention was focused on two phenotypes. The first, a rare subpopulation, stained positive for c-kit (CD117) and negative for many differentiation markers including CD34, was described recently by Kajstura et al., mainly in adult lung tissue, but also in embryonic tissue, the authors suggested that these cells represent a multipotent lung stem cell, with self-renewing capacity [Kajstura J. et al., N Engl J Med. (2011) 364(19): 1795-806; Anversa P. et al., Nat Med. (2011) 17(9):1038-9] and with regenerative potential for all lung lineages. However, Suzuki et al. maintain that in the embryonic lung, the $C-Kit^+$ cells also express CD34 and are likely endothelial progenitors [Moodley Y. et al., N Engl J Med. (2011) 365(5):464-6; Suzuki T. et al., American Journal of Respiratory and Critical Care Medicine (2010) 181 (1 Meeting Abstracts): A4898], therefore, the presence of $C-Kit^+CD34^+$ cells was also evaluated (FIGS. 2P-Z).

To that end, single cell suspensions obtained from enzymatically treated human embryonic lung tissues, harvested at 16, 18 and 20 weeks of gestation, were analyzed for the expression of several differentiation markers including CD34 (specific for hematopoietic and endothelial progenitors), CD45 (hematopoietic cells), CD31 (marker for endothelial cells), CD117 (c-KIT, to identify early progenitors), CD271 (NGFR, mesenchymal stem cell marker), and CD326 (EPCAM, epithelial differentiation marker).

Strikingly, the non-hematopoietic, CD45 negative population was found to comprise three distinct $C-Kit^+$ progenitor populations, including $CD34^{high}CD_{34}^{intermediate}$, and $CD_{34}^{negative}$ cells (FIGS. 2P-T). While the latter population is compatible with the early pluripotential adult lung stem cells, the other $CD34^+$ cells might be more strongly differentiated towards the endothelial lineage also expressing high levels of CD31 (FIGS. 5A-D).

Interestingly, the $C-Kit^+CD34^{neg}$ subpopulation was clearly more abundant in tissues harvested at 20 weeks (about up to 2-3% of $CD34^{neg}$ population) compared to earlier gestational ages (less than 0.15%) or to adult lung tissue used as a control (less than 0.45%, FIGS. 6A-L). These unique $C-Kit^+CD45^-CD34^-CD271^-$ cells, which are also negative for CD31 and CD326 (FIGS. 7A-I), in line with Kajstura et al. could also be identified by immunohistology. Thus, as shown in FIGS. 3A-C, these putative progenitors were present at low levels in close proximity to large airways, mainly in perivascular spaces.

Importantly, when lung tissues were analyzed by immunohistological staining for CD117 and CD34, several distinct cell sub-populations were found similar to those found by the FACS analysis. Analysis of a 20 week human lung is shown in FIGS. 4A-K; the majority of $CD117^+$ cells co-expressed CD34 and resided in blood vessels (FIGS. 4A-C) surrounding developing alveoli (FIGS. 4D-G), while the minor $CD117^+$ single positive cell sub-population were found in close proximity to large blood vessels and large airways (FIGS. 4H-K). Similar pattern of $CD117^+$ cell distribution was found in earlier gestational age lung tissues (FIGS. 8A-D), although the total percentage as revealed by FACS was significantly higher in the 20 week tissue (FIGS. 2A-Z). Furthermore, as shown in FIGS. 9A-D, the 20 week embryonic tissues also exhibit early and late endothelial progenitor cells (EPC) which may have a unique role in lung microvascular repair. Thus, this tissue was also found to exhibit the presence of two distinct $CD34^+CD31^+$ subpopulations. The first one identified by positive staining for CD14 and CD45, whereas the second subpopulation was $CD45^-CD105^+$. The former one termed 'early EPCs' are characterized by early growth in vitro, CD34/CD31/CD14 positivity, the inability to form tubes in a Matrigel tube forming assay, and high levels of cytokine secretion. The other type of EPC, termed 'late outgrowth EPCs', outgrowth endothelial cells (OECs)' or 'endothelial colony forming cells (ECFC)' is characterized by CD31 and CD105 positivity, lack of CD45 and CD14, and the unique ability to spontaneously form human blood vessels when implanted in a gel into immunodeficient mice, integrating with murine vessels of the systemic circulation.

EXAMPLE 2

Proof of Concept in Mouse Models for the Regenerative Potential of 'Window' Embryonic Lung Transplants Optimal 'Window' for Harvesting Mouse Embryonic Lung Precursor Tissue for Transplantation In order to assess the curative potential of embryonic lung derived tissue in appropriate mouse models, the optimal "window" for harvesting mouse embryonic lung for transplantation was initially defined, as for its human counterpart. Thus, mouse lung embryonic tissue was harvested at different gestational time points (E14-E17), implanted under the kidney capsule of syngeneic mice, and 8 weeks after transplantation, the implants were assessed for the presence of lung parenchyma, bronchial and alveolar structures, as well as for unwanted presence of fibrosis and cysts.

As can be seen in FIGS. 10A-E, twelve weeks after sub-capsular renal transplantation, E14 and E17 lung tissue resulted in formation of cystic and fibrotic tissue (FIGS. 10A-B), while E15-E16 mouse embryonic lung exhibited marked potential to further differentiate and to reach the alveolar stage (FIGS. 10C-E). Thus, similar to human lung tissue, the canalicular stage of lung development offers the optimal window for harvest of tissue for transplantation (FIG. 10F). Also, similarly to the human 'window' tissue, the E16 lung tissue exhibited no alveoli (FIG. 11A); CK-5 positive cells were abundant in large airways, and numerous neuroepithelial bodies were found within the entire sample, which stained positively for CGRP and were localized in niches (FIG. 11B) similarly to bone marrow and adult mouse lung (FIGS. 12A-F). Likewise, CCSP-positive cells were found in the regions of large airways, which were rich in nestin-positive cells (FIG. 11C), suggestive of stem cell niches, and were surrounded by alpha-SMA positive cells (FIG. 11D).

In addition, similarly to their human counterparts, the E15-E16 tissue was enriched with putative progenitors compared to early or later gestational tissues, as shown by FACS analysis of $CD45^-CD31^-EpCAM^+CD24^+CD49f^+CD104^+$ cells, recently established as putative lung progenitors in adult mouse lung [McQualter J L et al., Proceedings of the National Academy of Sciences. (2010) 107(4):1414-9]. Thus, as can be seen in FIGS. 11E-Y, depicting representative FACS analysis of E13, E14, E15 and E16 single cell suspensions, markedly higher levels of $CD45^-CD31^-EpCAM^+ CD24^+CD49f^+CD104^+$ cells were found in E15 and E16 lung tissue (0.062%±0.007 and 0.073%±0.005, respectively) compared to the level in E13 and E14 tissue (0.002±0.00057% and 0.012±0.0057%, respectively).

Transplantation of E16 Mouse Embryonic Lung Cells for the Treatment of Lung Injury Considering that E15-16 tissues exhibit marked growth and differentiation potential upon transplantation, this 'window' tissue was further evaluated in a mouse model for lung injury.

To that end, these cells were initially evaluated in a model based on injury induction with naphthalene, as previously described [Stripp B et al, American Journal of Physiology-Lung Cellular and Molecular Physiology. (1995) 269(6): 791]. This lung injury model mimics lung diseases caused by mild epithelial injury, detectable by changes in the expression of pulmonary Clara cells.

The particular anatomical localization of Clara cells in respiratory bronchioles and in broncho-alveolar junctions enabled to accurately localize the site of injury after naphthalene exposure, and to test the ability of a single cell suspension of embryonic "window" cells to colonize and restore the injured epithelial layer in syngeneic recipients.

Two days following naphthalene administration, recipient C57BL mice were infused with $1 \times 10^6$ E16 lung cells, derived from GFP-positive pregnant mice. Subsequently, the lungs of the treated animals were histologically assessed at different time points for the presence of GFP-positive cells. These initial experiments (not shown) revealed that ablation of Clara cells by naphthalene was transient and could not enable significant engraftment and development of donor-derived Clara cells. Thus, the present inventors contemplated that a more aggressive conditioning regimen, more effectively ablating resident stem cell proliferation, might be required for the assessment of the regenerative capacity of donor cells, as commonly found in studies measuring chimerism induction following bone marrow transplantation.

To test this theory, 40 hours following naphthalene injury, animals were additionally treated with sublethal TBI (6 Gy) so as to eliminate resident lung stem cells, which are potentially induced to proliferate by prior naphthalene treatment.

After 1 day, the mice received E16 lung cells, and were followed for engraftment and development of donor-derived cells in their lungs by immunohistological staining coupled with morphometric analysis, as well as by two-photon microscopy.

As shown in FIGS. 13A-C, GFP positive 'patches', indicating engraftment of donor-derived cells in the recipient lungs were markedly enhanced at 30 days post transplant, in mice conditioned with both naphthalene and 6 Gy TBI (FIG. 13C) compared to TBI alone (FIG. 13A), or naphthalene alone (FIG. 13B). This marked impact of conditioning on lung chimerism level is demonstrated quantitatively in FIG. 13D, depicting morphometric analysis of the GFP patches found in three independent experiments comprising a total of nine mice in each group. Thus, while 55 foci/mm$^3$ donor-derived foci were found in mice conditioned with naphthalene and 6 Gy TBY, only 10-12 foci/mm$^3$, and 2-3 foci/mm$^3$, were found in mice conditioned with naphthalene or TBI alone, respectively.

Immunohistological examination of mice exhibiting chimeric lungs, further revealed the level of integration into functional elements in the recipients lungs. As shown in FIG. 14A, lumens of the large airways of untreated control mice clearly exhibited the presence of CCSP$^+$ Clara cells, and these cells underwent ablation and peeling immediately after the conditioning (FIG. 14B). However, mice transplanted after the conditioning of choice, exhibited at day 30 post transplant, formation of a new epithelial layer, and engrafted GFP$^+$ cells were found in the bronchial lumens. These donor derived GFP$^+$ cells incorporated into the host bronchial and alveolar airways, and were vascularized, as shown by staining for V-cadherin (FIG. 14C); They also expressed CCSP (FIGS. 14D-F), and were positive for Sp-c (FIGS. 14G-I) and CFTR expression (FIGS. 14J-L), suggesting their ability to produce surfactant and engage in ion transport. As expected, these specific functional markers were exhibited differentially by the engrafted GFP$^+$ cells according to their location. Thus, in large airways, the cells were positive for CCSP, and in alveoli, the engrafted cells were positive for sp-C, but all the cells were found to express CFTR, which is of particular significance for potential correction of cystic fibrosis (CF).

Interestingly, when tested at later time points post transplant, the initial foci were clearly growing in size and thereby occupying a larger proportion of the engrafted lungs. This was further demonstrated by two-photon microscopy, enabling direct view of the lungs immediately after sacrifice, with or without intravital co-staining of blood vessels with red Quantum dots for fluorescent vascular labeling (data not shown). As can be seen in FIGS. 15A-C, while a moderate engraftment of the lung by donor type cells was found at 6 weeks post transplant, with a predominant integration of transplanted GFP$^+$ cells in the broncho-alveolar and vascular structures (FIGS. 15A-B), further progression of donor type cells occupying almost third of the lung tissue, was found at 4 months post transplant (FIG. 15C).

Furthermore, immunohistological assessment of these chimeric lungs at 16 weeks after transplantation, revealed the full integration of donor derived cells, in the gas exchange surface at the interface of blood vessels and in alveolar epithelial structures (FIGS. 16A-L). Thus, GFP$^+$ cells were found by triple staining with CD31 and anti-pan-cytokeratin antibodies to be incorporated into vascular and epithelial compartments of transplanted lungs, without signs of scarring or fibrosis (FIGS. 16A-D and FIGS. 17A-E). Likewise, the AQP (FIGS. 16E-H) and SP-C (FIGS. 16I-L) staining revealed incorporation of donor derived cells in the gas-exchange surface of type I and type II alveocytes, respectively.

Collectively, these results strongly suggest that embryonic lung cells harvested from 'window' tissue could offer a novel cell source for lung tissue repair. Furthermore, it is anticipated that therapy with such cells could be more effective if combined with sub-lethal conditioning, although this might be less critical in clinical situations at which host lung progenitors are markedly ablated by the ongoing injury.
Transplantation of a Single Cell Suspension Derived from 20-22 Week Human Embryonic Lung into NOD-SCID Mice, Following Lung Injury Induction with Naphthalene and TBI To investigate the ability of 'window' human embryonic lung cells to integrate into injured lungs, a lung injury model was established in immunodeficient SCID mice. Considering that NOD-SCID mice are more sensitive to TBI, 3.0 GY TBI were used instead of 6.0 Gy TBI used in the studies with mouse donor-tissue, described above. Furthermore, as a replacement for the genetic GFP labeling, immunohistology with mouse and human specific antibodies was used to distinguish between host and donor epithelial, endothelial, and mesenchymal cells.

Thus, while infusion of 1×10$^6$ cells harvested after enzymatic digestion of 20 week human embryonic lung cells into NOD-SCID mice, conditioned with NA alone, did not result in any appreciable level of engraftment (data not shown), marked chimerism was attained following infusion of the same number of cells into NOD-SCID mice conditioned with naphthalene and subsequent treatment with 3.0 Gy TBI (FIGS. 18A-I and 19A-F).

In an initial short term experiment, a human embryonic (20 w) lung-derived single cell suspension was stained with the tracking fluorescent dye, 5-(and-6)(((4Chloromethyl) Benzoyl)Amino)Tetramethylrhodamine) (CMTMR), and the cells were infused into conditioned NOD-SCID mice. When examined 2 weeks later, engrafted human cells could be visualized within distinct patches in the lung of the recipient mice (FIG. 24A), similar to GFP$^+$ patches found in the syngeneic transplantation model (FIG. 24B). As the CMTMR staining is transient, a second set of experiments was carried out to distinguish the human and mouse cells at later time points following transplantation, by immunohistological staining using an anti-mouse MHC antibody not cross reactive with control human tissue (FIGS. 24C-E), and the anti-human cytokeratin MNF 116 antibody (staining human epithelial cells), not cross reactive with control mouse tissue, as verified by double staining in FIGS. 24F-H.

Importantly, at 6 weeks post transplant, double staining with these antibodies clearly revealed a significant level of chimerism. As can be seen in FIGS. 18A-C, showing low magnification of mouse bronchi, double staining with the mouse and human markers clearly demonstrates incorporation of human derived cells into the lung structure, and this can be further appreciated under high magnification of two different fields (FIGS. 18D-F and 18G-I, respectively).

In a third set of experiments, human embryonic lung cells harvested at 20 week were transplanted into NOD-SCID treated with NA and slightly higher TBI (4 Gy).

The mouse lungs were stained 7 weeks after transplantation with additional distinguishing anti-mouse and anti-human markers. Thus, mouse anti-human cytokeratin MNF 116 antibody (staining human epithelial cells), mouse anti-human V9 (staining vimentin 9, typical of stromal cells), and mouse anti-human CD31 (staining endothelial cells) were mixed together and placed on the tissue section; sections were then incubated with a second anti-mouse IgG antibody labeled with Daylight 488 (green). FIGS. 19A and 19D show the selective staining by this antibody cocktail of human tissues in the bronchial structure of mouse lung. Cells of mouse origin in the mouse lung were stained with Banderia lectin. The latter is known to bind to α-Gal moiety expressed on mouse epithelial and endothelial cells, and as can be seen, it is not cross reactive with the human tissue when monitored alone (FIGS. 19B and 19E) or in conjunction with MNF staining FIGS. 19C and 19F). Furthermore, using similar markers, marked chimerism could also be detected in the alveoli of transplanted mice (FIGS. 20A-F). Importantly, the human lung cells derived from transplantation of human embryonic cells were also found to exhibit several important functional markers.

As can be seen in FIGS. 21A-C, double staining of the human cells marked in green by the cocktail described above (FIG. 21A) together with a general marker of cytokeratin, resulted in staining of all epithelial cells of both mouse and human origin (FIG. 21B), illustrating distinct epithelial cells within the human cell population in the engrafted lung (FIG. 21C). Likewise, human cells positive for aquaporin-5 (AQP-5), typical of type I alveocytes (FIGS. 22A-C) and human cells positive for surfactant protein C (SP-C) characteristic of type II alveocytes (FIGS. 23A-F) were clearly distinguished within the chimeric lungs of transplanted animals at 7 weeks following transplantation.

Thus, human derived lung cells are not only incorporated into the injured mouse lung but also express AQP-5, required to perform gas-exchange, or SP-C, indicating production of surfactant by the alveoli.
Treatment with Embryonic Lung Derived Stem Cells is not Associated with Teratoma Development One of the most controversial issues in embryonic stem cell transplantation, which limits their clinical application, is the potential tumorigenicity of the transplanted tissues. In previous studies in which the present inventors attempted to define the optimal 'window' for different pig embryonic precursor tissues, results showed that beyond E28, none of the tested tissues exhibit any risk for teratoma formation

[Eventov-Friedman S et al., Proceedings of the National Academy of Sciences. (2005) 102(8):2928]. Thus, considering that embryonic lungs develop late in embryogenesis, and that, accordingly, the 'window' of choice for mouse, pig or human embryonic lung tissue represents a relatively late stage of gestation, the risk for teratoma induction associated with such precursor tissues is likely very low. However, to further verify this important issue, a detailed histological analysis was performed of the transplanted mice (n=30) up to 12 months following transplantation; no evidence was found of any tumors in the transplanted lung tissue. Furthermore, long term follow up of transplanted mice by lung micro-CT (resolution of 80 μm) did not reveal any suspected space-occupying lesion in these mice. A summary of these results with representative images is demonstrated in FIGS. 25A-D.

DISCUSSION

The present results illustrate that mouse or human lung embryonic tissue, obtained at the canalicular stage, can offer an optimal source for tissue replacement by transplantation. Furthermore, it was proposed that human embryonic lung, rich in early progenitors, resembles in its attributes tissues of the bone marrow and cord blood, whose use for transplantation in hematopoietic diseases has dramatically increased over the past decade. The 'window' embryonic tissues, which exhibited optimal growth and differentiation upon implantation into syngeneic or SCID mice, are significantly enriched for various epithelial, mesenchymal, and endothelial progenitors, compared to tissue from earlier or later gestational time points. Moreover, detailed analysis of these early progenitors in their respective embryonic tissues, revealed that epithelial progenitors reside in specific niches, similar to those described extensively for hematopoietic stem cell niches in the bone marrow. Thus, the present results documented, in proximity to putative lung progenitor cells, the assembly of endothelial cells, nestin-positive cells, and mesenchymal cells, which are also typically innervated, as found by positive staining for CGRP and neurofilaments. These results are consistent with studies indicating the potential existence of stem cell niches in the adult mouse lung [Engelhardt J F. American journal of respiratory cell and molecular biology. (2001) 24(6): 649-52].

In addition to defining the optimal window for use of fetal tissue in transplantation, correlating with the appearance of human embryonic lung progenitor niches, the present study also sheds light on an ongoing debate regarding the phenotype of human lung progenitors. Thus, while Kajstura et al. [Kajstura et al. 2011, supra]described a small population of c-kit$^+$ cells that are negative for all other markers and reside in discrete perivascular areas close to large airway structures, the present inventors found in developing alveoli, another c-kit$^+$ cell population, which resides in blood vessels, in close proximity to CK5$^+$ progenitors, expressing both CD34 and CD31 antigens, as suggested by Suzuki et al. (Suzuki et al 2010, supra). Thus, the 'window' lung embryonic tissue, characterized here, contains both putative c-kit positive progenitor populations. The close proximity and potential interaction of c-kit positive cells with CK5$^+$ epithelial progenitors is consistent with the recent suggestion that c-kit triggering is crucial for normal development and maintenance of alveolar structures [Lindsey J Y et al., American Journal of Respiratory and Critical Care Medicine. (2011) 183 (1 MeetingAbstracts): A2445].

Importantly, the "optimal canalicular window" tissues exhibit the highest level of all types of progenitors relative to lung tissues from earlier developmental stages; thus, the present inventors contemplated that intravenous transplantation of the unfractionated cell mixture, similarly to the methodology used in bone marrow transplantation, could be the preferred approach. Indeed, transplantation of a single cell suspension of E15-E16 mouse lung or 20-22 week human lung tissue demonstrated the remarkable regenerative capacity of these cells following lung injury induced by combining naphthalene and 6.0 Gy sub-lethal TBI. Critically, this level of conditioning prior to transplantation was necessary to establish chimerism when host lung progenitors were present at significant levels, as found after injury induction with naphthalene. Similar observation was made recently by Duchesneau et al. [Duchesneau P et al., Molecular Therapy. (2010) 18(10): 1830-6] who demonstrated that the engraftment of bone marrow derived cells in lung structures can be markedly enhanced by intensification of the conditioning using the myeloablative agent busulfan in addition to naphthalene. Clearly, this requirement for conditioning might vary in its intensity in different clinical situations, depending on the level of lung injury to host progenitors affected by the pathological process.

Taken together, the present results revealed robust engraftment in different compartments of the host lung and formation of the entire respiratory unit including the following elements: a) Newly formed epithelial cells in small bronchioles, as manifested by GFP$^+$ CCSP$^+$ cells. b) Pneumocyte type 1 cells (GFP$^+$AQP-5$^+$), important for the gas-exchange surface within the alveoli. c) Pneumocyte type 2 cells (GFP$^+$ Sp-C$^+$), important for surfactant production in the alveoli. d) Robust presence of GFP$^+$CD31$^+$ cells in the vasculature. In addition, the engrafted tissue exhibits, along with respiratory elements, expression of CFTR required for ion transport, especially critical for CF patients.

This rather dramatic engraftment following "double injury", as opposed to conditioning with each agent alone, might be explained by competition between host and donor progenitors for their respective niches. Reynolds et al. [Reynolds S D et al., American Journal of Physiology-Lung Cellular and Molecular Physiology. (2004) 287(6): L1256-65] demonstrated that elimination of the CCSP-expressing cell population by naphthalene, results in secondary alveolar inflammation, edema, and depletion of the alveolar type II cell population. Thus, selective airway injury can serve as the inciting injury in diseases characterized by severely compromised alveolar function. Furthermore, Volscaert et al. [Volckaert T et al., J Clin Invest. (2011) 121(11):4409] demonstrated that the Wnt/Fgf10 embryonic signaling cascade is reactivated in mature parabronchial smooth muscle cells (PSMCs) after naphthalene-induced injury, in a manner that activates Notch signaling and subsequent epithelial to mesenchymal transition; this finding indicates that activation of this embryonic pathway could probably serve as a trigger for effective incorporation of the embryonic lung-derived tissue in the different lung compartments. Likewise, radiation-induced lung injury was shown to induce breakdown of the blood-alveolus barrier and microcirculation dysfunction, and could thereby enable the dominance of donor-derived endothelial cells (45-47).

Regardless of the mechanism involved, the marked engraftment in the mouse model of donor derived cells attained in both bronchiolar and alveolar structures is striking. This chimerism, which increases over time, can likely be attributed to the multiple donor progenitors in the implanted embryonic lung tissue, enabling progeny of early self-renewing pluripotential stem cells to gradually replace host or donor cells derived from later precursors.

Similar lung integration and development was also observed when testing human lung progenitors in NOD-SCID mice, although in this system, the potential loss of cross-talk with mouse cytokines might reduce engraftment. Thus, in three sets of experiments, the present results illustrated that donor-derived human cells incorporate into both bronchiolar and alveolar structures, exhibiting similar features to those described above for syngeneic embryonic mouse lung cells.

Further studies are required to define optimal immune suppression protocols that will enable successful transplantation in allogeneic recipients. In general, the early embryonic stage might render the implanted donor tissue less immunogenic; however, embryonic tissue transplants cannot evade the indirect pathway of rejection. Nevertheless, this challenge can be addressed by protocols including agents inducing co-stimulatory blockade. Alternatively, the marked level of hematopoietic progenitors (unpublished results) in the embryonic lung tissue might result in hematopoietic chimerism that could induce central tolerance towards donor-derived lung cells after transplantation. In addition, the possibility of cryopreserving single cell suspensions of 20-22 week lung tissue, which could markedly enhance transplant availability, might also enable to establish banks of HLA typed donors as for cord blood, and thereby could potentially reduce the immune suppression requirements.

Finally, the present 'window' mouse embryonic tissue exhibited no risk of teratoma when followed for prolonged time periods after transplantation, by high resolution (80 μm) micro-CT as well as by pathological examination at the end of the follow-up period.

In summary, the present results demonstrate for the first time that the canalicular stage of gestation offers an optimal 'window' for harvesting mouse and human embryonic lung precursor tissue for regenerative transplantation. This tissue, which is free of teratoma risk, is highly enriched for several progenitor types that were identified by immunohistology in their respective niches, similarly to HSCs in the bone marrow. Marked engraftment, differentiation, and robust incorporation of these progenitors into injured lungs, can be provided by infusion of a single cell suspension prepared by enzymatic digestion of the embryonic lung tissue. As in bone marrow transplantation, induction of lung chimerism is dependent on some form of conditioning, so as to reduce competition with host-type endogenous precursors. While various attempts to isolate pluripotential stem cells from adult lungs and to expand these cells in culture for the purpose of regenerative transplantation have been advocated, the present results demonstrate that embryonic lung tissue harvested at 20-22 weeks of gestation could potentially offer a more simple alternative modality for lung repair.

EXAMPLE 3

Ablation of Endogenous Lung Progenitors Occupying Niches

Based on the preliminary results described above, the present inventors tested the curative potential of non-fractionated single cell suspensions of canalicular-staged mouse lung cells, in the well-established NA-induced lung injury model. This model mimics lung diseases caused by epithelial injury, reflected by changes in the presence of pulmonary club cells (formerly referred to as Clara cells, which are marked by staining for Clara cell secretory protein (CCSP; formally known as Scgb1a1). Considering the observation of a marked analogy between the niches of progenitor cells in lung and in the BM, it was tempting to test the i.v. route for cell transfer, commonly used in HSCT. Thus, 2 days following NA administration, recipient C57BL/6 mice were intravenously infused with $1 \times 10^6$ syngeneic E16 lung cells, derived from GFP-positive embryos. Subsequently, the lungs of the treated animals were assessed at different time points for the presence of GFP-positive cells. These initial experiments (data not shown) failed to attain a detectable level of lung chimerism, indicating that either the progenitors did not home to the lung, or that NA-induced ablation of club cells was transient, and did not enable adequate engraftment or propagation of donor-derived CCSP$^+$ cells.

Figures 26F, 26G, 26H, 26I, 26J:
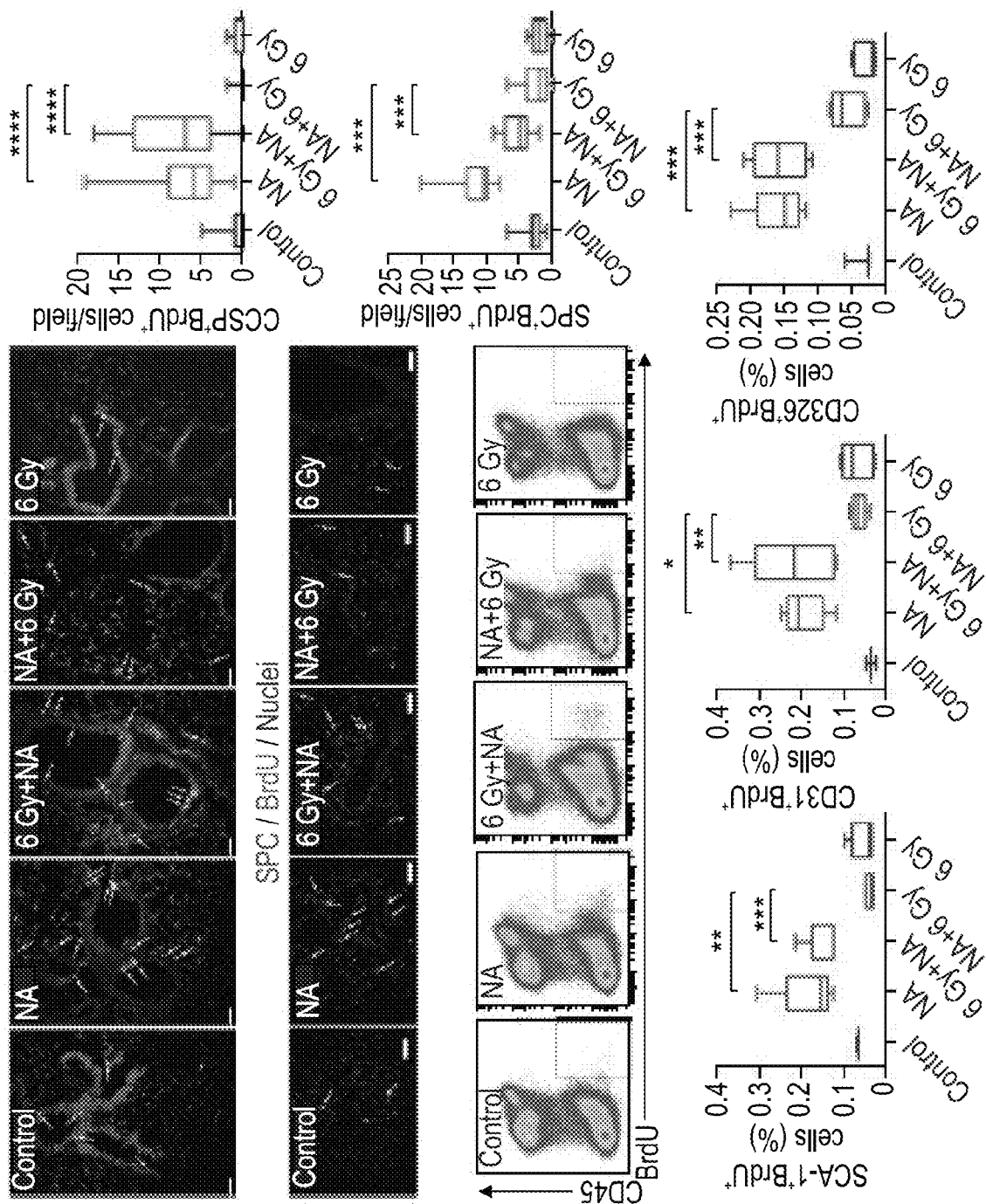

To address the latter possibility, the present inventors further explored the state of the niche using BrdU incorporation analysis of mice conditioned with NA alone, in the absence of transplantation. A marked signal of endogenous BrdU$^+$ proliferating cells could be detected (FIG. 26E), suggesting that a wave of endogenous progenitors can likely expand within the first week after NA exposure. This endogenous cell recovery, which could potentially compete with donor-derived progenitors and prevent their engraftment in the appropriate niches, was inhibited following exposure to 6 Grey (Gy) total body irradiation (TBI) 48 hrs after NA treatment. Exposure to 6 Gy TBI prior to NA treatment did not effectively ablate the endogenous pool of progenitors, as indicated by the marked BrdU incorporation if NA was given after, rather than before, exposure to 6 Gy TBI (FIG. 26E). Further immunohistological analysis revealed that both CCSP$^+$BrdU$^+$ (FIG. 26F) and BrdU$^+$ cells within the alveocytes type 2 (AT2) compartment marked by staining for surfactant protein C (SPC) (FIG. 26G) expanded after NA-induced lung injury. Quantitative morphometric analysis, using Fiji software, of the numbers of CCSP$^+$BrdU$^+$ and SPC$^+$BrdU$^+$ cells per assessed field following different conditioning protocols showed that indeed these cells could be effectively ablated upon subsequent exposure to 6 Gy TBI (P values for comparison of NA alone versus NA+6 Gy TBI, were 0.00017 and 0.0001 for CCSP$^+$BrdU$^+$ and SPC$^+$BrdU$^+$ cells, respectively). Evaluating the distribution of the number of proliferating cells per individual assessed field, collected in more than 20 fields from three different mice demonstrated the enhanced efficiency of elimination of proliferating cells induced by TBI administration after NA (FIG. 26H). Notably, ablation of both CCSP$^+$BrdU$^+$ cells and SPC$^+$BrdU$^+$ cells by NA followed by 6 Gy TBI was significantly more effective compared to 6 Gy TBI prior to NA (P=0.000017 and 0.0001 for CCSP$^+$BrdU$^+$ and SPC$^+$BrdU$^+$ cells, respectively).

This immunohistological analysis of elements of the epithelial compartment was further extended to other cell lineages using more quantitative FACS analysis to determine the level of CD45$^-$BrdU$^+$ cells following different conditioning modalities (FIG. 26I). A detectable signal, representing endogenous endothelial (CD45$^-$CD31$^+$), epithelial (CD45$^-$CD326$^+$) and mesenchymal (CD45$^-$SCA-1$^+$) [28] cell populations capable of proliferating in response to the NA challenge was observed (FIG. 26J). Again, the level of BrdU$^+$ cells within these lineages was significantly reduced following exposure to 6 Gy TBI administered 48 hrs after NA (P values were 0.015, 0.0009 and 0.0004 for CD45$^-$CD31$^+$BrdU$^+$, CD45$^-$CD326$^+$BrdU$^+$ and CD45$^-$SCA-1$^+$BrdU$^+$ cells, respectively), while treatment with 6 Gy TBI prior to NA exposure was less effective (P values for comparison of NA+6 Gy TBI versus 6 Gy TBI+NA, were 0.004, 0.0009, and 0.006 for CD45$^-$CD31$^+$BrdU$^+$, CD45$^-$CD326$^+$BrdU$^+$ and CD45$^-$SCA-1$^+$BrdU$^+$ cells, respectively). Taken together, these results strongly indicated that, as in HSCT, induction of lung chimerism might require "niche clearance" of endogenous progenitors, and that this prerequisite could be met by adequate preconditioning.

EXAMPLE 4

Lung Chimerism in Different Lineages after Progenitor Ablation

To evaluate the impact of preconditioning on lung chimerism, the present inventors exposed mice to 6 Gy TBI 48 hrs after NA, and infused 1×10$^6$ lung cells from E16 GFP-positive mice, several hours following irradiation. Recipient mice were then monitored for engraftment and development of donor-derived cells using immunohistological staining, morphometric analysis, and two-photon microscopy. GFP$^+$ 'patches', indicating engraftment of donor-derived cells in the recipient lungs, were markedly enhanced at 30 days post-transplantation in mice conditioned with both NA and 6 Gy TBI (FIGS. 30A-H), compared to TBI alone or NA alone (FIGS. 30A-D). Further analysis at 8 weeks post-transplantation using Fiji software revealed that in mice conditioned with NA plus 6 Gy TBI, these donor-derived GFP$^+$ cells occupied on average 11±3% (mean±s.d.) of the recipient lung. Co-localization analysis using Imaris software showed that co-localized donor type cells comprised more than 20% of cytokeratin$^+$ (CK$^+$), or CD31$^+$ or nestin$^+$ cell subpopulations within defined regions of interest (ROI). ROI for co-localization (% ROI co-localized) was defined by a fixed threshold on the green channel (% ROI co-localized, mean±SD for CK=9.1±4.2, for CD31=18.06±6.1, for nestin=8.5±2.5% respectively), indicating chimerism in epithelial, vascular and mesenchymal compartments of the lung (FIGS. 30E-H). This lung chimerism markedly progressed in the absence of subsequent injury, with donor cells occupying 28±6% of the lung when tested at 16 weeks post-transplant (P<0.01) (FIGS. 31A-J).

Figure 32H:
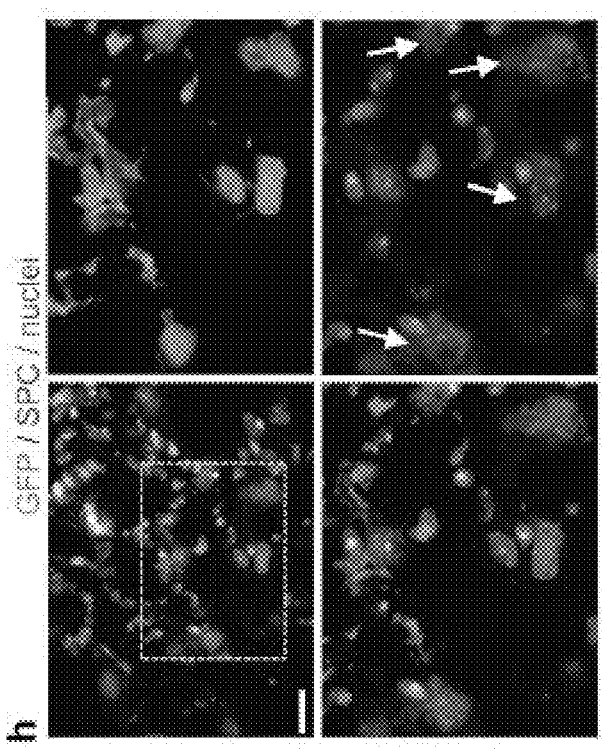

The three dimensional structure of the engrafted patches was visualized by two photon microscopy, enabling a direct view of the lungs immediately after sacrifice (FIGS. 31D-G and FIGS. 32A-I). While obvious engraftment of donor type cells was already evident at 6 weeks post-transplant, with predominant integration of transplanted GFP$^+$ cells into the bronchio-alveolar and vascular structures (FIGS. 31D-E and FIG. 32B), further proliferation of donor type cells continued, with donor cells occupying almost a third of the lung tissue after 4 months (FIGS. 31F-G and FIG. 32C).

Notably, these GFP$^+$ patches are likely derived from clonal expansion and differentiation of single progenitors, as indicated by transplantation of a 1:1 mixture of E16 fetal lung cells from GFP (green)- and 'tdTomato' (red)-marked mice (FIG. 32D), leading to distinct monochromatic patches, as revealed either by extended focus image of spinning disc confocal microscopy (FIG. 31H) or by two-photon microscopy (FIG. 31I and FIG. 32D). Likewise, histological staining of the recipient lung with anti-GFP and anti-DsRed antibody (cross-reactive with td-Tomato) and detailed examination by spinning disc confocal microscopy (FIG. 31J) demonstrated the absence of overlap between fully green and fully red donor-derived patches, supporting their clonal origin.

EXAMPLE 5

Functional Improvement after Transplantation

Figure 32E:
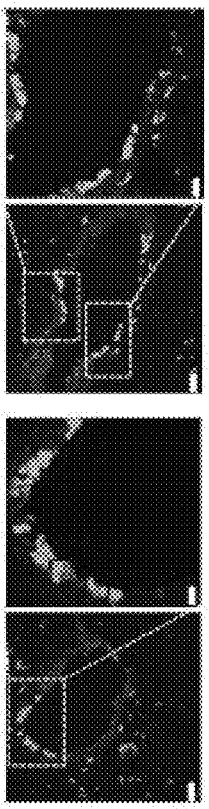
Figure 32F:
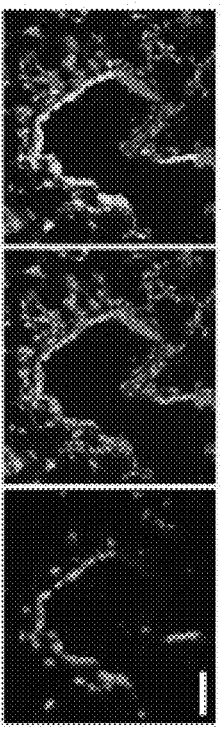
Figure 32G:
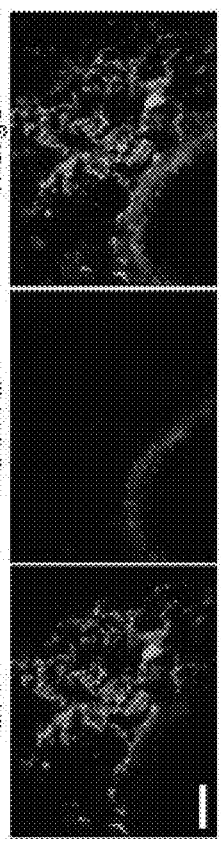
Figure 32I:
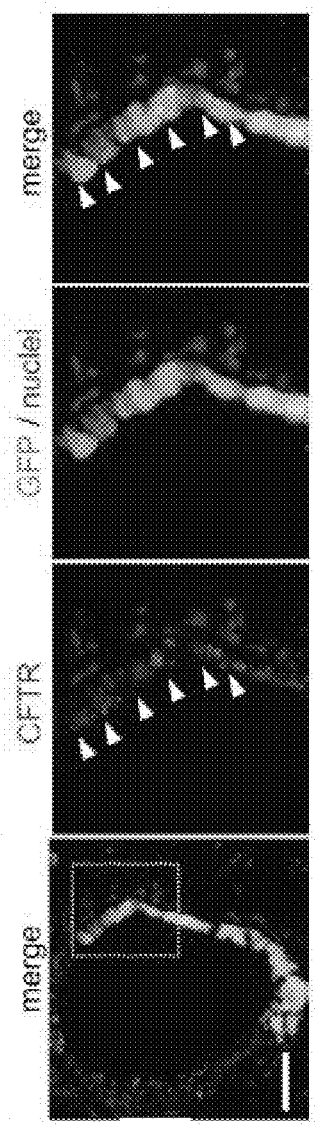

Having demonstrated that the donor-derived patches which were observed originated from a single progenitor, and considering the essential function of the epithelial compartment in the lung, inventors next characterized epithelial cell differentiation and cell types making up the distinct patches. Three types of patches—bronchiolar, bronchioalveolar and alveolar (FIG. 33A)—were identified on the basis of morphology and orientation vis-à-vis the bronchiolar lumen. Although these different patch types can be visualized well on the basis of morphology, further verification of the bronchioalveolar boundaries was carried out by immunostaining for SOX2, a transcription factor expressed by cells in conducting airways (FIGS. 32E-G). Quantitative analysis of the frequency of different types of patches suggested that most patches predominantly comprise alveolar structures (FIG. 32H) (159 out of 262 patches, 88 fields, n=3 mice), but some bronchiolar (15 out of 262) and bronchioalveolar patches (88 out of 262) were identified as well. Notably, some engrafted GFP$^+$ cells were positively stained for cystic fibrosis transmembrane conductance regulator (CFTR) (FIG. 32I) and potentially express wild-type CFTR critical for repair of cystic fibrosis, although the staining per se does not confirm appropriate functional activity.

To further evaluate the level of donor type chimerism in different functional lung cell subpopulations, CCSP staining was used to detect club cells, aquaporin-5 (AQP-5) or the receptor for advanced glycation end products (RAGE) to detect type I alveocytes (AT1 cells) and SPC to detect AT2 cells (FIGS. 33B-C). AQP-5 is a surface marker, and its colocalization with GFP is difficult to ascertain (as AT1 cells have long cytoplasmic extensions that are distant from the nucleus), so chimeric mice were generated by transplantation of major histocompatibility complex (MHC)-disparate E16 lung cells from C3H/HeJ donor mice, expressing H2$^k$ haplotype (H2K$^k$) into immunodeficient Rag1$^{-/-}$ mice of C57BL/6 background, expressing H2$^b$ haplotype (H2K$^b$) (FIGS. 34A-C). Although MHC class I is not expressed on all lung cells, it is highly expressed on the cell surface of alveolar and endothelial cells, and donor type lung patches in transplanted mice can be clearly distinguished by staining of cell surface MHC (FIG. 34D). Thus, this system is more suitable for studying colocalization on the cell surface with AQP-5 (FIGS. 33D-E and FIGS. 34E-F). The percentage of GFP colocalization with CCSP or SPC and of H2K$^k$ with AQP-5 was quantified using the Imaris 'colocalization module'. About 20%-50% colocalization was observed within defined ROIs in relevant chimeric structures within each of these epithelial lung subpopulations after infusion of GFP$^+$ or H2K$^k$ E16 lung cells (FIG. 33E). The percentage of ROI colocalized was defined by fixed threshold on the green (GFP) channel for CCSP and SPC (% ROI colocalized=18.8±10.3 for CCSP, 6.5±3.6 for SPC; mean±s.d.) or the red channel (H2K$^k$) for AQP-5 (% of ROI colocalized=28.5±12.1 for AQP-5). A marked colocalization on AT1 cells with donor type staining was also found when using an alternative cell-segmentation analysis (FIGS. 34F-G). Furthermore, the AT1 characteristics of these donor type AQP-5 positive cells were verified by RAGE staining (FIG. 34H).

The clear distinction of donor type patches from host type cells in this allogeneic model (FIG. 34D) strongly indicated that for most cells expressing donor MHC, fusion with host cells is unlikely. Indeed, FACS analysis of a single cell suspension of chimeric lung 8 weeks after transplantation confirmed this finding, revealing that although donor cells single-positive for H2K$^k$ represent about 5.2%±2.1%, mean±s.d. of the CD45− lung cell population (percentages in three mice were 7.3%, 5.1% and 3.1%), only 0.27%±0.16% of the cells were H2K$^k$H2K$^b$ double positive (double-positive percentages in these three mice were 0.17, 0.46 and 0.19, respectively), indicating that more than 90% of donor type cells were not fused with host cells (FIG. 34I).

Furthermore, the present inventors documented the predominance of single-positive donor cells not fused with host cells in the syngeneic model, in which GFP$^+$ E16 lung cells are infused into tdTomato-expressing recipients (detailed colocalization analysis and 3D confocal staining are presented in FIGS. 35A-F). Notably, in this mouse model, in contrast to the allogeneic model (in which donor cells are identified by their MHC class I expression), GFP and tdTomato markers are expressed in all lung cells.

Taken together, this chimerism data strongly indicate that the damage to different lung cell lineages may be reversed by infusion of lung cells from fetal E16 mice after NA and TBI conditioning. To further verify that lung function was indeed restored following transplantation, pulmonary function analysis was performed commonly used in the evaluation of mouse respiratory disease models and their repair. Compared to untreated injured mice, transplant recipient mice exhibited significantly improved (P=0.009) baseline compliance of injured lungs as measured by the oscillation technique at 6 weeks after transplant (FIG. 33F), resulting in performance similar to that of healthy, noninjured mice. Treated mice also showed significantly improved tissue damping compared to untreated injured mice (P=0.021) (FIG. 33G). Notably, detailed histological analysis and lung microcomputed tomography (micro-CT; resolution of 80 μm) of the treated mice (n=30) up to 12 months following transplantation did not detect any tumors in the transplanted lung tissue (FIGS. 25A-D).

EXAMPLE 6

Cell Types Needed for Regeneration by Epithelial Progenitors

Although several epithelial progenitors, including the putative CD45$^-$CD31$^-$EpCAM$^+$CD24$^+$ cells and the recently described common precursor of AT1 and AT2 cells, marked by double staining for mucin-1 and podoplanin, could give rise to the observed donor type patches, the present inventors found that when purified by FACS sorting, these subpopulations had very poor 'patch-forming' activity in vivo compared to that found with unsorted cells, even when the sorted cell fractions were recombined (data not shown). Thus, the present inventors attempted in subsequent experiments to use cell fractionation with magnetic beads, which is less time consuming and therefore less toxic when processing a large number of cells. In these experiments, the role of major E16 lung cell subpopulations was evaluated by defining the impact of their depletion on lung regeneration.

Using magnetic beads, CD45$^+$, SCA-1$^+$, CD31$^+$ or EpCAM$^+$ (also known as CD326) cells were depleted from the lung cells of E16 GFP$^+$ C57BL/6 donor mice. The remaining cells were then phenotyped by FACS analysis (FIG. 36A) and assayed for colony generation in a 3D culture system (FIG. 36B) and for their ability to form patches 8 weeks after infusion of 1×10$^6$ cells into C57BL/6 recipients conditioned with NA and 6 Gy TBI (FIGS. 36C-F). As expected, after removal of CD45$^+$ hematopoietic cells, the remaining cell preparation (the CD45− fraction) retained marked colony-forming activity in 3D culture and patch formation in vivo (FIG. 36C), whereas after removal of EpCAM$^+$ epithelial progenitors these activities were adversely affected (FIG. 36D) (83% and 98% reduction, compared to the CD45− fraction, P=0.00015 and P=0.00013, respectively). Interestingly, the lung patch assay also indicated a critical role for CD31$^+$ cells (FIG. 36E) (93% reduction in patch numbers compared to the CD45− fraction, P=0.00013); and a significant, but less pronounced, reduction of patches was found after removal of SCA-1$^+$ cells (FIG. 36F) (62% reduction, compared to removal of the CD45− population, P=0.005). In the 3D culture assay, the role of CD31$^+$ cells, although considerable, was less influential (FIG. 36G), and a similar reduction in activity was observed (compared to that after removal of CD45− cells) after removal of SCA-1$^+$ cells or CD31$^+$ cells (63% and 53%, respectively). Taken together, the present in vivo results (FIG. 36H) confirm that CD31$^+$ endothelial cells and SCA-1$^+$ mesenchymal cells could have an important role in facilitating growth and development of EpCAM$^+$ epithelial progenitors. Thus, the present results indicate that transplanting a single cell suspension without fractionation, as done in cord blood transplantation, could be advantageous for lung regeneration.

EXAMPLE 7

Human Fetal Lung Cell Transplantation into NOD-SCID Mice

To investigate the ability of canalicular-stage human embryonic lung cells to integrate into injured mouse lungs, the NA lung injury model was established in NOD-SCID mice. Because NOD-SCID mice are more sensitive to TBI than are wild-type mice, these mice were conditioned with 3-4 Gy TBI (instead of 6 Gy TBI). Infusion of 1×10$^6$ 20-week of gestation human embryonic lung cells into NOD-SCID mice conditioned with NA alone resulted in negligible engraftment (data not shown), but increased chimerism was observed after infusion of cells into NOD-SCID mice conditioned with NA followed by 3-4 Gy TBI. Inventors confirmed this pattern, which was found first after infusion of a single cell suspension stained with the fluorescent tracking dye CMTMR (data not shown), in a second experiment to verify donor type chimerism by double staining of the recipient lung with an antibody to mouse MHC (not cross-reactive with human tissue) (FIG. 37A), and an antibody (MNF116) to human cytokeratin (staining human epithelial cells and non-cross-reactive with control mouse tissue) (FIG. 37B). At 6 weeks after transplantation, double staining with these antibodies showed incorporation of human-derived cells into lung structures (data not shown).

In two subsequent experiments, lung cells from human embryos harvested at 20-weeks of gestation were infused into NOD-SCID mice treated with NA and 4 Gy TBI. Seven weeks after infusion, lungs were stained with *Bandeiraea simplicifolia* isolectin B4 (staining mouse and other species but non-cross-reactive with human tissue) alone or in conjunction with an antibody to a broad spectrum of human cytokeratins (clone MNF116, see Table 7 above), vimentinV9 and CD31 (non-cross-reactive with mouse tissue) (FIGS. 37C-E). The latter cocktail selectively stained cells of human origin in both alveolar and bronchial structures of chimeric mice (FIGS. 37F-G). Recipient mice showed varying degrees of chimerism. Thus, the morphometric analysis revealed more than 0.5% lung occupation in 6 of 13 mice [in one experiment, three out of these six positive mice (with more than 0.5% lung occupation) exhibited lung occupancy of 0.8%±0.4%, 0.6%±0.05% and 1.0%±0.9%, mean±s.d.; in the second experiment, three out of seven mice exhibited higher lung occupancy, of 4.2%±1.5%, 4.4%±1.4% and 5.15%±2.8%, respectively]. The average human cell lung occupancy in these six mice, identified using a mixture of anti-human antibodies at 7 weeks after transplant, was 3%±2.3% of the mouse lung parenchyma (FIG. 38A), compared to 11% found for syngeneic mouse E16 cells at 8 weeks after transplant (FIG. 30C). However, the patterns identified were similar to those found in the syngeneic transplantation model, and human-derived bronchioalveolar and alveolar patches (FIGS. 38B-C) comprising AT1 (FIG. 38D) and AT2 cells (FIG. 38E) were detected by double staining of human cells with anti-AQP-5 and anti-SPC antibodies, respectively.

Taken together, the present results (in individual mice showing relatively high lung occupancy) further establish the proof of concept attained in the above described studies using the syngeneic system. Additionally, the viability of $CD45^-$ human canalicular-stage lung cells after freezing and thawing (FIG. 37H) and their ability to form 3D lung structures in ex vivo culture (FIG. 37I), support the feasibility of 'banking' human embryonic lung cells for tissue typing and quality-control assays before transplantation.

EXAMPLE 8

Induction of Lung Chimerism after Transplantation of Fresh Adult Lung Cells

Adult lung cells were harvested from a GFP positive C57BL/6 mouse and a single cell suspension comprising $8 \times 10^6$ was injected i.v. into C57BL/6 recipient mice following conditioning with NA and 6 GY TBI.

Eight weeks after transplantation lung tissue from transplanted mice was obtained, fixed and analyzed for GFP positive patches. As evident from the results (FIGS. 39A-F) marked number of donor derived GFP positive patches were found in the recipient's lungs.

EXAMPLE 9

Induction of Lung Chimerism after Transplantation of Ex Vivo Expanded Lung Cells Lung cells were expanded ex vivo by first obtaining GFP positive C57BL E16 lung cells and seeding the cells on tissue culture plates with a suitable condition medium (iMEF) together with epithelial growth factor and Rock inhibitor. A single cell suspension comprising $2 \times 10^6$ expanded cells were injected i.v. into C57BL/6 recipient mice following conditioning with NA and 6 GY TBI.

Eight weeks after transplantation lung tissue from transplanted mice was obtained, fixed and analyzed for GFP positive patches. As evident from the results (FIGS. 40A-F) marked number of donor derived GFP positive patches were found in the recipient's lungs.

Although the invention has been described in conjunction with specific embodiments thereof, it is evident that many alternatives, modifications and variations will be apparent to those skilled in the art. Accordingly, it is intended to embrace all such alternatives, modifications and variations that fall within the spirit and broad scope of the appended claims.

All publications, patents and patent applications mentioned in this specification are herein incorporated in their entirety by into the specification, to the same extent as if each individual publication, patent or patent application was specifically and individually indicated to be incorporated herein by reference. In addition, citation or identification of any reference in this application shall not be construed as an admission that such reference is available as prior art to the present invention. To the extent that section headings are used, they should not be construed as necessarily limiting.

What is claimed is:

1. A method of transplanting progenitor cells in suspension from an adult lung tissue to a subject in need thereof, the method comprising:
   (a) conditioning the subject by:
      (i) administering to the subject a therapeutically effective amount of an agent capable of inducing damage to a pulmonary tissue, wherein said damage results in proliferation of resident stem cells in said pulmonary tissue, wherein said agent capable of inducing damage to said pulmonary tissue is selected from the group consisting of a chemical, an antibiotic, a therapeutic drug, a toxin, a surgical intervention and an herbal remedy, and wherein said agent capable of inducing damage to said pulmonary tissue is not naphthalene; and subsequently
      (ii) subjecting said subject to an agent which ablates said resident stem cells in said pulmonary tissue; and
   (b) transplanting progenitor cells in suspension from an adult lung tissue to said conditioned subject, wherein said transplanting is effected by an intravenous route.

2. The method of claim 1, wherein said agent capable of inducing damage to said pulmonary tissue is an agent causing pulmonary cell toxicity.

3. The method of claim 2, wherein said agent causing pulmonary cell toxicity is selected from the group consisting of a chemotherapeutic agent, an immunosuppressive agent, an amiodarone, a beta blockers, an ACE inhibitor, a nitrofurantoin, a procainamide, a quinidine, a tocainide, and a minoxidil.

4. The method of claim 1, wherein said agent which ablates said resident stem cells comprises a sublethal or lethal conditioning regimen.

5. The method of claim 4, wherein said sublethal or lethal conditioning regimen comprises a partial body irradiation, a total body irradiation (TBI) or an Alkylating agent.

6. The method of claim 5, wherein
   said Alkylating agent is selected from the group consisting of a cyclophosphamide and a busulfan.

7. The method of claim 1, wherein said agent capable of inducing damage to said pulmonary tissue is administered to the subject 1-3 days prior to said agent which ablates said resident stem cells.

8. The method of claim 1, wherein said subject has a disease selected from the group consisting of a malignant disease, a pulmonary disease, an infectious disease, an inflammatory disease, an immunodeficiency and an autoimmune disease.

9. The method of claim 1, wherein said progenitor cells comprise human progenitor cells.

10. The method of claim 1, wherein said progenitor cells are capable of regenerating a structural/functional tissue.

11. The method of claim 10, wherein said structural/functional tissue comprises generation of a chimeric tissue.

12. The method of claim 9, wherein said subject is a human being.

13. The method of claim 1, further comprising treating the subject with an immunosuppressive regimen.

* * * * *